US011590167B2

United States Patent
Ports et al.

(10) Patent No.: US 11,590,167 B2
(45) Date of Patent: Feb. 28, 2023

(54) METHODS AND COMPOSITIONS FOR USE OF THERAPEUTIC T CELLS IN COMBINATION WITH KINASE INHIBITORS

(71) Applicants: Juno Therapeutics, Inc., Seattle, WA (US); ACERTA PHARMA, LLC, Redwood City, CA (US); ACERTA PHARMA B.V., AB Oss (NL)

(72) Inventors: Michael Ports, Seattle, WA (US); Jim Qin, Renton, WA (US); Ruth Salmon, Bainbridge Island, WA (US); Oleksandr Baturevych, Seattle, WA (US)

(73) Assignees: Juno Therapeutic, Inc., Seattle, WA (US); ACERTA PHARMA B.V., AB Oss (NL)

( * ) Notice: Subject to any disclaimer, the term of this patent is extended or adjusted under 35 U.S.C. 154(b) by 678 days.

(21) Appl. No.: 16/465,542

(22) PCT Filed: Dec. 1, 2017

(86) PCT No.: PCT/US2017/064362
§ 371 (c)(1),
(2) Date: May 30, 2019

(87) PCT Pub. No.: WO2018/102785
PCT Pub. Date: Jun. 7, 2018

(65) Prior Publication Data
US 2019/0328786 A1 Oct. 31, 2019

Related U.S. Application Data

(60) Provisional application No. 62/581,644, filed on Nov. 3, 2017, provisional application No. 62/429,732, filed on Dec. 3, 2016.

(51) Int. Cl.
| | | |
|---|---|---|
| A61K 31/05 | (2006.01) | |
| A61K 35/17 | (2015.01) | |
| A61K 9/00 | (2006.01) | |
| C07K 16/28 | (2006.01) | |
| C12N 5/0783 | (2010.01) | |
| C12N 15/85 | (2006.01) | |
| A61K 45/06 | (2006.01) | |

(52) U.S. Cl.
CPC ............ *A61K 35/17* (2013.01); *A61K 9/0053* (2013.01); *A61K 31/05* (2013.01); *C07K 16/2809* (2013.01); *C12N 5/0638* (2013.01); *C12N 15/85* (2013.01); *A61K 45/06* (2013.01)

(58) Field of Classification Search
CPC ................................ A61K 35/17; A61K 31/05
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 4,795,698 A | 1/1989 | Owen et al. |
| 5,200,084 A | 4/1993 | Liberti et al. |
| 5,219,740 A | 6/1993 | Miller et al. |
| 6,040,177 A | 3/2000 | Riddell et al. |
| 6,207,453 B1 | 3/2001 | Maass et al. |
| 6,410,319 B1 | 6/2002 | Raubitschek et al. |
| 6,451,995 B1 | 9/2002 | Cheung et al. |
| 7,070,995 B2 | 7/2006 | Jensen |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,459,554 B2 | 12/2008 | Dong et al. |
| 8,324,353 B2 | 12/2012 | Jensen |
| 8,339,645 B2 | 12/2012 | Nakawaki |

(Continued)

FOREIGN PATENT DOCUMENTS

| | | |
|---|---|---|
| CN | 101084218 | 12/2007 |
| CN | 102209729 A | 10/2011 |

(Continued)

OTHER PUBLICATIONS

US 8,252,592 B2, 08/2012, Sadelain (withdrawn)

(Continued)

*Primary Examiner* — Rei Tsang Shiao
(74) *Attorney, Agent, or Firm* — Morrison Foerster LLP

(57) ABSTRACT

The present disclosure relates to methods, compositions and uses involving immunotherapies and inhibitors of a target protein tyrosine kinase in which the kinase is not IL-2-inducible T cell kinase (ITK) and/or is selected from Bruton's tyrosine kinase (BTK), tec protein tyrosine kinase (TEC), BMX non-receptor tyrosine kinase (Etk), TXK tyrosine kinase (TXK) and/or receptor tyro-sine-protein kinase ErbB4 (ErbB4). The provided methods, compositions and uses include administration of one or more such inhibitor with another agent, such as an immunotherapeutic agent targeting T cells and/or genetically engineered T cells, such as CAR-expressing T cells. Also provided are methods of manufacturing engineered cells, cells, compositions, methods of administration, nucleic acids, articles of manufacture and kits. In some aspects, features of the methods and cells provide for improved activity, efficacy, persistence, expansion and/or proliferation of T cells for adoptive cell therapy or endogenous T cells recruited by immunotherapeutic agents.

37 Claims, 46 Drawing Sheets

Specification includes a Sequence Listing.

(56) References Cited

U.S. PATENT DOCUMENTS

| | | | |
|---|---|---|---|
| 8,389,282 B2 | 3/2013 | Sadelain et al. | |
| 8,479,118 B2 | 7/2013 | Lindersay | |
| 8,802,374 B2 | 8/2014 | Jensen | |
| 8,822,647 B2 | 9/2014 | Jensen | |
| 8,911,993 B2 | 12/2014 | June et al. | |
| 9,278,919 B1 | 3/2016 | Xu | |
| 9,662,343 B2 * | 5/2017 | Tabuteau | A61K 31/675 |
| 10,392,446 B2 | 8/2019 | Stephan | |
| 2002/0131960 A1 | 9/2002 | Sadelain et al. | |
| 2003/0170238 A1 | 9/2003 | Gruenberg et al. | |
| 2011/0003380 A1 | 1/2011 | Miltenyi et al. | |
| 2013/0149337 A1 | 6/2013 | Cooper et al. | |
| 2013/0287748 A1 | 10/2013 | June et al. | |
| 2014/0134265 A1 | 5/2014 | Buggy et al. | |
| 2014/0271635 A1 | 9/2014 | Brogdon et al. | |
| 2014/0371241 A1 | 12/2014 | Buggy et al. | |
| 2015/0283178 A1 | 10/2015 | June et al. | |
| 2015/0299317 A1 | 10/2015 | Orentas et al. | |
| 2016/0362472 A1 | 12/2016 | Bitter et al. | |
| 2017/0210811 A1 | 7/2017 | Wong et al. | |
| 2018/0140602 A1 | 5/2018 | Angst et al. | |
| 2019/0161553 A1 | 5/2019 | Sather et al. | |
| 2019/0169572 A1 | 6/2019 | Shi et al. | |
| 2019/0233500 A1 | 8/2019 | Jantz et al. | |
| 2019/0292238 A1 | 9/2019 | Bitter et al. | |
| 2019/0298772 A1 | 10/2019 | Ports et al. | |
| 2019/0388471 A1 | 12/2019 | June et al. | |
| 2020/0016199 A1 | 1/2020 | Turtle et al. | |
| 2020/0031904 A1 | 1/2020 | Jantz et al. | |
| 2020/0277353 A1 | 1/2020 | Takahashi et al. | |
| 2020/0071670 A1 | 3/2020 | Shi et al. | |
| 2020/0172879 A1 | 6/2020 | Suri et al. | |
| 2020/0191774 A1 | 6/2020 | Christin et al. | |
| 2021/0121466 A1 | 4/2021 | Frankel et al. | |
| 2021/0147507 A1 | 5/2021 | Bayle et al. | |
| 2021/0161959 A1 | 6/2021 | Bot et al. | |
| 2021/0177896 A1 | 6/2021 | Porter et al. | |
| 2021/0213063 A1 | 7/2021 | Isaacs et al. | |
| 2021/0223248 A1 | 7/2021 | Turtle et al. | |
| 2022/0031746 A1 | 2/2022 | Gillenwater et al. | |

FOREIGN PATENT DOCUMENTS

| | | |
|---|---|---|
| CN | 104844573 | 8/2015 |
| CN | 105153154 | 12/2015 |
| CN | 105392888 A | 3/2016 |
| CN | 105399756 | 3/2016 |
| CN | 105732638 | 7/2016 |
| CN | 105884747 | 8/2016 |
| CN | 106163547 | 11/2016 |
| EP | 0 452 342 | 11/1994 |
| EP | 2 537 416 | 11/2014 |
| EP | 3747472 | 12/2020 |
| TH | 112298 | 2/2012 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/014257 | 3/2000 |
| WO | WO 2003/020763 | 3/2003 |
| WO | WO 2004/033685 | 4/2004 |
| WO | WO 2005/037836 | 4/2005 |
| WO | WO 2006/000830 | 1/2006 |
| WO | WO 2006/012422 | 2/2006 |
| WO | WO 2006/065946 | 6/2006 |
| WO | WO 2008/039218 | 4/2008 |
| WO | WO 2008/071937 | 6/2008 |
| WO | WO 2008/121742 | 10/2008 |
| WO | WO 2009/033140 | 3/2009 |
| WO | WO 2009/051822 | 4/2009 |
| WO | WO 2009/072003 | 6/2009 |
| WO | WO 2009/124119 | 10/2009 |
| WO | WO 2009/158571 | 12/2009 |
| WO | WO 2010/009342 | 1/2010 |
| WO | WO 2010/100070 | 9/2010 |
| WO | WO 2011/029046 | 3/2011 |
| WO | WO 2011/044186 | 4/2011 |
| WO | WO 2011/046964 | 4/2011 |
| WO | WO 2011/152351 | 12/2011 |
| WO | WO 2011/153514 | 12/2011 |
| WO | WO 2011/162515 | 12/2011 |
| WO | WO 2012/021444 | 2/2012 |
| WO | WO 2012/129514 | 9/2012 |
| WO | WO 2013/026837 | 2/2013 |
| WO | WO 2013/060098 | 5/2013 |
| WO | WO 2013/067274 | 5/2013 |
| WO | WO 2013/067277 | 5/2013 |
| WO | WO 2013/071154 | 5/2013 |
| WO | WO 2013/081016 | 6/2013 |
| WO | WO 2013/100631 | 7/2013 |
| WO | WO 2013/113097 | 8/2013 |
| WO | WO 2013/123061 | 8/2013 |
| WO | WO 2013/126726 | 8/2013 |
| WO | WO 2013/166321 | 11/2013 |
| WO | WO 2014/011984 | 1/2014 |
| WO | WO 2014/031687 | 2/2014 |
| WO | WO 2014/055668 | 4/2014 |
| WO | WO 2014/068527 | 5/2014 |
| WO | WO 2014/078578 | 5/2014 |
| WO | WO 2014/104757 | 7/2014 |
| WO | WO 2014/153270 | 9/2014 |
| WO | WO 2014/187262 | 11/2014 |
| WO | WO 2014/210085 | 12/2014 |
| WO | WO 2015/048689 | 4/2015 |
| WO | WO 2015/057992 | 4/2015 |
| WO | WO 2015/082499 | 6/2015 |
| WO | WO 2015/083008 | 6/2015 |
| WO | WO 2015/084892 | 6/2015 |
| WO | WO 2015083008 * | 6/2015 |
| WO | WO 2015/127310 | 8/2015 |
| WO | WO 2015/142675 | 9/2015 |
| WO | WO 2015/146159 | 10/2015 |
| WO | WO 2015/157252 | 10/2015 |
| WO | WO 2015/157384 | 10/2015 |
| WO | WO 2015/165279 | 11/2015 |
| WO | WO 2015/169233 | 11/2015 |
| WO | WO 2015/192658 | 12/2015 |
| WO | WO 2016/014530 | 1/2016 |
| WO | WO 2016/020901 | 2/2016 |
| WO | WO 2016/024230 | 2/2016 |
| WO | WO 2016/112637 | 7/2016 |
| WO | WO 2016/164580 | 10/2016 |
| WO | WO 2017/214207 | 12/2017 |
| WO | WO 2018/085731 | 5/2018 |
| WO | WO 2019/109053 | 6/2019 |
| WO | WO 2019/213184 | 11/2019 |
| WO | WO 2020/113188 | 3/2020 |
| WO | WO 2010/052013 | 5/2020 |

OTHER PUBLICATIONS

Deniger et al. PLOS One, 2015, DOI: 10.137.*
Abramson et al., "High durable CR rates and preliminary safety profile for JCAR017 in R/R aggressive b-NHL (TRANSCEND NHL 001 Study): A defined composition CD19-directed CAR T-cell product with potential for outpatient administration," J Clin Oncol (2018) 36(5_suppl):120.
Abramson et al., "TRANSCEND NHL 001: Immunotherapy with the CD19-directed CAR T-cell Product JCAR017 Results in High Complete Response Rates in Relapsed or Refractory B-Cell Non-Hodgkin Lymphoma," Blood (2016) 128:4192 Abstract.
Advani et al., "Bruton tyrosine kinase inhibitor ibrutinib (PCI-32765) has significant activity in patients with relapsed/refractory B-cell malignancies," J Clin Oncol. (2013)31:88-94.
Sidaway et al., "Ibrutinib supercharges CAR T cells," Nature Reviews Clin Oncol (2016) 13(4):204. doi:10.1038/nrclinonc.2016.28.
Barf et al., "Acalabrutinib (ACP-196): A Covalent Bruton Tyrosine Kinase Inhibitor with a Differentiated Selectivity and In Vivo Potency Profile," J Pharmacol Exp Ther (2017) 363(2):240-252.

(56) References Cited

OTHER PUBLICATIONS

Bridgeman et al., "The optimal antigen response of chimeric antigen receptors harboring the CD3 transmembrane domain is dependent upon incorporation of the receptor into the endogenous TCR/CD3 complex," J Immunol (2010) 184:6938-6949.
Buggy et al., "Bruton tyrosine kinase (BTK) and its role in B-cell malignancy," Int Rev Immunol. (2012) 31:119-132.
Chiron et al., "Cell-cycle reprogramming for PI3K inhibition overrides a relapse-specific C481S BTK mutation revealed by longitudinal functional genomics in mantle cell Tymphoma," Cancer Discov (2014) 4(9):1022-1035.
Gardner et al., "Intent-to-treat leukemia remission by CD19 CAR T cells of defined formulation and dose in children and young adults," Blood (2017) 129(25):3322-3331.
Gauthier et al., "Comparison of efficacy and toxicity of CD19-specific chimeric antigen receptor T-cells alone or in combination with ibrutinib for relapsed and/or refractory CLL," Blood. 2018;132:299.
Herman et al., "The Bruton tyrosine kinase (BTK) inhibitor acalabrutinib demonstrates potent on-target effects and efficacy in two mouse models of chronic lymphocytic Teukemia," Clin Cancer Res. (2017)23: 2831-2841.
Jackson et al., "Driving CAR T-cells forward," Nat Rev Clin Oncol (2016) 13(6):370-383.
Kahl et al., "Advances and issues in mantle cell lymphoma research: report of the 2014 mantle cell lymphoma consortium workshop," Leukemia & Lymphoma (2015) 56(9):2505.
Kandalaft et al., "A phase I clinical trial of adoptive transfer of folate receptor-alpha redirected autologous T cells for recurrent ovarian cancer," J Transl Med (2012) 10:157.
Kedmi et al., "Ibrutinib, bendamustine, rituximab combination for relapsed and refractory aggressive B cell lymphoma—Interim analysis of phase II clinical trial," Blood. Nov. 21, 2018; 132:4186.
Kokhaei et al., Ibrutinib—A double-edge sword in cancer and autoimmune disorders. J Drug Target. 2016;24:373-385.
Lee et al., "Current concepts in the diagnosis and management of cytokine release syndrome," Blood. (2014) 124(2):188-95.
Nastoupil et al., "Safety and efficacy of ibrutinib in combination with rituximab and lenalidomide in previously untreated subjects with follicular and marginal zone lymphoma: An open label, phase II study," Blood. Nov. 21, 2018; 132:447.
Patel et al., "Comparison of acalabrutinib, a selective bruton tyrosine kinase inhibitor, with ibrutinib in chronic lymphocytic leukemia cells," Clin Cancer Res (2017) 23(14):3734-3743.
Podhorecka et al., "Changes in T-cell subpopulations and cytokine network during early period of ibrutinib therapy in chronic lymphocytic leukemia patients: the significant decrease in T regulatory cells number," Oncotarget (2017) 8(21):34661-34669.
Porter et al., "Chimeric antigen receptor-modified T cells in chronic lymphoid Teukemia," N Engl J Med. Aug. 25, 2011;365(8):725-33.
Qin et al., "Antitumor Potency of an Anti-CD19 Chimeric Antigen Receptor T-Cell Therapy, Lisocabtagene Maraleucel in Combination With Ibrutinib or Acalabrutinib," J Immunother (2020) 43(4):107-120.
Ritchie et al., "Persistence and efficacy of second generation CAR T cell against the LeY antigen in acute myeloid leukemia," Mol Ther (2013) 21(11):2122-2129.
Sahaf B, Tebaykin D, Hopper M, Cheung P, Bittencourt F, Cutler CS, et al. Ibrutinib-Mediated Inhibition of cGVHD Pathogenic Pre-Germinal Center B Cells and Follicular Helper Cells While Preserving Immune Memory and Th1 T Cells. ASBMT 2018.
Sommermeyer et al., "Chimeric antigen receptor-modified T cells derived from defined CD8+ and CD4+ subsets confer superior antitumor reactivity in vivo," Leukemia (2016) 30(2):492-500.
Turtle et al., "Therapy of B Cell Malignancies with CD19-Specific Chimeric Antigen Receptor-Modified T Cells of Defined Subset Composition," Blood. (2014) 124 (21): 384.
Wang et al., "Acalabrutinib in relapsed or refractory mantle cell lymphoma (ACE-LY-004): a singlearm, multicentre, phase 2 trial," Lancet. (2018) 391:659-667.

Wang et al., "Bruton's tyrosine kinase and its isoforms in cancer," Front Cell Dev Biol (2021) 9:668996.
Wilson et al., "Targeting B cell receptor signaling with ibrutinib in diffuse large B cell Tymphoma," Nat Med. (2015) 21:922-926.
Younes et al., "A global, randomized, placebo-controlled, phase 3 study of ibrutinib plus rituximab, cyclophosphamide, doxorubicin, vincristine, and prednisone (RCHOP) in patients with previously untreated non-germinal center B-cell-like (GCB) diffuse large B-cell lymphoma (DLBCL)" Blood. Nov. 21, 2018; 132:784.
Afar et al., "Regulation of Btk by Src family tyrosine kinases," Mol Cell Biol (1996) 16(7):3465-3471.
AG1478 (Tyrphostin) Kinase Profiling Inhibitor Database, retrieved from the internet URL: http://www.kinase-screen.mrc.ac.uk/screening-compounds/348815; retrieved Feb. 21, 2020.
Ahmed et al., "Human Epidermal Growth Factor Receptor 2 (HER2)—Specific Chimeric Antigen Receptor-Modified T Cells for the Immunotherapy of HER2-Positive Sarcoma." J Clin Oncol. May 20, 2015; 33(15): 1688-1696.
Akinleye et al., "Ibrutinib and novel BTK inhibitors in clinical development," J Hematol Oncol (2013) 6:59.
Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.
Anastassiadis et al., "Comprehensive assay of kinase catalytic activity reveals features of kinase inhibitor selectivity," Nat Biotechnol (2011) 29(11):1039-1045.
Apsel et al., "Targeted polypharmacology: discovery of dual inhibitors of tyrosine and phosphoinositide kinases," Nat Chem Biol. (2008) 4(11):691-699.
Bair et al., "Accelerating chimeric antigen receptor therapy in chronic lymphocytic leukemia: The development and challenges of chimeric antigen receptor T-cell therapy for chronic lymphocytic leukemia," Am J Hematol. (2019) 94(S1):S10-S17.
Bamborough et al., "Assessment of chemical coverage of kinome space and its implications for kinase drug discovery," J Med Chem (2008) 51(24)7898-7914.
Bamborough et al., "N-4-Pyrimidinyl-1H-indazol-4-amine inhibitors of Lck: indazoles as phenol isosteres with improved pharmacokinetics," Bioorg Med Chem Lett. (2007) 17(15):4363-4368.
Barf et al., "Irreversible protein kinase inhibitors: balancing the benefits and risks," J Med Chern (2012) 55(14):6243-6262.
Barrett et al., "Chimeric Antigen Receptor Therapy for Cancer," Annual Review of Medicine (2013) 65:333-347.
Berg et al., "Tec family kinases in T lymphocyte development and function," Annu Rev Immunol (2005) 23:549-600.
Berglof et al., "Targets for Ibrutinib Beyond B Cell Malignancies," Scandinavian Journal of Immunology (2015) 82:208-217.
Boris-Lawrie et al., "Recent advances in retrovirus vector technology," Current Opinion in Genetics & Development (1993) 3(1):102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Britschgi et al., "HIC1 tumour suppressor gene is suppressed in acute myeloid leukaemia and induced during granulocytic differentiation," British Journal of Haematology (2008) 141(2):179-187.
BTK Target Report Card CHEMBL5251, retrieved from the internet URL: https://www.ebi.ac.uk/chembl/target_report_card/CHEMBL5251/ retrieved Feb. 21, 2020.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

(56) References Cited

OTHER PUBLICATIONS

Busch et al., "Role of memory T cell subsets for adoptive immunotherapy," Semin Immunol (2016) 28(1):28-34.

Byrd et al., "Acalabrutinib (ACP-196) in Relapsed Chronic Lymphocytic Leukemia" N Engl J Med. Jan. 28, 2016; 374(4): 323-332.

Byrd et al., "Three-year follow-up of treatment-naive and previously treated patients with CLL and SLL receiving single-agent ibrutinib," Blood (2015) 125(16):2497-2506.

Byrd, "Dr. John Byrd Discusses ACP 196 or Acalabrutinib, a new BTK inhibitor," ASH 2015.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carrillo et al., "The Multiple Sequence Alignment Problem in Biology," SIAM J Appl Math (1988) 48(5):1073-1082.

Cavalieri et al., "Human T lymphocytes transduced by lentiviral vectors in the absence of TCR activation maintain an intact immune competence," Blood (2003) 102(2): 497-505.

Cheadle et al., "Chimeric antigen receptors for T-cell based therapy," Methods Mol Biol. (2012);907:645-66.

Cheng et al., "Relationship between the inhibition constant (KI) and the concentration of inhibitor which causes 50 per cent inhibition (150) of an enzymatic reaction," Biochem Pharmacol. (1973) 22: 3099-3108.

Chervin et al., "Engineering higher affinity T cell receptors using a T cell display system," J Immunol Methods (2008) 339(2):175-184.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," EMBO J (1988) 7(12):3745-3755.

Clinical Trial Study Record No. NCT01865617. First posted May 31, 2013. Updated Oct. 26, 2017. Accessed Jun. 5, 2018.

Clinical Trial Study Record No. NCT02631044. First posted Dec. 15, 2015. Updated Aug. 26, 2019. Accessed Sep. 23, 2019.

Clinicaltrials.gov Identifier NCT01822652. First posted Apr. 2, 2013. Last updated May 3, 2019.

Clinicaltrials.gov Identifier NCT02029443. First posted Jan. 9, 2014. Last updated Feb. 1, 2019.

Clinicaltrials.gov identifier NCT02213926. First posted on Aug. 12, 2014. Last update posted Jul. 10, 2019.

Clinicaltrials.gov Identifier NCT02315612. First posted Dec. 12, 2014. Last updated Oct. 9, 2019.

Clinicaltrials.gov identifier NCT02717624. First posted on Mar. 24, 2016. Last update posted Mar. 28, 2019.

Clinicaltrials.gov identifier NCT02735876. First posted on Apr. 13, 2016. Last update posted May 13, 2016.

Clinicaltrials.gov Identifier NCT03331198. First posted Nov. 6, 2017. Last updated Sep. 18, 2019.

Cooper et al., "T-cell clones can be rendered specific for CD19: toward the selective augmentation of the graft-versus-B-lineage leukemia effect," Blood (2003) 101:1637-1644.

Corvus Pharmaceuticals, "Our Pipeline | CPI-444 | CPI-006 | CPI-818 |," (2019) https://www.corvuspharma.com/our-science/our-pipeline/.

Covey et al., "ACP-196: a novel covalent Bruton's tyrosine kinase (Btk) inhibitor with improved selectivity and in vivo target coverage in chronic lymphocytic leukemia (CLL)." Cancer Res 2015;75(15 Suppl):Abstract No. 2596.

D'Arena et al., "Regulatory T-cell No. is increased in chronic lymphocytic leukemia patients and correlates with progressive disease," Leuk Res (2011) 35(3):363-368.

Davids et al., "Ibrutinib: a first in class covalent inhibitor of Bruton's tyrosine kinase," Future Oncology (2014) 10(6):957-967.

Davila et al., "CD19 CAR-Targeted T Cells Induce Long-Term Remission and B Cell Aplasia in an Immunocompetent Mouse Model of B Cell Acute Lymphoblastic Leukemia," PLOS One (2013) 8(4):e61338.

Davila et al., "How do CARs work?: Early insights from recent clinical studies targeting CD19," Oncoimmunology (2012) 1(9):1577-1583.

Davis et al., "Comprehensive analysis of kinase inhibitor selectivity," Nat Biotechnol (2011) 29(11):1046-1051.

Di Paolo et al., "Specific Btk inhibition suppresses B cell- and myeloid cell-mediated arthritis," Nat Chem Biol (2011) 7(1):41-50.

Dimauro et al., "Discovery of aminoquinazolines as potent, orally bioavailable inhibitors of Lck: synthesis, SAR, and in vivo anti-inflammatory activity," J Med Chem. (2006) 49(19): 5671-86.

Dubovsky et al., "Ibrutinib is an irreversible molecular inhibitor of ITK driving a Th1-selective pressure in T lymphocytes." Blood. Oct. 10, 2013;122(15):2539-49.

Dudley et al., "Cancer regression and autoimmunity in patients after clonal repopulation with antitumor lymphocytes," Science (2002) 298(5594):850-854.

Emanuel et al., "Cellular and in vivo activity of JNJ-28871063, a nonquinazoline pan-ErbB kinase inhibitor that crosses the blood-brain barrier and displays efficacy against intracranial tumors," Mol Pharmacol. Feb. 2008;73(2):338-48.

Evans et al., "Clinical Development of AVL-292: A Potent, Selective Covalent Btk Inhibitor for the Treatment of B Cell Malignancies," ASH Annual Meeting. Dec. 10-13, 2011. Poster.

Evans et al., "Inhibition of Btk with CC-292 Provides Early Pharmacodynamic Assessment of Activity in Mice and Humans," JPET #203489. Retrieved on Sep. 27, 2019. Retrieved on http://jpet.aspetjournals.org/content/jpet/suppl/2013/05/24/jpet.113.203489.DC1/jpet203489SupplMethTabsREV.pdf.

Fabian et al., "A small molecule-kinase interaction map for clinical kinase inhibitors," Nat Biotechnol. (2005) 23(3): 329-36.

Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.

Fidanze et al., "Imidazo[2,1-b]thiazoles: multitargeted inhibitors of both the insulin-like growth factor receptor and members of the epidermal growth factor family of receptor tyrosine kinases," Bioorg Med Chem Lett. (2010) 20(8): 2452-2455.

Fraietta et al., "Ibrutinib enhances chimeric antigen receptor T-cell engraftment and efficacy in leukemia." Blood. Mar. 3, 2016;127(9):1117-27.

Gabrilovich et al., "Myeloid-derived suppressor cells as regulators of the immune system," Nat Rev Immunol (2009) 9(3):162-174.

Geyer et al., "Implications of Concurrent Ibrutinib Therapy on CAR T-Cell Manufacturing and Phenotype and on Clinical Outcomes Following CD19-Targeted CAR T-Cell administration in Adults with Relapsed/Refractory CLL." Blood 2016 128:58.

Gill et al., "CD19 CAR-T cells combined with ibrutinib to induce complete remission in CLL." J. Clin. Oncol. May 2017;35(15 Supp.):7509.

Godin et al., "Microfluidics and photonics for Bio-System-on-a-Chip: a review of advancements in technology towards a microfluidic flow cytometry chip," J Biophotonics (2008) 1(5):355-376.

Goldberg et al., "Optimization of 2-phenylaminoimidazo[4,5-h]isoquinolin-9-ones: orally active inhibitors of lck kinase," J Med Chem. Apr. 10, 2003;46(8):1337-49.

Gunderson et al., "Bruton Tyrosine Kinase-Dependent Immune Cell Cross-talk Drives Pancreas Cancer," Cancer Discov (2016) 6(3):270-285.

Hall et al., "Synthesis, activity, and pharmacophore development for isatin-beta-thiosemicarbazones with selective activity toward multidrug-resistant cells," J Med Chem (2009) 52(10):3191-3204.

Han et al., "Chimeric antigen receptor-engineered T cells for cancer immunotherapy: progress and challenges," J Hematology & Oncology (2013) 6:47.

Heim et al., "Selective repression of retinoic acid target genes by RIP140 during induced tumor cell differentiation of pluripotent human embryonal carcinoma cells," Mol Cancer (2007) 6:57.

Hendriks et al., "Targeting Bruton's tyrosine kinase in B cell malignancies," Nat Rev Cancer (2014) 14(4):219-232.

(56) References Cited

OTHER PUBLICATIONS

Hermans et al., "The VITAL assay: a versatile fluoro metric technique for assessing CTL- and NKT-mediated cytotoxicity against multiple targets in vitro and in vivo," J Immunol Methods (2004) 285(1):25-40.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Holliger et al., "Specific killing of lymphoma cells by cytotoxic T-cells mediated by a bispecific diabody," Protein Engineering Design and Selection (1996) 9(3):299-305.
Honda et al., "The kinase Btk negatively regulates the production of reactive oxygen species and stimulation-induced apoptosis in human neutrophils," Nat Immunol (2012) 13(4):369-378.
Honigberg et al., "The Bruton tyrosine kinase inhibitor PCI-32765 blocks B-cell activation and is efficacious in models of autoimmune disease and B-cell malignancy," Proc Natl Acad Sci USA (2010) 107(29):13075-13080.
Huang et al., "Discovery of 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a potent, orally active pan-inhibitor of breakpoint cluster region-abelson (BCR-ABL) kinase including the T315I gatekeeper mutant," J Med Chem. Jun. 24, 2010;53(12):4701-4719.
Huang et al., "DNA transposons for modification of human primary T lymphocytes," Methods Mol Biol (2009) 506:115-126.
Hudecek et al., "Receptor affinity and extracellular domain modifications affect tumor Yecognition by ROR1-specific chimeric antigen receptor T cells," Clin Cancer Res (2013) 19(12):3153-3164.
Hur et al., "Clinical stage EGFR inhibitors irreversibly alkylate Bmx kinase," Bioorg Med Chem Lett. Nov. 15, 2008;18(22):5916-5919.
Ibrutinib (RX) dosing and uses. Retrieved on Sep. 27, 2019. Retrieved on https://reference.medscape.com/drug/imbruvica-ibrutinib-999896.
IKK-2 Inhibitor IV (TPCA-1) Kinase Profiling Inhibitor Database, retrieved from the internet URL: http://www.kinase-screen.mrc.ac.uk/screening-compounds/345889; retrieved Feb. 21, 2020.
Imbruvica capsules and tablets, Highlights of Prescribing Information. Initial US Approval 2013. Revised Jul. 2019.
Imbruvica capsules, Highlights of Prescribing Information. Initial US Approval 2013. Revised Jan. 2015.
Jain et al., "Initial treatment of CLL: integrating biology and functional status," Blood (2015) 126(4):463-470.
Janeway et al., Immunobiology: The Immune System in Health and Disease, 3rd ED., Current Biology Publications (1997), p. 4:33.
Jensen et al., "Antitransgene rejection responses contribute to attenuated persistence of adoptively transferred CD20/CD19-specific chimeric antigen receptor redirected T cells in humans," Biol Blood Marrow Transplant (2010) 16(9):1245-1256.
Jiang et al., "LZTFL1 Upregulated by All-Trans Retinoic Acid during CD4+T Cell Activation Enhances IL-5 Production," J Immunol (2016) 196(3):1081-1090.
Johnson et al., "Kinomics: methods for deciphering the kinome," Nat Methods (2005) 2(1):17-25.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity.," PNAS (1990) 87(23):9138-9142.
Juno Corporate Presentation. Retrieved on http://ir.junotherapeutics.com. Retrieved on Jan. 2018.
Juno Corporate Presentation. Retrieved on http://ir.junotherapeutics.com. Retrieved on Sep. 2017.
Juno Therapeutics, "Juno's Investigational CAR T Cell Product Candidates JCAR014 and JCAR018 Demonstrate Encouraging Clinical Responses in Patients with B-Cell Cancers," Published on Dec. 6, 2015. Retrieved on http://ir.junotherapeutics.com/news-releases/news-release-details/junos-investigational-car-t-cell-product-candidates-jcar014-and Retrieved on Mar. 6, 2018.
Kalos et al., "T cells with chimeric antigen receptors have potent antitumor effects and can establish memory in patients with advanced leukemia," Sci Transl Med (2011) 3(95):95ra73.
Karaman et al., "A quantitative analysis of kinase inhibitor selectivity," Nat Biotechnol. Jan. 2008;26(1):127-32.
Kipriyanov et al., "Bispecific tandem diabody for tumor therapy with improved antigen binding and pharmacokinetics," J Mol Biol (1999) 293(1):41-56.
Klebanoff et al., "Sorting through subsets: Which T cell populations mediate highly effective adoptive immunotherapy?" J Immunother (2012) 35(9):651-660.
Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol (2015) 33(6):540-549.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol (2013) 10(5):267-276.
Koste et al., "T-cell receptor transfer into human T cells with ecotropic retroviral vectors," Gene Therapy (2014) 21:533-538.
Kotb et al., "Bacterial pyrogenic exotoxins as superantigens," Clinical Microbiology Reviews (1995) 8:411-426.
Kurucz et al., "A bacterially expressed single-chain Fv construct from the 2B4 T-cell receptor," PNAS (1993) 90(9):3830-3834.
Lamers et al., "Immune responses to transgene and retroviral vector in patients treated with ex vivo-engineered T cells," Blood (2011) 117(1):72-82.
Lannutti et al., "ACP-196, an orally bioavailable covalent selective inhibitor of Btk, modulates the innate tumor microenvironment, exhibits antitumor efficacy and enhances gemcitabine activity in pancreatic cancer," AACR; Cancer Res 2015;75(15 Suppl):Abstract nr 408. and retraction, published in Cancer Res 2017; 77(17).
Lee et al., "T cells expressing CD19 chimeric antigen receptors for acute lymphoblastic Teukaemia in children and yound adults: a phase 1 dose escalation trial," The Lancet (2015) 385(9967): 517-528.
Lefranc et al., "IMGT unique numbering for immunoglobulin and T cell receptor variable domains and Ig superfamily V-like domains," Dev Comp Immunol (2003) 27(1):55-77.
Legouill, S., "ACP-196 (Acalabrutinib) in MCL"; presented in Bologna, 2016, available at http://www.ercongressi.it/slides-NDH-Carlton/10-05/Le-Gouill.pdf.
LFM-A13 Product Page, Adooq Bioscience, retrieved from the internet URL: https://www.adooq.com/lfm-a13.html, retrieved Feb. 21, 2020.
Li et al., "Directed evolution of human T-cell receptors with picomolar affinities by phage display," Nat Biotechnol (2005) 23(3):349-354.
Li et al., "Discovery of a Series of 2,5-Diaminopyrimidine Covalent Irreversible Inhibitors of Bruton's Tyrosine Kinase with in Vivo Antitumor Activity," J. Med. Chem. (2014) 57(12):5112-5128.
Locke et al., "Phase 1 Clinical Results of the ZUMA-1 (KTE-C19-101) Study: a Phase 1-2 Multi-Center Study Evaluating the Safety and Efficacy of Anti-CD19 CAR T Cells (KTE-C19) in Subjects with Refractory Aggressive Non-Hodgkin Lymphoma (NHL)," Blood (2015) 126:3991.
Logan et al., "Minimal residual disease quantification using consensus primers and high-throughput IGH sequencing predicts post-transplant relapse in chronic lymphocytic Teukemia," Leukemia (2013) 27(8): 1659-1665.
Long et al., "Ibrutinib treatment improves T cell number and function in CLL patients," J Clin Invest. Aug. 1, 2017;127(8):3052-3064.

(56) References Cited

OTHER PUBLICATIONS

Long et al., "Ibrutinib Treatment Reduces Both T-Regulatory Cells and B-Regulatory Cell Phenotype in Malignant B Cells in Chronic Lymphocytic Leukemia Patients," Blood (2015) 126:2940.

Long et al., "Ilbrutinib Represents a Novel Class of Immune Modulating Therapeutics That Enhances the Survival of Activated T Cells in Vitro and In Vivo through a Non-BTK Mediated Mechanism." Blood 2016 128:3238.

Lou et al., "Bruton's tyrosine kinase inhibitors: approaches to potent and selective inhibition, preclinical and clinical evaluation for inflammatory diseases and B cell malignancies," J Med Chem (2012) 55(10):4539-4550.

Lupton et al., "Dominant positive and negative selection using a hygromycin phosphotransferase-thymidine kinase fusion gene," Mol and Cell Biol (1991) 11(6):3374-3378.

Ma et al., "The challenge of selecting protein kinase assays for lead discovery optimization," Expert Opin Drug Discov (2008) 3(6):607-621.

Maddocks et al., "Etiology of Ibrutinib Therapy Discontinuation and Outcomes in Patients With Chronic Lymphocytic Leukemia." JAMA Oncol. Apr. 2015;1(1):80-7.

Mahajan et al., "Rational design and synthesis of a novel anti-leukemic agent targeting Bruton's tyrosine kinase (BTK), LFM-A13 [alpha-cyano-beta-hydroxy-beta-methyl-N-(2, 5-dibromophenyl)propenamide]." J Biol Chem (1999) 274(14):9587-9599.

Mamonkin et al., "A T-cell-directed chimeric antigen receptor for the selective treatment of T-cell malignancies." Blood. Aug. 20, 2015;126(8):983-92.

Manuri et al., "piggyBac Transposon/Transposase System to Generate CD19-Specific T Cells for the Treatment of B-Lineage Malignancies," Hum Gene Ther (2010) 21(4):427-437.

Maude et al., "Chimeric antigen receptor T cells for sustained remissions in leukemia," N Engl J Med. Oct. 16, 2014;371(16):1507-17.

Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.

Miller et al., "Improved retroviral vectors for gene transfer and expression," Biotechniques (1989) 7(9):980-982.

Miller, "Retrovirus packaging cells," Hum Gene Ther (1990) 1(1):5-14.

Mirams et al., "Prediction of Thorough QT study results using action potential simulations based on ion channel screens," J Pharmacol Toxicol Methods. (2014) 70(3):246-54.

Moreira et al., "Infectious complications among individuals with clinical monoclonal B-cell lymphocytosis (MBL): a cohort study of newly diagnosed cases compared to controls," Leukemia (2013) 27(1):136-141.

Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.

Muranski et al., "Increased intensity lymphodepletion and adoptive immunotherapy—how far can we go?" Nat Clin Pract Oncol (2006) 3(12):668-681.

Nagorsen et al., "Immunomodulatory therapy of cancer with T cell-engaging BiTE antibody blinatumomab," Exp Cell Res (2011) 317(9):1255-1260.

Nijhof et al., "Upregulation of CD38 expression on multiple myeloma cells by all-trans retinoic acid improves the efficacy of daratumumab," Leukemia (2015) 29(10):2039-2049.

Palmer et al., "Prognostic importance of T and NK-cells in a consecutive series of newly diagnosed patients with chronic lymphocytic leukaemia," Br J Haematol (2008) 141(5):607-614.

Park et al., "Adoptive transfer of chimeric antigen receptor re-directed cytolytic T Tymphocyte clones in patients with neuroblastoma," Mol Ther (2007) 15(4):825-833.

Park et al., "CD19-targeted CAR T-cell therapeutics for hematologic malignancies: interpreting clinical outcomes to date." Blood. Jun. 30, 2016; 127(26): 3312-3320.

Park et al., "HM71224, a novel Bruton's tyrosine kinase inhibitor, suppresses B cell and monocyte activation and ameliorates arthritis in a mouse model: a potential drug for rheumatoid arthritis," Arthritis Res Ther (2016) 18:91.

Park et al., "Treating cancer with genetically engineered T cells," Trends Biotechnol (2011) 29(11):550-557.

PCI 29732 Product Page, Adooq Bioscience, retrieved from the internet URL: https://www.adooq.com/pci-29732.html retrieved Feb. 21, 2020.

Porter et al., "Chimeric antigen receptor T cells persist and induce sustained remissions in relapsed refractory chronic lymphocytic leukemia," Sci Transl Med (2015) 7(303):303ra139.

Porter et al., "Randomized, Phase II Dose Optimization Study of Chimeric Antigen Receptor Modified T Cells Directed Against CD19 (CTL019) in Patients with Relapsed, Refractory CLL." Blood 2014 124:1982.

Pott et al., "MRD detection in B-cell non-hodgkin lymphomas using Ig gene rearrangements and chromosomal translocations as targets for real-time quantitative PCT," Methods Mol Biol (2013) 971:175-200.

Qin et al., "Preclinical Analyses Support Clinical Investigation of Combined Anti-CD19 CAR-T Cell, JCAR017 with Ibrutinib and Acalabrutinib for the Treatment of Chronic Lymphocytic Leukemia," Blood 2016, 128:3231.

Qin et al., "Preclinical Analyses Support Clinical Investigation of Combined Anti-CD19 CAR-T Cell, JCAR017 with Ibrutinib and Acalabrutinib for the Treatment of Chronic Lymphocytic Leukemia," poster, presented at American Society of Hematology (ASH) 2016 Annual Meeting, Dec. 3-6, 2016, San Diego, CA. Poster 3231.

Qiu et al., "Current understanding of tyrosine kinase BMX in inflammation and its inhibitors," Burns & Trauma (2014) 2(3): 121-124.

QL47 Product Page, Adooq Bioscience, retrieved from the internet URL: https://www.adooq.com/ql47.html, retrieved Feb. 21, 2020.

Ramsay et al., "Chronic lymphocytic leukemia T cells show impaired immunological synapse formation that can be reversed with an immunomodulating drug." J Clin Invest. Jul. 2008;118(7):2427-37.

Remsing et al., "Global target profile of the kinase inhibitor bosutinib in primary chronic myeloid leukemia cells," Leukemia. Mar. 2009;23(3):477-485.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.

Rosen et al., "Identification of Small Molecule Modulators to Enhance the Therapeutic Properties of Chimeric Antigen Receptor T Cells," Blood (2016) 128(22):4712.

Rosenberg et al., "Durable Complete Responses in Heavily Pre-treated Patients with Metastatic Melanoma Using T-Cell Transfer Immunotherapy," Clin Cancer Res (2011) 17(13):4550-4557.

Rosenberg, "Cell transfer immunotherapy for metastatic solid cancer—what clinicians need to know," Nat Rev Clin Oncol (2011) 8(10):577-585.

Ruella et al., "Kinase Inhibitor Ibrutinib Prevents Cytokine-Release Syndrome after Anti-CD19 Chimeric Antigen Receptor T Cells (CART) for B Cell Neoplasms" Blood 2016 128:2159.

Ruella et al., "Kinase inhibitor ibrutinib to prevent cytokine-release syndrome after anti-CD19 chimeric antigen receptor T cells for B-cell neoplasms." Leukemia. Jan. 2017;31(1):246-248.

Ruella et al., "The Addition of the BTK Inhibitor Ibrutinib to Anti-CD19 Chimeric Antigen Receptor T Cells (CART19) Improves Responses against Mantle Cell Lymphoma." Clin Cancer Res. Jun. 1, 2016;22(11):2684-96.

Sadelain et al., "The basic principles of chimeric antigen receptor (CAR) design," Cancer Discov (2013) 3(4):388-398.

Sagiv-Barfi et al., "Therapeutic antitumor immunity by checkpoint blockade is enhanced by ibrutinib, an inhibitor of both BTK and ITK," Proc Natl Acad Sci USA (2015) 112(9):E966-972.

(56) References Cited

OTHER PUBLICATIONS

Savoldo et al., "CD28 costimulation improves expansion and persistence of chimeric antigen receptor-modified T cells in lymphoma patients," J Clin Invest (2011) 121(5):1822-1826.
Scarpa et al., "Characterization of recombinant helper retroviruses from Moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 256(5):859-869.
Schuler et al., "SYFPEITHI: database for searching and T-cell epitope prediction," Methods Mol Biol. (2007) 409: 75-93.
Schwartzberg et al., "TEC-family kinases: regulators of T-helper-cell differentiation," Nature Reviews Immunology (2005) 5:284-295.
Seimetz et al., "Development and approval of the trifunctional antibody catumaxomab (anti-EpCAM x anti-CD3) as a targeted cancer immunotherapy," Cancer Treat Rev (2010) 36:458-467.
Sharma et al., "Efficient Sleeping Beauty DNA Transposition From DNA Minicircles," Molec Ther Nucl Acids (2013) 2:e74.
Shimomura et al., "MK-5108, a highly selective Aurora-A kinase inhibitor, shows antitumor activity alone and in combination with docetaxel," Mol Cancer Ther. Jan. 2010;9(1):157-166.
Sidaway et al., "Haematological cancer: Ibrutinib supercharges CAR T cells." Nat Rev Clin Oncol. Apr. 2016;13(4):204.
Singh et al., "ProPred: prediction of HLA-DR binding sites," Bioinformatics (2001) 17(12):1236-1237.
Soo Hoo et al., "Characterization of a single-chain T-cell receptor expressed in *Escherichia coli*," PNAS (1992) 89(10):4759-4763.
Stiff et al., "Myeloid-Derived Suppressor Cells Express Bruton's Tyrosine Kinase and Can Be Depleted in Tumor-Bearing Hosts by Ibrutinib Treatment." Cancer Res. Apr. 15, 2016;76(8):2125-36.
Terakura et al., "Generation of CD19-chimeric antigen receptor modified CD8+ T cells derived from virus-specific central memory T cells," Blood (2012) 119(1):72-82.
Themeli et al., "Generation of tumor-targeted human T lymphocytes from induced pluripotent stem cells for cancer therapy," Nat Biotechnol (2013) 31(10):928-933.
Tsou et al., "6-Substituted-4-(3-bromophenylamino)quinazolines as putative irreversible inhibitors of the epidermal growth factor receptor (EGFR) and human epidermal growth factor receptor (HER-2) tyrosine kinases with enhanced antitumor activity," J Med Chem. (2001) 44(17): 2719-34.
Tsou et al., "Optimization of 6,7-disubstituted-4-(arylamino)quinoline-3-carbonitriles as orally active, irreversible inhibitors of human epidermal growth factor receptor-2 kinase activity," J Med Chem. (2005) 48(4): 1107-31.
Tsukahara et al., "CD19 target-engineered T-cells accumulate at tumor lesions in human B-cell lymphoma xenograft mouse models," Biochem Biophys Res Commun (2013) 438(1):84-89.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Improves In Vivo Expansion and Persistence of CAR-T Cells and Clinical Outcomes," Blood (2015) 126:184.
Turtle et al., "CD19 CAR-T Cells Are Highly Effective in Ibrutinib-Refractory Chronic Lymphocytic Leukemia," Blood (2016) 128(22): 56.
Turtle et al., "CD19 Car-T cells of defined CD4+:CD8+ composition in adult B cell ALL patients." J Clin Invest. Jun. 1, 2016;126(6):2123-38.
Turtle et al., "Durable Molecular Remissions in Chronic Lymphocytic Leukemia Treated With CD19-Specific Chimeric Antigen Receptor-Modified T Cells After Failure of Ibrutinib." J Clin Oncol. Sep. 10, 2017;35(26):3010-3020.
Turtle et al., "Engineered T cells for anti-cancer therapy," Engineered T cells for anti-cancer therapy, Curr Opin Immunol (2012) 24(5):633-639.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.

Turtle et al., "Rate of durable complete response in All, Nhl, and CLL after immunotherapy with optimized lymphodepletion and defined composition CD19 CAR-T cells," 2016 ASCO meeting abstract 102, J. Clin. Oncol. (2016) 34(15):Suppl. Abstr 102.
Van Tendeloo et al., "High-level transgene expression in primary human T Tymphocytes and adult bone marrow CD34+ cells via electroporation-mediated gene delivery," Gene Therpay (2000) 7(16):1431-1437.
Verhoeyen et al., "Lentiviral vector gene transfer into human T cells," Methods Mol Biol (2009) 506:97-114.
Wang et al., "Discovery of Disubstituted lmidazo[4,5-b]pyridines and Purines as Potent TrkA Inhibitors," ACS Med Chem Lett (2012) 3(9):705-709.
Wang et al., "Phenotypic and Functional Attributes of Lentivirus Modified CD19-specific Human CD8+ Central Memory T Cells Manufactured at Clinical Scale," J Immunother (2012) 35(9):689-701.
Wigler et al., "Transfer of Purified Herpes Virus Thymidine Kinase Gene to Cultured Mouse Cells," Cell (1997) 2:223.
Wilson, W.H., "Progress in Chronic Lymphocytic Leukemia with Targeted Therapy." N Engl J Med. Jan. 28, 2016;374(4):386-8.
Wong et al., "Antitumor and antiangiogenic activities of BMS-690514, an inhibitor of human EGF and VEGF receptor kinase families," Clin Cancer Res. Jun. 15, 2011;17(12):4031-4041.
Woyach et al., "Resistance mechanisms for the Bruton's tyrosine kinase inhibitor ibrutinib," N Engl J Med (2014) 370(24):2286-2294.
Woyach et al., "Targeted therapies in CLL: mechanisms of resistance and strategies for management." Blood. Jul. 23, 2015;126(4):471-7.
Wu et al., "Acalabrutinib (ACP-196): a selective second-generation BTK inhibitor," Journal of Hematology & Oncology (2016) 9:Article No. 21.
Wu et al., "Adoptive T-cell therapy using autologous tumor-infiltrating lymphocytes for metastatic melanoma: current status and future outlook," Cancer J (2012) 18(2):160-175.
Wu et al., "Second-generation inhibitors of Bruton tyrosine kinase," J Hematol Oncol (2016) 9:80.
Wu et al., "The transcription factor musculin promotes the unidirectional development of peripheral Treg cells by suppressing the TH2 transcriptional program," Nat Immunol (2017) 18(3):344-353.
Wulfing et al., "Correctly folded T-cell receptor fragments in the periplasm of *Escherichia coli*. Influence of folding catalysts," J Mol Biol (1994) 242(5):655-669.
Xu et al., "RN486, a selective Bruton's tyrosine kinase inhibitor, abrogates immune hypersensitivity responses and arthritis in rodents," J Pharmacol Exp Ther (2012) 341(1):90-103.
Younes, A. "Promising Novel Agents for Aggressive B-Cell Lymphoma." Hematol Oncol Clin North Am. Dec. 2016;30(6):1229-1237.
Young et al., "Potent and selective Bruton's tyrosine kinase inhibitors: discovery of GDC-0834," Bioorg Med Chem Lett (2015) 25(6):1333-1337.
Zhao et al., "Structural Design of Engineered Costimulation Determines Tumor Rejection Kinetics and Persistence of Car T Cells," Cancer Cell (2015) 28(4):415-428.
Zhong et al., "Targeting interleukin-2-inducible T-cell kinase (ITK) and resting Tymphocyte kinase (RLK) using a novel covalent inhibitor PRN694," J Biol Chem (2015) 290(10):5960-5978.
Zhou et al., "Novel mutant-selective EGFR kinase inhibitors against EGFR T790M," Nature (2009) 432(7276):1070-1074.
Zirn et al., "All-trans retinoic acid treatment of Wilms tumor cells reverses expression of genes associated with high risk and relapse in vivo," Oncogene (2005) 24(33):5246-5251.
Butler et al., "Human cell-based artificial antigen-presenting cells for cancer immunotherapy," Immunol Rev. (2014) 257(1):191-209.
Clinical Trial Study Record No. NCT02435849, "Study of Efficacy and Safety of CTL019 in Pediatric ALL Patients," (Eliana), May 6, 2015.
Clinical Trial Study Record No. NCT02445248, "Study of Efficacy and Safety of CTL019 in Adult DLBCL Patients," (Juliet), May 15, 2015.

(56) References Cited

OTHER PUBLICATIONS

Meisenberg et al., "Reduced charges and costs associated with outpatient autologous stem cell transplantation," Bone Marrow Transplant. (1998) 21(9):927-32.

Myers et al., "Perspectives on outpatient administration of CAR-T cell therapy in aggressive B-cell lymphoma and acute lymphoblastic leukemia," J Immunother Cancer. (2021) 9(4):e002056.

Park et al. "Phase I trial of autologous CD19-targeted CAR-modified T cells as consolidation after purine analog-based first-line therapy in patients with previously untreated CLL," Blood (Nov. 2013) 122(21):874.

Slovin et al., "Adoptive Transfer of Autologous T Cells Targeted to Prostate Specific Membrane Antigen (PSMA) for the Treatment of Castrate Metastatic Prostate Cancer (CMPC) DOD," Grant Log# PC081632, https://cdmrp.army.mil/pubs/video/pc/pdf/slovin_poster.pdf, 2013, poster presentation.

Stiff et al., "Autologous hematopoietic stem cell transplants that utilize total body irradiation can safely be carried out entirely on an outpatient basis," Bone Marrow Transplant. (2006) 38(11):757-64.

\* cited by examiner

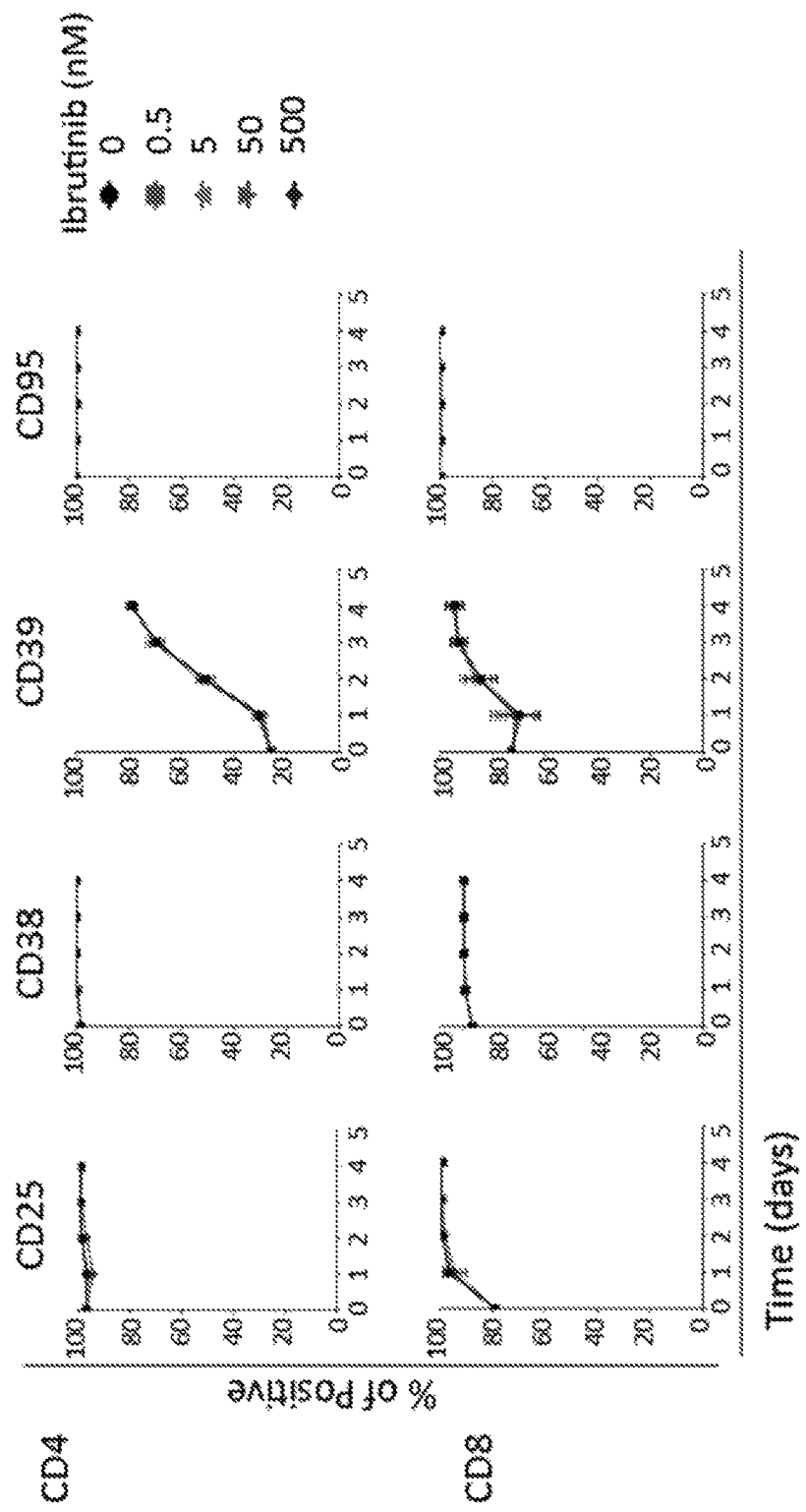

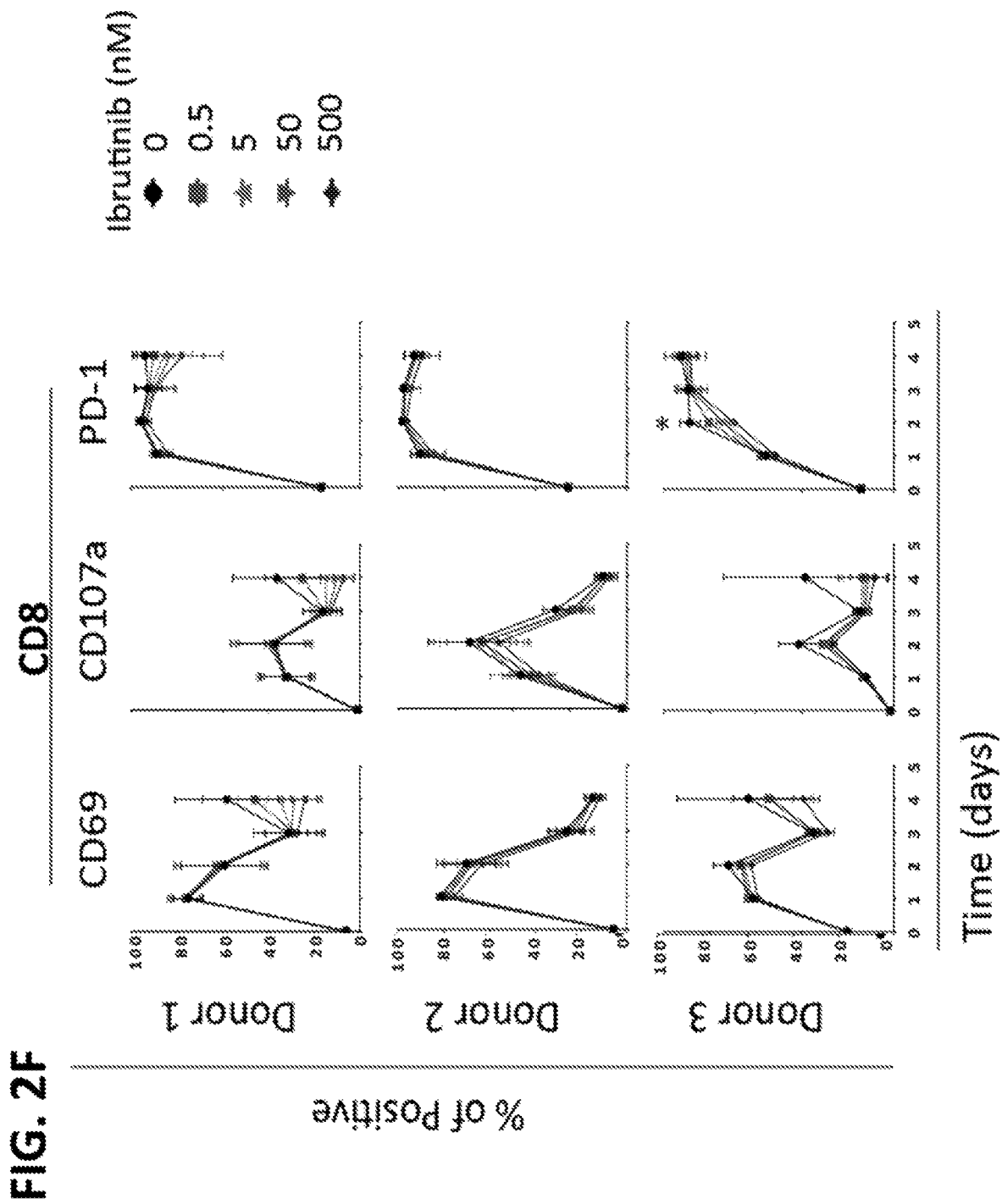

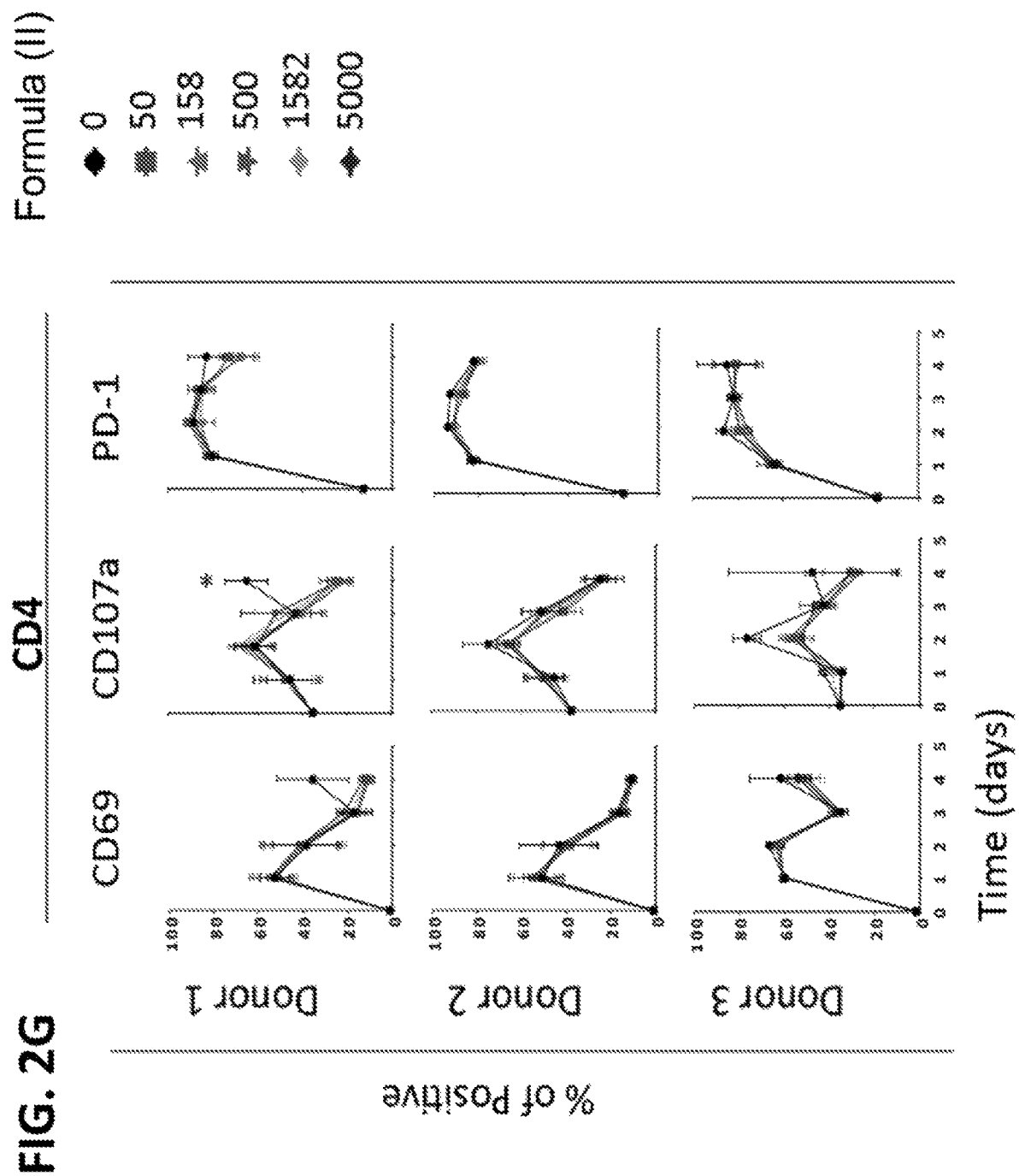

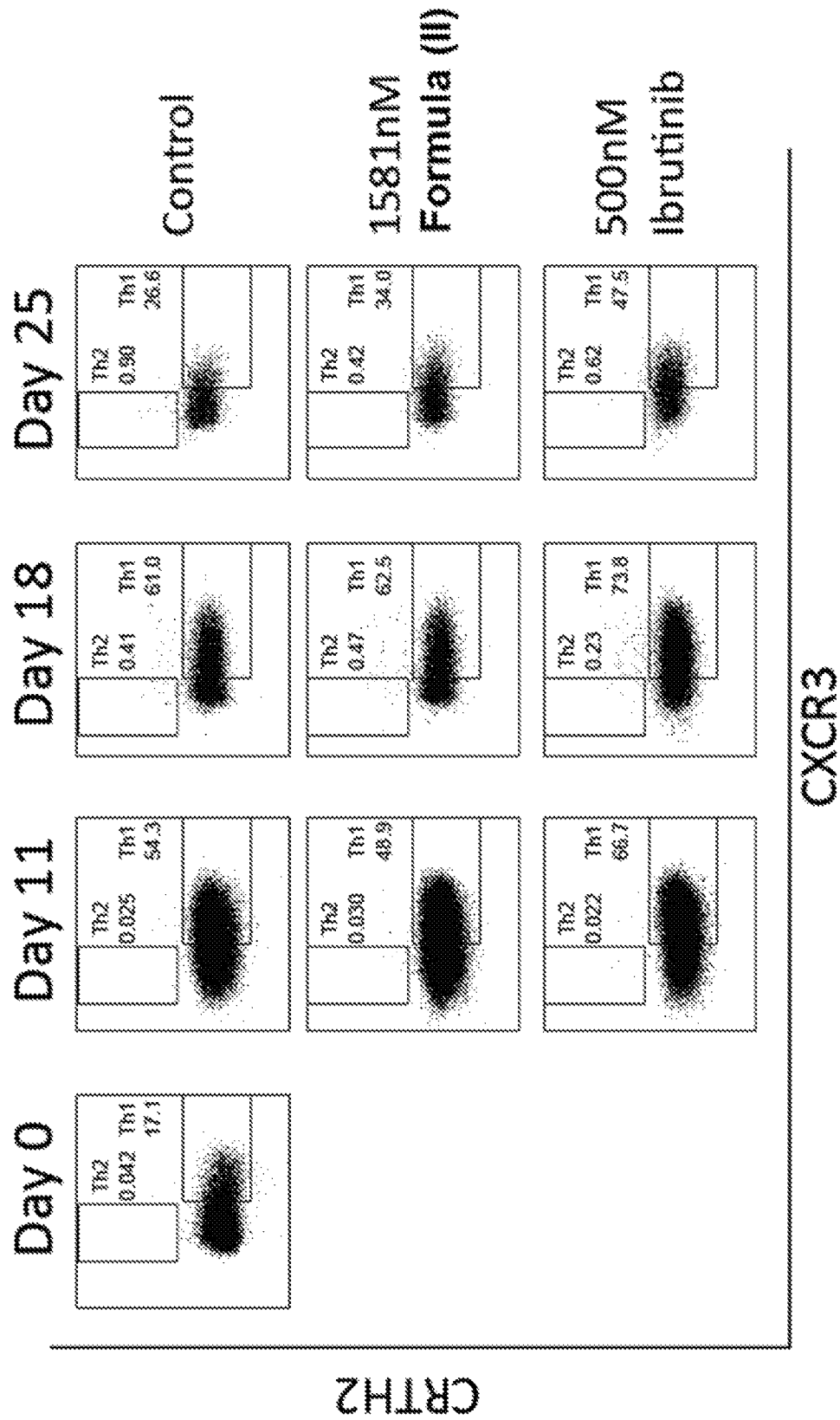

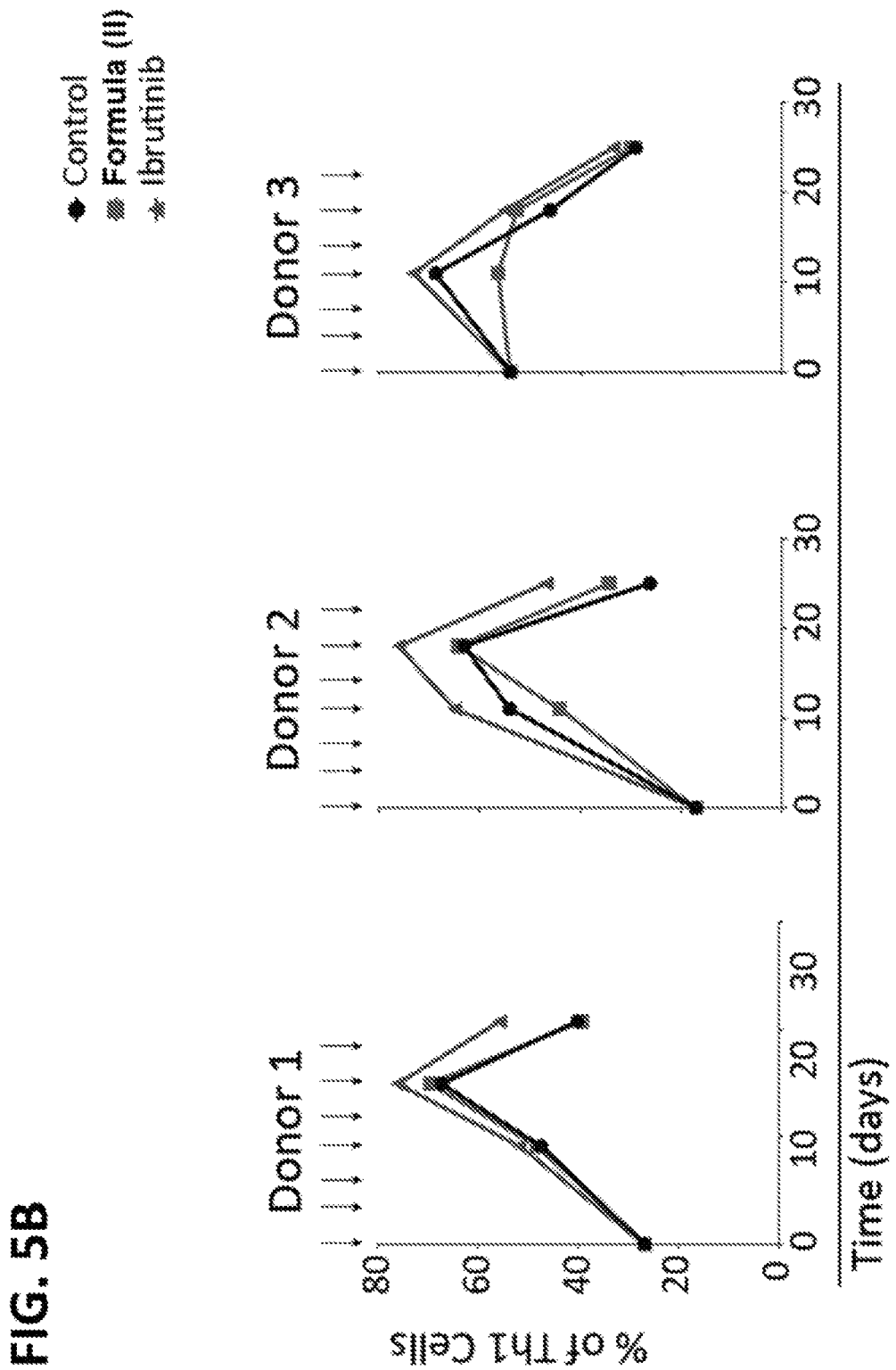

FIG. 5D

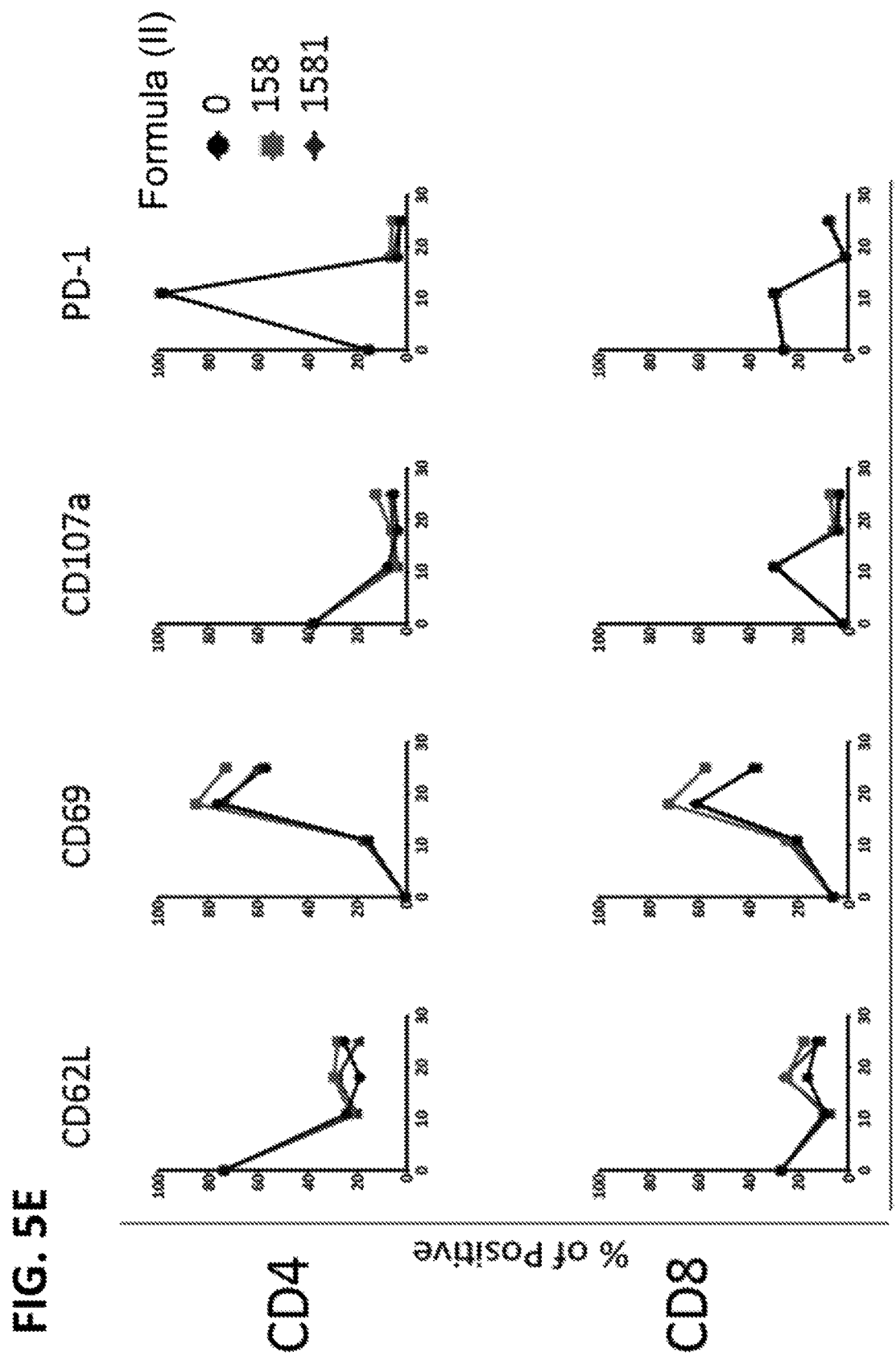

FIG. 5F

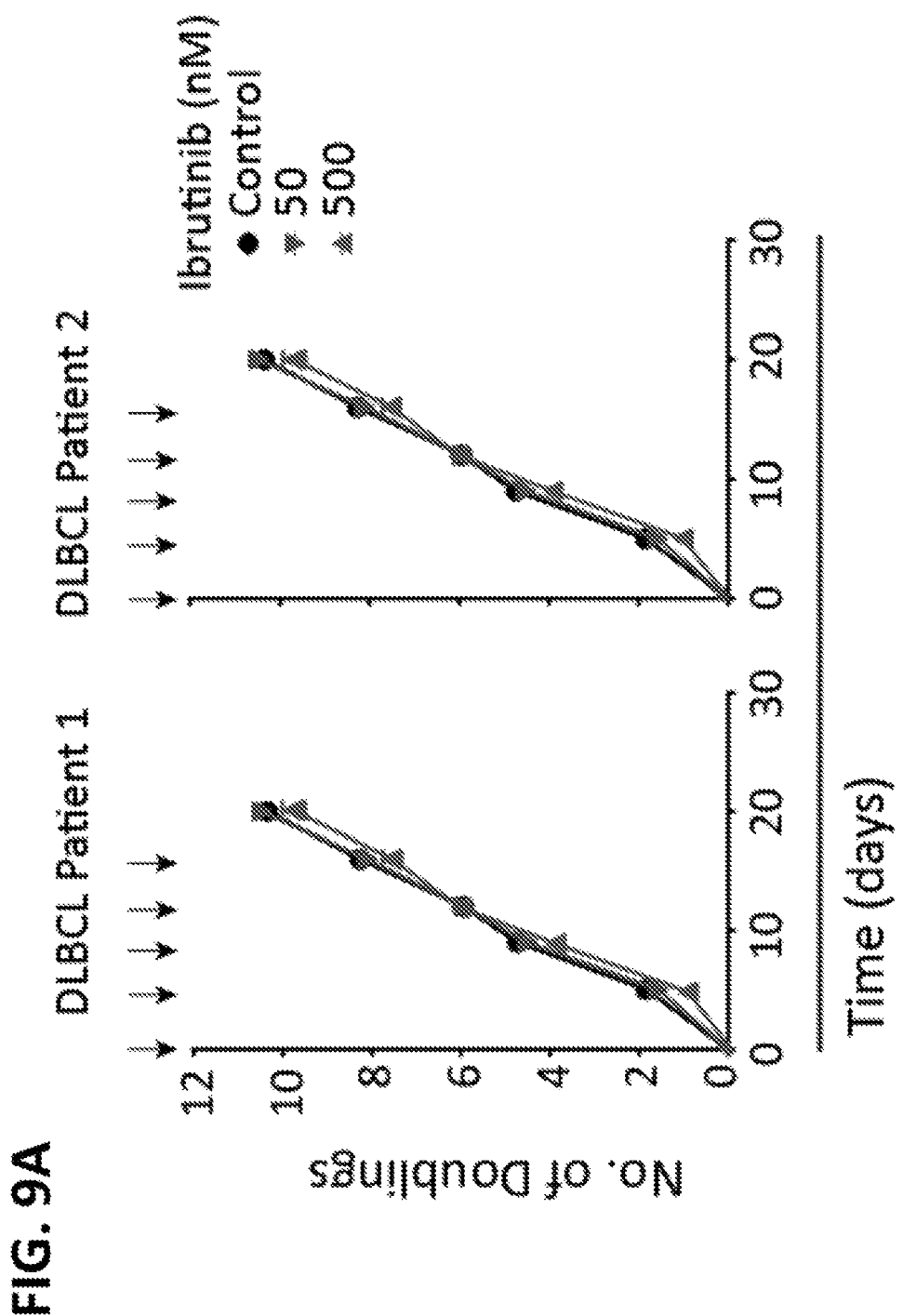

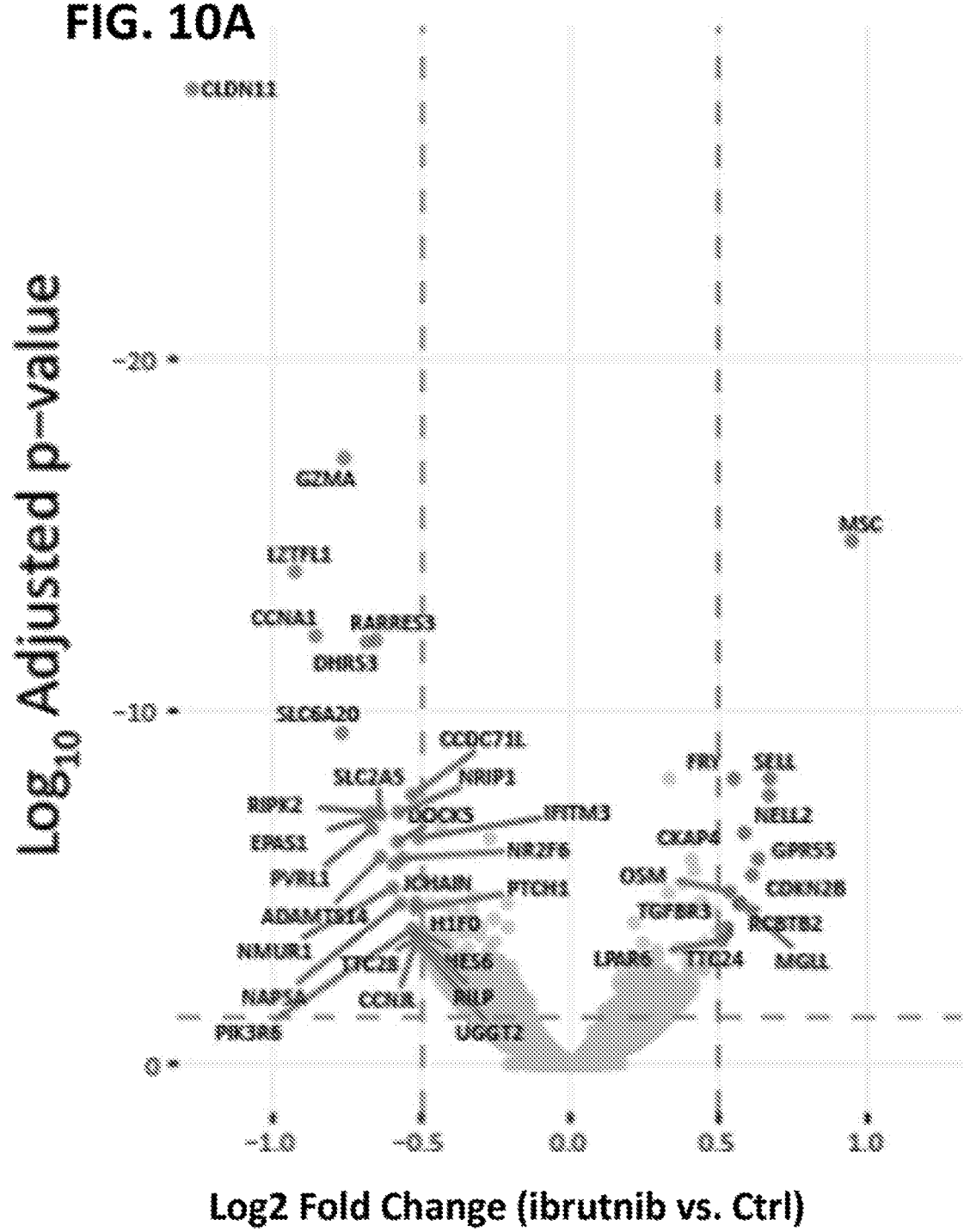

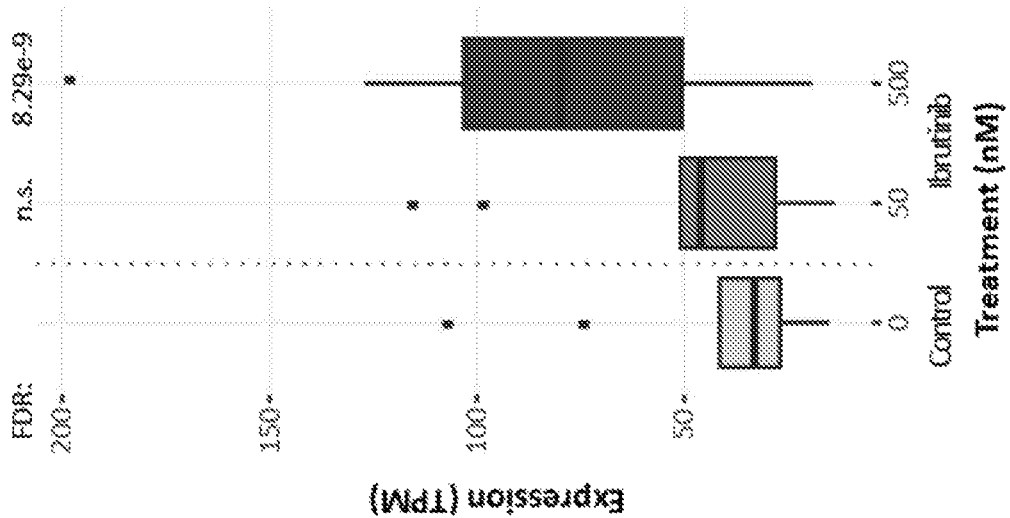
FIG. 11B SELL
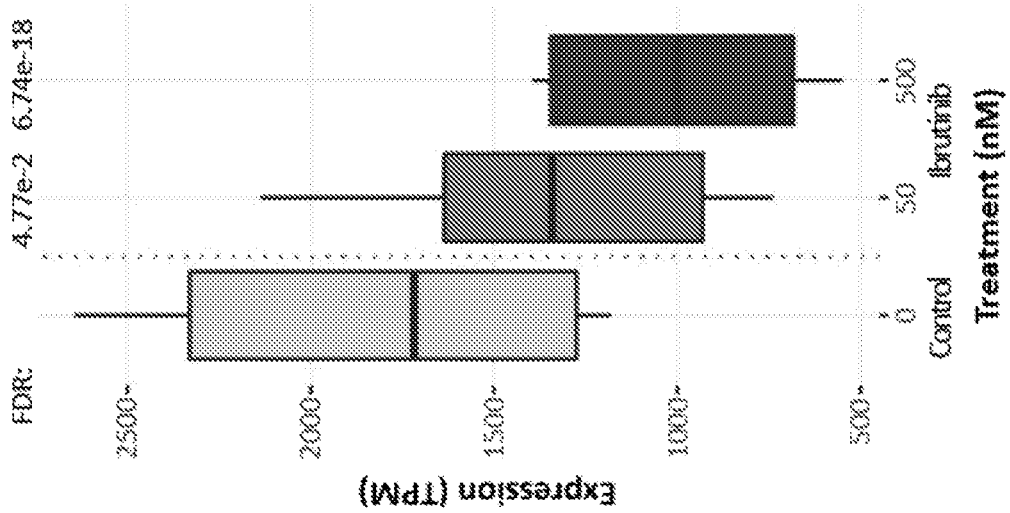
FIG. 11A GZMA

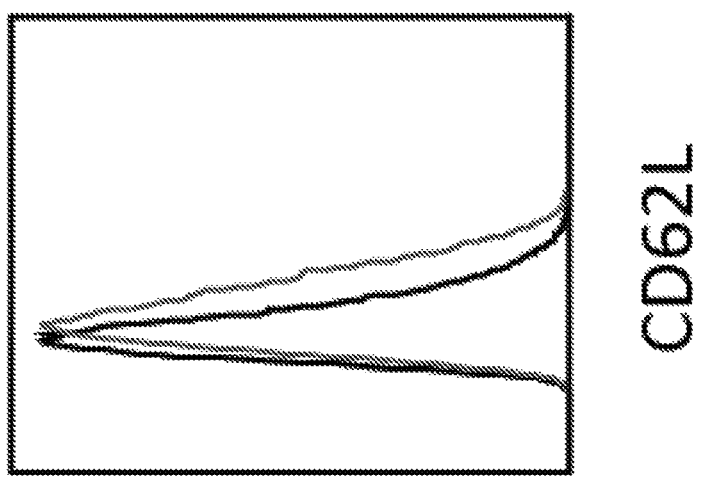
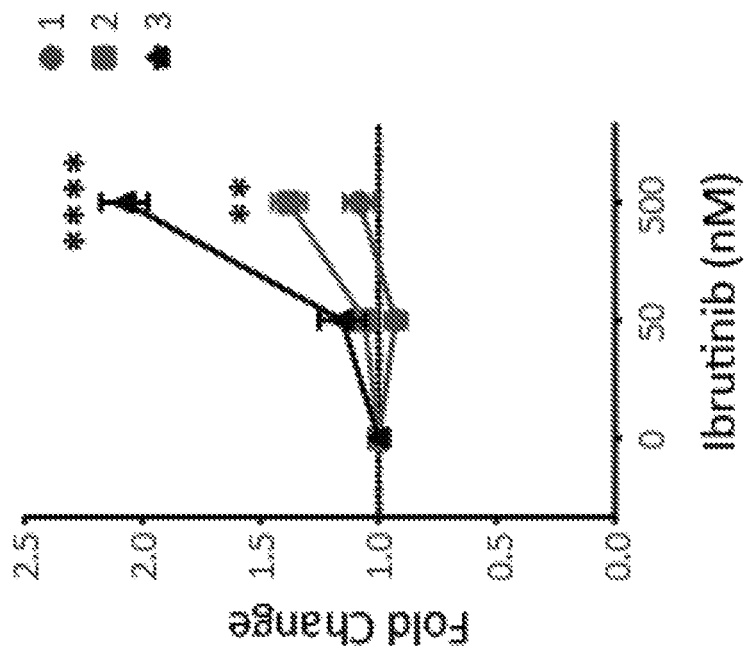

SEQUENCE LISTING

<160> NUMBER OF SEQ ID NOS: 19

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge)

<400> SEQUENCE: 2
gaatctaagt acggaccgcc ctgccccct tgccct                                 36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser Gln Glu Asp Pro Glu Val Gln Phe Asn Trp Tyr Val Asp Gly Val
     50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                  10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175
```

```
Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280
```

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

```
Leu Glu Gly Gly Gly Glu Gly Arg Gly Ser Leu Leu Thr Cys Gly Asp
1               5                   10                  15

Val Glu Glu Asn Pro Gly Pro Arg
            20
```

<210> SEQ ID NO 7
<211> LENGTH: 335
<212> TYPE: PRT
<213> ORGANISM: Artificial Sequence
<220> FEATURE:
<223> OTHER INFORMATION: tEGFR

<400> SEQUENCE: 7

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
```

```
                 165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt Accession No P10747
<309> DATABASE ENTRY DATE: 1989-07-01

<400> SEQUENCE: 8

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt Accession No P10747
<309> DATABASE ENTRY DATE: 1989-07-01

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65
```

-continued

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt Accession No P10747
<309> DATABASE ENTRY DATE: 1989-07-01

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Accession No Q07011.1
<309> DATABASE ENTRY DATE: 1995-02-01

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
 1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110

<210> SEQ ID NO 16

```
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 16

Pro Gly Gly Gly Ser Gly Gly Gly Gly Pro
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Linker

<400> SEQUENCE: 17

Gly Ser Ala Asp Asp Ala Lys Lys Asp Ala Ala Lys Lys Asp Gly Lys
1               5                   10                  15

Ser

<210> SEQ ID NO 18
<211> LENGTH: 659
<212> TYPE: PRT
<213> ORGANISM: Homo sapiens
<220> FEATURE:
<223> OTHER INFORMATION: Tyrosine-protein kinase BTK

<400> SEQUENCE: 18

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
                20                  25                  30

Thr Val His Lys Leu Ser Tyr Tyr Glu Tyr Asp Phe Glu Arg Gly Arg
            35                  40                  45

Arg Gly Ser Lys Lys Gly Ser Ile Asp Val Glu Lys Ile Thr Cys Val
        50                  55                  60

Glu Thr Val Val Pro Glu Lys Asn Pro Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala
        195                 200                 205
```

```
Ala Pro Val Ser Thr Ser Glu Leu Lys Lys Val Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
                260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
                355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Glu Ala Lys Val
        435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
                500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
                580                 585                 590

Leu Gly Lys Met Pro Tyr Glu Arg Phe Thr Asn Ser Glu Thr Ala Glu
                595                 600                 605

His Ile Ala Gln Gly Leu Arg Leu Tyr Arg Pro His Leu Ala Ser Glu
610                 615                 620

Lys Val Tyr Thr Ile Met Tyr Ser Cys Trp His Glu Lys Ala Asp Glu
```

| | 625 | | | 630 | | | | 635 | | | | 640 | |
|---|---|---|---|---|---|---|---|---|---|---|---|---|---|
| Arg | Pro | Thr | Phe | Lys | Ile | Leu | Leu | Ser | Asn | Ile | Leu | Asp | Val | Met | Asp |
| | | | | 645 | | | | | 650 | | | | | 655 |

Glu Glu Ser

<210> SEQ ID NO 19
<211> LENGTH: 2611
<212> TYPE: DNA
<213> ORGANISM: Homo sapiens
<220> FEATURE:
<223> OTHER INFORMATION: Tyrosine-protein kinase BTK

<400> SEQUENCE: 19

```
aactgagtgg ctgtgaaagg gtggggtttg ctcagactgt ccttcctctc tggactgtaa      60
gaatatgtct ccagggccag tgtctgctgc gatcgagtcc caccttccaa gtcctggcat     120
ctcaatgcat ctgggaagct acctgcatta agtcaggact gagcacacag gtgaactcca     180
gaaagaagaa gctatggccg cagtgattct ggagagcatc tttctgaagc gatcccaaca     240
gaaaaagaaa acatcaccct aaacttcaa gaagcgcctg tttctcttga ccgtgcacaa      300
actctcctac tatgagtatg actttgaacg tgggagaaga ggcagtaaga agggttcaat     360
agatgttgag aagatcactt gtgttgaaac agtggttcct gaaaaaaatc ctcctccaga     420
aagacagatt ccgagaagag gtgaagagtc cagtgaaatg gagcaaattt caatcattga     480
aaggttccct tatccttcc aggttgtata tgatgaaggg cctctctacg tcttctcccc      540
aactgaagaa ctaaggaagc ggtggattca ccagctcaaa aacgtaatcc ggtacaacag     600
tgatctggtt cagaaatatc acccttgctt ctggatcgat gggcagtatc tctgctgctc     660
tcagacagcc aaaaatgcta tgggctgcca aatttttggag aacaggaatg gaagcttaaa    720
acctgggagt tctcaccgga gacaaaaaa gcctcttccc ccaacgcctg aggaggacca     780
gatcttgaaa aagccactac cgcctgagcc agcagcagca ccagtctcca caagtgagct    840
gaaaaaggtt gtggccttt atgattacat gccaatgaat gcaaatgatc tacagctgcg    900
gaagggtgat gaatatttta tcttggagga aagcaactta ccatggtgga gagcacgaga    960
taaaaatggg caggaaggct acattcctag taactatgtc actgaagcag aagactccat   1020
agaaatgtat gagtggtatt ccaaacacat gactcggagt caggctgagc aactgctaaa   1080
gcaagagggg aaagaaggag gtttcattgt cagagactcc agcaaagctg caaatatac    1140
agtgtctgtg tttgctaaat ccacagggga ccctcaaggg gtgatacgtc attatgttgt   1200
gtgttccaca cctcagagcc agtattacct ggctgagaag cacctttca gcaccatccc    1260
tgagctcatt aactaccatc agcacaactc tgcaggactc atatccaggc tcaaatatcc   1320
agtgtctcaa caaacaaga atgcaccttc cactgcaggc ctgggatacg gatcatggga    1380
aattgatcca aaggacctga ccttcttgaa ggagctgggg actggacaat tggggtagt    1440
gaagtatggg aaatggagag gccagtacga cgtggccatc aagatgatca agaaggctc    1500
catgtctgaa gatgaattca ttgaagaagc caaagtcatg atgaatcttt cccatgagaa   1560
gctggtgcag ttgtatggcg tctgcaccaa gcagcgcccc atcttcatca tcactgagta   1620
catgccaat ggctgcctcc tgaactacct gagggagatg cgccaccgct tccagactca    1680
gcagctgcta gagatgtgca aggatgtctg tgaagccatg gaatacctgg agtcaaagca   1740
gttccttcac cgagacctgg cagctcgaaa ctgtttggta aacgatcaag agttgttaa    1800
agtatctgat ttcggcctgt ccaggtatgt cctggatgat gaatacacaa gctcagtagg   1860
```

```
ctccaaattt ccagtccggt ggtccccacc ggaagtcctg atgtatagca agttcagcag    1920
caaatctgac atttgggctt ttggggtttt gatgtgggaa atttactccc tggggaagat    1980
gccatatgag agatttacta acagtgagac tgctgaacac attgcccaag gcctacgtct    2040
ctacaggcct catctggctt cagagaaggt atataccatc atgtacagtt gctggcatga    2100
gaaagcagat gagcgtccca ctttcaaaat tcttctgagc aatattctag atgtcatgga    2160
tgaagaatcc tgagctcgcc aataagcttc ttggttctac ttctcttctc cacaagcccc    2220
aatttcactt tctcagagga aatcccaagc ttaggagccc tggagccttt gtgctcccac    2280
tcaatacaaa aaggccgctg tctacatctg ggaatgcacc tcttctttga ttccctggga    2340
tagtggcttc tgagcaaagg ccaagaaatt attgtgcctg aaatttcccg agagaattaa    2400
gacagactga atttgcgatg aaaatatttt ttaggaggga ggatgtaaat agccgcacaa    2460
aggggtccaa cagctctttg agtaggcatt tggtagagct tgggggtgtg tgtgtggggg    2520
tggaccgaat ttggcaagaa tgaaatggtg tcataaagat gggaggggag ggtgttttga    2580
taaaataaaa ttactagaaa gcttgaaagt c                                   2611
```

METHODS AND COMPOSITIONS FOR USE OF THERAPEUTIC T CELLS IN COMBINATION WITH KINASE INHIBITORS

CROSS-REFERENCE TO RELATED APPLICATIONS

This application is a U.S. National Stage of International Application No. PCT/US2017/064362, filed Dec. 1, 2017, which claims priority from U.S. provisional application No. 62/429,732 filed Dec. 3, 2016, entitled "Methods and Compositions for Use of Therapeutic T cells in Combination with Kinase Inhibitors" and to U.S. provisional application No. 62/581,644 filed Nov. 3, 2017, entitled "Methods and Compositions for Use of Therapeutic T cells in Combination with Kinase Inhibitors," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042008900SeqList.txt, created May 30, 2019, which is 24,363 bytes in size. The information in electronic format of the Sequence Listing is incorporated by reference in its entirety.

FIELD

The present disclosure relates in some aspects to methods, compositions and uses involving immunotherapies, such as adoptive cell therapy, e.g., T cell therapy, in combination or conjunction with modulators, e.g., inhibitors, of a target kinase, such as a target protein tyrosine kinase. Also provided are methods of manufacturing such engineered cells, cells, compositions, such as methods in which the cells are produced in the presence of one or more of the kinase inhibitors. Also provided are methods of administration to subjects, nucleic acids, articles of manufacture and kits for use in the methods.

BACKGROUND

Various strategies are available for immunotherapy, for example, adoptive cell therapy methods involving administering T cells, such as genetically engineered antigen receptors, such as CARs. In some aspects, available methods may not be entirely satisfactory. There is a need for additional strategies for immunotherapy and adoptive cell therapy, e.g., strategies to enhance persistence, activity and/or proliferation of administered cells and responses and strategies for modulating T cell phenotype. Provided are methods, cells, compositions, kits, and systems that meet such needs.

SUMMARY

Provided herein are methods of enhancing or modulating proliferation and/or activity of T cell activity associated with administration of an immunotherapy or immunotherapeutic agent, such as a composition including cells for adoptive cell therapy, e.g., such as a T cell therapy (e.g. CAR-expressing T cells) or a T cell-engaging therapeutic agent, such as a bispecific or multispecific agent or antibody, capable of recruiting one or more T cells or other immune cells. In some aspects, such methods included combination administration of the immunotherapy or immunotherapeutic agent and an inhibitor of one or more non-receptor protein tyrosine kinases such as TEC family kinases. In some aspects, the protein tyrosine kinase is not IL-2-inducible T cell kinase (not an ITK) and/or the inhibitor does not inhibit ITK, e.g., does not inhibit ITK with an IC50 value less than 1000 or less than 500 nM. In some aspects, the target protein tyrosine kinase is a Bruton's tyrosine kinase (BTK), a tec protein tyrosine kinase (TEC), a BMX non-receptor tyrosine kinase (Etk), a TXK tyrosine kinase (TXK) and/or a receptor tyrosine-protein kinase ErbB4 (ErbB4). The provided methods, compositions and uses include those for combination therapies involving the administration or use of one or more such inhibitor in conjunction with another agent, such as an immunotherapeutic agent that involves, recruits or engages T cells targeting a disease or condition, such as a therapeutic antibody, e.g., a multispecific (e.g., T cell engaging) antibody, and/or therapeutic compositions containing immune cells, such as T cells, such as genetically engineered T cells, such as chimeric antigen receptor (CAR)-expressing T cells. In some aspects, features of the methods and cells provide for increased or improved activity, efficacy, persistence, expansion and/or proliferation of T cells for adoptive cell therapy or endogenous T cells recruited by immunotherapeutic agents.

In some embodiments, the methods generally involve administrating a combination therapy of the immunotherapy or immunotherapeutic agent, such as a composition including cells for adoptive cell therapy, e.g., such as a T cell therapy (e.g. CAR-expressing T cells) or a T cell-engaging therapeutic agent and an inhibitor of a target protein tyrosine kinase that is not IL-2-inducible T cell kinase (ITK) and/or in which the target protein tyrosine kinase is selected from Bruton's tyrosine kinase (BTK), tec protein tyrosine kinase (TEC), BMX non-receptor tyrosine kinase (Etk), TXK tyrosine kinase (TXK) and/or receptor tyrosine-protein kinase ErbB4 (ErbB4).

Provided herein are methods of treatment that involve: (a) administering, to a subject having a disease or condition, T cells that specifically recognize or specifically bind to an antigen associated with, or expressed or present on cells of, the disease or condition and/or a tag comprised by a therapeutic agent that specifically targets the disease or condition and has been or is to be administered to the subject; and (b) administering to the subject an inhibitor of a target protein tyrosine kinase, wherein the inhibitor does not inhibit ITK and/or inhibits ITK with a half-maximal inhibitory concentration (IC50) of greater than or greater than about 1000 nM, wherein the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the protein tyrosine kinase is not ordinarily expressed or is not suspected of being expressed in cells from which the disease or condition is derived.

Provided in some aspects are methods of treatment that involve administering, to a subject having a disease or condition, T cells that specifically recognize or specifically bind to an antigen associated with, or expressed or present on cells of, the disease or condition and/or a tag comprised by a therapeutic agent that specifically targets the disease or condition and has been or is to be administered to the subject, wherein: the subject has been administered an inhibitor of a target protein tyrosine kinase, wherein the inhibitor does not inhibit ITK and/or inhibits ITK with a half-maximal inhibitory concentration (IC50) of greater than or greater than about 1000 nM; and the disease or condition (i) is not a B cell-derived disease or condition (ii) is not associated with expression of CD19, CD22, or CD20; (iii) does not express the protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the protein tyrosine kinase is not ordinarily expressed or is not suspected of being expressed in cells from which the disease or condition is derived.

Provided herein are methods of treatment that involve administering, to a subject having a disease or condition, an inhibitor of a target protein tyrosine kinase, wherein the inhibitor does not inhibit ITK and/or inhibits ITK with a half-maximal inhibitory concentration (IC50) of greater than or greater than about 1000 nM, wherein: the subject has been administered T cells that specifically recognize or specifically bind to an antigen associated with, or expressed or present on cells of, the disease or condition and/or a tag comprised by a therapeutic agent that specifically targets the disease or condition and has been or is to be administered to the subject; and the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the TEC family kinase is not ordinarily expressed or is not suspected of being expressed in cells from which the disease or condition is derived.

In some embodiments of any of the methods provided herein, the target protein tyrosine kinase is tyrosine kinase expressed in hepatocellular carcinoma (TEC), a resting lymphocyte kinase (RLK/TXK), a BMX/ETK, or an ERBB4. In some embodiments, the target protein tyrosine kinase is a TEC family kinase.

In some embodiments of any of the methods provided herein, the inhibitor is selected from Formula (II), ONO/GS-4059, Compound 30 or Compound 38,GDC-0834; RN-486; CGI-560; CGI-1764; HM-71224; CC-292; ONO-4059; CNX-774; and LFM-A13.

In some embodiments of any of the methods provided herein, the inhibitor is a selective inhibitor of the target protein tyrosine kinase. In some embodiments, the inhibitor inhibits the target protein tyrosine kinase with a half-maximal inhibitory concentration (IC50) that is at least 10 or at least 100 times lower than that of the IC50 of the inhibitor for any additional protein tyrosine kinase or TEC family kinase, and/or inhibits the target protein tyrosine kinase with an IC50 at least 2, at least 10 or at least 100 times lower than that the IC50 value of the inhibitor for both ITK and BTK. In some embodiments, the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less Provided herein are methods that involve: (1) administering, to a subject having a disease or condition, T cells that specifically recognize or specifically bind to an antigen associated with the disease or condition and/or a tag comprised by a therapeutic agent that specifically targets the disease or condition and has been or is to be administered to the subject; and (2) administering to the subject an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4. In some embodiments, the inhibitor is a selective inhibitor of the target protein tyrosine kinase. In some embodiments, the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK. In some embodiments, the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

Provided herein are methods that involve administering, to a subject having a disease or condition, T cells that specifically recognize or specifically bind to an antigen associated with the disease or condition and/or a tag comprised by a therapeutic agent that specifically targets the disease or condition and has been or is to be administered to the subject, said subject having been administered an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4. In some embodiments, the inhibitor is a selective inhibitor of the target protein tyrosine kinase. In some embodiments of any of the methods provided herein, the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK. In some embodiments of any of the methods provided herein, the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

Provided herein are methods of treatment that involve administering to a subject, having a disease or condition, an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4, said subject having been administered T cells that specifically recognize or specifically bind to an antigen associated with the disease or condition and/or a tag comprised by a therapeutic agent that specifically targets the disease or condition and has been or is to be administered to the subject. In some embodiments, the inhibitor is a selective inhibitor of the target protein tyrosine kinase. In some embodiments of any of the methods provided herein, the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK. In some embodiments of any of the methods provided herein, the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

In some embodiments of any of the methods provided herein, the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or the target kinase is not ordinarily expressed or is not suspected of being expressed in cells from which the disease or condition is derived. In some embodiments of any of the methods provided herein, the target protein tyrosine kinase is a RLK/TXK.

In some embodiments of any of the methods provided herein, the target protein tyrosine kinase is a BMX/ETK and the inhibitor inhibits Bmx/Etk with an a half-maximal inhibitory concentration (IC50) that is at least 10 or at least 100 times lower than that of the IC50 of the inhibitor for any other TEC family kinase and/or for ITK, and/or inhibits Bmx/Etk with a half-maximal inhibitory concentration (IC50) of less than or less than about 1000 nM, 900 nM, 800 nM, 600 nM, 500 nM, 400 nM, 300 nM, 200 nM, 100 nM or less. In some embodiments of any of the methods provided herein, the target kinase is or contains an ErbB4.

In some embodiments of any of the methods provided herein, the inhibitor contains is a compound of formula (II):

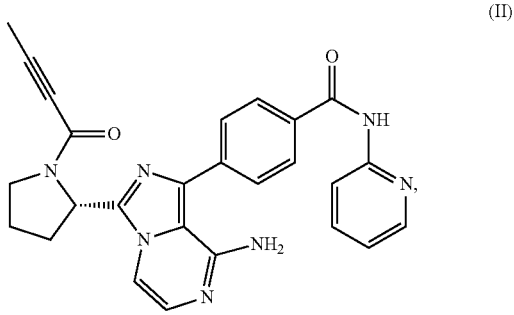 [SMILES: CC#CC(=O)N1CCC[C@H]1c1nc(-c2ccc(C(=O)Nc3ccccn3)cc2)c2c(N)nccn12]

(II)

or a pharmaceutically acceptable salt, solvate, hydrate, co-crystal, polymorph or prodrug thereof thereof.

In some embodiments of any of the methods provided herein, the inhibitor contains the compound of Formula (II), or an enantiomer, pharmaceutically-acceptable salt, solvate, hydrate, co-crystal, polymorph or prodrug thereof or a pharmaceutical composition comprising any of the foregoing.

Provided in some aspects are methods of treatment that involve (1) administering, to a subject having a disease or condition, T cells comprising a recombinant antigen receptor that specifically binds to an antigen associated with the disease or condition and/or a tag comprised by a therapeutic agent that specifically targets the disease or condition and has been or is to be administered to the subject; and (2) administering to the subject a kinase inhibitor or a pharmaceutical composition comprising the inhibitor, wherein the inhibitor contains the compound of Formula (II), or an enantiomer, pharmaceutically-acceptable salt, solvate, hydrate, co-crystal, polymorph or prodrug thereof.

Provided in some aspects are methods of treatment that involve administering, to a subject having a disease or condition, T cells comprising a recombinant antigen receptor that specifically binds to an antigen associated with the disease or condition and/or a tag comprised by a therapeutic agent that specifically targets the disease or condition and has been or is to be administered to the subject, said subject having been administered a kinase inhibitor or a pharmaceutical composition comprising the inhibitor, wherein the inhibitor contains the compound of Formula (II) or an enantiomer, pharmaceutically-acceptable salt, solvate, hydrate, co-crystal, polymorph or prodrug thereof.

Provided in some aspects are methods of treatment that involve administering, to a subject having a disease or condition, a kinase inhibitor or a pharmaceutical composition comprising the inhibitor, wherein the inhibitor contains the compound of Formula (II), or an enantiomer, pharmaceutically-acceptable salt, solvate, hydrate, co-crystal, polymorph or prodrug thereof, said subject having been administered T cells comprising a recombinant antigen receptor that specifically binds to an antigen associated with the disease or condition and/or a tag comprised by a therapeutic agent that specifically targets the disease or condition and has been or is to be administered to the subject.

In some embodiments of any of the methods provided herein, the disease or condition is a cancer.

In some embodiments of any of the methods provided herein, (i) the subject and/or the disease or condition (a) is resistant to inhibition of Bruton's tyrosine kinase (BTK) and/or (b) comprises a population of cells that are resistant to inhibition by the inhibitor; (ii) the subject and/or the disease or condition contains a mutation or disruption in a nucleic acid encoding BTK, capable of reducing or preventing inhibition of the BTK by the inhibitor and/or by ibrutinib; and/or (iii) at the time of the administration in (1) and at the time of the administration in (2) the subject has relapsed following remission after treatment with, or been deemed refractory to treatment with the inhibitor and/or with a BTK inhibitor therapy. In some embodiments, the population of cells is or comprises a population of B cells and/or does not include T cells. In some embodiments, the mutation in the nucleic acid encoding BTK contains a substitution at position C481, optionally C481S or C481R, and/or a substitution at position T474, optionally T474I or T474M.

In some embodiments of any of the methods provided herein, the target protein tyrosine kinase is not expressed by cells of the disease or condition, is not ordinarily expressed or is not suspected of being expressed in cells from which the disease or condition is derived, and/or the disease or condition is not sensitive to the inhibitor; and/or at least a plurality of the T cells express the target protein tyrosine kinase; and/or the target protein tyrosine kinase is expressed in T cells.

In some embodiments of any of the methods provided herein, the disease or condition is a cancer not expressing a B cell antigen, a non-hematologic cancer, is not a B cell malignancy, is not a B cell leukemia, or is a solid tumor.

In some embodiments of any of the methods provided herein, the disease or condition is a cancer selected from sarcomas, carcinomas, lymphomas, non-Hodgkin lymphomas (NHLs), diffuse large B cell lymphoma (DLBCL), leukemia, CLL, ALL, AML and myeloma.

In some embodiments of any of the methods provided herein, the disease or condition is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments of any of the methods provided herein, the T cells recognize or target an antigen selected from ROR1, B cell maturation antigen (BCMA), tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, and a pathogen-specific antigen.

In some embodiments of any of the methods provided herein, the antigen is not a B cell antigen; and/or the antigen is not a B cell antigen selected from CD19, CD20, CD22, and ROR1. In some embodiments, the antigen is not a B cell antigen selected from CD19, CD20, CD22, and ROR1; and/or the disease or condition does not express a B cell antigen selected from CD19, CD20, CD22 and ROR1 and/or kappa light chain.

In some embodiments of any of the methods provided herein, the T cells contains tumor infiltrating lymphocytes (TILs) or contains genetically engineered T cells expressing a recombinant receptor that specifically binds to the antigen. In some embodiments, the T cells comprise genetically engineered T cells expressing a recombinant receptor that specifically binds to the antigen or the tag, which receptor optionally is a chimeric antigen receptor. In some embodiments, the recombinant receptor is a transgenic T cell receptor (TCR) or a functional non-T cell receptor. In some embodiments, the recombinant receptor is a chimeric receptor, which optionally is a chimeric antigen receptor (CAR). In some embodiments, the chimeric antigen receptor (CAR) includes an extracellular antigen-recognition domain that specifically binds to the antigen and an intracellular signaling domain comprising an ITAM. In some embodiments, the intracellular signaling domain includes an intracellular domain of a CD3-zeta (CD3) chain. In some embodiments, the chimeric antigen receptor (CAR) further contains a costimulatory signaling region. In some embodiments, the costimulatory signaling region contains a signaling domain of CD28 or 4-1BB. In some embodiments, the costimulatory domain is a domain of CD28.

In some embodiments of any of the methods provided herein, the inhibitor is a small molecule, peptide, protein, antibody or antigen-binding fragment thereof, an antibody mimetic, an aptamer, or a nucleic acid molecule.

In some embodiments of any of the methods provided herein, the inhibitor irreversibly reduces or eliminates the activation of the target protein tyrosine kinase, specifically binds to a binding site in the active site of the target protein tyrosine kinase comprising an amino acid residue corresponding to residue C481 in the sequence set forth in SEQ ID NO:18, and/or reduces or eliminates autophosphorylation activity of the target protein tyrosine kinase.

In some embodiments of any of the methods provided herein, the inhibitor is not ibrutinib. In some embodiments of any of the methods provided herein, the inhibitor is not the compound of Formula (II). In some embodiments of any of the methods provided herein, the inhibitor is not GDC-0834; RN-486; CGI-560; CGI-1764; HM-71224; CC-292; ONO-4059; CNX-774; and LFM-A13.

In some embodiments of any of the methods provided herein, the inhibitor is administered concurrently with or subsequently to initiation of administration of the composition comprising the T cells.

In some embodiments of any of the methods provided herein, the inhibitor is administered subsequently to initiation of administration of the T cells.

In some embodiments of any of the methods provided herein, the inhibitor is administered within, or within about, 1 hour, 2 hours, 6 hours, 12 hours, 24 hours, 48 hours, 72 hours, 96 hours or 1 week of the initiation of the administration of the T cells.

In some embodiments of any of the methods provided herein, the inhibitor is administered at a time in which: the number of administered T cells detectable in the blood from the subject is decreased compared to in the subject at a preceding time point after initiation of the administration of the T cells; the number of administered T cells detectable in the blood is less than or less than about 1.5-fold, 2-fold, 3-fold, 4-fold, 5-fold, 10-fold, 50-fold or 100-fold or less the peak or maximum number of the cells of the T cell therapy detectable in the blood of the subject after initiation of administration of the administration of the T cells; and/or at a time after a peak or maximum level of the administered T cells are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject.

In some embodiments, the increase or decrease is by greater than or greater than about 1.2-fold, 1.5-fold, 2-fold, 3-fold, 4-fold, 5-fold, 10-fold or more.

In some embodiments of any of the methods provided herein, the inhibitor is administered for a time period up to 2 days, up to 7 days, up to 14 days, up to 21 days, up to one month, up to two months, up to three months, up to 6 months or up to 1 year after initiation of the administration of the administration of the T cells.

In some embodiments of any of the methods provided herein, the inhibitor is administered up to 3 months after initiation of the administration of the T cells.

In some embodiments of any of the methods provided herein, the administration of the inhibitor is continued, from at least after initiation of administration of the T cells, until: the number of cells of or derived from the T cells administered detectable in the blood from the subject is increased compared to in the subject at a preceding time point just prior to administration of the inhibitor or compared to a preceding time point after administration of the T-cell therapy; the number of cells of or derived from the T cells detectable in the blood is within 2.0-fold (greater or less) the peak or maximum number observed in the blood of the subject after initiation of administration of the T cells; the number of cells of the T cells detectable in the blood from the subject is greater than or greater than about 10%, 15%, 20%, 30%, 40%, 50%, or 60% total peripheral blood mononuclear cells (PBMCs) in the blood of the subject; and/or the subject exhibits a reduction in tumor burden as compared to tumor burden at a time immediately prior to the administration of the T cells or at a time immediately prior to the administration of the inhibitor; and/or the subject exhibits complete or clinical remission.

In some embodiments of any of the methods provided herein, the inhibitor is administered orally, subcutaneously or intravenously. In some embodiments, the inhibitor is administered orally.

In some embodiments of any of the methods provided herein, the inhibitor is administered six times daily, five times daily, four times daily, three times daily, twice daily, once daily, every other day, three times a week or at least once a week. In some embodiments of any of the methods provided herein, the inhibitor is administered once daily or twice a day.

In some embodiments of any of the methods provided herein, the inhibitor is administered at a total daily dosage amount of at least or at least about 50 mg/day, 100 mg/day, 150 mg/day, 175 mg/day, 200 mg/day, 250 mg/day, 300 mg/day, 350 mg/day, 400 mg/day, 450 mg/day, 500 mg/day, 600 mg/day, 700 mg/day, 800 mg/day or more. In some embodiments, the inhibitor is administered in an amount less than or about less than or about or 420 mg per day.

In some embodiments of any of the methods provided herein, the administered T cells contain T cells that are CD4+ or CD8+. In some embodiments of any of the methods provided herein, the administered T cells contain cells that are autologous to the subject. In some embodiments of any of the methods provided herein, the administered T cells contain T cells that are allogeneic to the subject. In some embodiments of any of the methods provided herein, the administered T cells include administration of a dose comprising a number of cells between or between about $5\times10^5$ cells/kg body weight of the subject and $1\times10^7$ cells/kg, $0.5\times10^6$ cells/kg and $5\times10^6$ cells/kg, between or between about $0.5\times10^6$ cells/kg and $3\times10^6$ cells/kg, between or between about $0.5\times10^6$ cells/kg and $2\times10^6$ cells/kg, between or between about $0.5\times10^6$ cells/kg and $1\times10^6$ cell/kg, between or between about $1.0\times10^6$ cells/kg body weight of the subject and $5\times10^6$ cells/kg, between or between about $1.0\times10^6$ cells/kg and $3\times10^6$ cells/kg, between or between about $1.0\times10^6$ cells/kg and $2\times10^6$ cells/kg, between or between about $2.0\times10^6$ cells/kg body weight of the subject and $5\times10^6$ cells/kg, between or between about $2.0\times10^6$ cells/kg and $3\times10^6$ cells/kg, or between or between about $3.0\times10^6$ cells/kg body weight of the subject and $5\times10^6$ cells/kg, each inclusive.

In some embodiments of any of the methods provided herein, the dose of cells administered is less than the dose in a method in which the administered T cells are administered without administering the inhibitor. In some embodiments, the dose is at least 1.5-fold, 2-fold, 3-fold, 4-fold, 5-fold or 10-fold less.

In some embodiments of any of the methods provided herein, the T cells are administered in a single dose, which optionally is a single pharmaceutical composition comprising the cells.

In some embodiments of any of the methods provided herein, the T cells are administered as a split dose, wherein the cells of a single dose are administered in a plurality of compositions, collectively comprising the cells of the dose, over a period of no more than three days and/or the method further includes administering one or more additional doses of the T cells.

In some embodiments of any of the methods provided herein, the method further includes administering a lymphodepleting chemotherapy prior to administration of the T cells and/or wherein the subject has received a lymphodepleting chemotherapy prior to administration of the T cells.

In some embodiments of any of the methods provided herein, the lymphodepleting chemotherapy includes administering fludarabine and/or cyclophosphamide to the subject.

In some embodiments of any of the methods provided herein, the method further includes: administering an immune modulatory agent to the subject, wherein the administration of the cells and the administration of the immune modulatory agent are carried out simultaneously, separately or in a single composition, or sequentially, in either order. In some embodiments, the immune modulatory agent is capable of inhibiting or blocking a function of a molecule, or signaling pathway involving said molecule, wherein the molecule is an immune-inhibitory molecule and/or wherein the molecule is an immune checkpoint molecule.

In some embodiments, the immune checkpoint molecule or pathway is selected from PD-1, PD-L1, PD-L2, CTLA-4, LAG-3, TIM3, VISTA, adenosine 2A Receptor (A2AR), or adenosine or a pathway involving any of the foregoing.

In some embodiments of any of the methods provided herein, the immune modulatory agent is or contains an antibody, which optionally is an antibody fragment, a single-chain antibody, a multispecific antibody, or an immunoconjugate.

In some embodiments, the antibody specifically binds to the immune checkpoint molecule or a ligand or receptor thereof; and/or the antibody is capable of blocking or impairing the interaction between the immune checkpoint molecule and a ligand or receptor thereof.

In some embodiments of any of the methods provided herein, the administered T cells exhibit increased or prolonged expansion and/or persistence in the subject as compared to a method in which the administered T cells are administered to the subject in the absence of the inhibitor.

In some embodiments of any of the methods provided herein, the method reduces tumor burden to a greater degree and/or for a greater period of time as compared to the reduction that would be observed with a comparable method in which the administered T cells are administered to the subject in the absence of the inhibitor.

Provided in some aspects are combinations containing: genetically engineered T cells expressing a recombinant receptor that binds to an antigen other than a B cell antigen or other than a B cell antigen selected from CD19, CD20, CD22 and ROR1, and an inhibitor of a target protein tyrosine kinase, wherein the inhibitor does not inhibit ITK and/or inhibits ITK with a half-maximal inhibitory concentration (IC50) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

In some embodiments of any of the combinations herein, the antigen is selected from among Her2, L1-CAM, mesothelin, CEA, hepatitis B surface antigen, anti-folate receptor, CD23, CD24, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, Lewis Y, L1-cell adhesion molecule (L1-CAM), Melanoma-associated antigen (MAGEMAGE-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, c-Met, GD-2 O-acetylated GD2 (OGD2), CE7, Wilms Tumor 1 (WT-1), a cyclin, cyclin A2, CCL-1, CD138, and a pathogen-specific antigen.

In some embodiments of any of the combinations herein, the antigen is a pathogen-specific antigen, which is a viral antigen, bacterial antigen or parasitic antigen.

In some embodiments of any of the combinations herein, the recombinant receptor is a transgenic T cell receptor (TCR) or a functional non-T cell receptor.

In some embodiments of any of the combinations herein, the recombinant receptor is a chimeric receptor, which optionally is a chimeric antigen receptor (CAR).

In some embodiments of any of the combinations herein: the inhibitor is a selective inhibitor of the target protein tyrosine kinase; and/or the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

In some embodiments of any of the combinations herein, the inhibitor is a small molecule, peptide, protein, antibody or antigen-binding fragment thereof, an antibody mimetic, an aptamer, or a nucleic acid molecule.

In some embodiments of any of the combinations herein, the inhibitor is selected from Formula (II), ONO/GS-4059, Compound 30 or Compound 38,GDC-0834; RN-486; CGI-560; CGI-1764; HM-71224; CC-292; ONO-4059; CNX-774; and LFM-A13.

In some embodiments of any of the combinations herein, the inhibitor contains the compound of Formula (II), or an enantiomer, pharmaceutically-acceptable salt, solvate, hydrate, co-crystal, polymorph or prodrug thereof or a pharmaceutical composition comprising any of the foregoing.

In some embodiments of any of the combinations herein, the combination is formulated in the same composition. In some embodiments of any of the combinations herein, the combination is formulated in separate compositions.

Provided herein are kits that contain the combination of any of claims 76-86 and instructions for administering, to a subject for treating a disease or condition, optionally a cancer, the genetically engineered cells and the inhibitor.

Provided herein are kits that contain a composition comprising a therapeutically effective amount of genetically engineered T cells expressing a recombinant receptor that binds to an antigen other than a B cell antigen or other than a B cell antigen selected from CD19, CD20, CD22 and ROR1; and instructions for administering, to a subject for treating a cancer, the genetically engineered cells in a combined therapy with an inhibitor of a target protein tyrosine kinase, wherein the inhibitor does not inhibit ITK and/or inhibits ITK with a half-maximal inhibitory concentration (IC50) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

Provided herein are kits that contain a composition comprising a therapeutically effective amount of an inhibitor of a target protein tyrosine kinase, wherein the inhibitor does not inhibit ITK and/or inhibits ITK with a half-maximal inhibitory concentration (IC50) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4; and instructions for administering, to a subject for treating a disease or condition, optionally a cancer, the inhibitor in a combined therapy with genetically engineered T cells, said T cells expressing a recombinant receptor that binds to an antigen other than a B cell antigen or other than a B cell antigen selected from CD19, CD20, CD22 and ROR1.

In some embodiments of any of the embodiments herein, the cancer is not a cancer expressing a B cell antigen, is a non-hematologic cancer, is not a B cell malignancy, is not a B cell leukemia, or is a solid tumor.

In some embodiments of any of the embodiments herein, the cancer is a sarcoma, a carcinoma or a lymphoma, optionally a non-Hodgkin lymphomas (NHLs), diffuse large B cell lymphoma (DLBCL), leukemia, CLL, ALL, AML and myeloma.

In some embodiments of any of the embodiments herein, the cancer is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments of any of the embodiments herein, (i) the subject and/or the disease or condition (a) is resistant to inhibition of Bruton's tyrosine kinase (BTK) and/or (b) contains a population of cells that are resistant to inhibition by the inhibitor; (ii) the subject and/or the disease or condition contains a mutation or disruption in a nucleic acid encoding BTK, capable of reducing or preventing inhibition of the BTK by the inhibitor and/or by ibrutinib; and/or (iii) at the time of the administering the subject has relapsed following remission after treatment with, or been deemed refractory to treatment with the inhibitor and/or with a BTK inhibitor therapy.

In some embodiments of any of the embodiments herein, the population of cells is or contains a population of B cells and/or does not contain T cells.

In some embodiments of any of the embodiments herein, the mutation in the nucleic acid encoding BTK contains a substitution at position C481, optionally C481S or C481R, and/or a substitution at position T474, optionally T474I or T474M.

In some embodiments of any of the embodiments herein, the antigen is selected from among Her2, L1-CAM, mesothelin, CEA, hepatitis B surface antigen, anti-folate receptor, CD23, CD24, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, Lewis Y, L1-cell adhesion molecule (L1-CAM), Melanoma-associated antigen (MAGEMAGE-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Fetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, c-Met, GD-2 O-acetylated GD2 (OGD2), CE7, Wilms Tumor 1 (WT-1), a cyclin, cyclin A2, CCL-1, CD138, and a pathogen-specific antigen.

In some embodiments of any of the embodiments herein, the antigen is a pathogen-specific antigen, which is a viral antigen, bacterial antigen or parasitic antigen.

In some embodiments of any of the embodiments herein, the recombinant receptor is a transgenic T cell receptor (TCR) or a functional non-T cell receptor.

In some embodiments of any of the embodiments herein, the recombinant receptor is a chimeric receptor, which optionally is a chimeric antigen receptor (CAR).

In some embodiments of any of the embodiments herein, the inhibitor is a selective inhibitor of the target protein tyrosine kinase; and/or the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

In some embodiments of any of the kits herein, the inhibitor is a small molecule, peptide, protein, antibody or antigen-binding fragment thereof, an antibody mimetic, an aptamer, or a nucleic acid molecule. In some embodiments of any of the embodiments herein, the inhibitor is selected from Formula (II), ONO/GS-4059, Compound 30 or Compound 38,GDC-0834; RN-486; CGI-560; CGI-1764; HM-71224; CC-292; ONO-4059; CNX-774; and LFM-A13.

In some embodiments of any of the kits herein, the inhibitor contains the compound of Formula (II), or an enantiomer, pharmaceutically-acceptable salt, solvate, hydrate, co-crystal, polymorph or prodrug thereof or a pharmaceutical composition comprising any of the foregoing.

In some embodiments of any of the kits herein, the instructions are for administering the inhibitor concurrently with or subsequently to initiation of administration of the composition comprising the T cells. In some embodiments of any of the kits herein, the instructions are for administering the inhibitor subsequently to initiation of administration of the T cells.

In some embodiments of any of the kits herein, the instructions are for administering the inhibitor within, or within about, 1 hour, 2 hours, 6 hours, 12 hours, 24 hours, 48 hours, 72 hours, 96 hours or 1 week of the initiation of the administration of the T cells.

In some embodiments of any of the kits herein, the instructions are for administering the inhibitor at a time in which: the number of cells of the T cell therapy detectable in the blood from the subject is decreased compared to in the subject at a preceding time point after initiation of the administration of the T cells; the number of cells of the T cell therapy detectable in the blood is less than or less than about 1.5-fold, 2-fold, 3-fold, 4-fold, 5-fold, 10-fold, 50-fold or 100-fold or less the peak or maximum number of the cells of the T cell therapy detectable in the blood of the subject after initiation of administration of the administration of the T cells; and/or at a time after a peak or maximum level of the cells of the T cell therapy are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject.

In some embodiments of any of the embodiments herein, the increase or decrease is by greater than or greater than about 1.2-fold, 1.5-fold, 2-fold, 3-fold, 4-fold, 5-fold, 10-fold or more.

In some embodiments of any of the embodiments herein, the instructions are for administering the inhibitor for a time period up to 2 days, up to 7 days, up to 14 days, up to 21 days, up to one month, up to two months, up to three months, up to 6 months or up to 1 year after initiation of the administration of the administration of the T cells.

In some embodiments of any of the embodiments herein, the instructions are for further administering the inhibitor from at least after initiation of administration of the T cells, until:

the number of cells of or derived from the T cells administered detectable in the blood from the subject is increased compared to in the subject at a preceding time point just prior to administration of the inhibitor or compared to a preceding time point after administration of the T-cell therapy; the number of cells of or derived from the T cells detectable in the blood is within 2.0-fold (greater or less) the peak or maximum number observed in the blood of the subject after initiation of administration of the T cells; the number of cells of the T cells detectable in the blood from the subject is greater than or greater than about 10%, 15%, 20%, 30%, 40%, 50%, or 60% total peripheral blood mononuclear cells (PBMCs) in the blood of the subject; and/or the subject exhibits a reduction in tumor burden as compared to tumor burden at a time immediately prior to the administration of the T cells or at a time immediately prior to the administration of the inhibitor; and/or the subject exhibits complete or clinical remission.

In some embodiments of any of the embodiments herein, the genetically engineered T cells contain cells that are autologous to the subject. In some embodiments of any of the embodiments herein, the genetically engineered T cells contain T cells that are allogeneic to the subject.

Provided in some aspects are methods of engineering immune cells expressing a recombinant receptor, comprising: contacting a population of cells comprising T cells with an inhibitor of a target protein tyrosine kinase, wherein the inhibitor does not inhibit ITK and/or inhibits ITK with a half-maximal inhibitory concentration (IC50) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4; and introducing a nucleic acid encoding a recombinant receptor into the population of T cells under conditions such that the recombinant receptor is expressed.

In some embodiments of any of the methods herein, the population of cells is or contains T cells, optionally CD4+ or CD8+.

In some embodiments of any of the methods herein, the population of cells are isolated from a subject, optionally a human subject.

In some embodiments of any of the methods herein, the contacting occurs prior to and/or during the introducing.

Provided in some aspects are methods of producing genetically engineered T cells, comprising introducing a nucleic acid molecule encoding a recombinant receptor into a primary T cell, wherein the T cells is from a subject having been administered an inhibitor of a target protein tyrosine kinase, wherein the inhibitor does not inhibit ITK and/or inhibits ITK with a half-maximal inhibitory concentration (IC50) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

In some embodiments of any of the methods herein, the subject has been administered the inhibitor no more than 30 days, 20 days, 10 days, 9 days, 8 days, 7 days, 6 days, 5 days, 4 days, 3 days, 2 days, or 1 day prior to introducing the nucleic acid molecule.

In some embodiments of any of the methods herein: the inhibitor is a selective inhibitor of the target protein tyrosine kinase; and/or the inhibitor inhibits the target protein tyrosine kinase with a half-maximal inhibitory concentration (IC50) that is at least 10 or at least 100 times lower than that of the IC50 of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration (IC50) of less than or less than about 1000 nM, 900 nM, 800 nM, 600 nM, 500 nM, 400 nM, 300 nM, 200 nM, 100 nM or less.

In some embodiments of any of the methods herein, the inhibitor is a small molecule, peptide, protein, antibody or antigen-binding fragment thereof, an antibody mimetic, an aptamer, or a nucleic acid molecule.

In some embodiments of any of the methods herein, the inhibitor is selected from the compound of Formula (II), ONO/GS-4059, Compound 30 or Compound 38,GDC-0834; RN-486; CGI-560; CGI-1764; HM-71224; CC-292; ONO-4059; CNX-774; and LFM-A13.

In some embodiments of any of the methods herein, the inhibitor contains the compound of Formula (II), or an enantiomer, pharmaceutically-acceptable salt, solvate, hydrate, co-crystal, polymorph or prodrug thereof or a pharmaceutical composition comprising any of the foregoing.

In some embodiments of any of the methods herein, the T cells contain CD4+ or CD8+ cells.

BRIEF DESCRIPTION OF THE DRAWINGS

FIG. 2A and FIG. 2B show CAR T cell expression of CD25, CD28, CD39 and CD95 following culture of CD4+ and CD8+ cells in the presence or absence of indicated concentrations of ibrutinib or the compound of Formula (II), respectively.

FIG. 2E and FIG. 2F show CAR-T cell expression of CD69, CD107a and PD-1 following culture of CD4+ and CD8+ cells, respectively, in the presence or absence of indicated concentrations of ibrutinib.

FIG. 2G and FIG. 2H show CAR-T cell expression of CD69, CD107a and PD-1 following culture of CD4+ and CD8+ cells, respectively, in the presence or absence of indicated concentrations of the compound of Formula (II).

Arrows indicate the time point of each re-stimulation where CAR T cells were counted and new target cells along with the compound of Formula (II) were added.

Figure 4A:
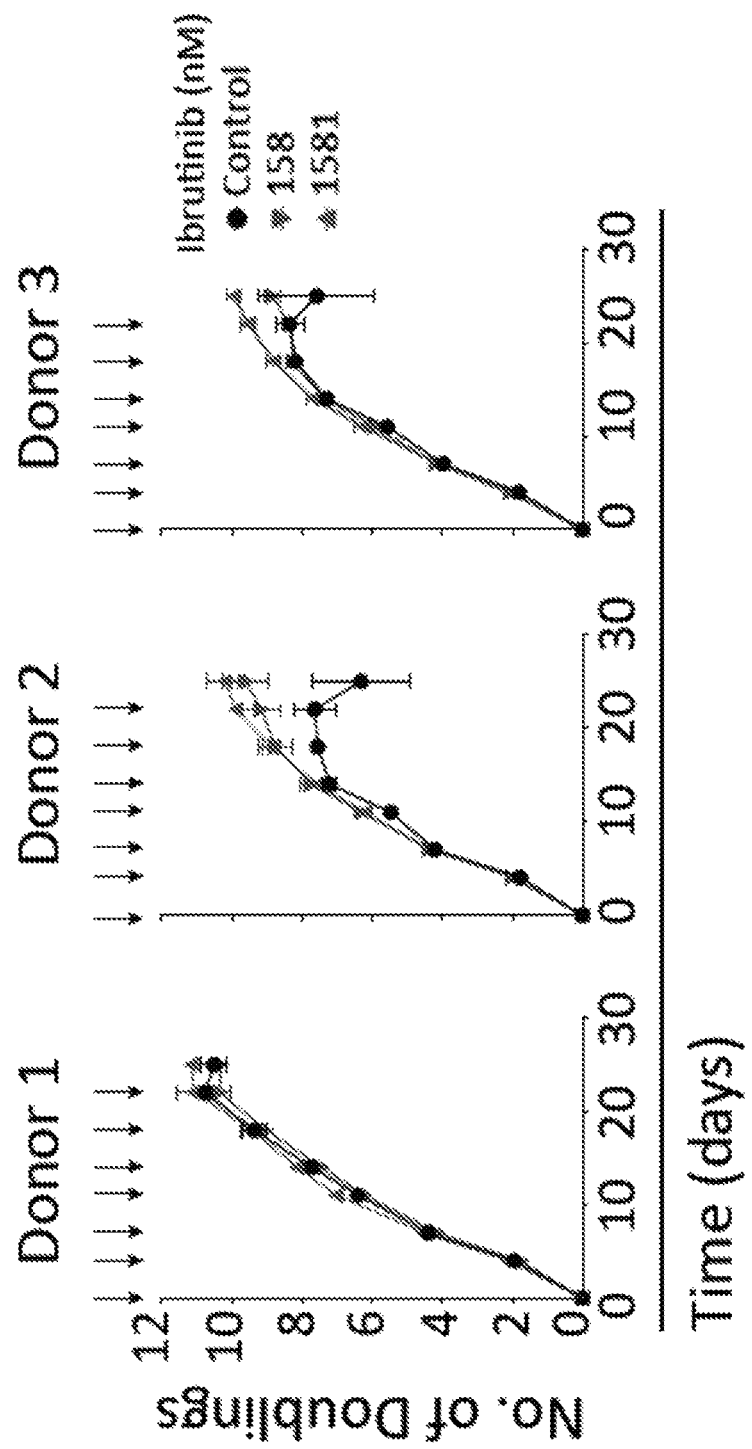
FIG. 4A shows the number of population doublings of CAR-T cells after individual round of restimulation in a serial stimulation assay, in the absence (control) or presence of 50 nM or 500 nM ibrutinib. Arrows indicate the time point of each re-stimulation where CAR T cells were counted and new target cells along with ibrutinib were added.
Figure 4B:
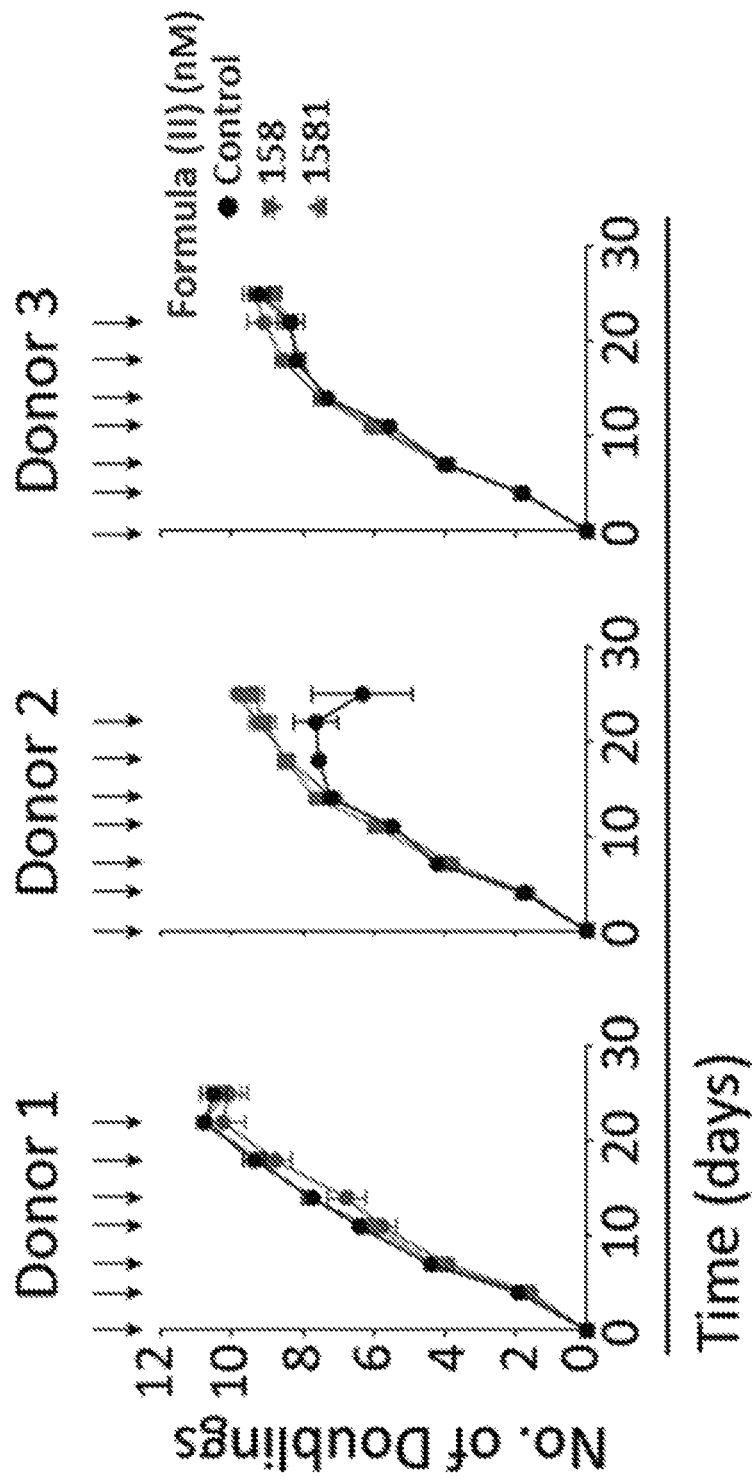
FIG. 4B shows the number of population doublings of CAR-T cells after individual round of restimulation in a serial stimulation assay, in the absence (control) or presence of 158 nM or 1581 nM of the compound of Formula (II).
Figure 4C:
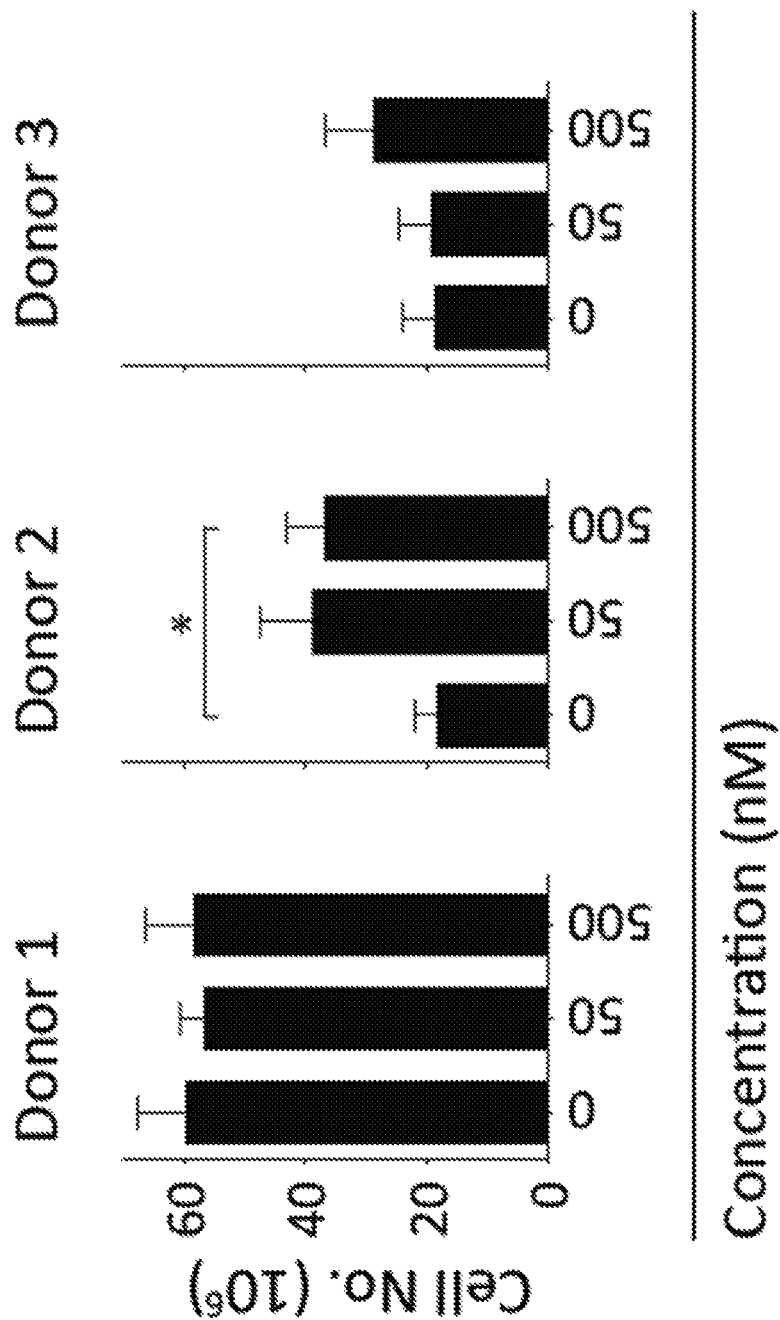

FIG. 4C shows the number of cells at day 18 after 5 rounds of restimulation in the presence or absence of the indicated concentrations of ibrutinib in a serial stimulation assay, P<0.05 (*).

Figure 4D:
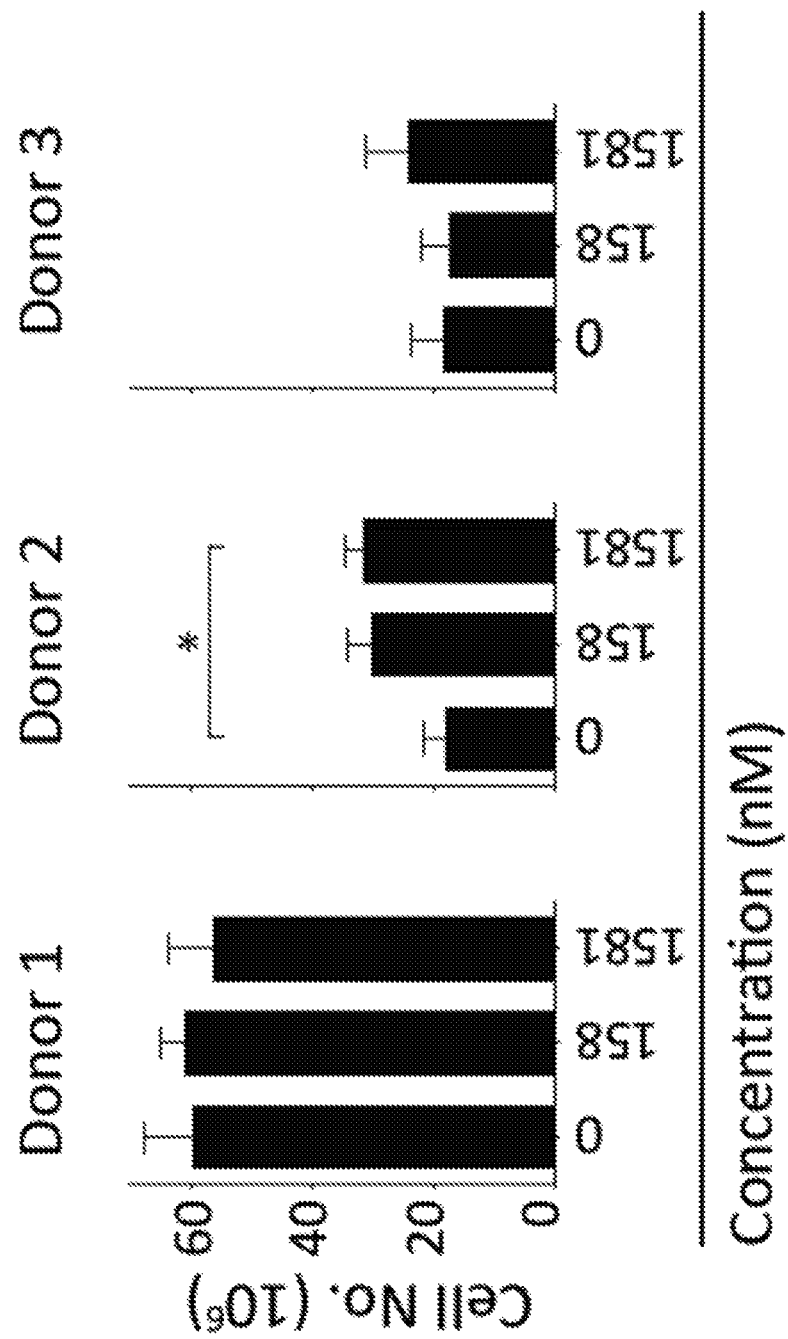

FIG. 4D shows the number of cells at day 18 after 5 rounds of restimulation in the presence or absence of the indicated concentrations of the compound of Formula (II) in a serial stimulation assay, P<0.05 (*).

FIG. 5A shows the results of a flow cytometry study assessing surface expression levels of cell surface markers used to differentiate TH2 versus TH1 phenotype T cells, following stimulation of T cells in the presence of the compound of Formula (II) or ibrutinib.

FIG. 5B shows the percentage of TH1 cells observed over time, as measured by the flow cytometry assay, for T cells cultured in the presence or absence of the compound of Formula (II) or ibrutinib.

Figure 5C:
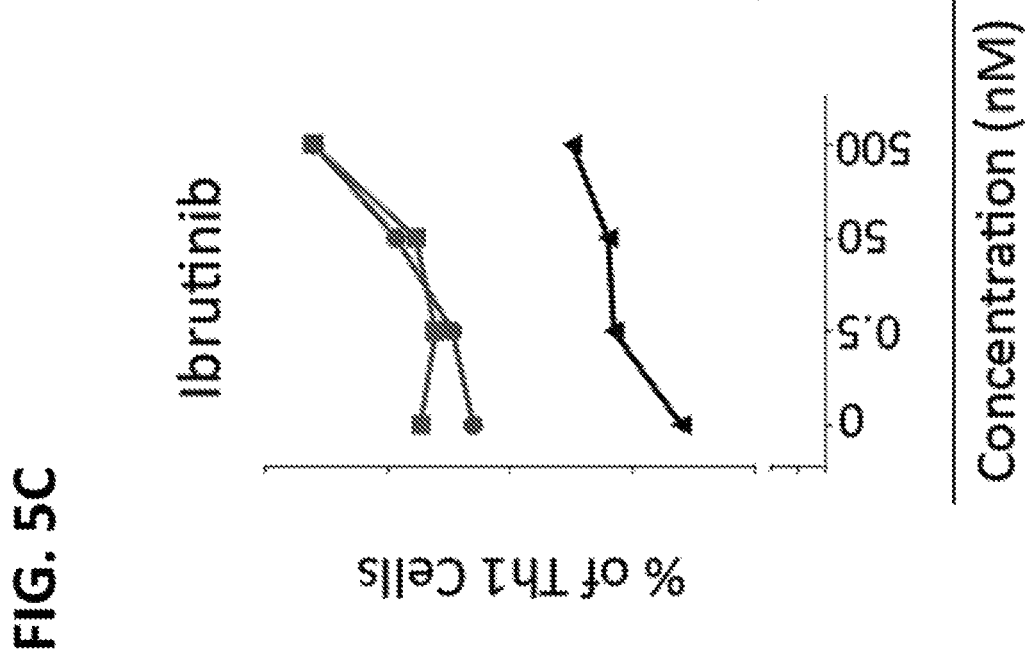

FIG. 5C shows the percentage of TH1 cells, as measured by the flow cytometry assay, at day 18 following serial restimulation of T cells in the absence or presence of the indicated concentrations of the compound of Formula (II) or ibrutinib.

Figure 5D:
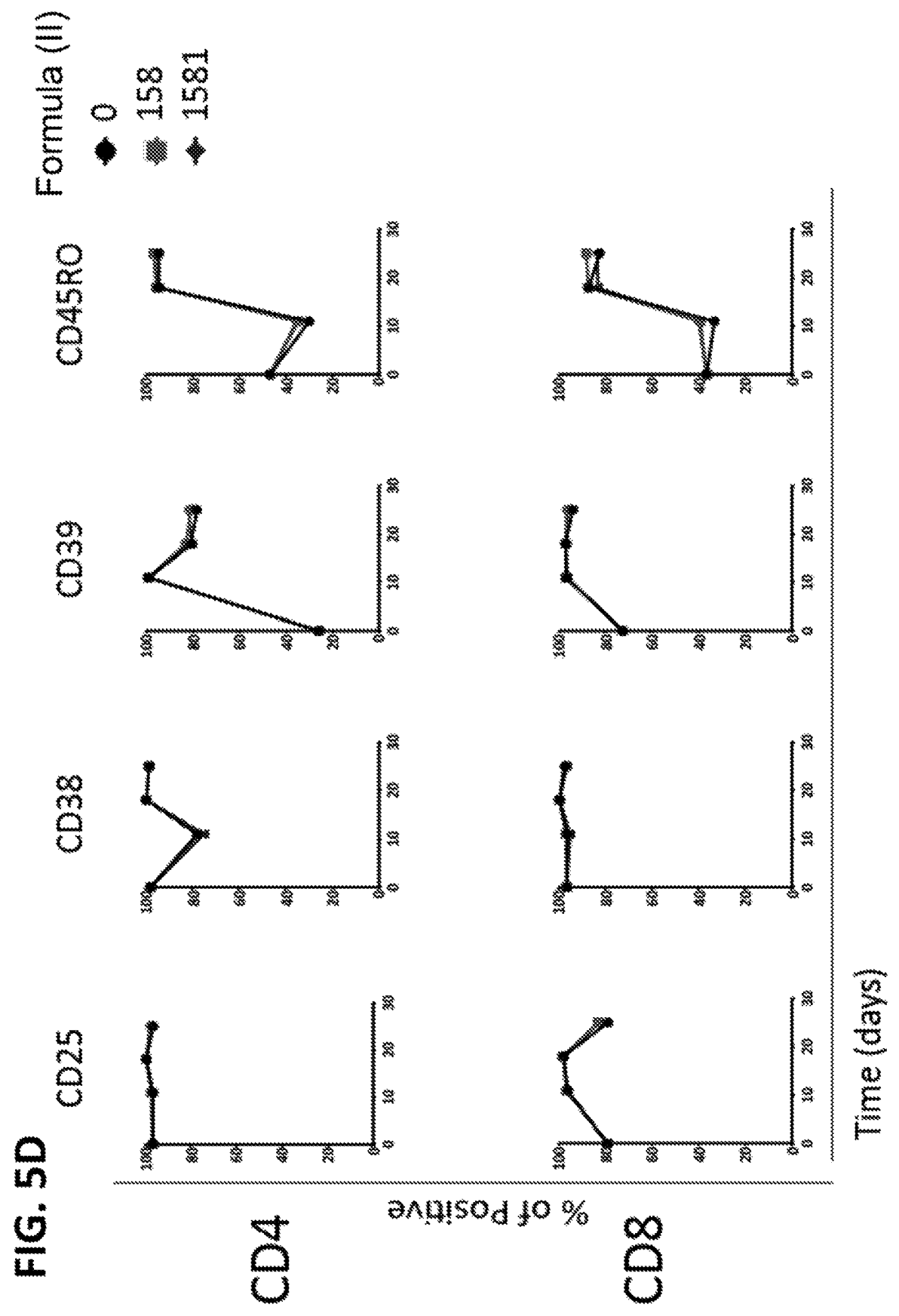

FIG. 5D shows expression of CD25, CD38, CD39 and CD45RO (FIG. 5D) at days 0, 11, 18 and 21 of serial stimulation in the presence of the compound of Formula (II). Representative results from CAR T cells from one donor-derived cells are shown.

FIG. 5E shows expression of CD62L, CD69, CD107a and PD-1 (FIG. 5E) at days 0, 11, 18 and 21 of serial stimulation in the presence of the compound of Formula (II). Representative results from CAR T cells from one donor-derived cells are shown.

Figure 5F:
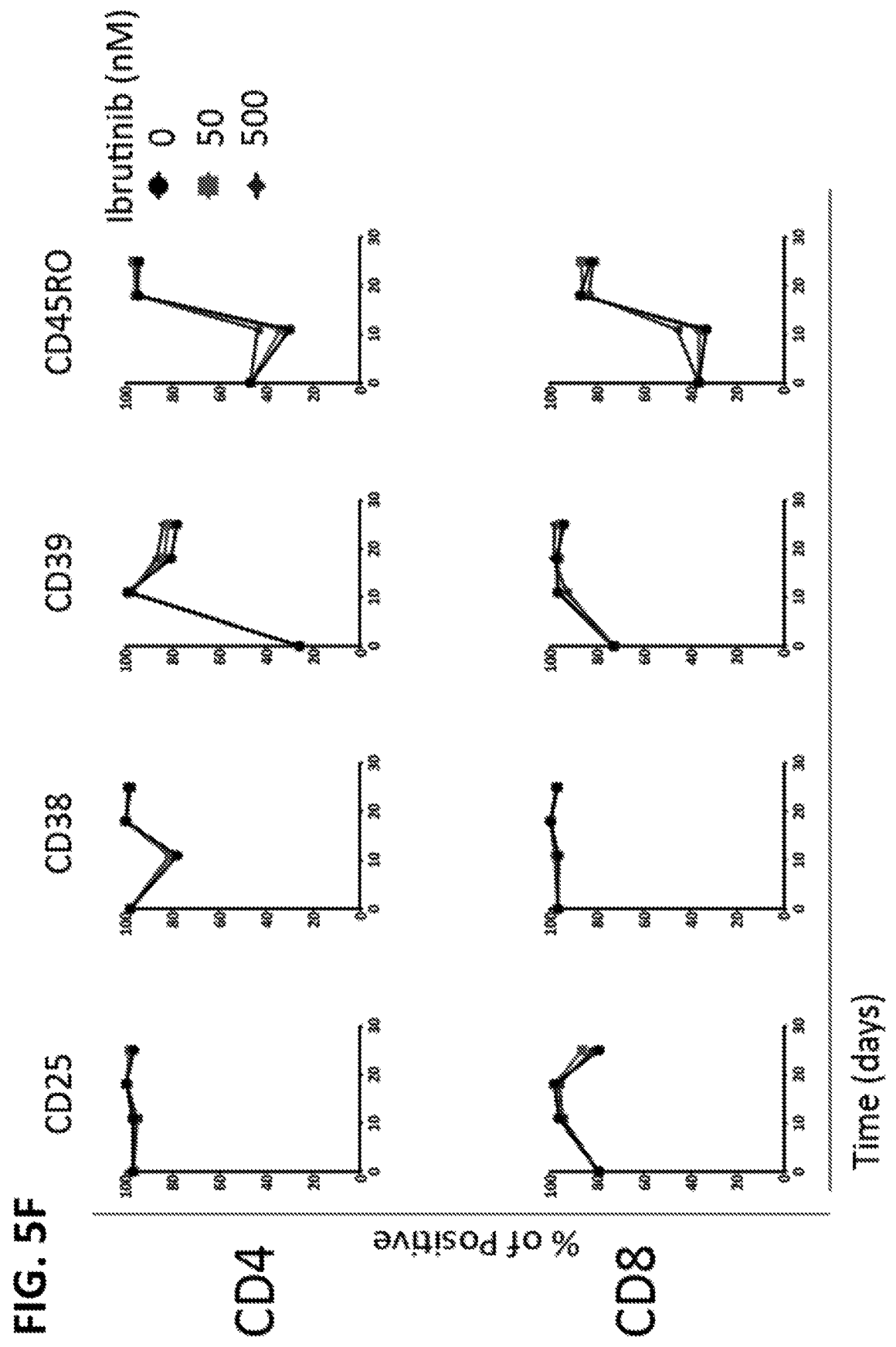
Figure 5G:
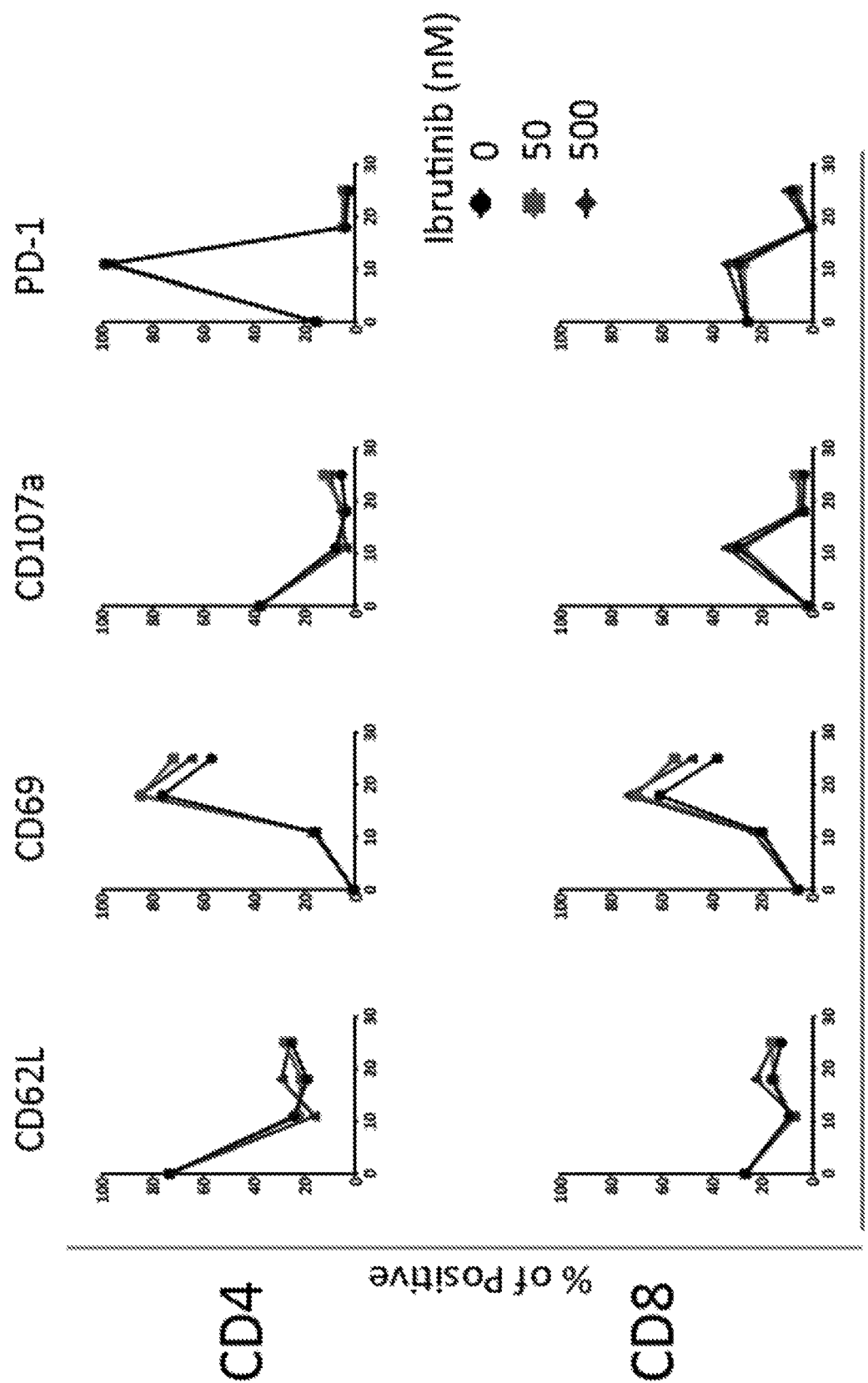

FIG. 5F and FIG. 5G expression of CD25, CD38, CD39 and CD45RO (FIG. 5D) and CD62L, CD69, CD107a and PD-1 (FIG. 5E) at days 0, 11, 18 and 21 of serial stimulation in the presence of ibrutinib. Representative results from CAR T cells from one donor-derived cells are shown.

Figure 6A:
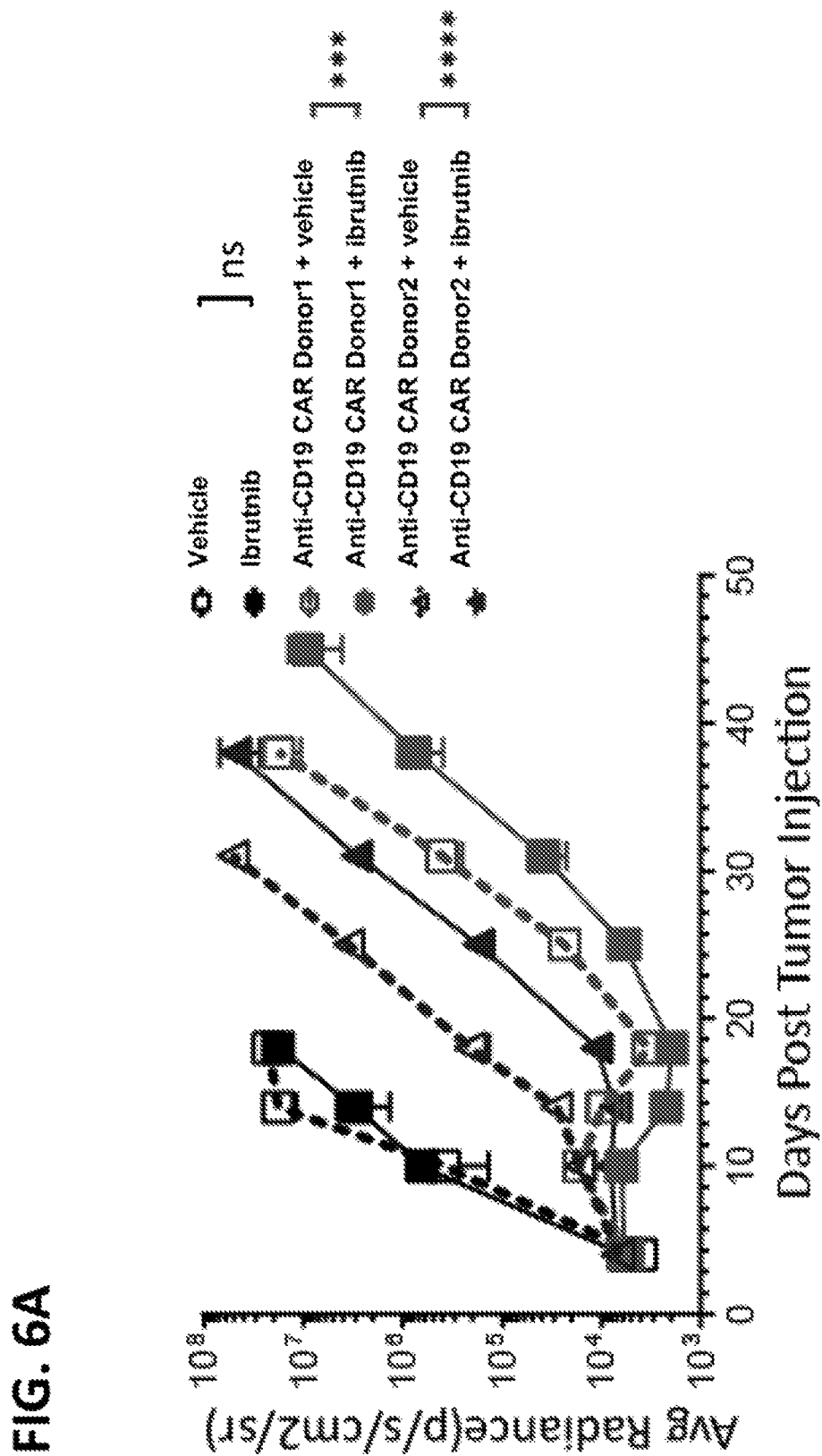
Figure 6B:
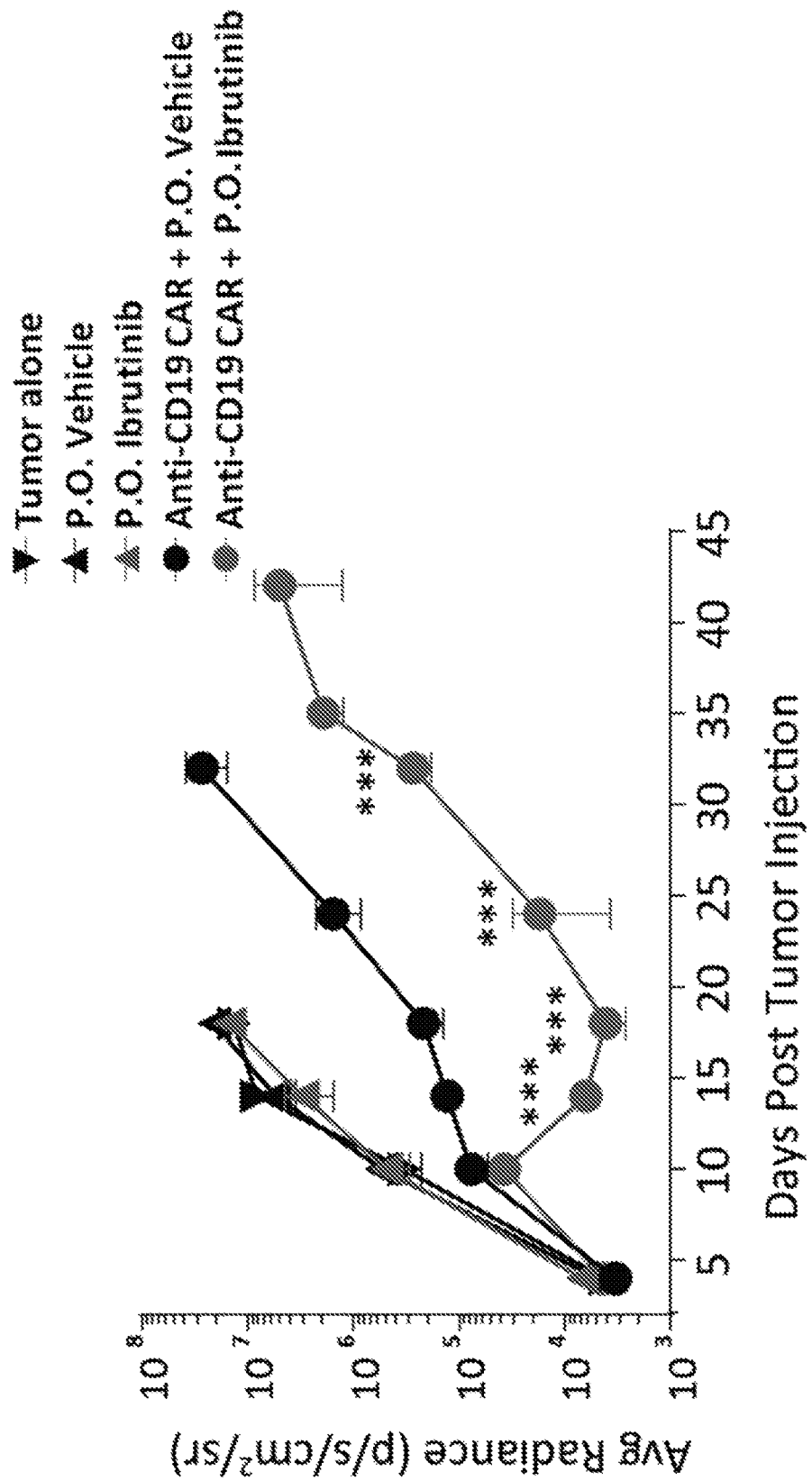

FIG. 6A shows results of a study assessing tumor burden over time in a disseminated tumor xenograft mouse model (the model identified as being resistant to BTK inhibition), following administration of a sub-optimal dose of CAR+ T cells (Anti-CD19 CAR), in combination with oral administration of (a) vehicle alone (P.O. vehicle) or (b) ibrutinib (P.O. Ibrutinib), (iii) oral administration of vehicle alone (vehicle) or (iv) oral administration of ibrutinib alone (ibrutinib). FIG. 6B shows results of the same study at greater time points after post-tumor rejection in mice that were treated with CAR+ T cells from two different donor-derived cells in the presence or absence of ibrutinib or vehicle control. The results in FIG. 6A and FIG. 6B depict tumor growth over time as indicated by measuring average radiance by bioluminescence.

Figure 6C:
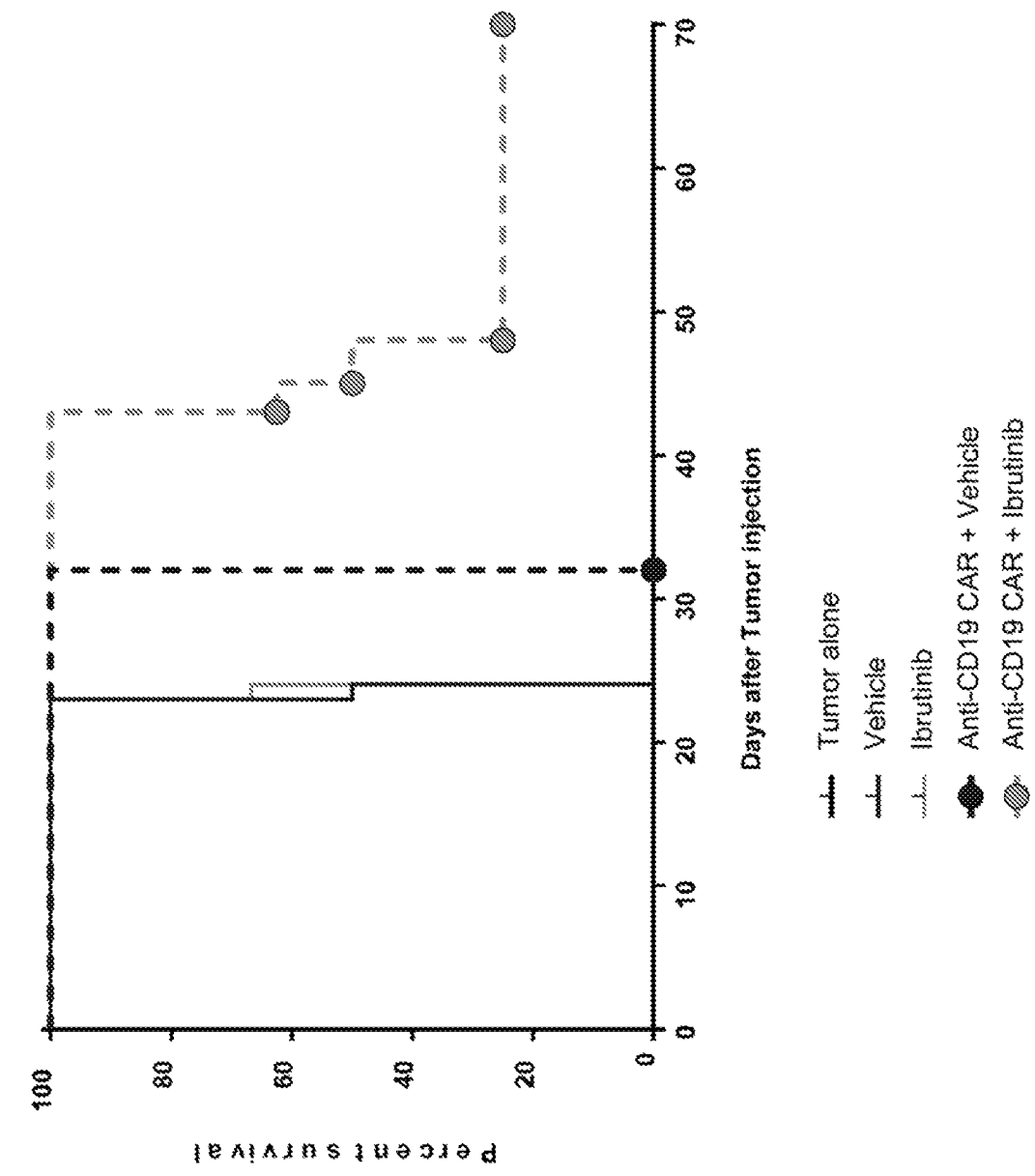
Figure 6D:
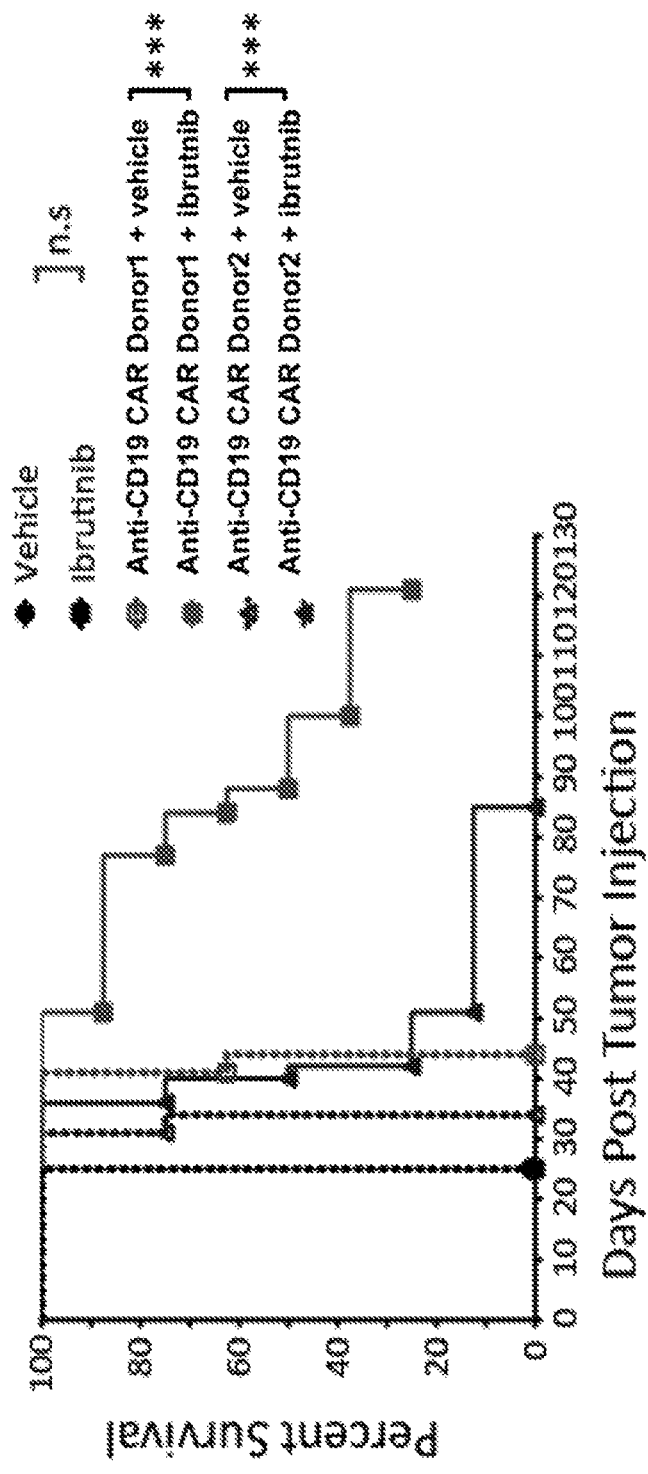

FIG. 6C shows a Kaplan Meier curve for survival of the animals in these treatment groups described with reference to FIG. 6A. FIG. 6D shows results of survival in the same study at greater time points after post-tumor rejection in mice that were treated with CAR+ T cells from two different donor-derived cells in the presence or absence of ibrutinib or vehicle control.

Figure 7A:
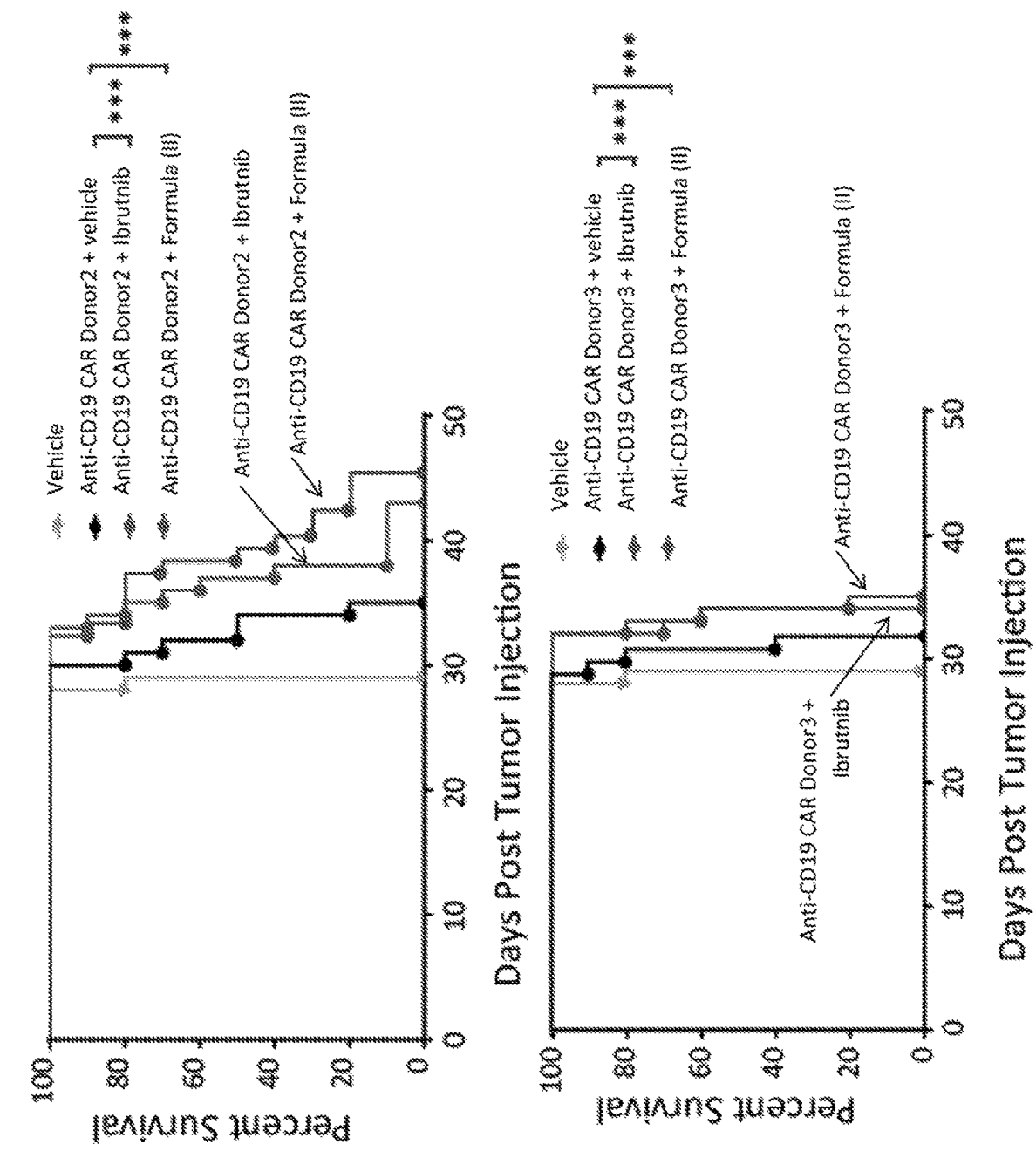

FIG. 7A shows a Kaplan meier curve depicting observed survival of tumor-bearing mice administered CAR-T cells generated from two different donors, alone or in combination with administration of daily ibrutinib or the compound of Formula (II), each administered via drinking water. Statistically significant differences are shown, P<0.001 (***).

Figure 7B:
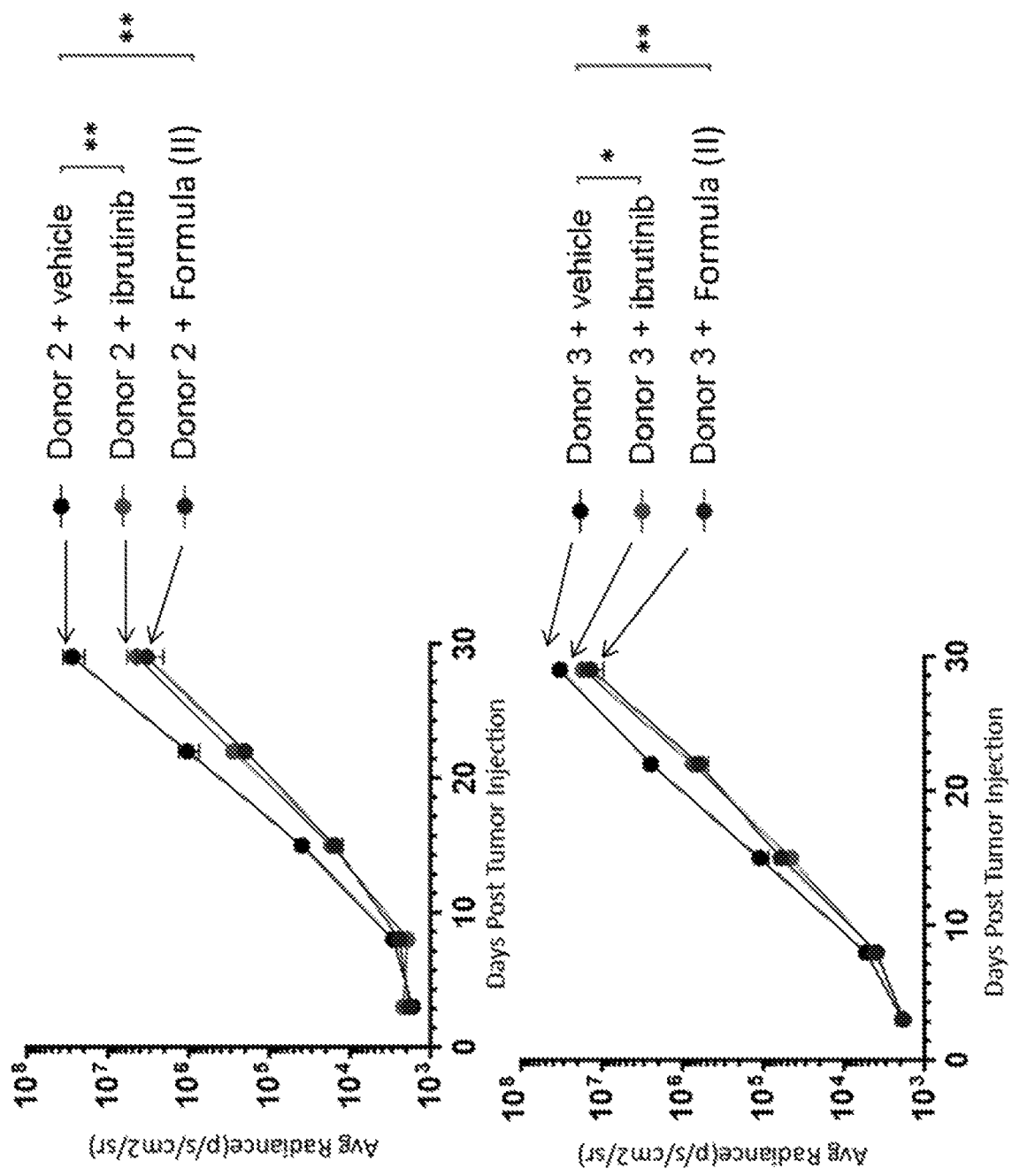

FIG. 7B shows tumor growth over time as indicated by measuring average radiance by bioluminescence from mice administered CAR-T cells generated from two different donors and treated with ibrutinib or the compound of Formula (II), each administered via drinking water. Statistically significant differences are shown, two-way ANOVA P<0.05 (*), P<0.01 (**).

Figure 7D:
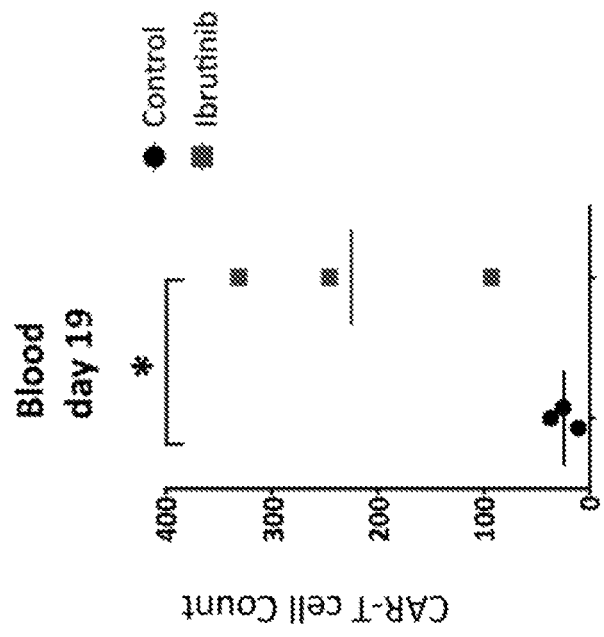
Figure 7C:
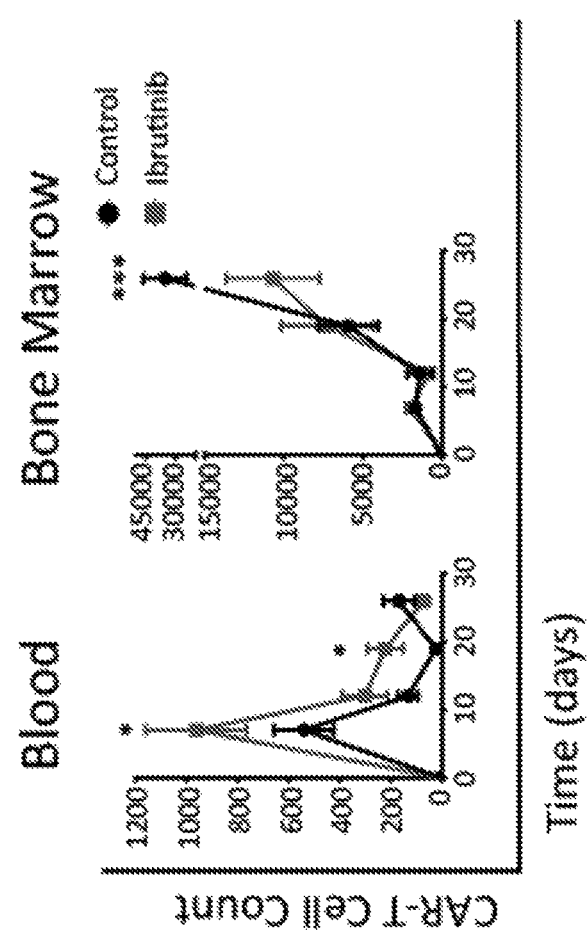

FIG. 7C shows results of a study assessing numbers of CAR-T cells in the blood and bone marrow of mice treated with or without ibrutinib. Statistically significant differences are indicated as P<0.05 (*), P<0.001 (***).

FIG. 7D shows the number of cells in the blood at day 19 post CAR-T cell transfer after treatment or with or without ibrutinib. Statistically significant differences are indicated as P<0.05 (*).

Figure 7E:
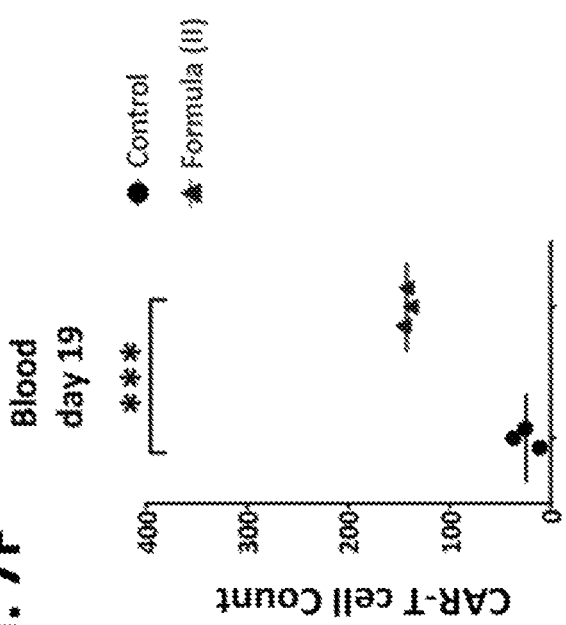

FIG. 7E shows results of a study assessing numbers of CAR-T cells in the blood and bone marrow of mice treated with or without the compound of Formula (II). Statistically significant differences are indicated as P<0.001 (*) and P<0.0001 (**).

Figure 7F:
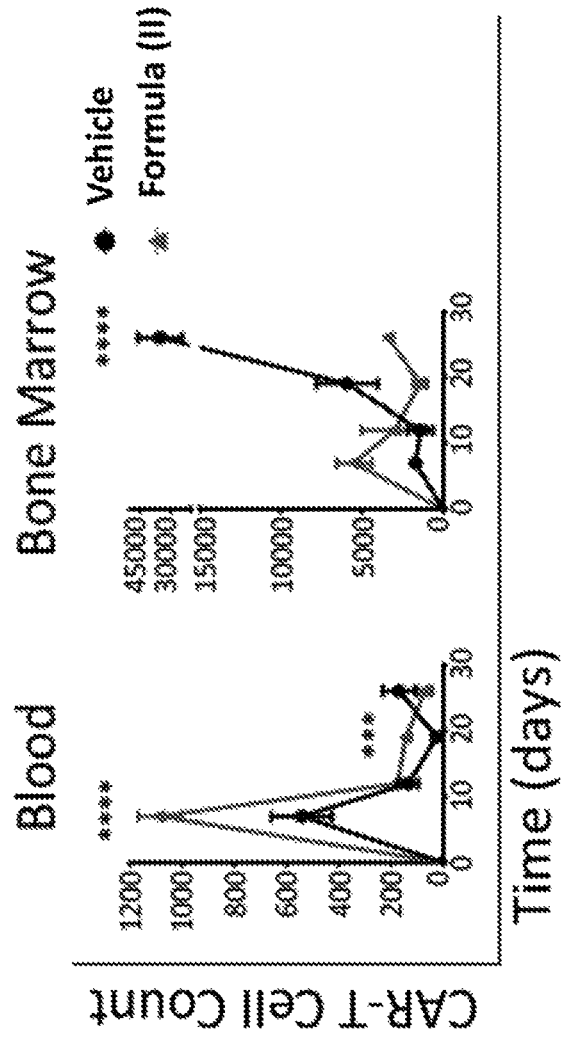

FIG. 7F shows the number of cells in the blood at day 19 post CAR-T cell transfer after treatment or with or without the compound of Formula (II). Statistically significant differences are indicated as P<0.001 (***).

Figure 7G:
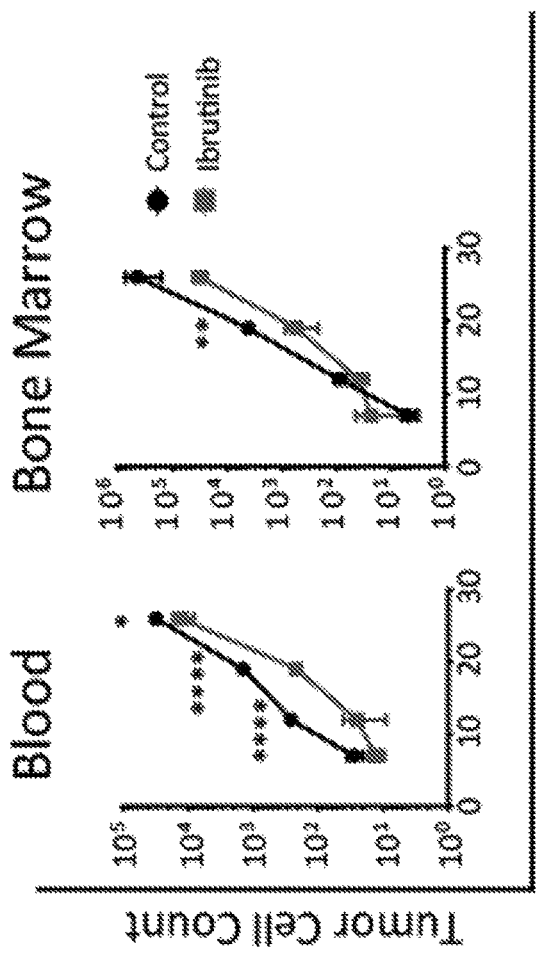

FIG. 7G shows the tumor cell count at days 7, 12, 19 and 26 post CAR T transfer in the blood and bone marrow of mice treated with CAR-T cells alone or with ibrutinib. Statistically significant differences are indicated as P<0.05 (*), P<0.01 (), P<0.001 (*) and P<0.0001 (****).

Figure 7H:
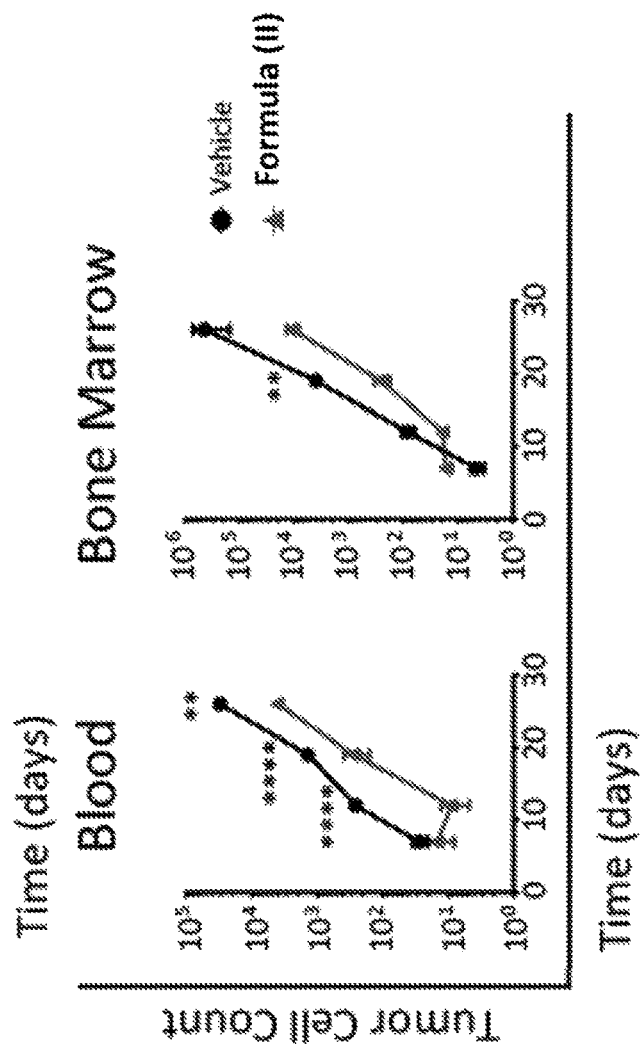

FIG. 7H shows the tumor cell count at days 7, 12, 19 and 26 post CAR T transfer in the blood, bone marrow of mice treated with CAR-T cells alone or with the compound of Formula (II). Statistically significant differences are indicated as P<0.05 (*), P<0.01 (), P<0.001 (*) and P<0.0001 (****).

Figure 8A:
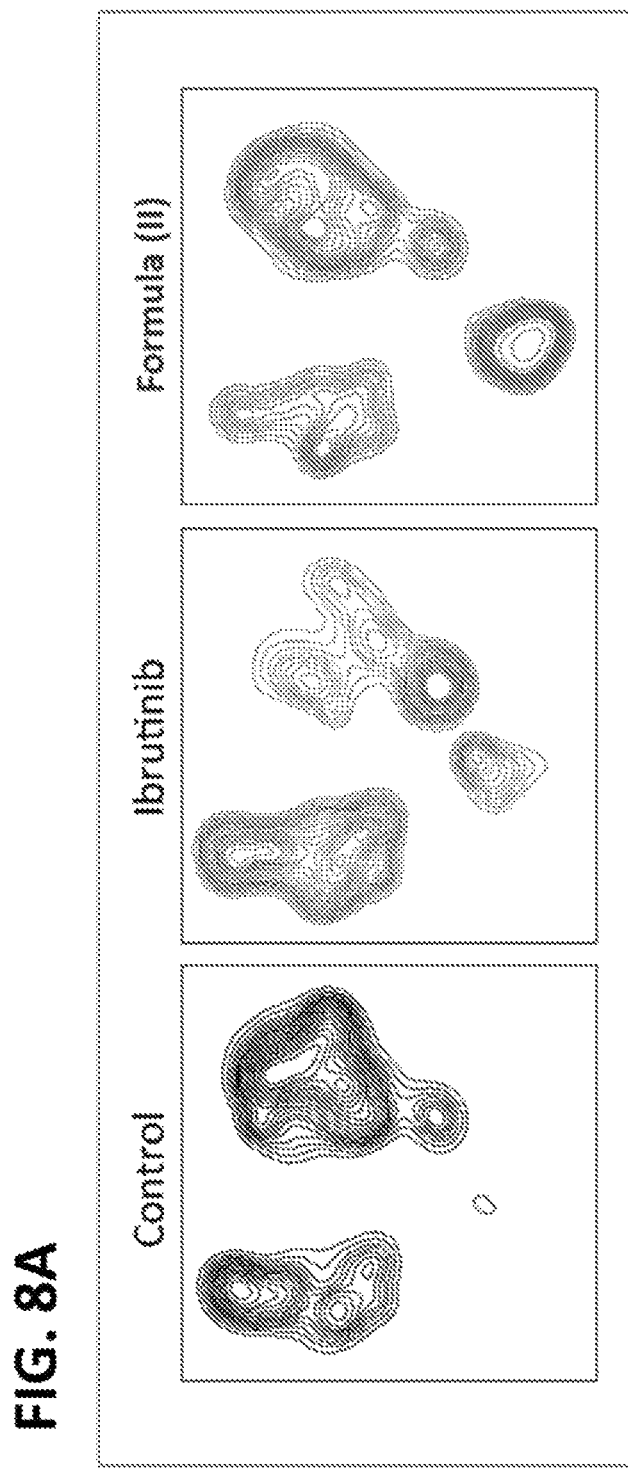

FIG. 8A depicts T-distributed stochastic neighbor embedding (t-SNE) high dimensional analysis of surface markers on CAR-engineered T cells harvested from the bone marrow of animals at day 12 after treatment with the CAR-T cells either in the absence of inhibitor (control) or in the presence of ibrutinib or the compound of Formula (II).

Figure 8B:
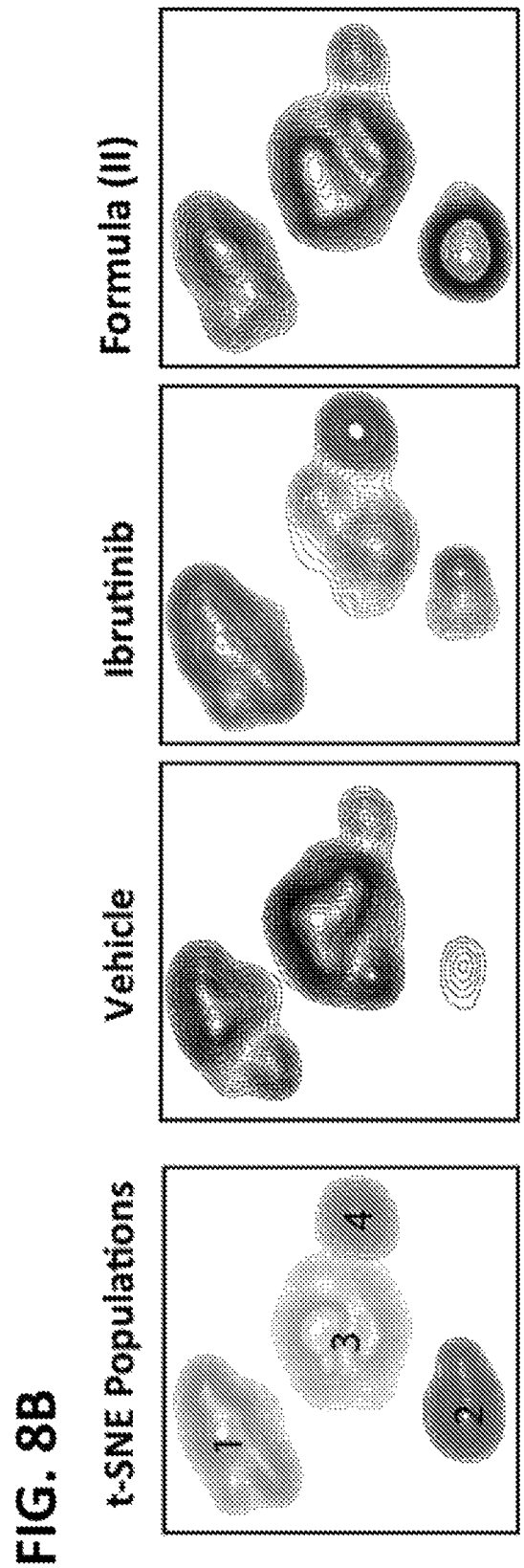

FIG. 8B depicts four populations derived from T-distributed stochastic neighbor embedding (t-SNE) high dimensional analysis of surface markers on CAR-engineered T cells harvested from the bone marrow of animals at day 12 after treatment with the CAR-T cells either in the absence of inhibitor (control) or in the presence of ibrutinib or the compound of Formula (II). The results represent pooled analysis from three mice per group.

Figure 8C:
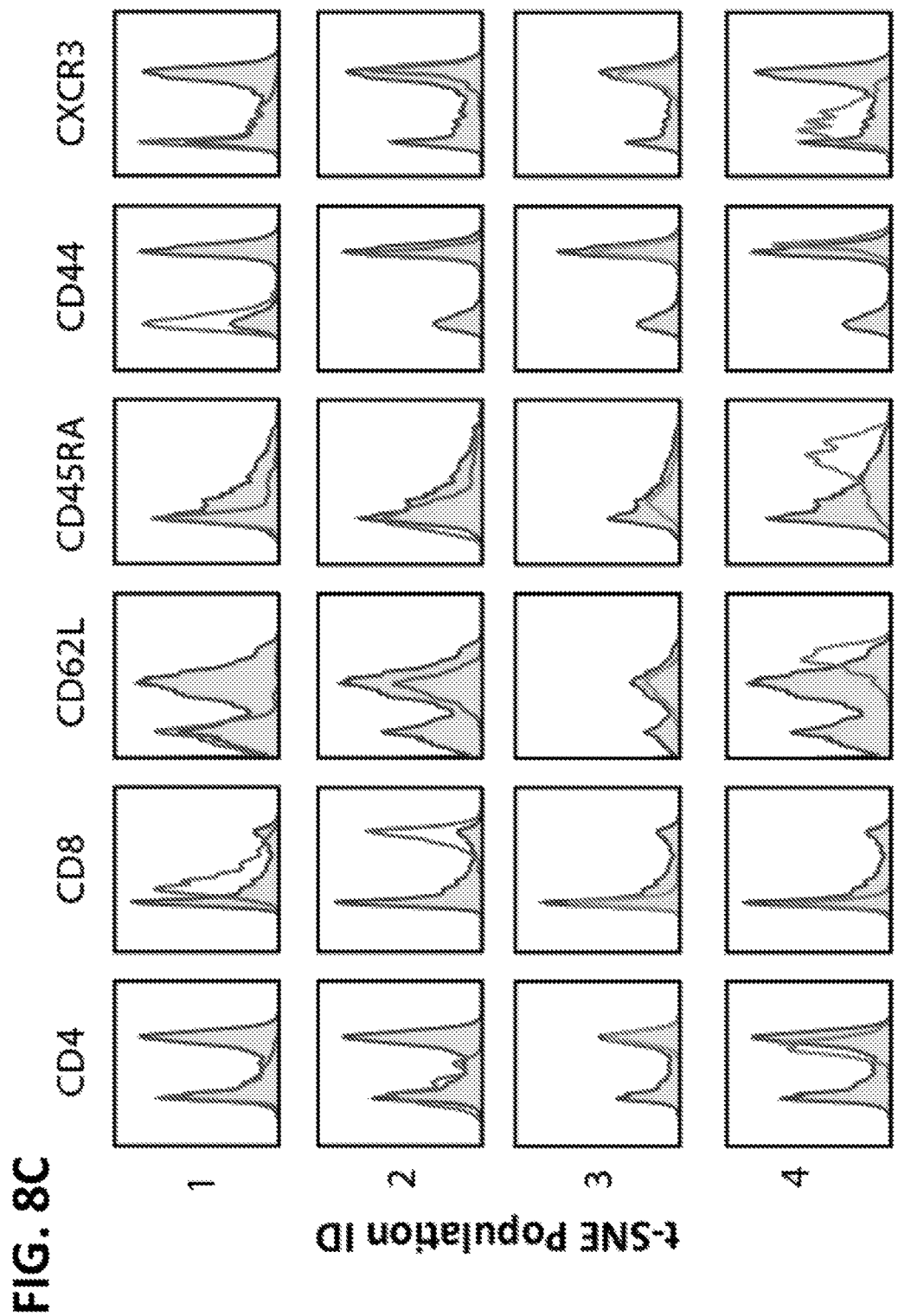

FIG. 8C depicts histograms showing the individual expression profiles of CD4, CD8, CD62L, CD45RA, CD44 and CXCR3 from the 4 gated t-SNE overlaid on the expression of the total population (shaded histogram).

Figure 8D:
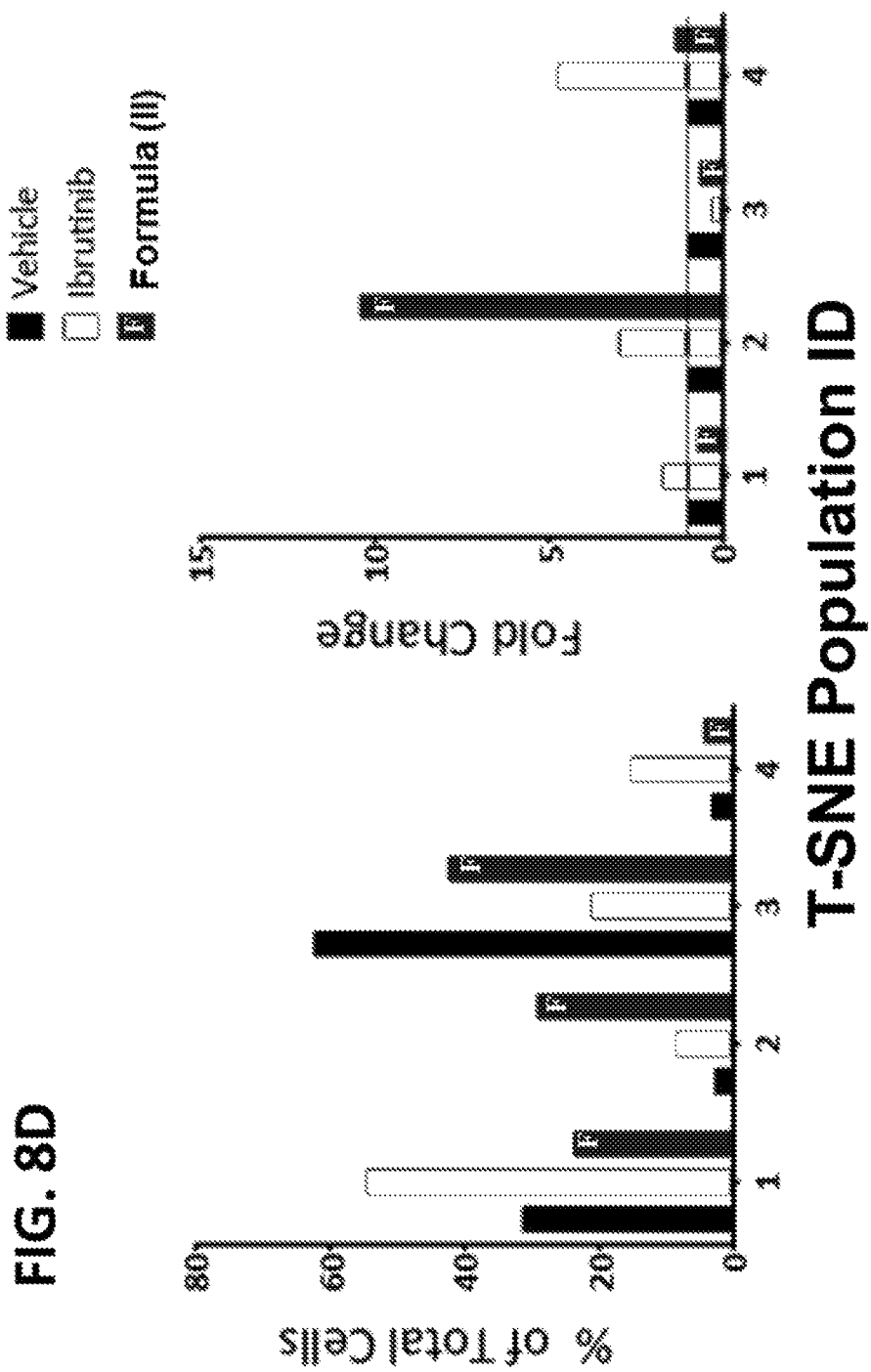

FIG. 8D depicts the percentage and fold change of each t-SNE population from control mice or mice treated with ibrutinib or the compound of Formula (II).

FIG. 9A shows the number of population doublings in a serial stimulation assay over a 21 day culture period of CAR-engineered cells, generated from cells obtained from subjects with diffuse large B-cell lymphoma (DLBCL), with cells cultured in the absence of ibrutinib (control) or in the presence of 50 nM or 500 nM ibrutinib. Arrows indicate the time point of each re-stimulation where CAR T cells were counted and new target cells along with ibrutinib was added.

Figure 9B:
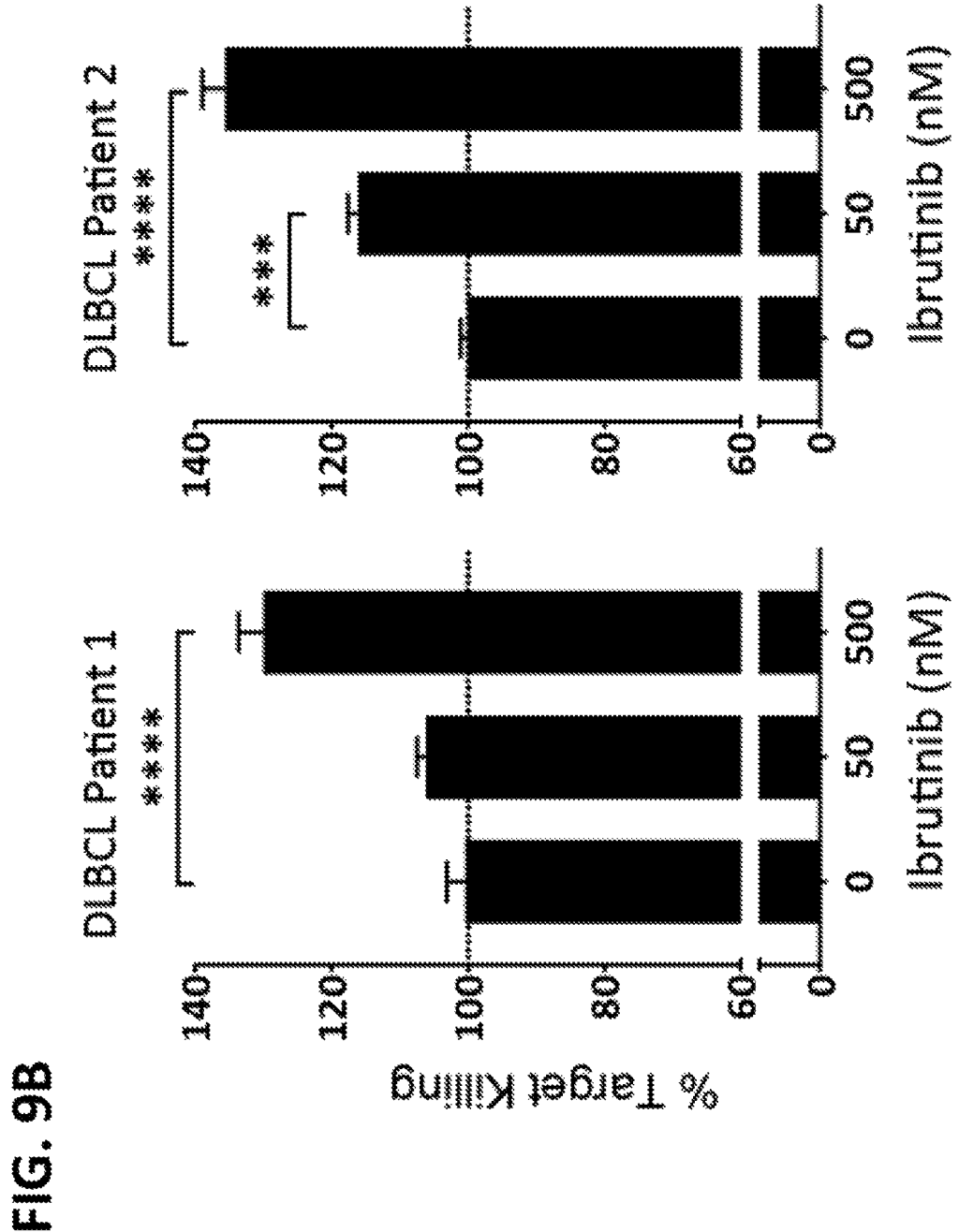

FIG. 9B shows results of an assay for cytolytic activity of the CAR-T cells for CD19-expressing target cells after 16 days of serial restimulation in the presence or absence of ibrutinib. Percent killing was normalized to untreated control (100%). Data shown as mean±SEM from replicate wells. Statistically significant differences are indicated as P<0.001 (*), P<0.0001 (**).

FIG. 10A is a Volcano plot depicting differentially expressed genes from day 18 serially stimulated CAR T cells treated with 500 nM ibrutinib compared with control. Significantly differentially upregulated genes are on the right side of right dashed line and significantly differentially downregulated genes are on left side of left dashed line (FDR<0.05, abslog2FC>0.5).

Figure 10B:
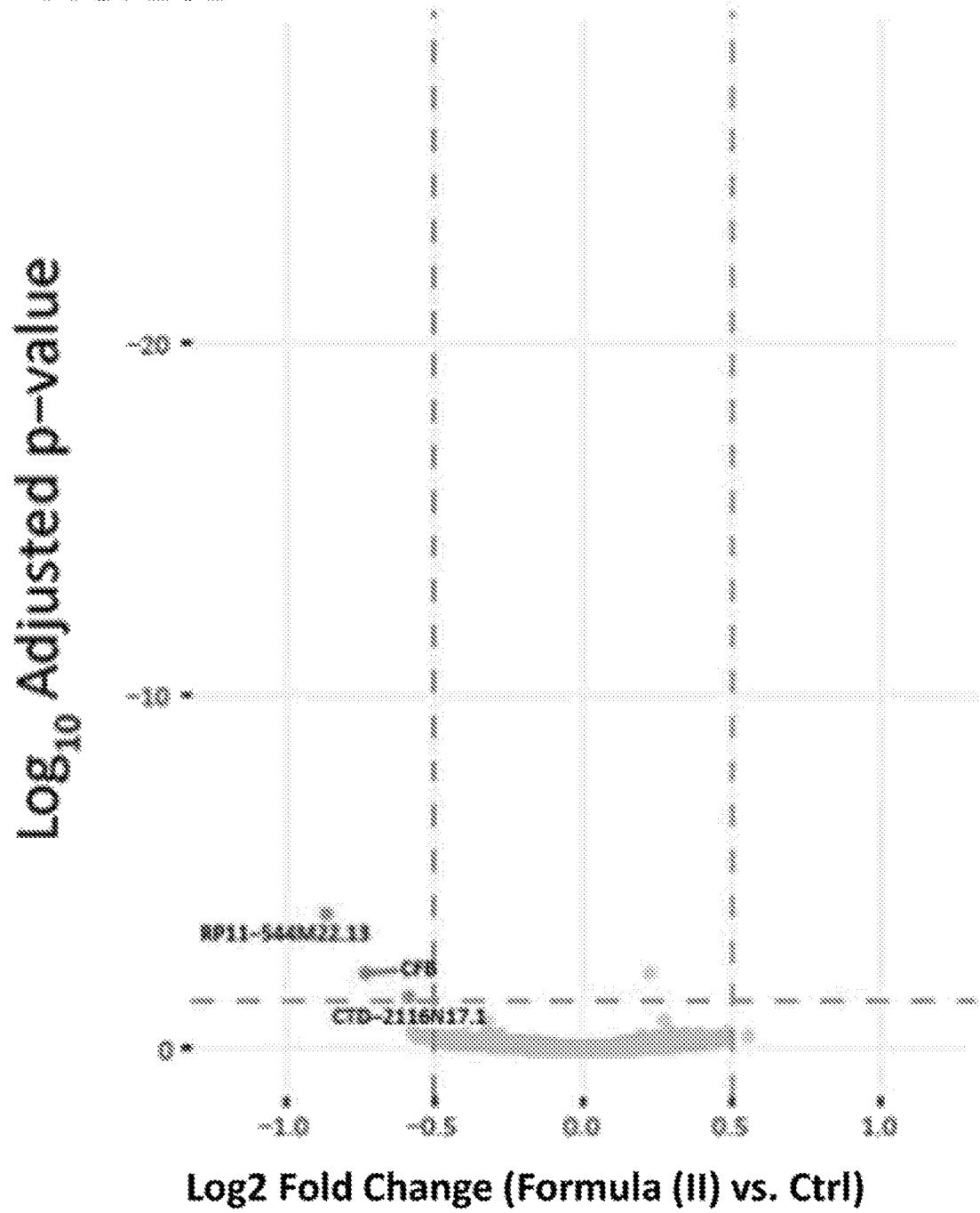

FIG. 10B depicts a Volcano plot of expressed genes from day 18 serially stimulated CAR T cells treated with 1581 nM of the compound of Formula (II) compared with control. Significantly differentially upregulated genes are on the right side of right dashed line and significantly differentially downregulated genes are on left side of left dashed line (FDR<0.05, abslog2FC>0.5).

Figure 10C:
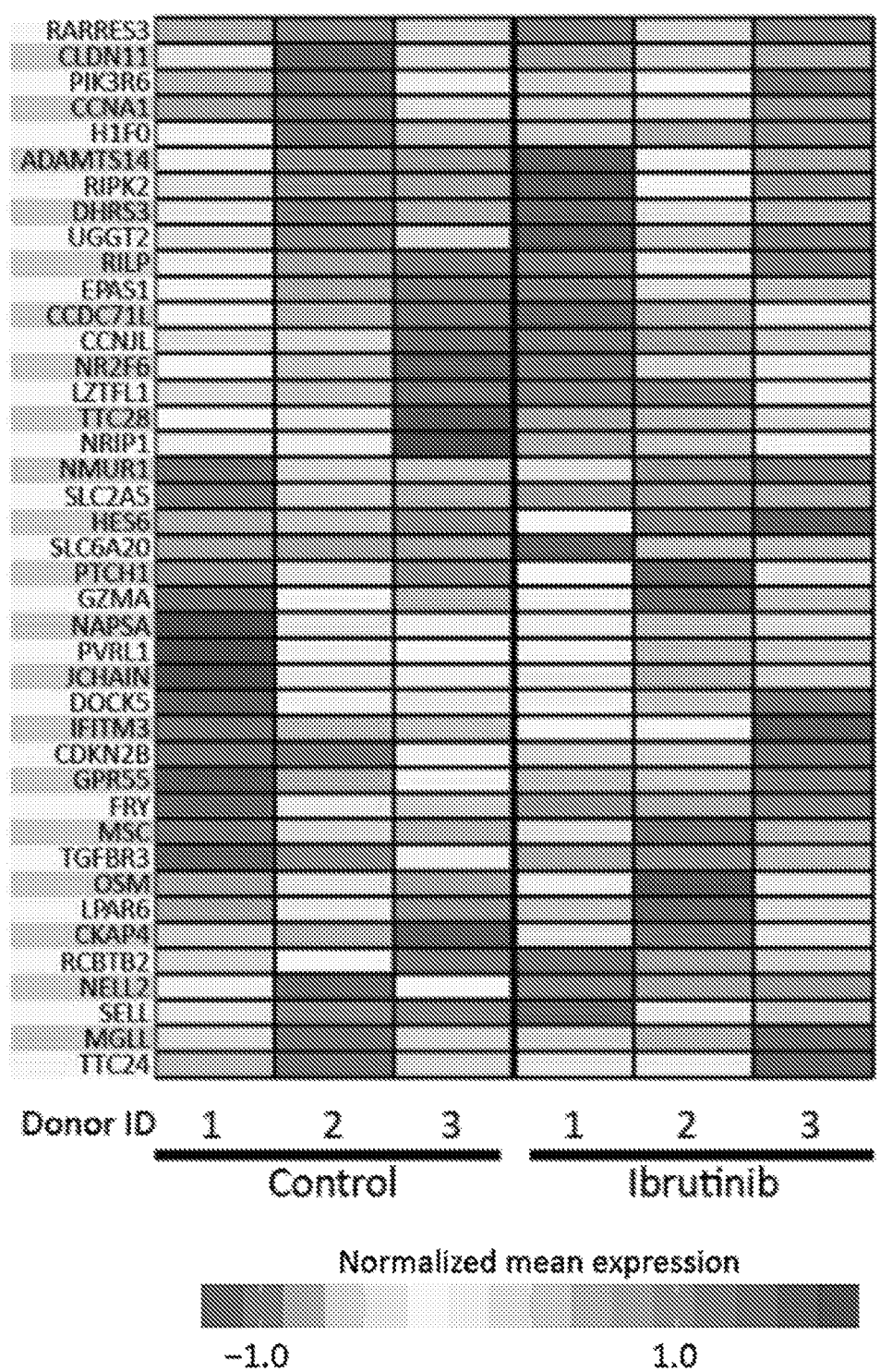

FIG. 10C is a heat map depicting normalized expression across 3 donors (mean Transcripts per Million per donor+ condition, z-score normalized per gene) of the differentially expressed genes from FIG. 10A in the control and 500 nM ibrutinib groups.

FIG. 11A-11B depict the expression (TPM, transcrips per million) box plot profiles of GZMA and SELL (CD62L) summarized across donors and experiments per condition from serially stimulated CAR T cells treated with 50 nM or 500 nM ibrutinib compared with control.

FIG. 12A is a representative histogram of CD62L expression in CAR T cells from one donor-derived cells after 18 days of serial stimulation, as measured by flow cytometry.

FIG. 12B depicts the fold change in the percentage of CD62L+ CAR T cells from one donor-derived cells after 18 days of serial stimulation normalized to control, as measured by flow cytometry. The data are from two independent experiments (mean±SEM).

DETAILED DESCRIPTION

Provided herein are methods of enhancing or modulating proliferation and/or activity of T cell activity associated with administration of an immunotherapy or immunotherapeutic agent, such as a composition including cells for adoptive cell therapy, e.g., such as a T cell therapy (e.g. CAR-expressing T cells) or a T cell-engaging therapeutic agent, such as a bispecific or multispecific agent or antibody, capable of recruiting one or more T cells or other immune cells. In some embodiments, the combination therapy involves administration of an inhibitor of a target protein tyrosine kinase that is not IL-2-inducible T cell kinase (ITK) and/or in which the target protein tyrosine kinase is one or more protein-tyrosine kinase selected from Bruton's tyrosine kinase (Btk), tec protein tyrosine kinase (TEC), BMX non-receptor tyrosine kinase (Etk), TXK tyrosine kinase (TXK) and/or receptor tyrosine-protein kinase ErbB4 (ErbB4), e.g. the compound of Formula (II) the compound of Formula (II), and administration of the immunotherapy or immunotherapeutic agent, such as a composition including cells for adoptive cell therapy, e.g., such as a T cell therapy (e.g. CAR-expressing T cells) or a T cell-engaging therapeutic agent.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

I. OVERVIEW

Provided herein are combination therapies involving administration of a cell therapy or other immunotherapeutic agent that contains or modulates the engagement or activity of T cells, in combination with an inhibitor. Among such agents are agents for T cell therapy, such engineered T cells (e.g., CAR-expressing T cells) and other agents for use in adoptive T cell therapy. The inhibitors generally are inhibitors of target kinases, such as target protein tyrosine kinases, including non-receptor tyrosine kinases such as those of the TEC family of kinases. In some aspects, the inhibitor is an inhibitor of a protein tyrosine kinase that is not IL-2-inducible T cell kinase (ITK) and/or does not inhibit ITK. In some embodiments, the target protein tyrosine kinase is one or more of Bruton's tyrosine kinase (Btk), tec protein tyrosine kinase (TEC), BMX non-receptor tyrosine kinase (Etk), TXK tyrosine kinase (TXK) and/or receptor tyrosine-protein kinase ErbB4 (ErbB4), Among the inhibitors are the compound of Formula (II).

T cell-based therapies, such as adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. The engineered expression of recombinant receptors, such as chimeric antigen receptors (CARs), on the surface of T cells enables the redirection of T-cell specificity. In clinical studies, CAR-T cells, for example anti-CD19 CAR-T cells, have produced durable, complete responses in both leukemia and lymphoma patients (Porter et al. (2015) Sci Transl Med., 7:303ra139; Kochenderfer (2015) J. Clin. Oncol., 33: 540-9; Lee et al. (2015) Lancet, 385:517-28; Maude et al. (2014) N Engl J Med, 371:1507-17).

In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof. In some contexts, optimal efficacy can depend on the ability of the administered cells to become activated, expand, to exert various effector functions, including cytotoxic killing and secretion of various factors such as cytokines, to persist, including long-term, to differentiate, transition or engage in reprogramming into certain phenotypic states (such as long-lived memory, less-differentiated, and effector states), to avoid or reduce immunosuppressive conditions in the local microenvironment of a disease, to provide effective and robust recall responses following clearance and re-exposure to target ligand or antigen, and avoid or reduce exhaustion, anergy, peripheral tolerance, terminal differentiation, and/or differentiation into a suppressive state.

In some cases, responses can be improved by administration or preconditioning with a lymphodepleting therapy, which in some aspects increases the persistence and/or efficacy of the cells following administration, as compared to methods in which the preconditioning is not carried out or is carried out using a different lymphodepleting therapy. The lymphodepleting therapy generally includes the administration of fludarabine, typically in combination with another chemotherapy or other agent, such as cyclophosphamide, which may be administered sequentially or simultaneously in either order. In a recent phase I/II clinical study, complete response (CR) in acute lymphoblastic leukemia (ALL), non-Hodgkin's lymphoma (NHL) and chronic lymphocytic leukemia (CLL) patients was 94%, 47% and 50% respectively, and disease free survival rates were greater in patients that received cyclophosphamide and fludarabine lymphodepletion compared to those who received cyclophosphamide but not fludarabine (Cameron et al. (2016) J Clin Oncol, 34 (suppl; abstr 102). In some aspects, however, even with lymphodepleting therapies, CAR-T cell therapies are not always consistently effective in all subjects.

In some aspects, the provided methods and uses provide for or achieve improved or more durable responses or efficacy as compared to certain alternative methods, such as in particular groups of subjects treated. In some embodiments, the methods are advantageous by virtue of administering an immunotherapy or immunotherapeutic agent, such as a composition including cells for adoptive cell therapy, e.g., such as a T cell therapy (e.g. CAR-expressing T cells) or a T cell-engaging therapeutic agent, such as a bispecific or multispecific agent or antibody, and an inhibitor of a target protein-tyrosine kinase that inhibits, targets or reduces the activity of a target protein tyrosine kinase other than IL-2-inducible T cell kinase (ITK), such as one or more of Bruton's tyrosine kinase (Btk), tec protein tyrosine kinase (TEC), BMX non-receptor tyrosine kinase (Etk), TXK tyrosine kinase (TXK) and/or receptor tyrosine-protein kinase ErbB4 (ErbB4) e.g. the compound of Formula (II).

The provided methods are based on observations that BTK inhibitors, e.g. ibrutinib and Formula (II), improve T cell function, including functions related to the expansion, proliferation and persistence of T cells. It is found herein that this effect, and extent and degree of this effect, is substantially the same whether using ibrutinib or the compound of Formula (II). Yet, ibrutinib and the compound of Formula (II) do not completely exhibit the same specificity for protein tyrosine kinases. Ibrutinib is an irreversible small molecule inhibitor (SMI) that blocks the activity of Bruton's tyrosine kinase (Btk) and also exhibits activity on ITK and numerous other TEC family kinases and other kinases. The compound of Formula (II) was developed as the next generation of Btk inhibitor with greater specificity and potency compared to ibrutinib (Wu et al. (2016) J Hematol Oncol, 9:21; Byrd et al. (2016) N Engl J Med., 374:323-332). Of interest, the compound of Formula (II) does not exhibit activity towards interleukin-2-inducible kinase (ITK), which is a kinase that is highly expressed in both CD4 and CD8 T cells and believed to be involved in effects on downstream T cell receptor signaling (Berg et al. (2005) Annu Rev. Immunol., 23:549-600). Thus, this finding indicates that the effect of the inhibitors on T cell function is not mediated by ITK but is mediated by inhibition of one or more of the other kinases targeted by these inhibitors, such as one or more of BTK, TEC, BMX/ETK, RLK/TXK and/or ERBB4.

BTK inhibitors are generally used for the treatment of B cell malignancies. For example, ibrutinib, is approved for use in mantle cell lymphoma (MCL) and Waldenström's Macroglobulinemia in the relapsed refractory setting (Davids et al. (2014) Future Oncol., 10:957-67). In some cases, aberrant activation of the B-cell receptor (BCR) signaling pathway is the main mechanism underlying B cell malignancies such as MCL and CLL, whereby chronic Btk signaling can initiate a phosphorylation cascade through NF-kB and MAP kinases promoting B cell survival and aberrant activation. Thus, existing methods of employing BTK inhibitors, e.g. ibrutinib, are used for treating B cell malignancies.

The provided findings indicate that combination therapy of the inhibitor in methods involving T cells, such as involving administration of adoptive T cell therapy, achieves improved function of the T cell therapy. In some embodiments, combination of the cell therapy (e.g., administration of engineered T cells) with the inhibitor of one or more target protein tyrosine kinase from among BTK, TEC, BMX/ETK, RLK/TXK and/or ERBB4 (such as a selective and/or irreversible inhibitor of such kinase), improves or enhances one or more functions and/or effects of the T cell therapy, such as persistence, expansion, cytotoxicity, and/or therapeutic outcomes, e.g., ability to kill or reduce the burden of tumor or other disease or target cell. In some embodiments, an inhibitor of one or more target protein tyrosine kinase from among BTK, TEC, BMX/ETK, RLK/TXK and/or ERBB4 (such as a selective and/or irreversible inhibitor of such kinase) may dampen CAR T activation at higher concentrations while increasing activation at lower concentrations.

In some aspects, such effects are observed despite that the tumor or disease or target cell itself is insensitive to the inhibitor, to inhibitors targeting the kinase to which the inhibitor is selective, and/or is resistant to the inhibition of BTK, TEC, BMX/ETK, RLK/TXK and/or ERBB4 by the inhibitor. For example, in some embodiments, the cancer is insensitive to or has become resistant to the inhibitor, or to inhibition of BTK, TEC, BMX/ETK, RLK/TXK and/or ERBB4 by the inhibitor, e.g., by the compound of Formula (II). In some embodiments, the combination with the inhibitor, while improving one or more outcomes or functional attributes, does not affect one or more side effects or unwanted changes in the T cells, such as does not reduce the ability of the cells to become activated, secrete one or more desired cytokines, expand and/or persist, e.g., as measured in an in vitro assay as compared to such cells cultured under conditions otherwise the same but in the absence of the inhibitor. Thus in some embodiments, provided are methods and combinations that result in improvements in T cell function or phenotype, e.g., in intrinsic T cell functionality and/or intrinsic T cell phenotype, generally without compromising one or more other desired properties of functionality, e.g., of CAR-T cell functionality.

Hence, in some embodiments, the provided methods can potentiate CAR-T cell therapy, which, in some aspects, can improve outcomes for treatment of subjects that have a cancer that is resistant or refractory to other therapies, is an aggressive or high-risk cancer, and/or that is or is likely to exhibit a relatively lower response rate to a CAR-T cell therapy administered without the inhibitor compared to another type of cancer.

In some embodiments, the methods can be used for treating B cell malignancies or hematological malignancies, and in particular such malignancies in which responses, e.g. complete response, to treatment with the immunotherapy or immunotherapeutic agent, such as a composition including cells for adoptive cell therapy, e.g., such as a T cell therapy (e.g. CAR-expressing T cells) or a T cell-engaging therapeutic agent, alone is relatively low compared to other B cell malignancies (e.g. a CR in a less than or less than about 60%, less than about 50% or less than about 45% of the subjects so treated) and/or in which the subject is not responsive to treatment with the inhibitor alone. In some embodiments, the combination therapy provided herein is for use in a subject having a cancer in which the subject and/or the cancer is resistant to inhibition of BTK, TEC, BMX/ETK, RLK/TXK and/or ERBB4 or comprises a population of cells that are resistant to inhibition by the inhibitor. In some embodiments, the combination therapy provided herein is for use in a subject having a cancer in which the subject and/or the cancer comprises a mutation or disruption in a nucleic acid encoding BTK, in which such mutation is capable of reducing or preventing inhibition of the BTK by the inhibitor, e.g. the compound of Formula (II).

In some embodiments, the combination therapy provided herein is for use in a subject having a cancer in which at the time of administration of the immunotherapy or immunotherapeutic agent, such as a composition including cells for adoptive cell therapy, e.g., such as a T cell therapy (e.g. CAR-expressing T cells) or a T cell-engaging therapeutic agent, and at the time of administering the inhibitor, the subject has relapsed following remission after treatment with, or been deemed refractory to treatment with the inhibitor and/or with a BTK inhibitor therapy.

In some embodiments, certain cancers, such as NHL, e.g. high-risk or aggressive NHL, such as DLBCL, and/or chronic lymphocytic leukemia (CLL) can be associated with defects in or reduction in intrinsic T cell functionality, which, in some cases, is influenced by the disease itself. For example, the pathogenesis of many cancers, such as CLL and NHL, e.g. DLBCL, can be associated with immunodeficiency, leading to promotion of tumor growth and immune evasion, such as due to immunosuppression of T cells, e.g. driven by one or more factors in the tumor microenvironment. In some cases, alleviating intrinsic T cell defects obtained from cancers of such patients for use in connection with adoptive cell therapy could provide for more potent responses to adoptive T cell therapy, e.g. CAR-T cell therapy.

In some embodiments, the provided methods are for treating a cancer in a subject in which such subject's T cells display or have been observed to display a decreased level of a factor indicative of T cell function, health, or activity, as compared to a reference population of T cells or a reference or threshold level, e.g. T cells from a subject not having or suspected of having a cancer, such as from a healthy or normal subject. In some embodiments, the provided methods are for treating subjects identified as having high-risk NHL and/or aggressive NHL, diffuse large B cell lymphoma (DLBCL), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL). For example, as shown herein, in the presence of the exemplary BTK inhibitor ibrutinib, T cells engineered from subjects having DLBCL exhibit a greater T cell functional activity, indicating that the function of the T cells is potentiated in the presence of the inhibitor. In some embodiments, the subject has DLBCL. In some embodiments, the provided methods are for treating a subject having chronic lymphocytic leukemia (CLL). In some embodiments of such methods, the administered engineered T cells are autologous to the subject.

In some embodiments, the provided methods also include methods in which the cancer is not a B cell malignancy, is not a B cell leukemia or lymphoma, is a non-hematologic cancer or is a solid tumor; and/or the antigen is not a B cell antigen, such as is not CD19, CD20, CD22, and ROR1. In some embodiments, the combination therapy includes administration to a subject with a solid tumor, such as a sarcoma or carcinoma, 1) T cells that specifically recognize and/or target an antigen associated with the cancer and/or present on a universal tag and 2) an inhibitor of a target protein tyrosine kinase that is other than ITK, such as is one or more of BTK, TEC, BMX/ETK, RLK/TXK and/or ERBB4, e.g. the compound of Formula (II). In some embodiments, the antigen recognized or targeted by the T cells is Her2, L1-CAM, mesothelin, CEA, hepatitis B surface antigen, anti-folate receptor, CD23, CD24, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, Lewis Y, L1-cell adhesion molecule (L1-CAM), Melanoma-associated antigen (MAGEMAGE-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, c-Met, GD-2 O-acetylated GD2 (OGD2), CE7, Wilms Tumor 1 (WT-1), a cyclin, cyclin A2, CCL-1, CD138, or a pathogen-specific antigen.

In some embodiments of the provided methods, one or more properties of administered genetically engineered cells can be improved or increased or greater compared to administered cells of a reference composition, such as increased or longer expansion and/or persistence of such administered cells in the subject or an increased or greater recall response upon restimulation with antigen. In some embodiments, the increase can be at least a 1.2-fold, at least 1.5-fold, at least 2-fold, at last 3-fold, at least 4-fold, at least 5-fold, at least 6-fold, at least 7-fold, at least 8-fold, at least 9-fold, or at least 10-fold increase in such property or feature compared to the same property or feature upon administration of a reference cell composition. In some embodiments, the increase in one or more of such properties or features can be observed or is present within one months, two months, three months, four months, five months, six months, or 12 months after administration of the genetically engineered cells.

In some embodiments, a reference cell composition can be a composition of T cells from the blood of a subject not having or not suspected of having the cancer or is a population of T cells obtained, isolated, generated, produced, incubated and/or administered under the same or substantially the conditions, except not having been incubated or administered in the presence of an inhibitor of a target protein tyrosine kinase that is other than ITK, such as is one or more of BTK, TEC, BMX/ETK, RLK/TXK and/or ERBB4. In some embodiments, the reference cell composition contains genetically engineered cells that are substantially the same, including expression of the same recombinant receptor, e.g. CAR. In some aspects, such T cells are treated identically or substantially identically, such as manufactured similarly, formulated similarly, administered in the same or about the same dosage amount and other similar factors.

In some embodiments, a genetically engineered cell with increased persistence exhibit better potency in a subject to which it is administered. In some embodiments, the persistence of genetically engineered cells, such as CAR-expressing T cells, in the subject upon administration is greater as compared to that which would be achieved by alternative methods, such as those involving administration of a reference cell composition. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

Also provided are methods for engineering, preparing, and producing the cells, compositions containing the cells and/or inhibitor, and kits and devices containing and for using, producing and administering the cells and/or inhibitor, such as in accord with the provided combination therapy methods.

II. COMBINATION THERAPY

Provided herein are methods for combination therapy for treating a disease or disorder, e.g. a cancer or proliferative disease, that includes administering to a subject a combination therapy of 1) an inhibitor of a target protein tyrosine kinase that does not inhibit ITK and/or that inhibits one or more of BTK, TEC, BMX/ETK, RLK/TXK and/or ERBB4 and 2) an immunotherapy or immunotherapeutic agent, such as an adoptive immune cell therapy, e.g. T cell therapy (e.g. CAR-expressing cell, e.g. T cells) or a T-cell engaging or immune modulatory therapy, e.g. a multispecific T cell recruiting antibody and/or checkpoint inhibitor. In some embodiments, the immunotherapy is an adoptive immune cell therapy comprising T cells that specifically recognize and/or target an antigen associated with a disease or disorder, e.g. a cancer or proliferative disease. Also provided are combinations and articles of manufacture, such as kits, that contain a composition comprising the T cell therapy and/or a composition comprising the inhibitor, such as an inhibitor of one or more of BTK, TEC, BMX/ETK, RLK/TXK and/or ERBB4, and uses of such compositions and combinations to treat or prevent diseases, conditions, and disorders, including cancers. Such methods can include administration of the inhibitor prior to, simultaneously with, during, during the course of (including once and/or periodically during the course of), and/or subsequently to, the administration (e.g., initiation of administration) of the T cell therapy (e.g. CAR-expressing T cells) or other therapy such as the T cell-engaging therapy. In some embodiments, the administrations can involve sequential or intermittent administrations of the inhibitor and/or the immunotherapy or immunotherapeutic agent, e.g. T cell therapy.

In some embodiments, the cell therapy is adoptive cell therapy. In some embodiments, the cell therapy is or comprises a tumor infiltrating lymphocytic (TIL) therapy, a transgenic TCR therapy or a recombinant-receptor expressing cell therapy (optionally T cell therapy), which optionally is a chimeric antigen receptor (CAR)-expressing cell therapy. In some embodiments, the therapy targets CD19 or is a B cell targeted therapy. In some embodiments, the cells and dosage regimens for administering the cells can include any as described in the following subsection A under "Administration of Cells."

In some embodiments, the inhibitor selectively inhibits one or more target protein tyrosine kinase from among BTK, TEC, BMX/ETK, RLK/TXK and/or ERBB4 compared to other protein tyrosine kinases or compared to other TEC family kinases. In some embodiments, the inhibitor does not inhibit ITK or has an IC50 or Kd for ITK of greater than 1000 nM and/or selectively inhibits one or more of BTK, TEC, BMX/ETK, RLK/TXK and/or ERBB4 compared to ITK. In some embodiments, the inhibitor exhibits at least 1.5-fold, 2.5-fold, 5.0-fold, 10.0-fold, 25-fold, 50-fold, 100-fold, 200-fold, 300-fold, 400-fold, 500-fold, 1000-fold or more activity for one or more of BTK, TEC, BMX/ETK, RLK/TXK and/or ERBB4 compared to ITK. In some embodiments, the inhibitor selectively inhibits one of TEC, TEC, BMX/ETK, RLK/TXK and/or ERBB4 compared to BTK, ITK and/or compared to the others kinase from TEC, Etk, Txk and/or ErbB4, e.g. the inhibitor exhibits at least 1.5-fold, 2.5-fold, 5.0-fold, 10.0-fold, 25-fold, 50-fold, 100-fold, 200-fold, 300-fold, 400-fold, 500-fold, 1000-fold or more activity for one of TEC, BMX/ETK, RLK/TXK and/or ERBB4 compared to BTK, ITK and/or compared to another kinase from TEC, BMX/ETK, RLK/TXK and/or ERBB4 that is distinct from the protein tyrosine kinase. In some embodiments, the cells and dosage regimens for administering the inhibitor can include any as described in the following subsection B under "Administration of Inhibitor."

In some embodiments, the immunotherapy, such as a T cell therapy (e.g. CAR-expressing T cells) or a T cell-engaging therapy, and inhibitor are provided as pharmaceutical compositions for administration to the subject. In some embodiments, the pharmaceutical compositions contain therapeutically effective amounts of one or both of the agents for combination therapy, e.g., T cells for adoptive cell therapy and an inhibitor as described. In some embodiments, the agents are formulated for administration in separate pharmaceutical compositions. In some embodiments, any of the pharmaceutical compositions provided herein can be formulated in dosage forms appropriate for each route of administration.

In some embodiments, the combination therapy, which includes administering the immunotherapy (e.g. T cell therapy, including engineered cells, such as CAR-T cell therapy) and the inhibitor are administered to a subject or patient having a disease or condition to be treated (e.g. cancer) or at risk for having the disease or condition (e.g. cancer). In some aspects, the methods treat, e.g., ameliorate one or more symptom of, the disease or condition, such as by lessening tumor burden in a cancer expressing an antigen recognized by the immunotherapy or immunotherapeutic agent, e.g. recognized by an engineered T cell.

In some embodiments, the disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by bacterial, viral or other pathogens. Exemplary antigens, which include antigens associated with various diseases and conditions that can be treated, include any of antigens described herein. In particular embodiments, the recombinant receptor expressed on engineered cells of a combination therapy, including a chimeric antigen receptor or transgenic TCR, specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the cancer or proliferative disease is a B cell malignancy or hematological malignancy. In some embodiments the cancer or proliferative disease is lymphoblastic leukemia (ALL), non-Hodgkin's lymphoma (NHL), or chronic lymphocytic leukemia (CLL). In some embodiments, the cancer is CLL. In some embodiments, the methods can be used to treat a myeloma, a lymphoma or a leukemia. In some embodiments, the methods can be used to treat a non-Hodgkin lymphoma (NHL), an acute lymphoblastic leukemia (ALL), a chronic lymphocytic leukemia (CLL), a diffuse large B-cell lymphoma (DLBCL), acute myeloid leukemia (AML), or a myeloma, e.g., a multiple myeloma (MM). In some embodiments, the methods can be used to treat a MM or a DBCBL.

In some embodiments, the antigen associated with the disease or disorder is selected from the group consisting of ROR1, B cell maturation antigen (BCMA), tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Fetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, and a pathogen-specific antigen. In some embodiments, the antigen is associated with or is a universal tag.

In some embodiments the cancer or proliferative disease is not a cancer expressing a B cell antigen. In some embodiments, the B cell antigen is selected from the group consisting of CD19, CD20, CD22 and ROR1. In some embodiments the cancer or proliferative disease is a non-hematologic cancer. In some embodiments the cancer or proliferative disease is a solid tumor. In some embodiments the cancer or proliferative disease does not express CD19, CD20, CD22 or ROR1. In some embodiments, the provided methods employ a recombinant receptor-expressing T cell (e.g. CAR-T cell) that does not target or specifically bind CD19, CD20, CD22 or ROR1.

In some embodiments, the methods can be used to treat a non-hematologic cancer, such as a solid tumor. In some embodiments, the methods can be used to treat a bladder, lung, brain, melanoma (e.g. small-cell lung, melanoma), breast, cervical, ovarian, colorectal, pancreatic, endometrial, esophageal, kidney, liver, prostate, skin, thyroid, or uterine cancers. In some embodiments, the cancer or proliferative disease is cancer is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Graves disease, Crohn's disease, multiple sclerosis, asthma, and/or a disease or condition associated with transplant.

For the prevention or treatment of disease, the appropriate dosage of the inhibitor, such as selective inhibitor, of one or more of BTK, TEC, BMX/ETK, RLK/TXK and/or ERBB4, and/or immunotherapy, such as a T cell therapy (e.g. CAR-expressing T cells) or a T cell-engaging therapy, may depend on the type of disease to be treated, the particular inhibitor, cells and/or recombinant receptors expressed on the cells, the severity and course of the disease, route of administration, whether the inhibitor and/or the immunotherapy, e.g., T cell therapy, are administered for preventive or therapeutic purposes, previous therapy, frequency of administration, the subject's clinical history and response to the cells, and the discretion of the attending physician. The compositions and cells are in some embodiments suitably administered to the subject at one time or over a series of treatments. Exemplary dosage regimens and schedules for the provided combination therapy are described.

In some embodiments, the immunotherapy, e.g. T cell therapy, and the inhibitor, such as selective inhibitor, of one or more of BTK, TEC, BMX/ETK, RLK/TXK and/or ERBB4 are administered as part of a further combination treatment, which can be administered simultaneously with or sequentially to, in any order, another therapeutic intervention. In some contexts, the immunotherapy, e.g. engineered T cells, such as CAR-expressing T cells, are co-administered with another therapy sufficiently close in time such that the immunotherapy enhances the effect of one or more additional therapeutic agents, or vice versa. In some embodiments, the cells are administered prior to the one or more additional therapeutic agents. In some embodiments, the immunotherapy, e.g. engineered T cells, such as CAR-expressing T cells, are administered after the one or more additional therapeutic agents. In some embodiments, the combination therapy methods further include a lymphodepleting therapy, such as administration of a chemotherapeutic agent. In some embodiments, the combination therapy further comprises administering another therapeutic agent, such as an anti-cancer agent, a checkpoint inhibitor, or another immune modulating agent. Uses include uses of the combination therapies in such methods and treatments, and uses of such compositions in the preparation of a medicament in order to carry out such combination therapy methods. In some embodiments, the methods and uses thereby treat the disease or condition or disorder, such as a cancer or proliferative disease, in the subject.

Prior to, during or following administration of the immunotherapy (e.g. T cell therapy, such as CAR-T cell therapy) and/or an inhibitor, such as selective inhibitor, of one or more of BTK, TEC, BMX/ETK, RLK/TXK and/or ERBB4, the biological activity of the immunotherapy, e.g. the biological activity of the engineered cell populations, in some embodiments is measured, e.g., by any of a number of known methods. Parameters to assess include the ability of the engineered cells to destroy target cells, persistence and other measures of T cell activity, such as measured using any suitable method known in the art, such as assays described further below in Section IV below. In some embodiments, the biological activity of the cells, e.g., T cells administered for the T cell based therapy, is measured by assaying cytotoxic cell killing, expression and/or secretion of one or more cytokines, proliferation or expansion, such as upon restimulation with antigen. In some aspects the biological activity is measured by assessing the disease burden and/or clinical outcome, such as reduction in tumor burden or load. In some embodiments, administration of one or both agents of the combination therapy and/or any repeated administration of the therapy, can be determined based on the results of the assays before, during, during the course of or after administration of one or both agents of the combination therapy.

In some embodiments, the combined effect of the inhibitor in combination with the cell therapy can be synergistic compared to treatments involving only the inhibitor or monotherapy with the cell therapy. For example, in some embodiments, the methods provided herein result in an increase or an improvement in a desired therapeutic effect, such as an increased or an improvement in the reduction or inhibition of one or more symptoms associated with cancer.

In some embodiments, the inhibitor increases the expansion or proliferation of the engineered T cells, such as CAR T-Cells. In some embodiments, the increase in expansion or proliferation is observed in vivo upon administration to a subject. In some embodiments, the increase in the number of engineered T cells, e.g. CAR-T cells, is increased by greater than or greater than about 1.2-fold, 1.5-fold, 2.0-fold, 3.0-fold, 4.0-fold, 5.0-fold, 6.0-fold, 7.0-fold, 8.0-fold, 9.0-fold, 10.0 fold or more.

A. Administration of Immunotherapy (e.g. T Cell Therapy or T Cell-Engaging Therapy)

In some embodiments of the methods, compositions, combinations, kits and uses provided herein, the combination therapy includes administering to a subject an immunotherapy, such as a T cell therapy (e.g. CAR-expressing T cells) or a T cell-engaging therapy. Such therapies can be administered prior to, subsequent to, simultaneously with administration of one or more inhibitor of a TEK family kinase as described.

In some embodiments, the immunotherapy is a cell-based therapy that is or comprises administration of cells, such as immune cells, for example T cell or NK cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject. Exemplary of such cell therapies, e.g. T cell therapies, for use in the provided methods are described below.

1. T Cell-Engaging Therapy

In some embodiments, the immunotherapy is or comprises a T cell-engaging therapy that is or comprises a binding molecule capable of binding to a surface molecule expressed on a T cell. In some embodiments, the surface molecule is an activating component of a T cell, such as a component of the T cell receptor complex. In some embodiments, the surface molecule is CD3 or is CD2. In some embodiments, the T cell-engaging therapy is or comprises an antibody or antigen-binding fragment. In some embodiments, the T cell-engaging therapy is a bispecific antibody containing at least one antigen-binding domain binding to an activating component of the T cell (e.g. a T cell surface molecule, e.g. CD3 or CD2) and at least one antigen-binding domain binding to a surface antigen on a target cell, such as a surface antigen on a tumor or cancer cell, for example any of the listed antigens as described herein, e.g. CD19. In some embodiments, the simultaneous or near simultaneous binding of such an antibody to both of its targets can result in a temporary interaction between the target cell and T cell, thereby resulting in activation, e.g. cytotoxic activity, of the T cell and subsequent lysis of the target cell.

Among such exemplary bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). In some embodiments, the T-cell engaging therapy is blinatumomab or AMG 330. Any of such T cell-engagers can be used in used in the provided methods.

2 T Cell Therapy

In some aspects, the T cell therapy is or comprises a tumor infiltrating lymphocytic (TIL) therapy, a transgenic TCR therapy or a T cell therapy comprising genetically engineered cells, such as a recombinant-receptor expressing cell therapy. In some embodiments, the recombinant receptor specifically binds to a ligand, such as one associated with a disease or condition, e.g. associated with or expressed on a cell of a tumor or cancer. In some embodiments, the T cell therapy includes administering T cells engineered to express a chimeric antigen receptor (CAR).

In some embodiments, the provided cells express and/or are engineered to express receptors, such as recombinant receptors, including those containing ligand-binding domains or binding fragments thereof, and T cell receptors (TCRs) and components thereof, and/or functional non-TCR antigen receptors, such as chimeric antigen receptors (CARs). In some embodiments, the recombinant receptor contains an extracellular ligand-binding domain that specifically binds to an antigen. In some embodiments, the recombinant receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Among the engineered cells, including engineered cells containing recombinant receptors, are described in Section III below. Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 Mar. 18(2): 160-75. In some aspects, the genetically engineered antigen receptors include a CAR as described in U.S. Pat. No. 7,446,190, and those described in International Patent Application Publication No.: WO/2014055668 A1.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means. The cells are administered in a dosing regimen to achieve a therapeutic effect, such as a reduction in tumor burden. Dosing and administration may depend in part on the schedule of administration of the inhibitor of a TEC family kinase, which can be administered prior to, subsequent to and/or simultaneously with initiation of administration of the T cell therapy. Various dosing schedules of the T cell therapy include but are not limited to single or multiple administrations over various time-points, bolus administration, and pulse infusion.

a. Compositions and Formulations

In some embodiments, the dose of cells of the T cell therapy, such a T cell therapy comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders.

In some embodiments, the T cell therapy, such as engineered T cells (e.g. CAR T cells), are formulated with a pharmaceutically acceptable carrier. In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

In some cases, the cell therapy is administered as a single pharmaceutical composition comprising the cells. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

b. Dosage Schedule and Administration

In some embodiments, a dose of cells is administered to subjects in accord with the provided methods. In some embodiments, the size or timing of the doses is determined as a function of the particular disease or condition in the subject. It is within the level of a skilled artisan to empirically determine the size or timing of the doses for a particular disease in view of the provided description.

In certain embodiments, the cells, or individual populations of sub-types of cells, are administered to the subject at a range of about 0.1 million to about 100 billion cells and/or that amount of cells per kilogram of body weight of the subject, such as, e.g., 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, the cell therapy comprises administration of a dose comprising a number of cells that is at least or at least about or is or is about $0.1 \times 10^6$ cells/kg body weight of the subject, $0.2 \times 10^6$ cells/kg, $0.3 \times 10^6$ cells/kg, $0.4 \times 10^6$ cells/kg, $0.5 \times 10^6$ cells/kg, $1 \times 10^6$ cell/kg, $2.0 \times 10^6$ cells/kg, $3 \times 10^6$ cells/kg or $5 \times 10^6$ cells/kg.

In some embodiments, the cell therapy comprises administration of a dose comprising a number of cells is between or between about $0.1 \times 10^6$ cells/kg body weight of the subject and $1.0 \times 10^7$ cells/kg, between or between about $0.5 \times 10^6$ cells/kg and $5 \times 10^6$ cells/kg, between or between about $0.5 \times 10^6$ cells/kg and $3 \times 10^6$ cells/kg, between or between about $0.5 \times 10^6$ cells/kg and $2 \times 10^6$ cells/kg, between or between about $0.5 \times 10^6$ cells/kg and $1 \times 10^6$ cell/kg, between or between about $1.0 \times 10^6$ cells/kg body weight of the subject and $5 \times 10^6$ cells/kg, between or between about $1.0 \times 10^6$ cells/kg and $3 \times 10^6$ cells/kg, between or between about $1.0 \times 10^6$ cells/kg and $2 \times 10^6$ cells/kg, between or between about $2.0 \times 10^6$ cells/kg body weight of the subject and $5 \times 10^6$ cells/kg, between or between about $2.0 \times 10^6$ cells/kg and $3 \times 10^6$ cells/kg, or between or between about $3.0 \times 10^6$ cells/kg body weight of the subject and $5 \times 10^6$ cells/kg, each inclusive.

In some embodiments, the dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, nor more than at or about $9 \times 10^5$ cells/kg, no more than at or about $1 \times 10^6$ cells/kg, or no more than at or about $2 \times 10^6$ cells/kg. In some embodiments, the dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values. In some embodiments, where the subject is a human, the dose includes between about $1 \times 10^6$ and $3 \times 10^8$ total recombinant receptor (e.g., CAR)-expressing cells, e.g., in the range of about $1 \times 10^7$ to $2 \times 10^8$ such cells, such as $1 \times 10^7$, $5 \times 10^7$, $1 \times 10^8$ or $1.5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^5$ to $5 \times 10^8$ total recombinant receptor-expressing T cells or total T cells, $1 \times 10^5$ to $1 \times 10^8$ total recombinant receptor-expressing T cells or total T cells, from or from about $5 \times 10^5$ to $1 \times 10^7$ total recombinant receptor-expressing T cells or total T cells, or from or from about $1 \times 10^6$ to $1 \times 10^7$ total recombinant receptor-expressing T cells or total T cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1 \times 10^6$ and $1 \times 10^8$ total recombinant receptor (e.g., CAR)-expressing CD8+ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$ or $1 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$ or $1\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" of cells encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, such as no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose. In some embodiments, the cells of a split dose are administered in a plurality of compositions, collectively comprising the cells of the dose, over a period of no more than three days.

Thus, the dose of cells may be administered as a split dose, e.g. a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, administration of the inhibitor in combination with the cells is able to increase, in some cases significantly increase, the expansion or proliferation of the cells, and thus a lower dose of cells can be administered to the subject. In some cases, the provided methods allow a lower dose of such cells to be administered, to achieve the same or better efficacy of treatment as the dose in a method in which the cell therapy is administered without administering the inhibitor, such as at least 1.5-fold, 2-fold, 3-fold, 4-fold, 5-fold or 10-fold less than the dose in a method in which the cell therapy is administered without administering the inhibitor.

In some embodiments, for example, the lower dose contains less than about $5 \times 10^6$ cells, recombinant receptor (e.g. CAR)-expressing cells, T cells, and/or PBMCs per kilogram body weight of the subject, such as less than about $4.5 \times 10^6$, $4 \times 10^6$, $3.5 \times 10^6$, $3 \times 10^6$, $2.5 \times 10^6$, $2 \times 10^6$, $1.5 \times 10^6$, $1 \times 10^6$, $5 \times 10^5$, $2.5 \times 10^5$, or $1 \times 10^5$ such cells per kilogram body weight of the subject. In some embodiments, the lower dose contains less than about $1 \times 10^5$, $2 \times 10^5$, $5 \times 10^5$, or $1 \times 10^6$ of such cells per kilogram body weight of the subject, or a value within the range between any two of the foregoing values. In some embodiments, such values refer to numbers of recombinant receptor-expressing cells; in other embodiments, they refer to number of T cells or PBMCs or total cells administered.

In some embodiments, one or more subsequent dose of cells can be administered to the subject. In some embodiments, the subsequent dose of cells is administered greater than or greater than about 7 days, 14 days, 21 days, 28 days or 35 days after initiation of administration of the first dose of cells. The subsequent dose of cells can be more than, approximately the same as, or less than the first dose. In some embodiments, administration of the T cell therapy, such as administration of the first and/or second dose of cells, can be repeated.

In some embodiments, initiation of administration of the cell therapy, e.g. the dose of cells or a first dose of a split dose of cells, is administered before (prior to), concurrently with or after (subsequently or subsequent to) the administration of the inhibitor.

In some embodiments, the dose of cells, or the subsequent dose of cells, is administered concurrently with or after starting or initiating administration of the inhibitor o. In some embodiments, the dose of cells, or the subsequent dose of cells, is administered 0 to 90 days, such as 0 to 30 days, 0 to 15 days, 0 to 6 days, 0 to 96 hours, 0 to 24 hours, 0 to 12 hours, 0 to 6 hours, or 0 to 2 hours, 2 hours to 30 days, 2 hours to 15 days, 2 hours to 6 days, 2 hours to 96 hours, 2 hours to 24 hours, 2 hours to 12 hours, 2 hours to 6 hours, 6 hours to 90 days, 6 hours to 30 days, 6 hours to 15 days, 6 hours to 6 days, 6 hours to 96 hours, 6 hours to 24 hours, 6 hours to 12 hours, 12 hours to 90 days, 12 hours to 30 days, 12 hours to 15 days, 12 hours to 6 days, 12 hours to 96 hours, 12 hours to 24 hours, 24 hours to 90 days, 24 hours to 30 days, 24 hours to 15 days, 24 hours to 6 days, 24 hours to 96 hours, 96 hours to 90 days, 96 hours to 30 days, 96 hours to 15 days, 96 hours to 6 days, 6 days to 90 days, 6 days to 30 days, 6 days to 15 days, 15 days to 90 days, 15 days to 30 days or 30 days to 90 days after starting or initiating administration of the inhibitor. In some embodiments, the dose of cells is administered at least or about at least or about 1 hour, 2 hours, 6 hours, 12 hours, 24 hours, 2 days, 3 days, 6 days, 12 days, 15 days, 30 days, 60 days or 90 days after starting or initiating administration of the inhibitor.

In some embodiments, the dose of cells is administered at a time when one or more effects of the inhibitor are achieved.

In some embodiments, the dose of cells, or the subsequent dose of cells, is administered prior to starting or initiating administration of the inhibitor. In some embodiments, the dose of cells is administered at least or at least about 1 hour, at least or at least about 2 hours, at least or at least about 3 hours, at least or at least about 6 hours, at least or at least about 12 hours, at least or at least about 1 day, at least or at least about 2 days, at least or at least about 3 days, at least or about at least 4 days, at least or at least about 5 days, at least or about at least 6 days, at least or at least about 7 days, at least or about at least 12 days, at least or at least about 14 days, at least or about at least 15 days, at least or at least about 21 days, at least or at least about 28 days, at least or about at least 30 days, at least or at least about 35 days, at least or at least about 42 days, at least or about at least 60 days or at least or about at least 90 days prior to administering the inhibitor.

In some embodiments, the administration of the inhibitor is at a time in which the prior administration of the immunotherapy (e.g. T cell therapy, such as CAR-T cell therapy) is associated with, or is likely to be associated with, a decreased functionality of the T cells compared to the functionality of the T cells at a time just prior to initiation of the immunotherapy (e.g. T cell therapy, such as CAR-T cell therapy) or at a preceding time point after initiation of the immunotherapy. In some embodiments, the method involves, subsequent to administering the dose of cells of the T cell therapy, e.g., adoptive T cell therapy, but prior to administering the inhibitor, assessing a sample from the subject for one or more function of T cells, such as expansion or persistence of the cells, e.g. as determined by level or amount in the blood, or other phenotypes or desired outcomes as described herein, e.g., such as those described in Section III. Various parameters for determining or assessing the regimen of the combination therapy are described in Section III.

B. Administration of Inhibitor

The provided methods, compositions, combinations, kits and uses involve administration of an inhibitor of a protein-tyrosine kinase selected from Bruton's tyrosine kinase (Btk), tec protein tyrosine kinase (TEC), BMX non-receptor tyrosine kinase (BMX/ETK), TXK tyrosine kinase (TXK; RLK/TXK) and/or receptor tyrosine-protein kinase ErbB4 (ERBB4). The inhibitor can be administered prior to, subsequently to, during, simultaneously or near simultaneously, sequentially and/or intermittently with administration of the immunotherapeutic agent or immunotherapy, e.g., T cell therapy, e.g., administration of T cells expressing a chimeric antigen receptor (CAR).

In some embodiments, the inhibitor inhibits BTK with a half-maximal inhibitory concentration ($IC_{50}$) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibitor binds to BTK with a dissociation constant (Kd) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibition constant (Ki) of the inhibitor for BTK is less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM.

In some embodiments, the inhibitor inhibits TEC with a half-maximal inhibitory concentration ($IC_{50}$) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibitor binds to TEC with a dissociation constant (Kd) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibition constant (Ki) of the inhibitor for TEC is less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM.

In some embodiments, the inhibitor inhibits BMX/ETK with a half-maximal inhibitory concentration ($IC_{50}$) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibitor binds to BMX/ETK with a dissociation constant (Kd) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibition constant (Ki) of the inhibitor for BMX/ETK is less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM.

In some embodiments, the inhibitor inhibits RLK/TXK with a half-maximal inhibitory concentration ($IC_{50}$) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibitor binds to RLK/TXK with a dissociation constant (Kd) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibition constant (Ki) of the inhibitor for RLK/TXK is less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM.

In some embodiments, the inhibitor inhibits ERBB4 with a half-maximal inhibitory concentration ($IC_{50}$) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibitor binds to ERBB4 with a dissociation constant (Kd) of less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM. In some embodiments, the inhibition constant (Ki) of the inhibitor for ERBB4 is less than or less than about 1000 nM, less than or less than about 900 nM, less than or less than about 800 nM, less than or less than about 700 nM, less than or less than about 600 nM, less than or less than about 500 nM, less than or less than about 400 nM, less than or less than about 300 nM, less than or less than about 200 nM, or less than or less than about 100 nM.

In some embodiments, the inhibitor does not inhibit IL-2 inducible T-cell kinase (ITK). In some embodiments, the inhibitor exhibits a half-maximal inhibitory concentration ($IC_{50}$) for ITK of greater than or greater than about 1000 nM, greater than or greater than about 2 µM, greater than or greater than about 3 µM, greater than or greater than about 4 µM, greater than or greater than about 5 µM, greater than or greater than about 10 µM, greater than or greater than about 50 µM, greater than or greater than about 100 µM, or greater than or greater than about 1000 µM. In some embodiments, the dissociation constant (Kd) of the inhibitor for ITK is greater than or greater than about 1000 nM, greater than or greater than about 2 µM, greater than or greater than about 3 µM, greater than or greater than about 4 µM, greater than or greater than about 5 µM, greater than or greater than about 10 µM, greater than or greater than about 50 µM, greater than or greater than about 100 µM, or greater than or greater than about 1000 µM.

In some embodiments, the inhibitor inhibits one of more of BTK, TEC, BMX/ETK, RLK/TXK or ERBB4 with a half-maximal inhibitory concentration ($IC_{50}$) that is lower than that of ITK by at least about 2-fold, at least about 3-fold, at least about 4-fold, at least about 5-fold, at least about 10-fold, at least about 20-fold, at least about 30-fold, at least about 40-fold, at least about 50-fold, at least about 100-fold, at least about 500-fold, at least about 1000-fold, at least about 10,000-fold, at least about 100,000-fold, or at least about 1,000,000-fold.

In some embodiments, the dissociation constant (Kd) of the inhibitor for one of more of BTK, TEC, BMX/ETK, RLK/TXK or ERBB4 is lower than that of ITK by at least about 2-fold, at least about 3-fold, at least about 4-fold, at least about 5-fold, at least about 10-fold, at least about 20-fold, at least about 30-fold, at least about 40-fold, at least about 50-fold, at least about 100-fold, at least about 500-fold, at least about 1000-fold, at least about 10,000-fold, at least about 100,000-fold, or at least about 1,000,000-fold.

In some embodiments, the inhibition constant (Ki) of the inhibitor for one of more of BTK, TEC, BMX/ETK, RLK/TXK or ERBB4 is lower than that of ITK by at least about 2-fold, at least about 3-fold, at least about 4-fold, at least about 5-fold, at least about 10-fold, at least about 20-fold, at least about 30-fold, at least about 40-fold, at least about 50-fold, at least about 100-fold, at least about 500-fold, at least about 1000-fold, at least about 10,000-fold, at least about 100,000-fold, or at least about 1,000,000-fold.

In some embodiments, the IC50, Kd and/or Ki is measured or determined using an in vitro assay. Assays to assess or quantitate or measure activity of protein tyrosine kinase inhibitors as described are known in the art. Such assays can be conducted in vitro and include assays to assess the ability of an agent to inhibit a specific biological or biochemical function. In some embodiments. In some embodiments, kinase activity studies can be performed. Protein tyrosine kinases catalyze the transfer of the terminal phosphate group from adenosine triphosphate (ATP) to the hydroxyl group of a tyrosine residue of the kinase itself or another protein substrate. In some embodiments, kinase activity can be measured by incubating the kinase with the substrate (e.g., inhibitor) in the presence of ATP. In some embodiments, measurement of the phosphorylated substrate by a specific kinase can be assessed by several reporter systems including colorimetric, radioactive, and fluorometric detection. (Johnson, S. A. & T. Hunter (2005) Nat. Methods 2:17.) In some embodiments, inhibitors can be assessed for their affinity for a particular kinase or kinases, such as by using competition ligand binding assays (Ma et al., *Expert Opin Drug Discov.* 2008 June; 3(6):607-621) From these assays, the half-maximal inhibitory concentration ($IC_{50}$) can be calculated. $IC_{50}$ is the concentration that reduces a biological or biochemical response or function by 50% of its maximum. In some cases, such as in kinase activity studies, $IC_{50}$ is the concentration of the compound that is required to inhibit the target kinase activity by 50%. In some cases, the dissociation constant (Kd) and/or the inhibition constant (Ki values) can be determined additionally or alternatively. $IC_{50}$ and Kd can be calculated by any number of means known in the art. The inhibition constant (Ki values) can be calculated from the $IC_{50}$ and Kd values according to the Cheng-Prusoff equation: $Ki=IC_{50}/(1+L/Kd)$, where L is the concentration of the inhibitor (Biochem Pharmacol 22: 3099-3108, 1973). Ki is the concentration of unlabeled inhibitor that would cause occupancy of 50% of the binding sites present in the absence of ligand or other competitors.

In some embodiments, the inhibitor is a peptide, protein, antibody, or antigen-binding fragment thereof, an antibody mimetic, an aptamer, or a nucleic acid molecule. In some embodiments, the inhibitor is a small molecule.

In some embodiments, the inhibitor is an inhibitor of a tyrosine protein kinase that has an accessible cysteine residue near the active site of the tyrosine kinase. In some embodiments, the inhibitor irreversibly reduces or eliminates the activation of tyrosine kinase. In some embodiments, the inhibitor forms a covalent bond with a cysteine residue on the protein tyrosine kinase. In some embodiments, the cysteine residue is a Cys 481 residue. In some embodiments, the inhibitor comprises a Michael acceptor moiety that forms a covalent bond with the appropriate cysteine residue of the tyrosine kinase. In some embodiments, the Michael acceptor moiety preferentially binds with the appropriate cysteine side chain of the tyrosine kinase protein relative to other biological molecules that also contain an assessable —SH moiety.

In some embodiments, the inhibitor exhibits inhibitory activity against Btk, e.g., with an $IC_{50}$ value of at or about 5.1 nM; does not exhibit inhibitory activity against Itk or exhibits any such activity with an $IC_{50}$ value of greater than at or about 1000 nM; exhibits inhibitory activity against Tec, e.g., with an $IC_{50}$ value of at or about 93 nM; exhibits inhibitory activity against RLK/TXK, e.g., with an $IC_{50}$ value of at or about 368 nM; exhibits inhibitory activity against BMX/ETK with an $IC_{50}$ value of at or about 46 nM; and/or exhibits inhibitory activity against ErbB4, e.g., with an $IC_{50}$ value of at or about 16 nM, in each case optionally as measured by a known in vitro assay and/or assay described herein. In some aspects, the inhibitor is Formula (II) or a pharmaceutically acceptable salt, solvate, hydrate, co-crystal, polymorph or prodrug thereof thereof. See Byrd J C, Harrington B, O'Brien S, Jones J A, Schuh A, Devereux S, et al. The compound of Formula (II) in relapsed chronic lymphocytic leukemia. N Engl J Med. 2016; 374(4):323-32; Wu et al., "The compound of Formula (II): a selective second-generation BTK inhibitor," Journal of Hematology & Oncology (2016) 9:21.

In some embodiments, the inhibitor exhibits inhibitory activity against Btk, e.g., with an $IC_{50}$ value of at or about 1 µM, such as, for example, as measured by a known in vitro assay and/or assay described herein. In some aspects, the inhibitor is BGB-3111 (described by Wu et al., "Second-generation inhibitors of Bruton tyrosine kinase," *Journal of Hematology & Oncology* (2016) 9:80 WO2016/024230), or a pharmaceutically acceptable salt, solvate, hydrate, co-crystal, polymorph or prodrug thereof. In some embodiments, the inhibitor exhibits inhibitory activity against Btk, e.g., with an $IC_{50}$ value of at or about 1.9 nM; does not exhibit inhibitory activity against Itk or exhibits any such activity with an $IC_{50}$ value of greater than at or about 1000 nM or at or about 4000 or 4270 nM, or has the same less inhibitory activity towards ITK as the compound of Formula (II). In some embodiments, the inhibitor does not inhibit TEC or exhibits any such inhibitory activity against $IC_{50}$ only with an $IC_{50}$ value greater than 1000 nM or greater than 10,000 nM. In some embodiments, the inhibitor does not inhibit BMX or exhibits any such inhibitory activity against $IC_{50}$ only with an $IC_{50}$ value greater than 1000 nM or at or about or greater than 1800 nM or greater than 10,000 nM. In some aspects, the inhibitor is CGI-1746 (see Hendriks et al., "Targeting Bruton's tyrosine kinase in B cell malignancies," Nature, 2014, 14: 219-232; Akinleye et al., "Ibrutinib and novel BTK inhibitors in clinical development." Journal of Hematology & Oncology 2013, 6:59; WO2016/024230; Di Paolo et al., Nat. Chem. Biol., 2011, 7(1): 41-50), or a pharmaceutically acceptable salt, solvate, hydrate, co-crystal, polymorph or prodrug thereof.

In some embodiments, the inhibitor exhibits inhibitory activity against Btk, e.g., with an $IC_{50}$ value of less than about 4.4 nM or about 5 nM; does not exhibit inhibitory activity against Itk or exhibits any such activity with an $IC_{50}$ value of greater than at or about 3000 nM; exhibits inhibitory activity against Tec, e.g., with an $IC_{50}$ value of at or about 8.2 nM or about 6.2 nM; exhibits inhibitory activity against RLK/TXK, e.g., with an $IC_{50}$ value of at or about 1.9 nM or 1.4 nM; and/or exhibits inhibitory activity against BMX/ETK with an $IC_{50}$ value of at or about 1.9 nM or 0.7 nM, in each case optionally as measured by a known in vitro assay and/or assay described herein. In some aspects, the inhibitor is N-(3-(2-(3-Aminophenylamino)pyrimidin-5-yl-carbamoyl)-4-methylphenyl)-2-naphthamidecompounds or N-(2-(3-(2-Acrylamidoacetamido)phenylamino)pyrimidin-5-yl)-2-methyl-5-(3-(trifluoromethyl)benzamido)benzamide (Compounds 31 or 38) (Li et. al., *J. Med. Chem.*, 2014, 57(12): 5112-28), or a pharmaceutically acceptable salt, solvate, hydrate, co-crystal, polymorph or prodrug thereof.

In some embodiments, the inhibitor exhibits inhibitory activity against ErbB4, e.g., with an $IC_{50}$ value of about 50 nM; and does not exhibit inhibitory activity against Itk or exhibits any such activity with an $IC_{50}$ value of greater than at or about 10 μM, in each case optionally as measured by a known in vitro assay and/or assay described herein. In some aspects, the inhibitor is 4557W (CAS ID 179248-61-4), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some embodiments, the inhibitor exhibits inhibitory activity against ErbB4, e.g., with an $IC_{50}$ value of about 5 nM to about 500 nM; and does not exhibit inhibitory activity against Itk or exhibits any such activity with an $IC_{50}$ value of greater than at or about 10 μM, in each case optionally as measured by a known in vitro assay and/or assay described herein. In some embodiments, the inhibitor exhibits inhibitory activity against ErbB4, e.g., with an $IC_{50}$ value of about 6.3 nM. In some aspects, the inhibitor is Afatinib (CAS ID 439081-18-2), or a pharmaceutically acceptable salt, solvate, hydrate, co-crystal, polymorph or prodrug thereof. See Davis, et al., *Nat Biotechnol,* 2011; 29:1046-51. In some embodiments, the inhibitor exhibits inhibitory activity against ErbB4, e.g., with an $IC_{50}$ value of about 250 nM. In some aspects, the inhibitor is AG1478 (CAS ID 175178-82-2) or Compound 56 (CAS ID 171745-13-4), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45. In some embodiments, the inhibitor exhibits inhibitory activity against ErbB4, e.g., with an $IC_{50}$ value of about 150 nM. In some aspects, the inhibitor is Gefitnib (CAS ID 184475-35-2), or a pharmaceutically acceptable salt, solvate, hydrate, co-crystal, polymorph or prodrug thereof. See Karaman et al., *Nat Biotechnol.* 2008 January; 26(1): 127-32. In some aspects, the inhibitor is WHI-P154 (CAS ID 211555-04-3), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45. In some embodiments, the inhibitor exhibits inhibitory activity against ErbB4, e.g., with an $IC_{50}$ value of about 21 nM. In some aspects, the inhibitor is JNJ-28871063 (CAS ID 944341-54-2), or a pharmaceutically acceptable salt, solvate, hydrate, co-crystal, polymorph or prodrug thereof. See Emanuel et al., *Mol Pharmacol.* 2008 February; 73(2):338-48. In some embodiments, the inhibitor exhibits inhibitory activity against ErbB4, e.g., with an $IC_{50}$ value of about 18 nM. In some aspects, the inhibitor is Kinome 714, or a pharmaceutically acceptable salt, solvate, hydrate, co-crystal, polymorph or prodrug thereof. See Fidanze et al., *Bioorg Med Chem Lett.* 2010 Apr. 15; 20(8):2452-5. In some embodiments, the inhibitor exhibits inhibitory activity against ErbB4, e.g., with a Kd value of about 21 nM. In some aspects, the inhibitor is Pelitinib (CAS ID 257933-82-7), or a pharmaceutically acceptable salt, solvate, hydrate, co-crystal, polymorph or prodrug thereof. See Fabian et al., *Nat Biotechnol.* 2005 March; 23(3)329-36. In some embodiments, the inhibitor exhibits inhibitory activity against ErbB4, e.g., with a Kd value of about 230 nM. In some aspects, the inhibitor is Erlotinib (CAS ID 183319-69-9), or a pharmaceutically acceptable salt, solvate, hydrate, co-crystal, polymorph or prodrug thereof. See Davis, et al., *Nat Biotechnol,* 2011; 29:1046-51. In some embodiments, the inhibitor exhibits inhibitory activity against ErbB4, e.g., with an $IC_{50}$ value of about 345 nM. In some aspects, the inhibitor is Lapatinib (CAS ID 183319-69-9), or a pharmaceutically acceptable salt, solvate, hydrate, co-crystal, polymorph or prodrug thereof. See Mirams et al., *J Pharmacol Toxicol Methods,* 2014; 70:246-54.

In some embodiments, the inhibitor exhibits inhibitory activity against Btk, e.g., with an $IC_{50}$ value of less than about 250 nM; does not exhibit inhibitory activity against Itk or exhibits any such activity with an $IC_{50}$ value of greater than at or about 5 μM; and/or exhibits inhibitory activity against RLK/TXK, e.g., with an $IC_{50}$ value of at or about 250 nM, in each case optionally as measured by a known in vitro assay and/or assay described herein. In some aspects, the inhibitor is Aloisine A (CAS ID 496864-16-5), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some embodiments, the inhibitor exhibits inhibitory activity against Btk, e.g., with an $IC_{50}$ value of about 545 nM; and does not exhibit inhibitory activity against Itk or exhibits any such activity with an $IC_{50}$ value of greater than at or about 25 μM, in each case optionally as measured by a known in vitro assay and/or assay described herein. In some aspects, the inhibitor is AMG-47a (CAS ID 882663-88-9), or a pharmaceutically acceptable salt, solvate, hydrate, co-crystal, polymorph or prodrug thereof. See DiMauro et al., *J Med Chem,* 2006 Sep. 21; 49(19): 5671-86.

In some embodiments, the inhibitor exhibits inhibitory activity against Btk, e.g., with an $IC_{50}$ value of less than about 500 nM; does not exhibit inhibitory activity against Itk or exhibits any such activity with an $IC_{50}$ value of greater than at or about 10 μM; and/or exhibits inhibitory activity against RLK/TXK, e.g., with an $IC_{50}$ value of at or about 500 nM, in each case optionally as measured by a known in vitro assay and/or assay described herein. In some aspects, the inhibitor is AS601245 (CAS ID 345987-15-7), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some embodiments, the inhibitor exhibits inhibitory activity against Btk, e.g., with an Kd value of less than about 50 nM; does not exhibit inhibitory activity against Itk or exhibits any such activity with an $IC_{50}$ value of greater than at or about 5000 nM; exhibits inhibitory activity against RLK/TXK, e.g., with an Kd value of at or about 50 nM; and/or exhibits inhibitory activity against ErbB4 with an $IC_{50}$ value of about 60 nM, in each case optionally as measured by a known in vitro assay and/or assay described herein. In some aspects, the inhibitor is BMS-690514 (CAS ID 859853-30-8), or a pharmaceutically acceptable salt, solvate, hydrate, co-crystal, polymorph or prodrug thereof. See Wong, et al., *Clin Cancer Res.* 2011 Jun. 15; 17(12): 4031-41.

In some embodiments, the inhibitor exhibits inhibitory activity against Btk, e.g., with an $IC_{50}$ value of less than about 2.5 nM; does not exhibit inhibitory activity against Itk or exhibits any such activity with an Kd value of greater than at or about 1700 nM; exhibits inhibitory activity against Tec, e.g., with an $IC_{50}$ value of at or about 282 nM; exhibits inhibitory activity against RLK/TXK, e.g., with an $IC_{50}$ value of at or about 40 nM; exhibits inhibitory activity against BMX/ETK with an $IC_{50}$ value of at or about 7.9 nM; and exhibits inhibitory activity against ErbB4 with an $IC_{50}$ value of at or about 2.5 nM, in each case optionally as measured by a known in vitro assay and/or assay described herein. In some aspects, the inhibitor is Bosutinib (CAS ID 380843-75-4), or a pharmaceutically acceptable salt, solvate, hydrate, co-crystal, polymorph or prodrug thereof. See Remsing et al., *Leukemia.* 2009 March; 23(3): 477-85.

In some embodiments, the inhibitor exhibits inhibitory activity against Btk, e.g., with an $IC_{50}$ value of about 185 nM; does not exhibit inhibitory activity against Itk or exhibits any such activity with an Kd value of greater than at or about 5600 nM; exhibits inhibitory activity against RLK/TXK, e.g., with an Kd value of at or about 700 nM; exhibits inhibitory activity against BMX/ETK with an $IC_{50}$ value of at or about 62 nM; and exhibits inhibitory activity against ErbB4 with an Kd value of at or about 6.5 nM, in each case optionally as measured by a known in vitro assay and/or assay described herein. In some aspects, the inhibitor is Canertinib (CAS ID 289499-45-2), or a pharmaceutically acceptable salt, solvate, hydrate, co-crystal, polymorph or prodrug thereof. See Hur et al., *Bioorg Med Chem Lett.* 2008 Nov. 15; 18(22):5916-9.

In some embodiments, the inhibitor exhibits inhibitory activity against Btk, e.g., with an $IC_{50}$ value of about 2 nM; does not exhibit inhibitory activity against Itk or exhibits any such activity with an Kd value of greater than at or about 10000 nM; exhibits inhibitory activity against RLK/TXK, e.g., with an $IC_{50}$ value of at or about 2 nM; and/or exhibits inhibitory activity against BMX/ETK with an Kd value of at or about 36 nM; in each case optionally as measured by a known in vitro assay and/or assay described herein. In some aspects, the inhibitor is CHEMBL249097, or a pharmaceutically acceptable salt, solvate, hydrate, co-crystal, polymorph or prodrug thereof. See Bamborough et al., *Bioorg Med Chem Lett.* 2007 Aug. 1; 17(15):4363-8.

In some aspects, the inhibitor is CHEMBL383899 (CAS ID 879127-16-9), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is CP724714 (CAS ID 537705-08-1), or a pharmaceutically acceptable salt, solvate, hydrate, co-crystal, polymorph or prodrug thereof. See Karaman et al., *Nat Biotechnol.* 2008 January; 26(1): 127-32.

In some aspects, the inhibitor is Dasatinib (CAS ID 302962-49-8), or a pharmaceutically acceptable salt, solvate, hydrate, co-crystal, polymorph or prodrug thereof. See Remsing et al., *Leukemia.* 2009 March; 23(3): 477-85.

In some aspects, the inhibitor is GSK-3 Inhibitor X (CAS ID 740841-15-0), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is HDS029 (CAS ID 881001-19-0), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is IKK-2 Inhibitor IV (CAS ID 507475-17-4), or a pharmaceutically acceptable salt, solvate, hydrate, co-crystal, polymorph or prodrug thereof.

In some aspects, the inhibitor is JNJ-10198409 (CAS ID 627518-40-5), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Ki11502(CAS ID 347155-76-4), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Lck Inhibitor (CAS ID 213743-31-8), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is MK5108 (CAS ID 1010085-13-8), or a pharmaceutically acceptable salt, solvate, hydrate, co-crystal, polymorph or prodrug thereof. See Shimomura et al., *Mol Cancer Ther.* 2010 January; 9(1): 157-66.

In some aspects, the inhibitor is N-Benzoylstaurosporine (CAS ID 120685-11-2), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Neratinib (CAS ID 698387-09-6), or a pharmaceutically acceptable salt, solvate, hydrate, co-crystal, polymorph or prodrug thereof. See Davis, et al., *Nat Biotechnol,* 2011; 29:1046-51.

In some aspects, the inhibitor is NU6140 (CAS ID 444723-13-1), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Pazopanib (CAS ID 444731-52-6), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is PD168393 (CAS ID 194423-15-9), or a pharmaceutically acceptable salt, solvate, hydrate, co-crystal, polymorph or prodrug thereof. See Hur et al., *Bioorg Med Chem Lett.* 2008 Nov. 15; 18(22): 5916-9.

In some aspects, the inhibitor is PD169316 (CAS ID 152121-53-4), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is PD173955 (CAS ID 260415-63-2), or a pharmaceutically acceptable salt, solvate, hydrate, co-crystal, polymorph or prodrug thereof. See Davis, et al., *Nat Biotechnol,* 2011; 29:1046-51.

In some aspects, the inhibitor is PDK1/Akt/Flt Dual Pathway Inhibitor (CAS ID 331253-86-2), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Ponatinib (CAS ID 943319-70-8), or a pharmaceutically acceptable salt, solvate, hydrate, co-crystal, polymorph or prodrug thereof. See Huang et al., *J Med Chem.* 2010 Jun. 24; 53(12):4701-19.

In some aspects, the inhibitor is PP1 Analog II; 1NM-PP1 (CAS ID 221244-14-0), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is PP121 (CAS ID 1092788-83-4), or a pharmaceutically acceptable salt, solvate, hydrate, co-crystal, polymorph or prodrug thereof. See Apsel et al., *Nat Chem Biol.* 2008 November; 4(11):691-9.

In some aspects, the inhibitor is Purvalanol A (CAS ID 212844-53-6), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Src Kinase Inhibitor I (CAS ID 179248-59-0), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is SureCN7018367, or a pharmaceutically acceptable salt, solvate, hydrate, co-crystal, polymorph or prodrug thereof. See Bamborough et al., *J Med Chem.* 2008 Dec. 25; 51(24):7898-914.

In some aspects, the inhibitor is TWS119 (CAS ID 601514-19-6), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is Vandetanib (CAS ID 443913-73-3), or a pharmaceutically acceptable salt, solvate, hydrate, co-crystal, polymorph or prodrug thereof. See Anastassiasdis et al., *Nat Biotechnol.* 2011 Oct. 30; 29(11): 1039-45.

In some aspects, the inhibitor is BDBM50126732 (2-(2,6-Dichloro-phenylamino)-7-(3-diethylamino-propenyl)-1,6-dimethyl-1,8-dihydro-imidazo[4,5-h]isoquinolin-9-one), or a pharmaceutically acceptable salt, solvate, hydrate, co-crystal, polymorph or prodrug thereof. See Goldberg, et al., *J Med Chem,* 2003; 46:1337-49.

In some aspects, the inhibitor is BDBM50020476 (CHEMBL3290148), or a pharmaceutically acceptable salt, solvate, hydrate, co-crystal, polymorph or prodrug thereof. See Li, et al., *J Med Chem,* 2014; 57:5112-28.

In some aspects, the inhibitor is BDBM4567 (N-{4-[(3-bromophenyl)amino]quinazolin-6-yl}prop-2-enamide), or a pharmaceutically acceptable salt, solvate, hydrate, co-crystal, polymorph or prodrug thereof. See Tsou et al., *J Med Chem,* 2001; 44:2719-34.

In some aspects, the inhibitor is BDBM4779 (N-{4-[(3-chloro-4-fluorophenyl)amino]-7-[3-(morpholin-4-yl)propoxy]quinazolin-6-yl}prop-2-enamide), or a pharmaceutically acceptable salt, solvate, hydrate, co-crystal, polymorph or prodrug thereof. See Davis, et al., *Nat Biotechnol,* 2011; 29:1046-51.

In some aspects, the inhibitor is BDBM36409 (PP242), or a pharmaceutically acceptable salt, solvate, hydrate, co-crystal, polymorph or prodrug thereof. See Davis, et al., *Nat Biotechnol,* 2011; 29:1046-51.

In some aspects, the inhibitor is BDBM50161957 (HKI-272), or a pharmaceutically acceptable salt, solvate, hydrate, co-crystal, polymorph or prodrug thereof. See Klumpers et al., *J Med Chem,* 2005; 48:1107-31.

In some aspects, the inhibitor is BDBM6568 (PD-173955), or a pharmaceutically acceptable salt, solvate, hydrate, co-crystal, polymorph or prodrug thereof. See Davis, et al., *Nat Biotechnol,* 2011; 29:1046-51.

In some embodiments, the inhibitor does not exhibit inhibitory activity against Itk or exhibits any such activity with an $IC_{50}$ value of greater than at or about 1000 nM or at or about 4000 or 4270 nM, or has the same inhibitory activity towards ITK as the compound of Formula (II); does not inhibit TEC or exhibits any such inhibitory activity against $IC_{50}$ only with an $IC_{50}$ value greater than 1000 nM or greater than 10,000 nM; does not inhibit BMX or exhibits any such inhibitory activity against $IC_{50}$ only with an $IC_{50}$ value greater than 1000 nM or at or about or greater than 1800 nM or greater than 10,000 nM. In some aspects, the inhibitor is not CGI-1746 (see Hendriks et al., "Targeting Bruton's tyrosine kinase in B cell malignancies," Nature, 2014, 14: 219-232; Akinleye et al., "Ibrutinib and novel BTK inhibitors in clinical development." Journal of Hematology & Oncology 2013, 6:59; WO2016/024230; Di Paolo et. al., Nat. Chem. Biol., 2011, 7(1): 41-50)), or a pharmaceutically acceptable salt, solvate, hydrate, co-crystal, polymorph or prodrug thereof. In some embodiments, the inhibitor is not an inhibitor that exhibits activity towards ITK with an $IC_{50}$ value of greater than at or about 1000 nM or at or about 4000 or 4270 nM, or has the same less inhibitory activity towards ITK as the compound of Formula (II); does not inhibit TEC or exhibits any such inhibitory activity against $IC_{50}$ only with an $IC_{50}$ value greater than 1000 nM or greater than 10,000 nM; does not inhibit BMX or exhibits any such inhibitory activity against $IC_{50}$ only with an $IC_{50}$ value greater than 1000 nM or at or about or greater than 1800 nM or greater than 10,000 nM.

In some embodiments, the inhibitor is a compound of Formula (I):

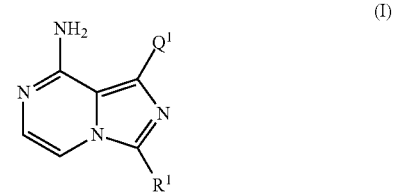

(I)

or a pharmaceutically acceptable salt thereof, wherein:

$Q^1$ is aryl$^1$, heteroaryl$^1$, cycloalkyl, heterocyclyl, cycloalkenyl, or heterocyclo alkenyl, any of which is optionally substituted by one to five independent $G^1$ substituents; $R^1$ is alkyl, cycloalkyl, bicycloalkyl, aryl, heteroaryl, aralkyl, heteroaralkyl, heterocyclyl, or heterobicycloalkyl, any of which is optionally substituted by one or more independent $G^{11}$ substituents;

$G^1$ and $G^{41}$ are each independently halo, oxo, —CF$_3$, —OCF$_3$, —OR$^2$, —NR$^2$R$^3$(R$^{3a}$)$_{j1}$, —C(O)R$^2$, —CO$_2$R$^2$, —CONR$^2$R$^3$, —NO$_2$, —CN, —S(O)$_{j1}$R$^2$, —SO$_2$NR$^2$R$^3$, NR$^2$(C=O)R$^3$, NR$^2$(C=O)OR$^3$, NR$^2$(C=O)NR$^2$R$^3$, NR$^2$S(O)$_{j1}$R$^3$, —(C=S)OR$^2$, —(C=O)SR$^2$, —NR$^2$(C=NR$^3$)NR$^{2a}$R$^{3a}$, —NR$^2$(C=NR$^3$)OR$^{2a}$, —NR$^2$(C=NR$^3$)SR$^{3a}$, —O(C=O)OR$^2$, —O(C=O)NR$^2$R$^3$, —O(C=O)SR$^2$, —S(C=O)OR$^2$, —S(C=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$ alkyl, cycloC$_{3-8}$ alkenyl, cycloC$_{3-8}$ alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$ alkylC$_{2-10}$alkynyl, cycloC$_{3-8}$alkenylC$_{2-10}$alkynyl, heterocyclyl-C$_{0-10}$ alkyl, heterocyclyl-C$_{2-10}$alkenyl, or heterocyclyl-C$_{2-10}$ alkynyl, any of which is optionally substituted with one or more independent halo, oxo, —CF$_3$, —OCF$_3$, —OR$^{222}$— NR$^{22}$R$^{333}$(R$^{333a}$)$_{j1a}$, —C(O)R$^{222}$, —CO$_2$R$^{222}$, —CONR$^{222}$R$^{333}$, —NO$_2$, —CN, —S(O)$_{j1a}$R$^{222}$, —SO$_2$NR$^{222}$R$^{333}$, NR$^{22}$ (C=O)R$^{333}$, NR$^{222}$(C=O)OR$^{333}$, NR$^{222}$(C=O)NR$^{222}$R$^{333}$, NR$^{222}$S(O)$_{j1a}$R$^{333}$, —(C=S)OR$^{222}$, —(C=O)SR$^{222}$, —NR$^{222}$ (C=NR$^{333}$)NR$^{222a}$R$^{333a}$, NR$^{222}$ (C=NR$^{333}$)OR$^{222a}$, NR$^{222}$ (C=R$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or —(X$^1$)$_n$—(Y$^1$)$_m$—R$^4$; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{222}$, —NR$^{222}$R$^{333}$(R$^{333a}$)$_{j2a}$, —C(O)R$^{222}$, —CO$_2$R$^{222}$, —CONR$^{222}$R$^{333}$, —NO$_2$, —CN, —S(O)$_{j2a}$R$^{222}$, —SO$_2$NR$^{222}$R$^{333}$, NR$^{222}$(C=O)R$^{333}$, NR$^{222}$(C=O)OR$^{333}$, NR$^{222}$, (C=O)NR$^{222}$R$^{333}$, NR$^{222}$S(O)$_{j2a}$R$^{333}$, —(C=S)OR$^{222}$, —(C=O)SR$^{222}$, —NR$^{22}$ (C=NR$^{333}$)NR$^{22a}$R$^{333a}$, —NR$^{222}$ (C=NR$^{333}$)OR$^{222a}$, —NR$^{222}$(C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$ (R$^{333a}$)$_{j3a}$, —C(O)R$^{222}$, —CO$_2$R$^{222}$, —CONR$^{222}$R$^{333}$, —NO$_2$, —CN, —S(O)$_{j3a}$R$^{222}$, —SO$_2$NR$^{222}$R$^{333}$, NR$^{222}$ (C=O)R$^{333}$, NR$^{222}$(C=O)OR$^{333}$, NR$^{222}$(C=O)NR$^{222}$R$^{333}$, NR$^{222}$S(O)$_{j3a}$R$^{333}$, —(C=S)OR$^{222}$, —(C=O)SR$^{222}$, —NR$^{222}$(C=NR$^{333}$)NR$^{222a}$R$^{333a}$, —NR$^{222}$ (C=NR$^{333}$)OR$^{222a}$, —NR$^{222}$ (C=NR$^{333}$)SR$^{333a}$, —O(C=O)OR$^{222}$, —O(C=O)NR$^{222}$R$^{333}$, —O(C=O)SR$^{222}$, —S(C=O)OR$^{222}$, or —S(C=O)NR$^{222}$R$^{333}$ substituents;

G$^{11}$ is halo, oxo, —CF$_3$, —OCF$_3$, —OR$^{21}$, —NR$^{21}$R$^{31}$ (R$^{3a1}$)$_{j4}$, —C(O)R$^{21}$, —CO$_2$R$^{21}$, —CONR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$(C=O)OR$^{31}$, NR$^{21}$(C=O)NR$^{21}$R$^{31}$, NR$^{21}$S(O)$_{j4}$R$^{31}$, —(C=S)OR$^{21}$, —(C=O)SR$^{21}$, —NR$^{21}$(C=NR$^{31}$) NR$^{2}$a1R$^{3a1}$, NR$^{21}$(C=NR$^{31}$)OR$^{2a1}$, —NR$^{21}$(C=NR$^{31}$)SR$^{3a1}$, —O(C=O)OR$^{21}$, —O(C=O)NR$^{21}$R$^{31}$, —O(C=O)SR$^{21}$, —S(C=O)OR$^{21}$, —S(C=O)NR$^{21}$R$^{31}$, —P(O)OR$^{21}$OR$^{31}$, C$_{0-10}$alkyl, C$_{2-10}$alkenyl, C$_{2-10}$alkynyl, C$_{1-10}$alkoxyC$_{2-10}$ alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$ alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$ alkylC$_{1-10}$alkyl, cycloC$_{3-8}$alkenylC$_{1-10}$alkyl, cycloC$_{3-8}$ alkylC$_{2-10}$ alkenyl, cycloC$_{3-8}$alkenylC$_{2-10}$alkenyl, cycloC$_{3-8}$alkylC$_{2-10}$ alkynyl, cycloC$_{3-8}$ alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$NR$^{2221}$R$^{3331}$(R$^{333a1}$)$_{j4a}$, C(O)R$^{2221}$, —CO$_2$R$^{2224}$, —CONR$^{2221}$R$^{3331}$, —NO$_2$, —CN, —S(O)$_{j4a}$R$^{2221}$, —SO$_2$NR$^{2221}$R$^{3331}$, NR$^{2221}$ (C=O)R$^{3331}$, NR$^{2221}$(C=O)OR$^{3331}$, NR$^{2221}$ (C=O)NR$^{2221}$R$^{3331}$, NR$^{2221}$S(O)$_{j4a}$R$^{3331}$, —(C=S) R$^{2221}$, —(CO)SR$^{221}$, —NR$^{2221}$(C=NR$^{3331}$)NR$^{222a1}$R$^{333a1}$, —NR$^{2221}$(C=NR$^{3331}$)OR$^{222a1}$, —NR$^{2221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —O(O)OR$^{2221}$OR$^{3331}$, or —S(C=O)NR$^{2221}$R$^{3331}$ substituents; or aryl-C$_{0-10}$alkyl, aryl-C$_{2-10}$alkenyl, or aryl-C$_{2-10}$alkynyl, any of which is optionally substituted with one or more independent halo, —CF$_3$, —OCF$_3$, —OR$^{2221}$, —NR$^{2221}$R$^{3331}$(R$^{333a1}$)$_{j5a}$, —C(O)R$^{2221}$, —CO$_2$R$^{2221}$, —CONR$^{2221}$R$^{3331}$, —NO$_2$, —CN, —S(O)$_{j5a}$R$^{2221}$, —SO$_2$NR$^{2221}$R$^{3331}$, NR$^{2221}$(C=O)R$^{3331}$, NR$^{2221}$(C=O)OR$^{3331}$, NR$^{2221}$ (C=O)NR$^{2221}$R$^{3331}$, NR$^{2221}$(O)$_{j5a}$R$^{3331}$, —(C=O)SR$^{2221}$, NR$^{2221}$(C=NR$^{3331}$)NR$^{222a1}$R$^{333a1}$, NR$^{2221}$ (C=NR$^{3331}$)OR$^{222a1}$, NR$^{221}$(C=NR$^{3331}$)SR$^{333a1}$, —O(C=O)OR$^{2221}$, —O(C=O) NR$^{2221}$R$^{3331}$, -0(C=O)SR$^{2221}$, —S(C=O)OR$^{2221}$, —P(O)OR$^{2221}$OR$^{3331}$, or —S(C=O)NR$^{2221}$R$^{3331}$ substituents; or hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR, —NR$^{2221}$R$^{3331}$ (R$^{333a1}$)$_{j6a}$, —C(O)R$^{2221}$, —CO$_2$R$^{2221}$, —CONR$^{2221}$R$^{3331}$, —NO$_2$, —CN, —S(O)$_{j6a}$R$^{2221}$, —SO$_2$NR$^{2221}$R$^{3331}$, NR$^{2221}$(C=O)R$^{3331}$, NR$^{21}$ (C=O)OR$^{3331}$, NR$^{2221}$ (C=O)NR$^{2221}$R$^{3331}$, NR$^{221}$S(O)$_{j6a}$R$^{3331}$, —(C=S)OR$^{2221}$, —(CO)SR$^{2221}$, —NR$^{2221}$ (C=NR$^{3331}$) NR$^{222a1}$R$^{333a1}$, —NR$^{2221}$ (C=NR$^{3331}$)OR$^{222a1}$, NR$^{221}$(C=NR$^{3331}$)SR$^{333a1}$, —O(C=O)OR$^{2221}$, —O(C=O)NR$^{2221}$R$^{3331}$, —O(C=O)SR$^{2221}$, —S(C=O)OR$^{2221}$, —P(O)OR$^{2221}$OR$^{3331}$, or —S(C=O)NR$^{2221}$—R$^{3331}$ substituents; or G$^{11}$ is taken together with the carbon to which it is attached to form a double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{3331}$ are each independently equal to C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$ alkylthioC$_{2-10}$alkenyl, C$_{1-10}$alkylthioC$_{2-10}$alkynyl, cyclo C$_{3-8}$alkyl, cycloC$_{3-8}$alkenyl, cycloC$_{3-8}$alkylC$_{1-10}$alkyl, cycloCs-salkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{-10}$ alkynyl, cyoloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted by one or more G$^{111}$ substituents; or aryl-C$_{0-10}$alkyl, aryl-C$_{2-10}$alkenyl, or aryl-C$_{2-10}$ alkynyl, hetaryl-C$_{0-10}$alkyl, hetaryl-C$_{2-10}$alkenyl, or hetaryl-C$_{2-10}$alkynyl, any of which is optionally substituted by one or more G$^{111}$ substituents; or in the case of —NR$^2$R$^3$(R$^{3a}$)$_{j1}$ or —NR$^{222}$R$^{333}$(R$^{333a}$)* or —NR$^{222}$R$^{333}$(R$^{333a}$)$_{j2a}$ or —NR$^{2221}$R$^{3331}$(R$^{333a1}$)$_{j3a}$ or —NR$^{2221}$R$^{3331}$(R$^{333a1}$)$_{j4a}$ or —NR$^{2221}$R$^{3331}$(R$^{333a1}$)$_{j5a}$ or —NR$^{2221}$R$^{3331}$(R$^{333a1}$)$_{j6a}$, R$^2$ and R$^3$ or R$^{222}$ and R$^{333}$ or R$^{2221}$ and R$^{3331}$ taken together with the nitrogen atom to which they are attached form a 3-10 membered saturated ring, unsaturated ring, heterocyclic saturated ring, or heterocyclic unsaturated ring, wherein said ring is optionally substituted by one or more G$^{111}$ substituents;

X$^1$ and Y$^1$ are each independently —O—, —NR$^7$—, —S(O)$_{j7}$— —CR$^5$R$^6$—, —N(C(O)OR$^7$)—, —N(C(O)R$^7$)—, —N(SO$_2$R$^7$)—, —CH$_2$O— —CH$_2$S— —CH$_2$N (R$^7$)— —CH(NR$^7$)—, —CH$_2$N(C(O)R$^7$)—, —CH$_2$N(C(O) O12$^7$)—, —CH$_2$N(SO$_2$R$^7$)—, —CH(NHR$^7$)—, —CH (NHC(O)R$^7$)—, —CH(NHSO$_2$R$^7$)—, —CH(NHC(O) OR$^7$)—, —CH(OC(O)R$^7$)—, —CH(OC(O)NHR$^7$)—, —CH—CH—, —C——C(=NOR$^7$)—, —C(O)—, —CH (OR$^7$)—, —C(O)N(R$^7$)—, —N(R$^7$)C(O)—, —N(R$^7$)S (O)—, —N(R$^7$)S(O)$_2$— —OC(O)N(R$^7$)—, —N(R$^7$)C(O)N (R$^7$)—, —NR$^7$C(O)O— —S(O)N(R$^7$)—, —S(O)$_2$N(R$^7$)—, —N(C(O)R$^7$)S(O)—, —N(C(O)R$^7$)S(O)$_2$—, —N(R$^7$)S(O) N(R$^7$)—, —N(R$^7$)S(O)$_2$N; (R$^7$)—, —C(O)N(R$^7$)C(O)—, —S(O)N(R$^7$)C(O)—, —S(O)$_2$N(R$^7$)C(O)—, —OS(O)N (R$^7$)—, —OS(O)$_2$N(R$^7$)—, —N(R$^7$)S(O)O—, —N(R$^7$)S (O)$_2$O—, —N(R$^7$)S(O)C(O)— —N(R$^7$)S(O)$_2$C(O)—, —SON(C(O)R$^7$)—, —SO$_2$N(C(O)R$^7$)—, —N(R$^7$)SON (R$^7$)—, —N(R$^7$)SO$_2$N(R$^7$)—, —C(O)O— —N(R$^7$)P(OR$^8$) O—, —N(R$^7$)P(OR$^8$)—, —N(R$^7$)P(O)(OR$^8$)O— —N(R$^7$)P (O)(OR$^8$)—, —N(C(O)R$^7$)P(OR$^8$)O— —N(C(O)R$^7$)P (OR$^8$)—, —N(C(O)R$^7$)P(O)(OR$^8$)O—, —N(C(O)R$^7$)P (OR$^8$)—, —CH(R)S(O)—, —CH(R$^7$)S(O)$_2$— —CH(R$^7$)N (C(O)OR$^7$)— —CH(R$^7$)N(C(O)R$^7$)— —CH(R$^7$)N (SO$_2$R$^7$)—, —CH(R$^7$)O— —CH(R$^7$)S— —CH(R$^7$)N (R$^7$)—, —CH(R$^7$)N(C(O)R$^7$)—, —CH(R$^7$)N(C(O)OR$^7$)—, —CH(R$^7$)N(SO$_2$R$^7$)—, —CH(R$^7$)C(=NOR$^7$)—, —CH $(R^7)C(O)$—, —$CH(R^7)CH(OR^7)$—, —$CH(R^7)C(O)N(R^7)$—, —$CH(R^7)N(R^7)C(O)$—, —$CH(R^7)N(R^7)S(O)$—, —$CH(R^7)N(R^7)S(O)_2$—, —$CH(R^7)OC(O)N(R^7)$—, —$CH(R^7)N(R^7)C(O)N(R^7)$—, —$CH(R^7)NR^7C(O)O$—, —$CH(R^7)S(O)N(R^7)$—, —$CH(R^7)S(O)_2N(R^7)$—, —$CH(R^7)N(C(O)R^7)S(O)$—, —$CH(R^7)N(C(O)R^7)S(O)$—, —$CH(R^7)N(R^7)S(O)N(R^7)$—, —$CH(R^7)N(R^7)S(O)_2N(R^7)$—, —$CH(R^7)C(O)N(R^7)C(O)$—, —$CH(R^7)S(O)N(R^7)C(O)$—, —$CH(R^7)S(O)_2N(R^7)C(O)$— —$CH(R^7)OS(O)N(R^7)$—, —$CH(R^7)OS(O)_2N(R^7)$—, —$CH(R^7)N(R^7)S(O)O$—, —$CH(R^7)N(R^7)S(O)_2O$—, —$CH(R^7)N(R^7)S(O)C(O)$—, —$CH(R^7)N(R^7)S(O)_2C(O)$—, —$CH(R^7)SON(C(O)R^7)$—, —$CH(R^7)SO_2N(C(O)R^7)$—, —$CH(R^7)N(R^7)SON(R^7)$—, —$CH(R^7)N(R^7)SO_2N(R^7)$—, —$CH(R^7)C(O)O$—, —$CH(R^7)N(R^7)P(OR^8)O$— —$CH(R^7)N(R^7)P(OR^8)$—, —$CH(R^7)N(R^7)P(O)(OR^8)O$—, —$CH(R^7)N(R^7)P(O)(OR^8)$—, —$CH(R^7)N(C(O)R^7)P(OR^8)O$—, —$CH(R^7)N(C(O)R^7)P(OR^8)$——$CH(R^7)N(C(O)R^7)P(O)(OR^8)O$—, or —$CH(R^7)N(C(O)R^7)P(OR^8)$—; or $X^1$ and $Y^1$ are each independently represented by one of the following structural formulas:

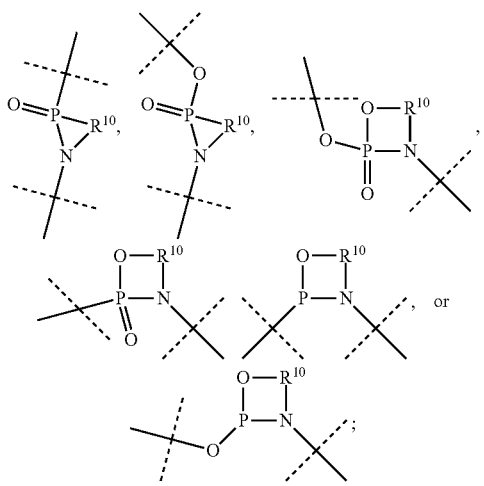

$R^{10}$, taken together with the phosphinamide or phosphonamide, is a 5-, 6-, or 7-membered aryl, heteroaryl or heterocyclyl ring system;

$R^5$, $R^6$, and $G^{111}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$ alkyl, cyclo$C_{3-8}$ alkenyl, cyclo$C_{3-8}$ alkyl$C_{1-10}$alkyl, cyclo$C_{3-8}$ alkenyl$C_{1-10}$alkyl, cyclo$C_{3-8}$ alkyl$C_{2-10}$alkenyl, cyclo$C_{3-8}$ alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, —$(C=S)OR^{77}$, —$C(=O)R^{87}$, —$NR^{77}(C=NR^{87})NR^{78}R^{88}$, —$NR^{77}(C=NR^{87})OR^{78}$, —$NR^{77}(C=NR^{87})SR^{78}$, —$O(C=O)OR^{77}$, —$O(C=O)NR^{77}R^{87}$, —$O(C=O)SR^{77}$, —$S(C=O)OR^{77}$, —$P(O)OR^{77}OR^{87}$, or —$S(C=O)NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, —$CF_3$, —$OCF_3$, —$OR^{77}$, —$NR^{77}R^{87}$, —$C(O)R^{77}$, —$CO_2R^{77}$, —$CONR^{77}R^{87}$, —$NO_2$, —$CN$, —$S(O)_{j5a}R^{77}$, —$SO_2NR^{77}R^{87}$, $NR^{77}(C=O)R^{87}$, $NR^{77}(C=O)OR^{87}$, $NR^{77}(C=O)NR^{78}R^{87}$, $NR^{77}S(O)_{j5a}R^{87}$, —$(C=S)OR^{77}$, —$C(=O)R^{87}$, —$NR^{77}(C=NR^{87})NR^{78}R^{88}$, —$NR^{77}(C=NR^{87})OR^{78}$, —$NR^{77}(C=NR^{87})SR^{78}$, —$O(C=O)OR^{77}$, —$O(C=O)NR^{77}R^{87}$, —$O(C=O)SR^{77}$, —$S(C=O)OR^{77}$, —$P(O)OR^{77}O$ $R^{87}$, or —$S(C=O)NR^{77}R^{87}$ substituents; or $R^5$ with $R^6$ taken together with the respective carbon atom to which they are attached, form a 3-10 membered saturated or unsaturated ring, wherein said ring is optionally substituted with $R^{69}$; or $R^5$ with $R^6$ taken together with the respective carbon atom to which they are attached, form a 3-10 membered saturated or unsaturated heterocyclic ring, wherein said ring is optionally substituted with $R^{69}$;

$R^7$ and $R^8$ are each independently H, acyl, alkyl, alkenyl, aryl, heteroaryl, heterocyclyl or cycloalkyl, any of which is optionally substituted by one or more $G^{111}$ substituents;

$R^4$ is H, alkyl, alkenyl, alkynyl, aryl, heteroaryl, cycloalkyl, heterocyclyl, cycloalkenyl, or heterocycloalkenyl, any of which is optionally substituted by one or more $G^{41}$ substituents;

$R^{69}$ is halo, —$OR^{78}$, —$SH$, —$NR^{78}R^{88}$, —$CO_2R^{78}$, —$CONR^{78}R^{88}$, —$NO_2$, —$CN$, —$S(O)_{j8}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$ alkynyl, $C_{1-10}$alkylthio$C_{1-10}$alkenyl, $C_{1-10}$alkoxy$C_{2-10}$ alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$ alkynyl, cyclo$C_{3-8}$alkenyl$C_{2-10}$alkynyl, heterocyclyl-$C_{0-10}$alkyl, heterocyclyl-$C_{2-10}$ alkenyl, or heterocyclyl-$C_{2-10}$ alkynyl, any of which is optionally substituted with one or more independent halo, cyano, nitro, —$OR^{778}$, —$SO_2NR^{778}R^{888}$, or —$NR^{778}R^{888}$ substituents; or aryl-$C_{0-10}$alkyl, aryl-$C_{2-10}$ alkenyl, or aryl-$C_{2-10}$alkynyl, any of which is optionally substituted with one or more independent halo, cyano, nitro, —$OR^{778}$, $C_{1-10}$alkyl, $C_{2-10}$ alkenyl, $C_{2-10}$alkynyl, halo$C_{1-10}$alkyl, halo$C_{2-10}$alkenyl, halo$C_{2-10}$alkynyl, —$COOH$, $C_{1-4}$alkoxycarbonyl, —$CONR^{778}R^{888}$, —$SO_2NR^{778}R^{888}$, or —$NR^{778}R^{888}$ substituents; or hetaryl-$C_{0-10}$alkyl, hetaryl-$C_{2-10}$ alkenyl, or hetaryl-$C_{2-10}$ alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —$COOH$, $C_{1-4}$alkoxycarbonyl, —$CONR^{778}R^{888}$, $SO_2NR^{778}R^{888}$, or —$NR^{778}R^{888}$ substituents; or mono($C_{1-6}$alkyl)amino$C_{1-6}$alkyl, di($C_{1-6}$alkyl)amino$C_{1-6}$ alkyl, mono(aryl)amino$C_{1-6}$alkyl, di(aryl)amino$C_{1-6}$alkyl, or —$N(C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$ alkenyl, $C_{2-10}$alkynyl, halo$C_{1-10}$alkyl, halo$C_{2-m}$alkenyl, halo$C_{2-m}$alkynyl, —$COOH$, $C_{1-4}$alkoxycarbonyl, —$CONR^{778}R^{888}$, —$SO_2NR^{778}R^{888}$, or —$NR^{778}R^{888}$ substituents; or in the case of —$NR^{78}R^{88}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$, or —$NR^{778}R^{888}$ substituents;

$R^{77}$, $R^{78}$, $R^{87}$, $R^{88}$, $R^{778}$, and $R^{888}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$ alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$ alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$ alkynyl, heterocyclyl-$C_{0-10}$alkyl, heterocyclyl-$C_{2-10}$alkenyl, heterocyclyl-$C_{2-10}$alkynyl, $C_{1-10}$ alkylcarbonyl, $C_{240}$alkenylcarbonyl, $C_{240}$alkynylcarbonyl, $C_{1-10}$alkoxycarbonyl, $C_{1-10}$ alkoxycarbonyl$C_{1-10}$alkyl, mono$C_{1-6}$alkylaminocarbonyl, di-$C_{1-6}$alkylaminocarbonyl, mono(aryl)aminocarbonyl, di(aryl)aminocarbonyl, or $C_{1-10}$alkyharyl) aminocarbonyl, any of which is optionally substituted with one or more independent halo, cyano, hydroxy, nitro, $C_{1-10}$ alkoxy, —$SO_2N(C_{0-4}$alkyl)($C_{0-4}$alkyl), or —$N(C_{0-4}$alkyl)($C_{0-4}$alkyl) substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl)($C_{0-10}$ alkyl), —$SO_2N(C_{0-4}$alkyl)($C_{0-4}$alkyl), or —$N(C_{0-4}$alkyl)($C_{0-4}$alkyl) substituents; or hetaryl-$C_{0-10}$ alkyl, hetaryl-$C_{2-10}$alkenyl, or hetaryl-$C_{2-10}$alkynyl, any of which is optionally substituted with one or more independent halo, cyano, nitro, —$O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl)($C_{0-4}$alkyl), —$SO_2N(C_{0-4}$alkyl)($C_{0-4}$alkyl), or —$N(C_{0-4}$alkyl)($C_{0-4}$alkyl) substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —$N(C_{1-6}$alkyl)-$C_{1-6}$alkyl-aryl, any of which is optionally substituted with one or more independent halo, cyano, nitro, —$O(C_{0-4}$alkyl), $C_{1-10}$alkyl, $C_{2-10}$alkenyl, $C_{2-10}$ alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl)($C_{0-4}$alkyl), —$SO_2N(C_{0-4}$alkyl)($C_{0-4}$alkyl), or —$N(C_{0-4}$alkyl)($C_{0-4}$alkyl) substituents; and n, m, j1, j1a, j2a, j3a, j4, j4a, j5a, j6a, j7, and j8 are each independently equal to 0, 1, or 2.

In some embodiments, the inhibitor is 4-18-Amino-3-[(2S)-1-(2-butynoyl)-2-pyrrolidinyl]imidazo[1,5-a]pyrazin-1-yl}-N-(2-pyridinyl)benzamide, or a pharmaceutically acceptable salt, solvate, hydrate, co-crystal, polymorph or prodrug thereof thereof. In some embodiments, the inhibitor has the CAS Number 1420477-60-6.

In some embodiments, the inhibitor is a compound of Formula (II):

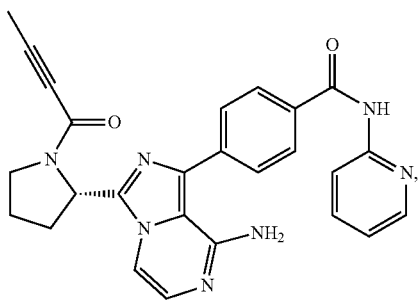

(II)

or a pharmaceutically acceptable salt, solvate, hydrate, co-crystal, polymorph or prodrug thereof.

In some embodiments, the inhibitor is an inhibitor as described in U.S. Pat. No. 7,459,554 and PCT Application No. WO2005/037836.

I. Compositions and Formulations

In some embodiments of the methods, compositions, combinations, kits and uses provided herein, the combination therapy can be administered in one or more compositions, e.g., a pharmaceutical composition containing an inhibitor of a TEC family kinase, e.g. a Btk inhibitor, and/or the cell therapy, e.g., T cell therapy.

In some embodiments, the composition, e.g., a pharmaceutical composition containing an inhibitor of a protein tyrosine kinase other than an inhibitor of ITK and/or an inhibitor of one or more of BTK, TEC, BMX/ETK, RLK/TXK and/or ERBB4, can include carriers such as a diluent, adjuvant, excipient, or vehicle with which the inhibitor, and/or the cells are administered. Examples of suitable pharmaceutical carriers are described in "Remington's Pharmaceutical Sciences" by E. W. Martin. Such compositions will contain a therapeutically effective amount of the tyrosine kinase inhibitor, e.g. Btk inhibitor, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Saline solutions and aqueous dextrose and glycerol solutions also can be employed as liquid carriers, particularly for injectable solutions. The pharmaceutical compositions can contain any one or more of a diluents(s), adjuvant(s), antiadherent(s), binder(s), coating(s), filler(s), flavor(s), color(s), lubricant(s), glidant(s), preservative(s), detergent(s), sorbent(s), emulsifying agent(s), pharmaceutical excipient(s), pH buffering agent(s), or sweetener(s) and a combination thereof. In some embodiments, the pharmaceutical composition can be liquid, solid, a lyophilized powder, in gel form, and/or combination thereof. In some aspects, the choice of carrier is determined in part by the particular inhibitor and/or by the method of administration.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), stabilizers and/or preservatives. The compositions containing the tyrosine kinase inhibitor, e.g. Btk inhibitor can also be lyophilized.

In some embodiments, the pharmaceutical compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. In some embodiments, other modes of administration also are contemplated. In some embodiments, the administration is by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, administration is by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration. In some embodiments, it is administered by multiple bolus administrations, for example, over a period of no more than 3 days, or by continuous infusion administration.

In some embodiments, the administration can be local, topical or systemic depending upon the locus of treatment. In some embodiments local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. In some embodiments, compositions also can be administered with other biologically active agents, either sequentially, intermittently or in the same composition. In some embodiments, administration also can include controlled release systems including controlled release formulations and device controlled release, such as by means of a pump. In some embodiments, the administration is oral.

In some embodiments, pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. In some embodiments, unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. In some embodiments, a multiple dose form is a plurality of identical unit dosage forms packaged in a single container to be administered in segregated unit dose form. Examples of multiple dose forms include vials, bottles of tablets or capsules or bottles of pints or gallons.

2. Inhibitor Dosage Schedule

In some embodiments, the method involves administering to the subject a therapeutically effective amount of an inhibitor of a protein tyrosine kinase other than an inhibitor of ITK and/or an inhibitor of one or more of BTK, TEC, BMX/ETK, RLK/TXK and/or ERBB4, and the cell therapy, such as a T cell therapy (e.g. CAR-expressing T cells) or a T cell-engaging therapy. In some embodiments, the inhibitor, is administered prior to, subsequently to, during, during the course of, simultaneously, near simultaneously, sequentially and/or intermittently with the administration of the cell therapy, such as a T cell therapy (e.g. CAR-expressing T cells) or a T cell-engaging therapy. In some embodiments, the method involves administering the inhibitor, prior to administration of the T cell therapy. In other embodiments, the method involves administering the inhibitor, after administration of the T cell therapy. In some embodiments, the inhibitor, is not further administered after initiation of the T cell therapy. In some embodiments, the dosage schedule comprises administering the inhibitor o, prior to and after initiation of the T cell therapy. In some embodiments, the dosage schedule comprises administering the inhibitor, simultaneously with the administration of the T cell therapy.

In some embodiments, the inhibitor of a protein tyrosine kinase other than an inhibitor of ITK and/or an inhibitor of one or more of BTK, TEC, BMX/ETK, RLK/TXK and/or ERBB4, is administered multiple times in multiple doses. In some embodiments, the inhibitor, is administered once. In some embodiments, the inhibitor, is administered six times daily, five times daily, four times daily, three times daily, twice daily, once daily, every other day, every three days, twice weekly, once weekly or only one time prior to or subsequently to initiation of administration of the cell therapy (e.g. T cell therapy, such as CAR-T cell therapy). In some embodiments, the inhibitor is administered in multiple doses in regular intervals prior to, during, during the course of, and/or after the period of administration of the cell therapy (e.g. T cell therapy, such as CAR-T cell therapy). In some embodiments, the inhibitor, is administered in one or more doses in regular intervals prior to the administration of the cell therapy (e.g. T cell therapy, such as CAR-T cell therapy). In some embodiments, the inhibitor is administered in one or more doses in regular intervals after the administration of the cell therapy (e.g. T cell therapy, such as CAR-T cell therapy). In some embodiments, one or more of the doses of the inhibitor can occur simultaneously with the administration of a dose of the cell therapy (e.g. T cell therapy, such as CAR-T cell therapy).

In some embodiments, the dose, frequency, duration, timing and/or order of administration of the inhibitor of a protein tyrosine kinase other than an inhibitor of ITK and/or an inhibitor of one or more of BTK, TEC, BMX/ETK, RLK/TXK and/or ERBB4, is determined, based on particular thresholds or criteria of results of the screening step and/or assessment of treatment outcomes described herein, e.g., those described in Section IV herein.

In some embodiments, the method involves administering the cell therapy to a subject that has been previously administered a therapeutically effective amount of the inhibitor. In some embodiments, the inhibitor is administered to a subject before administering a dose of cells expressing a recombinant receptor to the subject. In some embodiments, the treatment with the inhibitor occurs at the same time as the administration of the dose of cells. In some embodiments, the inhibitor is administered after the administration of the dose of cells. In some embodiments, the inhibitor is administered at a sufficient time prior to cell therapy so that the therapeutic effect of the combination therapy is increased.

In some embodiments, the inhibitor of a protein tyrosine kinase other than an inhibitor of ITK and/or an inhibitor of one or more of BTK, TEC, BMX/ETK, RLK/TXK and/or ERBB4, is administered prior to and/or concurrently with the administration of the cell therapy (e.g. T cell therapy, such as CAR-T cell therapy). In some embodiments, the inhibitor is administered from or from about 0 to 90 days, such as 0 to 30 days, 0 to 15 days, 0 to 6 days, 0 to 96 hours, 0 to 24 hours, 0 to 12 hours, 0 to 6 hours, or 0 to 2 hours, 2 hours to 30 days, 2 hours to 15 days, 2 hours to 6 days, 2 hours to 96 hours, 2 hours to 24 hours, 2 hours to 12 hours, 2 hours to 6 hours, 6 hours to 90 days, 6 hours to 30 days, 6 hours to 15 days, 6 hours to 6 days, 6 hours to 96 hours, 6 hours to 24 hours, 6 hours to 12 hours, 12 hours to 90 days, 12 hours to 30 days, 12 hours to 15 days, 12 hours to 6 days, 12 hours to 96 hours, 12 hours to 24 hours, 24 hours to 90 days, 24 hours to 30 days, 24 hours to 15 days, 24 hours to 6 days, 24 hours to 96 hours, 96 hours to 90 days, 96 hours to 30 days, 96 hours to 15 days, 96 hours to 6 days, 6 days to 90 days, 6 days to 30 days, 6 days to 15 days, 15 days to 90 days, 15 days to 30 days or 30 days to 90 days prior to initiation of the cell therapy (e.g. T cell therapy, such as CAR-T cell therapy). In some aspects, the inhibitor is administered no more than about 96 hours, 72 hours, 48 hours, 24 hours, 12 hours, 6 hours, 2 hours or 1 hour prior to initiation of the cell therapy (e.g. T cell therapy, such as CAR-T cell therapy).

In some embodiments, the inhibitor of a protein tyrosine kinase other than an inhibitor of ITK and/or an inhibitor of one or more of BTK, TEC, BMX/ETK, RLK/TXK and/or ERBB4, is administered at least or about at least 1 hours, at least or about at least 2 hours, at least or about at least 6 hours, at least or about at least 12 hours, at least or about at least 1 day, at least or about at least 2 days, at least or about at least 3 days, at least or about at least 4 days, at least or about at least 5 days, at least or about at least 6 days, at least or about at least 7 days, at least or at least about 12 days, at least or about at least 14 days, at least or at least about 15 days, at least or about at least 21 days, at least or at least about 24 days, at least or about at least 28 days, at least or about at least 30 days, at least or about at least 35 days or at least or about at least 42 days, at least or about at least 60 days, or at least or about at least 90 days prior to initiation of the administration of the cell therapy (e.g. T cell therapy, such as a CAR-T cell therapy). In some embodiments, the inhibitor of the TEC family kinase, e.g., a BTK inhibitor, is administered up to 2 days, up to 3 days, up to 4 days, up to 5 days, up to 6 days, up to 7 days, up to 8 days, up to 12 days, up to 14 days, up to 15 days, up to 21 days, up to 24 days, up to 28 days, up to 30 days, up to 35 days, up to 42 days, up to 60 days or up to 90 days prior to initiation of administration of the cell therapy (e.g. T cell therapy, such as CAR-T cell therapy).

In some of any such embodiments in which the inhibitor of a protein tyrosine kinase other than an inhibitor of ITK and/or an inhibitor of one or more of BTK, TEC, BMX/ETK, RLK/TXK and/or ERBB4 is given prior to the cell therapy (e.g. T cell therapy, such as CAR-T cell therapy), the administration of the inhibitor continues at regular intervals until the initiation of the cell therapy and/or for a time after the initiation of the cell therapy.

In some embodiments, the inhibitor of a protein tyrosine kinase other than an inhibitor of ITK and/or an inhibitor of one or more of BTK, TEC, BMX/ETK, RLK/TXK and/or ERBB4 is administered, or is further administered, after administration of the cell therapy (e.g. T cell therapy, such as CAR-T cell therapy). In some embodiments, the inhibitor is administered within or within about 1 hours, 2 hours, 6 hours, 12 hours, 24 hours, 48 hours, 96 hours, 4 days, 5 days, 6 days or 7 days, 14 days, 15 days, 21 days, 24 days, 28 days, 30 days, 36 days, 42 days, 60 days, 72 days or 90 days after initiation of administration of the cell therapy (e.g. T cell therapy). In some embodiments, the provided methods involve continued administration, such as at regular intervals, of the inhibitor after initiation of administration of the cell therapy.

In some embodiments, the inhibitor of a protein tyrosine kinase other than an inhibitor of ITK and/or an inhibitor of one or more of BTK, TEC, BMX/ETK, RLK/TXK and/or ERBB4r, is administered, such as is administered daily, for up to or up to about 1 day, up to or up to about 2 days, up to or up to about 3 days, up to or up to about 4 days, up to or up to about 5 days, up to or up to about 6 days, up to or up to about 7 days, up to or up to about 12 days, up to or up to about 14 days, up to or up to about 21 days, up to or up to about 24 days, up to or up to about 28 days, up to or up to about 30 days, up to or up to about 35 days, up to or up to about 42 days, up to or up to about 60 days or up to or up to about 90 days, up to or up to about 120 days, up to or up to about 180 days, up to or up to about 240 days, up to or up about 360 days, or up to or up to about 720 days or more after the administration of the cell therapy (e.g. T cell therapy, such as CAR-T cell therapy).

In some of any such above embodiments, the inhibitor of a protein tyrosine kinase other than an inhibitor of ITK and/or an inhibitor of one or more of BTK, TEC, BMX/ETK, RLK/TXK and/or ERBB4, is administered prior to and after initiation of administration of the cell therapy (e.g. T cell therapy, such as CAR-T cell therapy).

In some embodiments, the inhibitor of a protein tyrosine kinase other than an inhibitor of ITK and/or an inhibitor of one or more of BTK, TEC, BMX/ETK, RLK/TXK and/or ERBB4 is administered several times a day, twice a day, daily, every other day, three times a week, twice a week, or once a week after initiation of the cell therapy. In some embodiments, the inhibitor is administered daily. In some embodiments the inhibitor is administered twice a day. In some embodiments, the inhibitor is administered three times a day. In other embodiments, the inhibitor is administered every other day.

In some embodiments, the inhibitor of a protein tyrosine kinase other than an inhibitor of ITK and/or an inhibitor of one or more of BTK, TEC, BMX/ETK, RLK/TXK and/or ERBB4 is administered daily for a cycle of 7, 14, 21, 28, 35, or 42 days. In some embodiments, the inhibitor is administered twice a day for a cycle of 7, 14, 21, 28, 35, or 42 days. In some embodiments, the inhibitor is administered three times a day for a cycle of 7, 14, 21, 28, 35, or 42 days. In some embodiments, the inhibitor is administered every other day for a cycle of 7, 14, 21, 28, 35, or 42 days. In some embodiments, the inhibitor is administered for 1, 2, 3, 4, 5, 6, 7, 8, 9, 10, 11, 12, 13, 14, 15, 16, 17, 18, 19, 20, 21, 22, 23, or 24 cycles.

In some embodiments of the methods provided herein, the inhibitor of a protein tyrosine kinase other than an inhibitor of ITK and/or an inhibitor of one or more of BTK, TEC, BMX/ETK, RLK/TXK and/or ERBB4, and the cell therapy (e.g. T cell therapy, such as CAR-T cell therapy) are administered simultaneously or near simultaneously.

In some embodiments, the inhibitor of a protein tyrosine kinase other than an inhibitor of ITK and/or an inhibitor of one or more of BTK, TEC, BMX/ETK, RLK/TXK and/or ERBB4, is independently administered in a dosage amount of from or from about 0.2 mg per kg body weight of the subject (mg/kg) to 200 mg/kg, 0.2 mg/kg to 100 mg/kg, 0.2 mg/kg to 50 mg/kg, 0.2 mg/kg to 10 mg/kg, 0.2 mg/kg to 1.0 mg/kg, 1.0 mg/kg to 200 mg/kg, 1.0 mg/kg to 100 mg/kg, 1.0 mg/kg to 50 mg/kg, 1.0 mg/kg to 10 mg/kg, 10 mg/kg to 200 mg/kg, 10 mg/kg to 100 mg/kg, 10 mg/kg to 50 mg/kg, 50 mg/kg to 200 mg/kg, 50 mg/kg to 100 mg/kg or 100 mg/kg to 200 mg/kg. In some embodiments, the inhibitor is administered at a dose of about 0.2 mg per kg body weight of the subject (mg/kg) to 50 mg/kg, 0.2 mg/kg to 25 mg/kg, 0.2 mg/kg to 10 mg/kg, 0.2 mg/kg to 5 mg/kg, 0.2 mg/kg to 1.0 mg/kg, 1.0 mg/kg to 50 mg/kg, 1.0 mg/kg to 25 mg/kg, 1.0 mg/kg to 10 mg/kg, 1.0 mg/kg to 5 mg/kg, 5 mg/kg to 50 mg/kg, 5 mg/kg to 25 mg/kg, 5 mg/kg to 10 mg/kg, or 10 mg/kg to 25 mg/kg.

In some embodiments, the inhibitor of a protein tyrosine kinase other than an inhibitor of ITK and/or an inhibitor of one or more of BTK, TEC, BMX/ETK, RLK/TXK and/or ERBB4, is independently administered in a dosage amount of from or from about 25 mg to 2000 mg, 25 mg to 1000 mg, 25 mg to 500 mg, 25 mg to 200 mg, 25 mg to 100 mg, 25 mg to 50 mg, 50 mg to 2000 mg, 50 mg to 1000 mg, 50 mg to 500 mg, 50 mg to 200 mg, 50 mg to 100 mg, 100 mg to 2000 mg, 100 mg to 1000 mg, 100 mg to 500 mg, 100 mg to 200 mg, 200 mg to 2000 mg, 200 mg to 1000 mg, 200 mg to 500 mg, 500 mg to 2000 mg, 500 mg to 1000 mg or 1000 mg to 2000 mg, each inclusive.

In some embodiments, the inhibitor is the compound of Formula (II), which is administered, in a dosage amount of from or from about 50 mg to 420 mg, 50 mg to 400 mg, 50 mg to 380 mg, 50 mg to 360 mg, 50 mg to 340 mg, 50 mg to 320 mg, 50 mg to 300 mg, 50 mg to 280 mg, 100 mg to 400 mg, 100 mg to 380 mg, 100 mg to 360 mg, 100 mg to 340 mg, 100 mg to 320 mg, 100 mg to 300 mg, 100 mg to 280 mg, 100 mg to 200 mg, 140 mg to 400 mg, 140 mg to 380 mg, 140 mg to 360 mg, 140 mg to 340 mg, 140 mg to 320 mg, 140 mg to 300 mg, 140 mg to 280 mg, 140 mg to 200 mg, 180 mg to 400 mg, 180 mg to 380 mg, 180 mg to 360 mg, 180 mg to 340 mg, 180 mg to 320 mg, 180 mg to 300 mg, 180 mg to 280 mg, 200 mg to 400 mg, 200 mg to 380 mg, 200 mg to 360 mg, 200 mg to 340 mg, 200 mg to 320 mg, 200 mg to 300 mg, 200 mg to 280 mg, 220 mg to 400 mg, 220 mg to 380 mg, 220 mg to 360 mg, 220 mg to 340 mg, 220 mg to 320 mg, 220 mg to 300 mg, 220 mg to 280 mg, 240 mg to 400 mg, 240 mg to 380 mg, 240 mg to 360 mg, 240 mg to 340 mg, 240 mg to 320 mg, 240 mg to 300 mg, 240 mg to 280 mg, 280 mg to 420 mg, or 300 mg to 400 mg, each inclusive.

In some embodiments, the inhibitor of a protein tyrosine kinase other than an inhibitor of ITK and/or an inhibitor of one or more of BTK, TEC, BMX/ETK, RLK/TXK and/or ERBB4, is administered at a total daily dosage amount of at least or at least about 50 mg/day, 100 mg/day, 150 mg/day, 175 mg/day, 200 mg/day, 250 mg/day, 300 mg/day, 350 mg/day, 400 mg/day, 420 mg/day, 440 mg/day, 460 mg/day, 480 mg/day, 500 mg/day, 520 mg/day, 540 mg/day, 560 mg/day, 580 mg/day or 600 mg/day. In some embodiments, the inhibitor is administered in an amount less than 420 mg/day. In some embodiments, the inhibitor is administered once daily. In some embodiments, the inhibitor is administered twice daily.

In any of the aforementioned embodiments, the inhibitor, e.g. the compound of Formula (II), may be administered orally.

In some embodiments, dosages, such as daily dosages, are administered in one or more divided doses, such as 2, 3, or 4 doses, or in a single formulation. The inhibitor can be administered alone, in the presence of a pharmaceutically acceptable carrier, or in the presence of other therapeutic agents.

One skilled in the art will recognize that higher or lower dosages of the inhibitor could be used, for example depending on the particular agent and the route of administration. In some embodiments, the inhibitor may be administered alone or in the form of a pharmaceutical composition wherein the compound is in admixture or mixture with one or more pharmaceutically acceptable carriers, excipients, or diluents. In some embodiments, the inhibitor may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the route of administration is oral, parenteral, rectal, nasal, topical, or ocular routes, or by inhalation. In some embodiments, the inhibitor is administered orally. In some embodiments, the inhibitor is administered orally in solid dosage forms, such as capsules, tablets and powders, or in liquid dosage forms, such as elixirs, syrups and suspensions.

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. If symptoms have been alleviated to an appropriate level, treatment may cease. Patients may, however, require intermittent treatment on a long-term basis upon any recurrence of symptoms. Patients may also require chronic treatment on a long-term basis.

C. Lymphodepleting Treatment

In some aspects, the provided methods can further include administering one or more lymphodepleting therapies, such as prior to or simultaneous with initiation of administration of the immunotherapy, such as a T cell therapy (e.g. CAR-expressing T cells) or a T cell-engaging therapy. In some embodiments, the lymphodepleting therapy comprises administration of a phosphamide, such as cyclophosphamide. In some embodiments, the lymphodepleting therapy can include administration of fludarabine.

In some aspects, preconditioning subjects with immunodepleting (e.g., lymphodepleting) therapies can improve the effects of adoptive cell therapy (ACT). Preconditioning with lymphodepleting agents, including combinations of cyclosporine and fludarabine, have been effective in improving the efficacy of transferred tumor infiltrating lymphocyte (TIL) cells in cell therapy, including to improve response and/or persistence of the transferred cells. See, e.g., Dudley et al., *Science,* 298,850-54 (2002); Rosenberg et al., *Clin Cancer Res,* 17(13):4550-4557 (2011) Likewise, in the context of CAR+ T cells, several studies have incorporated lymphodepleting agents, most commonly cyclophosphamide, fludarabine, bendamustine, or combinations thereof, sometimes accompanied by low-dose irradiation. See Han et al. *Journal of Hematology & Oncology,* 6:47 (2013);

Kochenderfer et al., *Blood,* 119: 2709-2720 (2012); Kalos et al., *Sci Transl Med,* 3(95):95ra73 (2011); Clinical Trial Study Record Nos.: NCT02315612; NCT01822652.

Such preconditioning can be carried out with the goal of reducing the risk of one or more of various outcomes that could dampen efficacy of the therapy. These include the phenomenon known as "cytokine sink," by which T cells, B cells, NK cells compete with TILs for homeostatic and activating cytokines, such as IL-2, IL-7, and/or IL-15; suppression of TILs by regulatory T cells, NK cells, or other cells of the immune system; impact of negative regulators in the tumor microenvironment. Muranski et al., *Nat Clin Pract Oncol.* December; 3(12): 668-681 (2006).

Thus in some embodiments, the provided method further involves administering a lymphodepleting therapy to the subject. In some embodiments, the method involves administering the lymphodepleting therapy to the subject prior to the administration of the dose of cells. In some embodiments, the lymphodepleting therapy contains a chemotherapeutic agent such as fludarabine and/or cyclophosphamide. In some embodiments, the administration of the cells and/or the lymphodepleting therapy is carried out via outpatient delivery.

In some embodiments, the methods include administering a preconditioning agent, such as a lymphodepleting or chemotherapeutic agent, such as cyclophosphamide, fludarabine, or combinations thereof, to a subject prior to the administration of the dose of cells. For example, the subject may be administered a preconditioning agent at least 2 days prior, such as at least 3, 4, 5, 6, or 7 days prior, to the first or subsequent dose. In some embodiments, the subject is administered a preconditioning agent no more than 7 days prior, such as no more than 6, 5, 4, 3, or 2 days prior, to the administration of the dose of cells.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the fludarabine can be administered in a single dose or can be administered in a plurality of doses, such as given daily, every other day or every three days. In some embodiments, the cyclophosphamide is administered once daily for one or two days.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 30 mg/m$^2$, or 24 mg/m$^2$ and 26 mg/m$^2$. In some instances, the subject is administered 25 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the dose of cells.

In one exemplary dosage regime, prior to receiving the first dose, subjects receive a kinase inhibitor 1 day before the administration of cells and an lymphodepleting preconditioning chemotherapy of cyclophosphamide and fludarabine (CY/FLU), which is administered at least two days before the first dose of CAR-expressing cells and generally no more than 7 days before administration of cells. In some cases, for example, cyclophosphadmide is given from 24 to 27 days after the administration of the inhibitor of a protein tyrosine kinase other than an inhibitor of ITK and/or an inhibitor of one or more of BTK, TEC, BMX/ETK, RLK/TXK and/or ERBB4. After preconditioning treatment, subjects are administered the dose of CAR-expressing T cells as described above.

In some embodiments, the administration of the preconditioning agent prior to infusion of the dose of cells improves an outcome of the treatment. For example, in some aspects, preconditioning improves the efficacy of treatment with the dose or increases the persistence of the recombinant receptor-expressing cells (e.g., CAR-expressing cells, such as CAR-expressing T cells) in the subject. In some embodiments, preconditioning treatment increases disease-free survival, such as the percent of subjects that are alive and exhibit no minimal residual or molecularly detectable disease after a given period of time following the dose of cells. In some embodiments, the time to median disease-free survival is increased.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy,* 32(7): 689-702 (2009), and Herman et al. *J. Immunological Methods,* 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In some embodiments, the administration of the preconditioning agent prior to infusion of the dose of cells improves an outcome of the treatment such as by improving the efficacy of treatment with the dose or increases the persistence of the recombinant receptor-expressing cells (e.g., CAR-expressing cells, such as CAR-expressing T cells) in the subject. Therefore, in some embodiments, the dose of preconditioning agent given in the method which is a combination therapy with the inhibitor and cell therapy is higher than the dose given in the method without the inhibitor.

III. T CELL THERAPY AND ENGINEERING CELLS

In some embodiments, the T cell therapy for use in accord with the provided combination therapy methods includes administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

A. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

I. Chimeric Antigen Receptors (CARS)

Exemplary antigen receptors, including CARs, and methods for engineering and introducing such receptors into cells, include those described, for example, in international patent application publication numbers WO2000/14257, WO2013/126726, WO2012/129514, WO2014/031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.*, 3(4): 388-398 (2013); Davila et al., *PLoS ONE* 8(4): e61338 (2013); Turtle et al., *Curr. Opin. Immunol.*, 24(5): 633-39 (2012); Wu et al., *Cancer*, 18(2): 160-75 (2012). In some aspects, the antigen receptors include a CAR as described in U.S. Pat. No. 7,446,190, and those described in International Patent Application Publication No. WO/2014055668 A1. Examples of the CARs include CARs as disclosed in any of the aforementioned publications, such as WO2014031687, U.S. Pat. Nos. 8,339, 645, 7,446,179, US 2013/0149337, U.S. Pat. Nos. 7,446, 190, 8,389,282, Kochenderfer et al., *Nature Reviews Clinical Oncology*, 10, 267-276 (2013); Wang et al., *J. Immunother.* 35(9): 689-701 (2012); and Brentjens et al., *Sci Transl Med.* 5(177) (2013). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-$R^2$, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a $C_H1/C_L$ and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014/031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to $C_H2$ and $C_H3$ domains, or IgG4 hinge linked to the CH3 domain. Exemplary spacers include, but are not limited to, those described in Hudecek et al., *Clin. Cancer Res.*, 19:3153 (2013), international patent application publication number WO2014/031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD 134, CD137, or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25 or CD16. For example, in some aspects, the CAR or other chimeric receptor includes a chimeric molecule between CD3-zeta (CD3-0 or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker and/or cells expressing the CAR or other antigen receptor further includes a surrogate marker, such as a cell surface marker, which may be used to confirm transduction or engineering of the cell to express the receptor, such as a truncated version of a cell surface receptor, such as truncated EGFR (tEGFR). In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7. An exemplary T2A linker sequence comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as a 112 AA cytoplasmic domain of isoform 3 of human CD3ζ (Accession No. P20963.2) or a CD3 zeta signaling domain as described in U.S. Pat. Nos. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

2. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., *Immunobiology: The Immune System in Health and Disease,* 3rd Ed., *Current Biology Publications,* p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al., (2003) *Nat Immunol,* 4, 55-62; Holler et al., (2000) *Proc Natl Acad Sci USA,* 97, 5387-92), phage display (Li et al., (2005) *Nat Biotechnol,* 23, 349-54), or T cell display (Chervin et al., (2008) *J Immunol Methods,* 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models known to those of skill in the art. In some embodiments, for predicting MHC class I binding sites, such models include, but are not limited to, ProPred1 (Singh and Raghava (2001) *Bioinformatics* 17(12):1236-1237, and SYFPEITHI (see Schuler et al., (2007) *Immunoinformatics Methods in Molecular Biology,* 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known to those of skill in the art. For predicting MHC class I binding sites, such models include, but are not limited to, ProPred1 (described in more detail in Singh and Raghava, ProPred: prediction of HLA-DR binding sites. *BIOINFORMATICS* 17(12):1236-1237 2001), and SYFPEITHI (see Schuler et al., SYFPEITHI, Database for Searching and T-Cell Epitope Prediction. in *Immunoinformatics Methods in Molecular Biology,* vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, See e.g., Soo Hoo, W. F. et al., *PNAS (USA)* 89, 4759 (1992); Wülfing, C. and Plückthun, A., *J. Mol. Biol.* 242, 655 (1994); Kurucz, I. et al., *PNAS (USA)* 90 3830 (1993); International published PCT Nos. WO 96/13593, WO 96/18105, WO99/60120, WO99/18129, WO 03/020763, WO2011/044186; and Schlueter, C. J. et al., *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO: 16). In some embodiments, the linker has the sequence GSADDAKKDAAKKDGKS (SEQ ID NO: 17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about $10^{-5}$ and $10^{-12}$ M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

3. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in PCT Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptors include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Cells and Preparation of Cells for Genetic Engineering

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MALT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level (markerhigh) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al., *Blood*. 1:72-82 (2012); Wang et al., *J Immunother*. 35(9):689-701 (2012). In some embodiments, combining TCM-enriched $CD8^+$ T cells and $CD4^+$ T cells further enhances efficacy.

In embodiments, memory T cells are present in both $CD62L^+$ and CD62L- subsets of $CD8^+$ peripheral blood lymphocytes. PBMC can be enriched for or depleted of $CD62L-CD8^+$ and/or $CD62L^+$ $CD8^+$ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are CD45RO-, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are CD62L- and CD45RO-.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in PCT Pub. Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al., *J Immunother.* 35(9): 651-660 (2012), Terakura et al., *Blood.* 1:72-82 (2012), and Wang et al., *J Immunother.* 35(9):689-701 (2012).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al., *Lab Chip* 10,1567-1573 (2010); and Godin et al., *J Biophoton.* 1(5):355-376 (2008). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al., J Immunother. 35(9): 651-660 (2012), Terakura et al., *Blood.* 1:72-82 (2012), and/or Wang et al., *J Immunother.* 35(9):689-701 (2012).

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Vectors and Methods for Genetic Engineering

Introduction of the nucleic acid molecules encoding the recombinant receptor may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, prior to or during gene transfer, the cells are incubated or cultured in the presence of an inhibitor of a protein tyrosine kinase other than an inhibitor of ITK and/or an inhibitor of one or more of BTK, TEC, BMX/ETK, RLK/TXK and/or ERBB4, including any as described herein. In some embodiments, the inhibitor is added during the cell manufacturing process, for example, during the process of engineering CAR-T cells. In some aspects, the presence of the inhibitor can improve the quality of the population of cells produced. In some aspects, the inhibitor of a protein tyrosine kinase other than an inhibitor of ITK and/or an inhibitor of one or more of BTK, TEC, BMX/ETK, RLK/TXK and/or ERBB4 may increase the proliferation or expansion of cells or may alter one or more signaling pathways thereby resulting in cells with a less-differentiated or less activated surface phenotype, despite exhibiting substantial expansion and/or effector function.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphribosyltransferase (HPRT) gene, the cellular adenine phosphoriboslytransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

IV. EXEMPLARY TREATMENT OUTCOMES AND METHODS FOR ASSESSING SAME

In some embodiments of the methods, compositions, combinations, kits and uses provided herein, the provided combination therapy results in one or more treatment outcomes, such as a feature associated with any one or more of the parameters associated with the therapy or treatment, as described below. In some embodiments, the combination therapy can further include one or more screening steps to identify subjects for treatment with the combination therapy and/or continuing the combination therapy, and/or a step for assessment of treatment outcomes and/or monitoring treatment outcomes. In some embodiments, the step for assessment of treatment outcomes can include steps to evaluate and/or to monitor treatment and/or to identify subjects for administration of further or remaining steps of the therapy and/or for repeat therapy. In some embodiments, the screening step and/or assessment of treatment outcomes can be used to determine the dose, frequency, duration, timing and/or order of the combination therapy provided herein.

In some embodiments, any of the screening steps and/or assessment of treatment of outcomes described herein can be used prior to, during, during the course of, or subsequent to administration of one or more steps of the provided combination therapy, e.g., administration of the immunotherapy, such as a T cell therapy (e.g. CAR-expressing T cells) or a T cell-engaging therapy, and/or an inhibitor of a protein tyrosine kinase other than an inhibitor of ITK and/or an inhibitor of one or more of BTK, TEC, BMX/ETK, RLK/TXK and/or ERBB4. In some embodiments, assessment is made prior to, during, during the course of, or after performing any of the methods provided herein. In some embodiments, the assessment is made prior to performing the methods provided herein. In some embodiments, assessment is made after performing one or more steps of the methods provided herein. In some embodiments, the assessment is performed prior to administration of administration of one or more steps of the provided combination therapy, for example, to screen and identify patients suitable and/or susceptible to receive the combination therapy. In some embodiments, the assessment is performed during, during the course of, or subsequent to administration of one or more steps of the provided combination therapy, for example, to assess the intermediate or final treatment outcome, e.g., to determine the efficacy of the treatment and/or to determine whether to continue or repeat the treatments and/or to determine whether to administer the remaining steps of the combination therapy.

In some embodiments, treatment of outcomes includes improved immune function, e.g., immune function of the T cells administered for cell based therapy and/or of the endogenous T cells in the body. In some embodiments, exemplary treatment outcomes include, but are not limited to, enhanced T cell proliferation, enhanced T cell functional activity, changes in immune cell phenotypic marker expression, such as such features being associated with the engineered T cells, e.g. CAR-T cells, administered to the subject. In some embodiments, exemplary treatment outcomes include decreased disease burden, e.g., tumor burden, improved clinical outcomes and/or enhanced efficacy of therapy.

In some embodiments, the screening step and/or assessment of treatment of outcomes includes assessing the survival and/or function of the T cells administered for cell based therapy. In some embodiments, the screening step and/or assessment of treatment of outcomes includes assessing the levels of cytokines or growth factors. In some embodiments, the screening step and/or assessment of treatment of outcomes includes assessing disease burden and/or improvements, e.g., assessing tumor burden and/or clinical outcomes. In some embodiments, either of the screening step and/or assessment of treatment of outcomes can include any of the assessment methods and/or assays described herein and/or known in the art, and can be performed one or more times, e.g., prior to, during, during the course of, or subsequently to administration of one or more steps of the combination therapy. Exemplary sets of parameters associated with a treatment outcome, which can be assessed in some embodiments of the methods provided herein, include peripheral blood immune cell population profile and/or tumor burden.

In some embodiments, the methods affect efficacy of the cell therapy in the subject. In some embodiments, the persistence, expansion, and/or presence of recombinant receptor-expressing, e.g., CAR-expressing, cells in the subject following administration of the dose of cells in the method with the inhibitor is greater as compared to that achieved via a method without the administration of the inhibitor. In some embodiments of the immunotherapy methods provided herein, such as a T cell therapy (e.g. CAR-expressing T cells) or a T cell-engaging therapy, assessment of the parameter includes assessing the expansion and/or persistence in the subject of the administered T cells for the immunotherapy, e.g., T cell therapy, as compared to a method in which the immunotherapy is administered to the subject in the absence of the inhibitor. In some embodiments, the methods result in the administered T cells exhibiting increased or prolonged expansion and/or persistence in the subject as compared to a method in which the T cell therapy is administered to the subject in the absence of the inhibitor.

In some embodiments, the administration of the inhibitor of a protein tyrosine kinase other than an inhibitor of ITK and/or an inhibitor of one or more of BTK, TEC, BMX/

ETK, RLK/TXK and/or ERBB4 decreases disease burden, e.g., tumor burden, in the subject as compared to a method in which the dose of cells expressing the recombinant receptor is administered to the subject in the absence of the inhibitor. In some embodiments, the administration of the inhibitor decreases blast marrow in the subject as compared to a method in which the dose of cells expressing the recombinant receptor is administered to the subject in the absence of the inhibitor. In some embodiments, the administration of the inhibitor results in improved clinical outcomes, e.g., objective response rate (ORR), progression-free survival (PFS) and overall survival (OS), compared to a method in which the dose of cells expressing the recombinant receptor is administered to the subject in the absence of the inhibitor.

In some embodiments, the subject can be screened prior to the administration of one or more steps of the combination therapy. For example, the subject can be screened for characteristics of the disease and/or disease burden, e.g., tumor burden, prior to administration of the combination therapy, to determine suitability, responsiveness and/or susceptibility to administering the combination therapy. In some embodiments, the screening step and/or assessment of treatment outcomes can be used to determine the dose, frequency, duration, timing and/or order of the combination therapy provided herein.

In some embodiments, the subject can be screened after administration of one of the steps of the combination therapy, to determine and identify subjects to receive the remaining steps of the combination therapy and/or to monitor efficacy of the therapy. In some embodiments, the number, level or amount of administered T cells and/or proliferation and/or activity of the administered T cells is assessed prior to administration and/or after administration of the inhibitor.

In some embodiments, the inhibitor of a protein tyrosine kinase other than an inhibitor of ITK and/or an inhibitor of one or more of BTK, TEC, BMX/ETK, RLK/TXK and/or ERBB4 is administered until the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

In some embodiments, the inhibitor of a protein tyrosine kinase other than an inhibitor of ITK and/or an inhibitor of one or more of BTK, TEC, BMX/ETK, RLK/TXK and/or ERBB4 is administered until there is a clinical benefit to the treatment, such as at least or greater than a 50% decrease in the total tumor volume a complete response (CR) in which detectable tumor has disappeared, progression free survival or disease free survival for greater than 6 months or greater than 1 year or more.

In some embodiments, a change and/or an alteration, e.g., an increase, an elevation, a decrease or a reduction, in levels, values or measurements of a parameter or outcome compared to the levels, values or measurements of the same parameter or outcome in a different time point of assessment, a different condition, a reference point and/or a different subject is determined or assessed. For example, in some embodiments, a fold change, e.g., an increase or decrease, in particular parameters, e.g., number of engineered T cells in a sample, compared to the same parameter in a different condition, e.g., before or after administration of the inhibitor can be determined. In some embodiments, the levels, values or measurements of two or more parameters are determined, and relative levels are compared. In some embodiments, the determined levels, values or measurements of parameters are compared to the levels, values or measurements from a control sample or an untreated sample. In some embodiments, the determined levels, values or measurements of parameters are compared to the levels from a sample from the same subject but at a different time point. The values obtained in the quantification of individual parameter can be combined for the purpose of disease assessment, e.g., by forming an arithmetical or logical operation on the levels, values or measurements of parameters by using multi-parametric analysis. In some embodiments, a ratio of two or more specific parameters can be calculated.

A. T Cell Exposure, Persistence and Proliferation

In some embodiments, the parameter associated with therapy or a treatment outcome, which include parameters that can be assessed for the screening steps and/or assessment of treatment of outcomes and/or monitoring treatment outcomes, is or includes assessment of the exposure, persistence and proliferation of the T cells, e.g., T cells administered for the T cell based therapy. In some embodiments, the increased exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells used for the immunotherapy, e.g. T cell therapy, before or after administering one or more steps of the combination therapy provided herein.

In some embodiments, the administration of the inhibitor of a protein tyrosine kinase other than an inhibitor of ITK and/or an inhibitor of one or more of BTK, TEC, BMX/ETK, RLK/TXK and/or ERBB4 are designed to promote exposure of the subject to the cells, e.g., T cells administered for T cell based therapy, such as by promoting their expansion and/or persistence over time. In some embodiments, the T cell therapy exhibits increased or prolonged expansion and/or persistence in the subject as compared to a method in which the T cell therapy is administered to the subject in the absence of the inhibitor.

In some embodiments, the provided methods increase exposure of the subject to the administered cells (e.g., increased number of cells or duration over time) and/or improve efficacy and therapeutic outcomes of the immunotherapy, e.g. T cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the administration of the inhibitor of a protein tyrosine kinase other than an inhibitor of ITK and/or an inhibitor of one or more of BTK, TEC, BMX/ETK, RLK/TXK and/or ERBB4 kinase can increase the maximum, total, and/or duration of exposure to the cells, e.g. T cells administered for the T cell based therapy, in the subject as compared to administration of the T cells alone in the absence of the inhibitor. In some aspects, administration of the inhibitor, in the context of high disease burden (and thus higher amounts of antigen) and/or a more aggressive or resistant cancer enhances efficacy as compared with administration of the T cells alone in the absence of the inhibitor in the same context, which may result in immunosuppression, anergy and/or exhaustion which may prevent expansion and/or persistence of the cells.

In some embodiments, the presence and/or amount of cells expressing the recombinant receptor (e.g., CAR-expressing cells administered for T cell based therapy) in the subject following the administration of the T cells and before, during and/or after the administration of the inhibitor is detected. In some aspects, quantitative PCR (qPCR) is used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the T cells, e.g., CAR-expressing T cells. In some aspects, the cells are detected at or at least at 2, 4, or 6 weeks following, or 3, 6, or 12, 18, or 24, or 30 or 36 months, or 1, 2, 3, 4, 5, or more years, following the administration of the T cells, e.g., CAR-expressing T cells and/or the inhibitor.

In some embodiments, the persistence of receptor-expressing cells (e.g. CAR-expressing cells) in the subject by the methods, following the administration of the T cells, e.g., CAR-expressing T cells and/or the inhibitor, is greater as compared to that which would be achieved by alternative methods such as those involving the administration of the immunotherapy alone, e.g., administration the T cells, e.g., CAR-expressing T cells, in the absence of the inhibitor.

The exposure, e.g., number of cells, e.g. T cells administered for T cell therapy, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor expressing cells, e.g. CAR-expressing cells, expand in the subject following administration of the T cells, e.g., CAR-expressing T cells, and/or following administration of inhibitor. In some aspects, the methods result in greater expansion of the cells compared with other methods, such as those involving the administration of the T cells, e.g., CAR-expressing T cells, in the absence of administering the t inhibitor.

In some aspects, the method results in high in vivo proliferation of the administered cells, for example, as measured by flow cytometry. In some aspects, high peak proportions of the cells are detected. For example, in some embodiments, at a peak or maximum level following the administration of the T cells, e.g., CAR-expressing T cells and/or the inhibitor in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR, per microgram of DNA, or at least 0.1, 0.2, 0.3, 0.4, 0.5, 0.6, 0.7, 0.8, or 0.9 receptor-expressing, e.g., CAR-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the T cells, e.g., CAR-expressing T cells and/or the inhibitor or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject.

In some embodiments, cells expressing the receptor are detectable in the serum, plasma, blood or tissue, e.g., tumor sample, of the subject, e.g., by a specified method, such as qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the T cells, e.g., CAR-expressing T cells, or after administration of the inhibitor for at least at or about 2, 3, 4, 5, 6, 7, 8, 9, 10, 11, 12, 13, 14, 15, 16, 17, 18, 19, 20, 21, 22, 23, or 24 or more weeks following the administration of the T cells, e.g., CAR-expressing T cells, and/or the inhibitor.

In some aspects, at least about $1 \times 10^2$, at least about $1 \times 10^3$, at least about $1 \times 10^4$, at least about $1 \times 10^5$, or at least about $1 \times 10^6$ or at least about $5 \times 10^6$ or at least about $1 \times 10^7$ or at least about $5 \times 10^7$ or at least about $1 \times 10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, plasma, serum, tissue, or compartment thereof, such as in the blood, e.g., peripheral blood, or disease site, e.g., tumor, thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the T cells, e.g., CAR-expressing T cells, and/or following the administration of the inhibitor. Such cell numbers may be as detected by flow cytometry-based or quantitative PCR-based methods and extrapolation to total cell numbers using known methods. See, e.g., Brentjens et al., *Sci Transl Med.* 2013 5(177), Park et al, Molecular Therapy 15(4):825-833 (2007), Savoldo et al., *JCI* 121(5):1822-1826 (2011), Davila et al., (2013) *PLoS ONE* 8(4):e61338, Davila et al., *Oncoimmunology* 1(9):1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8, 9, 10, 11, or 12 months or at least 2 or 3 years following administration of the cells, e.g., CAR-expressing T cells, and/or the inhibitor. In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the T cells, e.g., CAR-expressing T cells, or inhibitor, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, plasma, serum, blood, tissue and/or disease site thereof, e.g., tumor site, at a time that is at least about 3 months, at least about 6 months, at least about 12 months, at least about 1 year, at least about 2 years, at least about 3 years, or more than 3 years, following the administration of the cells, e.g., following the initiation of the administration of the T cells, e.g., CAR-expressing T cells, and/or the inhibitor.

In some embodiments, the area under the curve (AUC) for concentration of receptor/- (e.g., CAR-) expressing cells in a fluid, plasma, serum, blood, tissue, organ and/or disease site, e.g. tumor site, of the subject over time following the administration of the T cells, e.g., CAR-expressing T cells and/or following the administration of the inhibitor, is greater as compared to that achieved via an alternative dosing regimen where the subject is administered the T cells, e.g., CAR-expressing T cells, in the absence of administering the inhibitor.

In some aspects, the method results in high in vivo proliferation of the administered cells, for example, as measured by flow cytometry. In some aspects, high peak proportions of the cells are detected. For example, in some embodiments, at a peak or maximum level following the T cells, e.g., CAR-expressing T cells and/or inhibitor, in the blood, plasma, serum, tissue or disease site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some aspects, the increased or prolonged expansion and/or persistence of the dose of cells in the subject administered with the inhibitor is associated with a benefit in tumor related outcomes in the subject. In some embodiments, the tumor related outcome includes a decrease in tumor burden or a decrease in blast marrow in the subject. In some embodiments, the tumor burden is decreased by or by at least at or about 10, 20, 30, 40, 50, 60, 70, 80, 90, or 100 percent after administration of the method. In some embodiments, disease burden, tumor size, tumor volume, tumor mass, and/or tumor load or bulk is reduced following the dose of cells by at least at or about 50%, 60%, 70%, 80%, 90% or more compared a subject that has been treated with a method that does not involve the administration of a inhibitor of a protein tyrosine kinase other than an inhibitor of ITK and/or an inhibitor of one or more of BTK, TEC, BMX/ETK, RLK/TXK and/or ERBB4.

B. T Cell Functional Activity

In some embodiments, parameters associated with therapy or a treatment outcome, which include parameters that can be assessed for the screening steps and/or assessment of treatment of outcomes and/or monitoring treatment outcomes, includes one or more of activity, phenotype, proliferation or function of T cells. In some embodiments, any of the known assays in the art for assessing the activity, phenotypes, proliferation and/or function of the T cells, e.g., T cells administered for T cell therapy, can be used. Prior to and/or subsequent to administration of the cells and/or inhibitor, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy*, 32(7): 689-702 (2009), and Herman et al., *J. Immunological Methods*, 285(1): 25-40 (2004). In certain embodiments, the biological activity of the cells is measured by assaying expression and/or secretion of one or more cytokines, such as CD107a, IFNγ, IL-2, GM-CSF and TNFα, and/or by assessing cytolytic activity.

In some embodiments, assays for the activity, phenotypes, proliferation and/or function of the T cells, e.g., T cells administered for T cell therapy include, but are not limited to, ELISPOT, ELISA, cellular proliferation, cytotoxic lymphocyte (CTL) assay, binding to the T cell epitope, antigen or ligand, or intracellular cytokine staining, proliferation assays, lymphokine secretion assays, direct cytotoxicity assays, and limiting dilution assays. In some embodiments, proliferative responses of the T cells can be measured, e.g. by incorporation of $^3$H-thymidine, BrdU (5-Bromo-2'-Deoxyuridine) or 2'-deoxy-5-ethynyluridine (EdU) into their DNA or dye dilution assays, using dyes such as carboxyfluorescein diacetate succinimidyl ester (CFSE), CellTrace Violet, or membrane dye PKH26.

In some embodiments, assessing the activity, phenotypes, proliferation and/or function of the T cells, e.g., T cells administered for T cell therapy, include measuring cytokine production from T cells, and/or measuring cytokine production in a biological sample from the subject, e.g., plasma, serum, blood, and/or tissue samples, e.g., tumor samples. In some cases, such measured cytokines can include, without limitation, interlekukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample.

In some embodiments, assessing the activity, phenotypes, proliferation and/or function of the T cells, e.g., T cells administered for T cell therapy, include assessing cell phenotypes, e.g., expression of particular cell surface markers. In some embodiments, the T cells, e.g., T cells administered for T cell therapy, are assessed for expression of T cell activation markers, T cell exhaustion markers, and/or T cell differentiation markers. In some embodiments, the cell phenotype is assessed before administration. In some embodiments, the cell phenotype is assessed after administration. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, CD62L$^{low}$, CCR7$^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some aspects, detecting the expression levels includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more factors, effectors, enzymes and/or surface markers are detected by an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, detection of cytokines and/or surface markers is determined using a binding reagent that specifically binds to at least one biomarker. In some cases, the binding reagent is an antibody or antigen-binding fragment thereof, an aptamer or a nucleic acid probe.

In some embodiments, the administration of the inhibitor increases the level of circulating CAR T cells. In some embodiments, treatment with the kinase inhibitor skews the development of T cells towards a Th1 immune phenotype. In some embodiments, treatment with ibrutinib or the compound of Formula (II) may skew CAR T cells towards a more memory-like phenotype that has been associated with increased CAR T in vivo persistence (Busch, D. H., et al. (2016) Semin Immunol, 28(1): 28-34).)

C. Disease Burden, Response, Efficacy and Survival

In some embodiments, parameters associated with therapy or a treatment outcome, which include parameters that can be assessed for the screening steps and/or assessment of treatment of outcomes and/or monitoring treatment outcomes, includes tumor or disease burden. The administration of the immunotherapy, such as a T cell therapy (e.g. CAR-expressing T cells) or a T cell-engaging therapy and/or the inhibitor, can reduce or prevent the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden.

In some embodiments, the provided methods result in a decreased tumor burden in treated subjects compared to alternative methods in which the immunotherapy, such as a T cell therapy (e.g. CAR-expressing T cells) or a T cell-engaging therapy is given without administration of the inhibitor. It is not necessary that the tumor burden actually be reduced in all subjects receiving the combination therapy, but that tumor burden is reduced on average in subjects treated, such as based on clinical data, in which a majority of subjects treated with such a combination therapy exhibit a reduced tumor burden, such as at least 50%, 60%, 70%, 80%, 90%, 95% or more of subjects treated with the combination therapy, exhibit a reduced tumor burden.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood, lymph or bone marrow in the context of certain hematological malignancies. Disease burden can include, in some embodiments, the mass of a tumor, the number or extent of metastases and/or the percentage of blast cells present in the bone marrow.

In some embodiments, the subject has a myeloma, a lymphoma or a leukemia. In some embodiments, the subject has a non-Hodgkin lymphoma (NHL), an acute lymphoblastic leukemia (ALL), a chronic lymphocytic leukemia (CLL), a diffuse large B-cell lymphoma (DLBCL) or a myeloma, e.g., a multiple myeloma (MM). In some embodiments, the subject has a MM or a DBCBL.

In some embodiments, the subject has a solid tumor.

In the case of MM, exemplary parameters to assess the extent of disease burden include such parameters as number of clonal plasma cells (e.g., >10% on bone marrow biopsy or in any quantity in a biopsy from other tissues; plasmacytoma), presence of monoclonal protein (paraprotein) in either serum or urine, evidence of end-organ damage felt related to the plasma cell disorder (e.g., hypercalcemia (corrected calcium >2.75 mmol/1); renal insufficiency attributable to myeloma; anemia (hemoglobin <10 g/dl); and/or bone lesions (lytic lesions or osteoporosis with compression fractures)).

In the case of DLBCL, exemplary parameters to assess the extent of disease burden include such parameters as cellular morphology (e.g., centroblastic, immunoblastic, and anaplastic cells), gene expression, miRNA expression and protein expression (e.g., expression of BCL2, BCL6, MUM1, LMO2, MYC, and p21).

In the case of leukemia, the extent of disease burden can be determined by assessment of residual leukemia in blood or bone marrow. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, for leukemia, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD$^-$, such that, in some cases, no leukemia cells are able to be detected in the subject using PCR or flow cytometry techniques.

In some embodiments, the methods and/or administration of an immunotherapy, such as a T cell therapy (e.g. CAR-expressing T cells) or a T cell-engaging therapy and/or inhibitor decrease(s) disease burden as compared with disease burden at a time immediately prior to the administration of the immunotherapy, e.g., T cell therapy and/or inhibitor.

In some aspects, administration of the immunotherapy, e.g. T cell therapy and/or inhibitor, may prevent an increase in disease burden, and this may be evidenced by no change in disease burden.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative therapy, such as one in which the subject receives immunotherapy, e.g. T cell therapy alone, in the absence of administration of the inhibitor. In some embodiments, disease burden is reduced to a greater extent or for a greater duration following the combination therapy of administration of the immunotherapy, e.g., T cell therapy, and the inhibitor, compared to the reduction that would be effected by administering each of the agent alone, e.g., administering the inhibitor to a subject having not received the immunotherapy, e.g. T cell therapy; or administering the immunotherapy, e.g. T cell therapy, to a subject having not received the inhibitor.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified. In some embodiments, exemplary parameters for determination include particular clinical outcomes indicative of amelioration or improvement in the disease or condition, e.g., tumor. Such parameters include: duration of disease control, including complete response (CR), partial response (PR) or stable disease (SD) (see, e.g., Response Evaluation Criteria In Solid Tumors (RECIST) guidelines), objective response rate (ORR), progression-free survival (PFS) and overall survival (OS). Specific thresholds for the parameters can be set to determine the efficacy of the method of combination therapy provided herein.

In some aspects, disease burden is measured or detected prior to administration of the immunotherapy, e.g. T cell therapy, following the administration of the immunotherapy, e.g. T cell therapy but prior to administration of the inhibitor following administration of the inhibitor but prior to the administration of the immunotherapy, e.g., T cell therapy, and/or following the administration of both the immunotherapy, e.g. T cell therapy and the inhibitor. In the context of multiple administration of one or more steps of the combination therapy, disease burden in some embodiments may be measured prior to or following administration of any of the steps, doses and/or cycles of administration, or at a time between administration of any of the steps, doses and/or cycles of administration.

In some embodiments, the burden is decreased by or by at least at or about 10, 20, 30, 40, 50, 60, 70, 80, 90, or 100 percent by the provided methods compared to immediately prior to the administration of the inhibitor and the immunotherapy, e.g. T cell therapy. In some embodiments, disease burden, tumor size, tumor volume, tumor mass, and/or tumor load or bulk is reduced following administration of the immunotherapy, e.g. T cell therapy and the inhibitor, by at least at or about 10, 20, 30, 40, 50, 60, 70, 80, 90% or more compared to that immediately prior to the administration of the immunotherapy, e.g. T cell therapy and/or the inhibitor.

In some embodiments, reduction of disease burden by the method comprises an induction in morphologic complete remission, for example, as assessed at 1 month, 2 months, 3 months, or more than 3 months, after administration of, e.g., initiation of, the combination therapy.

In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the method of combination therapy provided herein, is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the method of combination therapy, is less than about 80%, less than about 70%, less than about 60%, less than about 50%, less than about 40%, less than about 30%, less than about 20%, or less than about 10%.

V. ARTICLES OF MANUFACTURE AND KITS

Also provided are articles of manufacture containing an inhibitor of a protein tyrosine kinase other than an inhibitor of ITK and/or an inhibitor of one or more of BTK, TEC, BMX/ETK, RLK/TXK and/or ERBB4, e.g. the compound of Formula (II), and components for the immunotherapy, e.g., antibody or antigen binding fragment thereof or T cell therapy, e.g. engineered cells, and/or compositions thereof. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition.

The article of manufacture may include (a) a first container with a composition contained therein, wherein the composition includes the antibody or engineered cells used for the immunotherapy, e.g. T cell therapy; and (b) a second container with a composition contained therein, wherein the composition includes the second agent, such as an inhibitor of a protein tyrosine kinase other than an inhibitor of ITK and/or an inhibitor of one or more of BTK, TEC, BMX/ETK, RLK/TXK and/or ERBB4. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VI. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

VII. EXEMPLARY EMBODIMENTS

Among the provided embodiments are:

1. A method of treatment, the method comprising:
(a) administering, to a subject having a disease or condition, T cells that specifically recognize or specifically bind to an antigen associated with, or expressed or present on cells of, the disease or condition and/or a tag comprised by a therapeutic agent that specifically targets the disease or condition and has been or is to be administered to the subject; and (b) administering to the subject an inhibitor of a target protein tyrosine kinase, wherein the inhibitor does not inhibit ITK and/or inhibits ITK with a half-maximal inhibitory concentration ($IC_{50}$) of greater than or greater than about 1000 nM,
wherein the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the protein tyrosine kinase is not ordinarily expressed or is not suspected of being expressed in cells from which the disease or condition is derived.

2. A method of treatment, the method comprising administering, to a subject having a disease or condition, T cells that specifically recognize or specifically bind to an antigen associated with, or expressed or present on cells of, the disease or condition and/or a tag comprised by a therapeutic agent that specifically targets the disease or condition and has been or is to be administered to the subject, wherein:
the subject has been administered an inhibitor of a target protein tyrosine kinase, wherein the inhibitor does not inhibit ITK and/or inhibits ITK with a half-maximal inhibitory concentration ($IC_{50}$) of greater than or greater than about 1000 nM; and
the disease or condition (i) is not a B cell-derived disease or condition (ii) is not associated with expression of CD19, CD22, or CD20; (iii) does not express the protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the protein tyrosine kinase is not ordinarily expressed or is not suspected of being expressed in cells from which the disease or condition is derived.

3. A method of treatment, the method comprising administering, to a subject having a disease or condition, an inhibitor of a target protein tyrosine kinase, wherein the inhibitor does not inhibit ITK and/or inhibits ITK with a half-maximal inhibitory concentration ($IC_{50}$) of greater than or greater than about 1000 nM, wherein:
the subject has been administered T cells that specifically recognize or specifically bind to an antigen associated with, or expressed or present on cells of, the disease or condition and/or a tag comprised by a therapeutic agent that specifically targets the disease or condition and has been or is to be administered to the subject; and
the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or wherein the TEC family kinase is not ordinarily expressed or is not suspected of being expressed in cells from which the disease or condition is derived.

4. The method of any of embodiments 1-3, wherein the target protein tyrosine kinase is tyrosine kinase expressed in hepatocellular carcinoma (TEC), a resting lymphocyte kinase (RLK/TXK), a BMX/ETK, or an ERBB4

5. The method of any of embodiments 1-4, wherein the target protein tyrosine kinase is a TEC family kinase.

6. The method of any of embodiments 1-5, wherein the inhibitor is selected from the group consisting of the compound of Formula (II), ONO/GS-4059, Compound 30 or Compound 38,GDC-0834; RN-486; CGI-560; CGI-1764; HM-71224; CC-292; ONO-4059; CNX-774; and LFM-A13.

7. The method of any of embodiments 1-6, wherein:
the inhibitor is a selective inhibitor of the target protein tyrosine kinase; and/or the inhibitor inhibits the target protein tyrosine kinase with a half-maximal inhibitory concentration ($IC_{50}$) that is at least 10 or at least 100 times lower than that of the $IC_{50}$ of the inhibitor for any additional protein tyrosine kinase or TEC family kinase, and/or inhibits the target protein tyrosine kinase with an IC50 at least 2, at least 10 or at least 100 times lower than that the IC50 value of the inhibitor for both ITK and BTK; and/or
the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less 8. A method of treatment, the method comprising:
(1) administering, to a subject having a disease or condition, T cells that specifically recognize or specifically bind to an antigen associated with the disease or condition and/or a tag comprised by a therapeutic agent that specifically targets the disease or condition and has been or is to be administered to the subject; and
(2) administering to the subject an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4, wherein:
the inhibitor is a selective inhibitor of the target protein tyrosine kinase; and/or
the inhibitor inhibits the target protein tyrosine kinase with a half-maximal inhibitory concentration ($IC_{50}$) that is at least 10 or at least 100 times lower than that of the $IC_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or
the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

9. A method of treatment, the method comprising administering, to a subject having a disease or condition, T cells that specifically recognize or specifically bind to an antigen associated with the disease or condition and/or a tag comprised by a therapeutic agent that specifically targets the disease or condition and has been or is to be administered to the subject, said subject having been administered an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4, wherein:

the inhibitor is a selective inhibitor of the target protein tyrosine kinase; and/or the inhibitor inhibits the target protein tyrosine kinase with a half-maximal inhibitory concentration ($IC_{50}$) that is at least 10 or at least 100 times lower than that of the $IC_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

10. A method of treatment, the method comprising administering to a subject, having a disease or condition, an inhibitor of a target protein tyrosine kinase, which target protein tyrosine kinase is a tyrosine kinase expressed in hepatocellular carcinoma (TEC), a resting lymphocyte kinase (RLK/TXK), a BMX/ETK, or an ERBB4, said subject having been administered T cells that specifically recognize or specifically bind to an antigen associated with the disease or condition and/or a tag comprised by a therapeutic agent that specifically targets the disease or condition and has been or is to be administered to the subject, wherein: the inhibitor is a selective inhibitor of the target protein tyrosine kinase; and/or the inhibitor inhibits the target protein tyrosine kinase with a half-maximal inhibitory concentration ($IC_{50}$) that is at least 10 or at least 100 times lower than that of the $IC_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

11. The method of any of embodiments 8-10, wherein the disease or condition (i) is not a B cell-derived disease or condition (ii) is not associated with expression of CD19, CD22, or CD20; (iii) does not express the target protein tyrosine kinase, (iv) does not contain a form of the target protein tyrosine kinase that is sensitive to the inhibitor, (v) does not contain a kinase sensitive to the inhibitor and/or (vi) is not sensitive to inhibition by the inhibitor and/or wherein the subject or disease or condition is resistant or refractory to the inhibitor and/or to an inhibitor of BTK and/or the target kinase is not ordinarily expressed or is not suspected of being expressed in cells from which the disease or condition is derived.

12. The method of any of embodiments 4-11, wherein the target protein tyrosine kinase is a RLK/TXK.

13. The method of any of embodiments 4-12, wherein the target protein tyrosine kinase is a BMX/ETK and the inhibitor inhibits Bmx/Etk with a half-maximal inhibitory concentration ($IC_{50}$) that is at least 10 or at least 100 times lower than that of the $IC_{50}$ of the inhibitor for any other TEC family kinase and/or for ITK, and/or inhibits Bmx/Etk with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

14. The method of any of embodiments 4 and 7-13, wherein the target kinase is or comprises an ErbB4.

15. The method of any of embodiments 1-13, wherein the inhibitor comprises is a compound of formula (II):

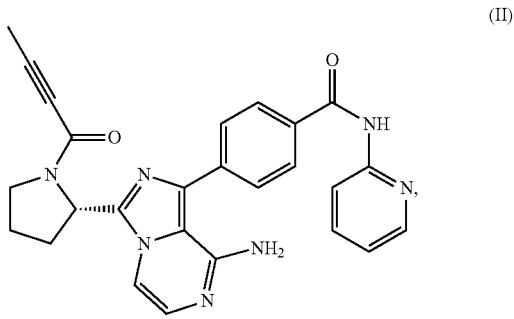 [SMILES: CC#CC(=O)N1CCC[C@H]1c1nc(-c2ccc(C(=O)Nc3ccccn3)cc2)c2c(N)nccn12]

or a pharmaceutically acceptable salt, solvate, hydrate, co-crystal, polymorph or prodrug thereof thereof.

16. The method of any of embodiments 1-15, wherein the inhibitor comprises the compound of Formula (II), or an enantiomer, pharmaceutically-acceptable salt, solvate, hydrate, co-crystal, polymorph or prodrug thereof or a pharmaceutical composition comprising any of the foregoing.

17. A method of treatment, the method comprising:

(1) administering, to a subject having a disease or condition, T cells comprising a recombinant antigen receptor that specifically binds to an antigen associated with the disease or condition and/or a tag comprised by a therapeutic agent that specifically targets the disease or condition and has been or is to be administered to the subject; and (2) administering to the subject a kinase inhibitor or a pharmaceutical composition comprising the inhibitor, wherein the inhibitor comprises the compound of Formula (II) comprises the compound of Formula (II), or an enantiomer, pharmaceutically-acceptable salt, solvate, hydrate, co-crystal, polymorph or prodrug thereof.

18. A method of treatment, the method comprising administering, to a subject having a disease or condition, T cells comprising a recombinant antigen receptor that specifically binds to an antigen associated with the disease or condition and/or a tag comprised by a therapeutic agent that specifically targets the disease or condition and has been or is to be administered to the subject, said subject having been administered a kinase inhibitor or a pharmaceutical composition comprising the inhibitor, wherein the inhibitor comprises the compound of Formula (II) or an enantiomer, pharmaceutically-acceptable salt, solvate, hydrate, co-crystal, polymorph or prodrug thereof.

19. A method of treatment, the method comprising administering, to a subject having a disease or condition, a kinase inhibitor or a pharmaceutical composition comprising the inhibitor, wherein the inhibitor comprises the compound of Formula (II), or an enantiomer, pharmaceutically-acceptable salt, solvate, hydrate, co-crystal, polymorph or prodrug thereof, said subject having been administered T cells comprising a recombinant antigen receptor that specifically binds to an antigen associated with the disease or condition and/or a tag comprised by a therapeutic agent that specifically targets the disease or condition and has been or is to be administered to the subject.

20. The method of any of embodiments 17-19, wherein the disease or condition is a cancer.

21. The method of any of embodiments 1-20, wherein:

(i) the subject and/or the disease or condition (a) is resistant to inhibition of Bruton's tyrosine kinase (BTK) and/or (b) comprises a population of cells that are resistant to inhibition by the inhibitor;

(ii) the subject and/or the disease or condition comprises a mutation or disruption in a nucleic acid encoding BTK, capable of reducing or preventing inhibition of the BTK by the inhibitor and/or by ibrutinib; and/or (iii) at the time of the administration in (1) and at the time of the administration in (2) the subject has relapsed following remission after treatment with, or been deemed refractory to treatment with the inhibitor and/or with a BTK inhibitor therapy.

22. The method of embodiment 21, wherein the population of cells is or comprises a population of B cells and/or does not comprise T cells.

23. The method of embodiment 21 or embodiment 22, wherein the mutation in the nucleic acid encoding BTK comprises a substitution at position C481, optionally C481S or C481R, and/or a substitution at position T474, optionally T474I or T474M.

24. The method of any of embodiments 1-23, wherein:
the target protein tyrosine kinase is not expressed by cells of the disease or condition, is not ordinarily expressed or is not suspected of being expressed in cells from which the disease or condition is derived, and/or
the disease or condition is not sensitive to the inhibitor; and/or
at least a plurality of the T cells express the target protein tyrosine kinase; and/or
the target protein tyrosine kinase is expressed in T cells.

25. The method of any of embodiments 1-24, wherein the disease or condition is a cancer not expressing a B cell antigen, a non-hematologic cancer, is not a B cell malignancy, is not a B cell leukemia, or is a solid tumor.

26. The method of any of embodiments 1-25, wherein the disease or condition is a cancer selected from the group consisting of sarcomas, carcinomas, lymphomas, non-Hodgkin lymphomas (NHLs), diffuse large B cell lymphoma (DLBCL), leukemia, CLL, ALL, AML and myeloma.

27. The method of any of embodiments 1-26, wherein the disease or condition is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

28. The method of any of embodiments 1-27, wherein the T cells recognize or target an antigen selected from ROR1, B cell maturation antigen (BCMA), tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Fetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, ROR1, TAG72, VEGF-$R^2$, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, and a pathogen-specific antigen.

29. The method of any of embodiments 1-28, wherein:
the antigen is not a B cell antigen; and/or
the antigen is not a B cell antigen selected from the group consisting of CD19, CD20, CD22, and ROR1.

30. The method of embodiment 29, wherein:
the antigen is not a B cell antigen selected from the group consisting of CD19, CD20, CD22, and ROR1; and/or
the disease or condition does not express a B cell antigen selected from the group consisting of CD19, CD20, CD22 and ROR1 and/or kappa light chain.

31. The method of any of embodiments 1-30, wherein the T cells comprise tumor infiltrating lymphocytes (TILs) or comprises genetically engineered T cells expressing a recombinant receptor that specifically binds to the antigen.

32. The method of embodiment 31, wherein the T cells comprise genetically engineered T cells expressing a recombinant receptor that specifically binds to the antigen or the tag, which receptor optionally is a chimeric antigen receptor.

33. The method of embodiment 31 or embodiment 32, wherein the recombinant receptor is a transgenic T cell receptor (TCR) or a functional non-T cell receptor.

34. The method of any of embodiments 31-33, wherein the recombinant receptor is a chimeric receptor, which optionally is a chimeric antigen receptor (CAR).

35. The method of embodiment 34, wherein the chimeric antigen receptor (CAR) comprises an extracellular antigen-recognition domain that specifically binds to the antigen and an intracellular signaling domain comprising an ITAM.

36. The method of embodiment 35, wherein the intracellular signaling domain comprises an intracellular domain of a CD3-zeta (CD3) chain.

37. The method of embodiment 35 or embodiment 36, wherein the chimeric antigen receptor (CAR) further comprises a costimulatory signaling region.

38. The method of embodiment 37, wherein the costimulatory signaling region comprises a signaling domain of CD28 or 4-1BB.

39. The method of embodiment 37 or embodiment 38, wherein the costimulatory domain is a domain of CD28.

40. The method of any of embodiments 1-39, wherein the inhibitor is a small molecule, peptide, protein, antibody or antigen-binding fragment thereof, an antibody mimetic, an aptamer, or a nucleic acid molecule.

41. The method of any of embodiments 1-40, wherein the inhibitor irreversibly reduces or eliminates the activation of the target protein tyrosine kinase, specifically binds to a binding site in the active site of the target protein tyrosine kinase comprising an amino acid residue corresponding to residue C481 in the sequence set forth in SEQ ID NO:18, and/or reduces or eliminates autophosphorylation activity of the target protein tyrosine kinase.

42. The method of any of embodiments 1-41, wherein the inhibitor is not ibrutinib.

43. The method of any of embodiments 1-41, wherein the inhibitor is not the compound of Formula (II).

44. The method of any of embodiments 1-41, wherein the inhibitor is not GDC-0834; RN-486; CGI-560; CGI-1764; HM-71224; CC-292; ONO-4059; CNX-774; and LFM-A13.

45. The method of any of embodiments 1, 2-8, 10-17 and 19-44, wherein the inhibitor is administered concurrently with or subsequently to initiation of administration of the composition comprising the T cells.

46. The method of any of embodiments 1, 2-8, 10-17 and 19-45, wherein the inhibitor is administered subsequently to initiation of administration of the T cells.

47. The method of embodiment 45 or embodiment 46, wherein the inhibitor is administered within, or within about, 1 hour, 2 hours, 6 hours, 12 hours, 24 hours, 48 hours, 72 hours, 96 hours or 1 week of the initiation of the administration of the T cells.

48. The method of any of embodiments 45-47, wherein the inhibitor is administered at a time in which:
the number of administered T cells detectable in the blood from the subject is decreased compared to in the subject at a preceding time point after initiation of the administration of the T cells;
the number of administered T cells detectable in the blood is less than or less than about 1.5-fold, 2-fold, 3-fold, 4-fold, 5-fold, 10-fold, 50-fold or 100-fold or less the peak or maximum number of the cells of the T cell therapy detectable in the blood of the subject after initiation of administration of the administration of the T cells; and/or
at a time after a peak or maximum level of the administered T cells are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject.

49. The method of embodiment 48, wherein the increase or decrease is by greater than or greater than about 1.2-fold, 1.5-fold, 2-fold, 3-fold, 4-fold, 5-fold, 10-fold or more.

50. The method of any of embodiments 1-49, wherein the inhibitor is administered for a time period up to 2 days, up to 7 days, up to 14 days, up to 21 days, up to one month, up to two months, up to three months, up to 6 months or up to 1 year after initiation of the administration of the administration of the T cells.

51. The method of any of embodiments 1, 2-8, 10-17 and 19-50, wherein the inhibitor is administered up to 3 months after initiation of the administration of the T cells.

52. The method of any of embodiments 1-51, wherein the administration of the inhibitor is continued, from at least after initiation of administration of the T cells, until:
the number of cells of or derived from the T cells administered detectable in the blood from the subject is increased compared to in the subject at a preceding time point just prior to administration of the inhibitor or compared to a preceding time point after administration of the T-cell therapy;
the number of cells of or derived from the T cells detectable in the blood is within 2.0-fold (greater or less) the peak or maximum number observed in the blood of the subject after initiation of administration of the T cells;
the number of cells of the T cells detectable in the blood from the subject is greater than or greater than about 10%, 15%, 20%, 30%, 40%, 50%, or 60% total peripheral blood mononuclear cells (PBMCs) in the blood of the subject; and/or
the subject exhibits a reduction in tumor burden as compared to tumor burden at a time immediately prior to the administration of the T cells or at a time immediately prior to the administration of the inhibitor; and/or
the subject exhibits complete or clinical remission.

53. The method of any of embodiments 1-52, wherein the inhibitor is administered orally, subcutaneously or intravenously.

54. The method of embodiment 53, wherein the inhibitor is administered orally.

55. The method of any of embodiments 1-54, wherein the inhibitor is administered six times daily, five times daily, four times daily, three times daily, twice daily, once daily, every other day, three times a week or at least once a week.

56. The method of embodiment 55, wherein the inhibitor is administered once daily or twice a day.

57. The method of any of embodiments 1-56, wherein the inhibitor is administered at a total daily dosage amount of at least or at least about 50 mg/day, 100 mg/day, 150 mg/day, 175 mg/day, 200 mg/day, 250 mg/day, 300 mg/day, 350 mg/day, 400 mg/day, 450 mg/day, 500 mg/day, 600 mg/day, 700 mg/day, 800 mg/day or more.

58. The method of any of embodiments 1-57, wherein the inhibitor is administered in an amount less than or about less than or about or 420 mg per day.

59. The method of any of embodiments 1-58, wherein the administered T cells comprise T cells that are CD4+ or CD8+.

60. The method of any of embodiments 1-59, wherein the administered T cells comprise cells that are autologous to the subject.

61. The method of any of embodiments 1-60, wherein the administered T cells comprise T cells that are allogeneic to the subject.

62. The method of any of embodiments 1-61, wherein the administered T cells comprise administration of a dose comprising a number of cells between or between about $5\times10^5$ cells/kg body weight of the subject and $1\times10^7$ cells/kg, $0.5\times10^6$ cells/kg and $5\times10^6$ cells/kg, between or between about $0.5\times10^6$ cells/kg and $3\times10^6$ cells/kg, between or between about $0.5\times10^6$ cells/kg and $2\times10^6$ cells/kg, between or between about $0.5\times10^6$ cells/kg and $1\times10^6$ cell/kg, between or between about $1.0\times10^6$ cells/kg body weight of the subject and $5\times10^6$ cells/kg, between or between about $1.0\times10^6$ cells/kg and $3\times10^6$ cells/kg, between or between about $1.0\times10^6$ cells/kg and $2\times10^6$ cells/kg, between or between about $2.0\times10^6$ cells/kg body weight of the subject and $5\times10^6$ cells/kg, between or between about $2.0\times10^6$ cells/kg and $3\times10^6$ cells/kg, or between or between about $3.0\times10^6$ cells/kg body weight of the subject and $5\times10^6$ cells/kg, each inclusive.

63. The method of any of embodiments 1-62, wherein the dose of cells administered is less than the dose in a method in which the administered T cells are administered without administering the inhibitor.

64. The method of embodiment 63, wherein the dose is at least 1.5-fold, 2-fold, 3-fold, 4-fold, 5-fold or 10-fold less.

65. The method of any of embodiments 1-64, wherein the T cells are administered in a single dose, which optionally is a single pharmaceutical composition comprising the cells.

66. The method of any of embodiments 1-65, wherein the T cells are administered as a split dose, wherein the cells of a single dose are administered in a plurality of compositions, collectively comprising the cells of the dose, over a period of no more than three days and/or the method further comprises administering one or more additional doses of the T cells.

67. The method of any of embodiments 1-66, wherein the method further comprises administering a lymphodepleting chemotherapy prior to administration of the T cells and/or wherein the subject has received a lymphodepleting chemotherapy prior to administration of the T cells.

68. The method of embodiment 67, wherein the lymphodepleting chemotherapy comprises administering fludarabine and/or cyclophosphamide to the subject.

69. The method of any of embodiments 1-68, further comprising:
administering an immune modulatory agent to the subject, wherein the administration of the cells and the administration of the immune modulatory agent are carried out simultaneously, separately or in a single composition, or sequentially, in either order.

70. The method of embodiment 69, wherein the immune modulatory agent is capable of inhibiting or blocking a function of a molecule, or signaling pathway involving said molecule, wherein the molecule is an immune-inhibitory molecule and/or wherein the molecule is an immune checkpoint molecule.

71. The method of embodiment 70, wherein the immune checkpoint molecule or pathway is selected from the group consisting of PD-1, PD-L1, PD-L2, CTLA-4, LAG-3, TIM3, VISTA, adenosine 2A Receptor (A2AR), or adenosine or a pathway involving any of the foregoing.

72. The method of any of embodiments 69-71, wherein the immune modulatory agent is or comprises an antibody, which optionally is an antibody fragment, a single-chain antibody, a multispecific antibody, or an immunoconjugate.

73. The method of embodiment 72, wherein:
the antibody specifically binds to the immune checkpoint molecule or a ligand or receptor thereof; and/or
the antibody is capable of blocking or impairing the interaction between the immune checkpoint molecule and a ligand or receptor thereof.

74. The method of any of embodiments 1-73, wherein the administered T cells exhibit increased or prolonged expansion and/or persistence in the subject as compared to a method in which the administered T cells are administered to the subject in the absence of the inhibitor.

75. The method of any of embodiments 1-74, wherein the method reduces tumor burden to a greater degree and/or for a greater period of time as compared to the reduction that would be observed with a comparable method in which the administered T cells are administered to the subject in the absence of the inhibitor.

76. A combination, comprising:
genetically engineered T cells expressing a recombinant receptor that binds to an antigen other than a B cell antigen or other than a B cell antigen selected from the group consisting of CD19, CD20, CD22 and ROR1, and
an inhibitor of a target protein tyrosine kinase, wherein the inhibitor does not inhibit ITK and/or inhibits ITK with a half-maximal inhibitory concentration ($IC_{50}$) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

77. The combination of embodiment 76, wherein the antigen is selected from among Her2, L1-CAM, mesothelin, CEA, hepatitis B surface antigen, anti-folate receptor, CD23, CD24, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, Lewis Y, L1-cell adhesion molecule (L1-CAM), Melanoma-associated antigen (MAGEMAGE-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Fetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, TAG72, VEGF-$R^2$, carcinoembryonic antigen (CEA), prostate specific antigen, PSMA, estrogen receptor, progesterone receptor, ephrinB2, CD123, c-Met, GD-2 O-acetylated GD2 (OGD2), CE7, Wilms Tumor 1 (WT-1), a cyclin, cyclin A2, CCL-1, CD138, and a pathogen-specific antigen.

78. The combination of embodiment 76 or embodiment 77, wherein the antigen is a pathogen-specific antigen, which is a viral antigen, bacterial antigen or parasitic antigen.

79. The combination of any of embodiments 76-78 wherein the recombinant receptor is a transgenic T cell receptor (TCR) or a functional non-T cell receptor.

80. The combination of any of embodiments 76-79, wherein the recombinant receptor is a chimeric receptor, which optionally is a chimeric antigen receptor (CAR).

81. The combination of any of embodiments 76-80, wherein:
the inhibitor is a selective inhibitor of the target protein tyrosine kinase; and/or
the inhibitor inhibits the target protein tyrosine kinase with a half-maximal inhibitory concentration ($IC_{50}$) that is at least 10 or at least 100 times lower than that of the $IC_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or
the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

82. The combination of any of embodiments 76-81, wherein the inhibitor is a small molecule, peptide, protein, antibody or antigen-binding fragment thereof, an antibody mimetic, an aptamer, or a nucleic acid molecule.

83. The combination of any of embodiments 76-82, wherein the inhibitor is selected from the group consisting of the compound of Formula (II), ONO/GS-4059, Compound 30 or Compound 38,GDC-0834; RN-486; CGI-560; CGI-1764; HM-71224; CC-292; ONO-4059; CNX-774; and LFM-A13.

84. The combination of any of embodiments 76-83, wherein the inhibitor comprises the compound of Formula (II), or an enantiomer, pharmaceutically-acceptable salt, solvate, hydrate, co-crystal, polymorph or prodrug thereof or a pharmaceutical composition comprising any of the foregoing.

85. The combination of any of embodiments 76-84 that is formulated in the same composition.

86. The combination of any of embodiments 76-84 that is formulated in separate compositions.

87. A kit, comprising the combination of any of embodiments 76-86 and instructions for administering, to a subject for treating a disease or condition, optionally a cancer, the genetically engineered cells and the inhibitor.

88. A kit, comprising:
a composition comprising a therapeutically effective amount of genetically engineered T cells expressing a recombinant receptor that binds to an antigen other than a B cell antigen or other than a B cell antigen selected from the group consisting of CD19, CD20, CD22 and ROR1; and instructions for administering, to a subject for treating a cancer, the genetically engineered cells in a combined therapy with an inhibitor of a target protein tyrosine kinase, wherein the inhibitor does not inhibit ITK and/or inhibits ITK with a half-maximal inhibitory concentration ($IC_{50}$) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

89. A kit, comprising:

a composition comprising a therapeutically effective amount of an inhibitor of a target protein tyrosine kinase, wherein the inhibitor does not inhibit ITK and/or inhibits ITK with a half-maximal inhibitory concentration ($IC_{50}$) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4; and instructions for administering, to a subject for treating a disease or condition, optionally a cancer, the inhibitor in a combined therapy with genetically engineered T cells, said T cells expressing a recombinant receptor that binds to an antigen other than a B cell antigen or other than a B cell antigen selected from the group consisting of CD19, CD20, CD22 and ROR1.

90. The kit of any of embodiments 87-89, wherein the cancer is not a cancer expressing a B cell antigen, is a non-hematologic cancer, is not a B cell malignancy, is not a B cell leukemia, or is a solid tumor.

91. The kit of any of embodiments 87-89, wherein the cancer is a sarcoma, a carcinoma or a lymphoma, optionally a non-Hodgkin lymphomas (NHLs), diffuse large B cell lymphoma (DLBCL), leukemia, CLL, ALL, AML and myeloma.

92. The kit of any of embodiments 87-91, wherein the cancer is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

93. The kit of any of embodiments 87-92, wherein (i) the subject and/or the disease or condition (a) is resistant to inhibition of Bruton's tyrosine kinase (BTK) and/or (b) comprises a population of cells that are resistant to inhibition by the inhibitor;

(ii) the subject and/or the disease or condition comprises a mutation or disruption in a nucleic acid encoding BTK, capable of reducing or preventing inhibition of the BTK by the inhibitor and/or by ibrutinib; and/or (iii) at the time of the administering the subject has relapsed following remission after treatment with, or been deemed refractory to treatment with the inhibitor and/or with a BTK inhibitor therapy.

94. The method of embodiment 93, wherein the population of cells is or comprises a population of B cells and/or does not comprise T cells.

95. The kit of embodiment 93 or embodiment 94, wherein the mutation in the nucleic acid encoding BTK comprises a substitution at position C481, optionally C481S or C481R, and/or a substitution at position T474, optionally T474I or T474M.

96. The kit of any of embodiments 87-95, wherein the antigen is selected from among Her2, L1-CAM, mesothelin, CEA, hepatitis B surface antigen, anti-folate receptor, CD23, CD24, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, Lewis Y, L1-cell adhesion molecule (L1-CAM), Melanoma-associated antigen (MAGEMAGE-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, TAG72, VEGF-$R^2$, carcinoembryonic antigen (CEA), prostate specific antigen, PSMA, estrogen receptor, progesterone receptor, ephrinB2, CD123, c-Met, GD-2 O-acetylated GD2 (OGD2), CE7, Wilms Tumor 1 (WT-1), a cyclin, cyclin A2, CCL-1, CD138, and a pathogen-specific antigen.

97. The kit of any of embodiments 87-96 wherein the antigen is a pathogen-specific antigen, which is a viral antigen, bacterial antigen or parasitic antigen.

98. The kit of any of embodiments 87-97, wherein the recombinant receptor is a transgenic T cell receptor (TCR) or a functional non-T cell receptor.

99. The kit of any of embodiments 87-98, wherein the recombinant receptor is a chimeric receptor, which optionally is a chimeric antigen receptor (CAR).

100. The kit of any of embodiments 87-99, wherein:

the inhibitor is a selective inhibitor of the target protein tyrosine kinase; and/or the inhibitor inhibits the target protein tyrosine kinase with a half-maximal inhibitory concentration ($IC_{50}$) that is at least 10 or at least 100 times lower than that of the $IC_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration ($IC_{50}$) of less than or less than about 1000 nM, 900 nM, 800 nM, 600 nM, 500 nM, 400 nM, 300 nM, 200 nM, 100 nM or less.

101. The kit of any of embodiments 87-100, wherein the inhibitor is a small molecule, peptide, protein, antibody or antigen-binding fragment thereof, an antibody mimetic, an aptamer, or a nucleic acid molecule.

102. The kit of any of embodiments 87-101, wherein the inhibitor is selected from the group consisting of the compound of Formula (II), ONO/GS-4059, Compound 30 or Compound 38,GDC-0834; RN-486; CGI-560; CGI-1764; HM-71224; CC-292; ONO-4059; CNX-774; and LFM-A13.

103. The kit of any of embodiments 87-102, wherein the inhibitor comprises the compound of Formula (II), or an enantiomer, pharmaceutically-acceptable salt, solvate, hydrate, co-crystal, polymorph or prodrug thereof or a pharmaceutical composition comprising any of the foregoing.

104. The kit of any of embodiments 87-103, wherein the instructions are for administering the inhibitor concurrently with or subsequently to initiation of administration of the composition comprising the T cells.

105. The kit of any of embodiments 87-104, wherein the instructions are for administering the inhibitor subsequently to initiation of administration of the T cells.

106. The kit of embodiment 104 or embodiment 105, wherein the instructions are for administering the inhibitor within, or within about, 1 hour, 2 hours, 6 hours, 12 hours, 24 hours, 48 hours, 72 hours, 96 hours or 1 week of the initiation of the administration of the T cells.

107. The kit of any of embodiments 104-106, wherein instructions are for administering the inhibitor at a time in which:

the number of cells of the T cell therapy detectable in the blood from the subject is decreased compared to in the subject at a preceding time point after initiation of the administration of the T cells;

the number of cells of the T cell therapy detectable in the blood is less than or less than about 1.5-fold, 2-fold, 3-fold, 4-fold, 5-fold, 10-fold, 50-fold or 100-fold or less the peak or maximum number of the cells of the T cell therapy detectable in the blood of the subject after initiation of administration of the administration of the T cells; and/or at a time after a peak or maximum level of the cells of the T cell therapy are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject.

108. The kit of embodiment 107, wherein the increase or decrease is by greater than or greater than about 1.2-fold, 1.5-fold, 2-fold, 3-fold, 4-fold, 5-fold, 10-fold or more.

109. The kit of any of embodiments 87-108, wherein the instructions are for administering the inhibitor for a time period up to 2 days, up to 7 days, up to 14 days, up to 21 days, up to one month, up to two months, up to three months, up to 6 months or up to 1 year after initiation of the administration of the administration of the T cells.

110. The kit of any of embodiments 87-109, wherein the instructions are for further administering the inhibitor from at least after initiation of administration of the T cells, until:

the number of cells of or derived from the T cells administered detectable in the blood from the subject is increased compared to in the subject at a preceding time point just prior to administration of the inhibitor or compared to a preceding time point after administration of the T-cell therapy;

the number of cells of or derived from the T cells detectable in the blood is within 2.0-fold (greater or less) the peak or maximum number observed in the blood of the subject after initiation of administration of the T cells;

the number of cells of the T cells detectable in the blood from the subject is greater than or greater than about 10%, 15%, 20%, 30%, 40%, 50%, or 60% total peripheral blood mononuclear cells (PBMCs) in the blood of the subject; and/or the subject exhibits a reduction in tumor burden as compared to tumor burden at a time immediately prior to the administration of the T cells or at a time immediately prior to the administration of the inhibitor; and/or the subject exhibits complete or clinical remission.

111. The kit of any of embodiments 87-110, wherein the genetically engineered T cells comprises cells that are autologous to the subject.

112. The kit of any of embodiments 87-111, wherein the genetically engineered T cells comprises T cells that are allogeneic to the subject.

113. A method of engineering immune cells expressing a recombinant receptor, comprising:

contacting a population of cells comprising T cells with an inhibitor of a target protein tyrosine kinase, wherein the inhibitor does not inhibit ITK and/or inhibits ITK with a half-maximal inhibitory concentration (IC$_{50}$) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4; and introducing a nucleic acid encoding a recombinant receptor into the population of T cells under conditions such that the recombinant receptor is expressed.

114. The method of embodiment 113, wherein the population of cells is or comprises T cells, optionally CD4+ or CD8+.

115. The method of embodiment 113 or embodiment 114, wherein the population of cells are isolated from a subject, optionally a human subject.

116. The method of any of embodiments 113-115, wherein the contacting occurs prior to and/or during the introducing.

117. A method of producing genetically engineered T cells, comprising introducing a nucleic acid molecule encoding a recombinant receptor into a primary T cell, wherein the T cells is from a subject having been administered an inhibitor of a target protein tyrosine kinase, wherein the inhibitor does not inhibit ITK and/or inhibits ITK with a half-maximal inhibitory concentration (IC$_{50}$) of greater than or greater than about 1000 nM and/or the target protein tyrosine kinase is a tyrosine kinase expressed in hepatocellular carcinoma (TEC), a resting lymphocyte kinase (RLK/TXK), a BMX/ETK, or an ERBB4.

118. The method of embodiment 117, wherein the subject has been administered the inhibitor no more than 30 days, 20 days, 10 days, 9 days, 8 days, 7 days, 6 days, 5 days, 4 days, 3 days, 2 days, or 1 day prior to introducing the nucleic acid molecule.

119. The method of any of embodiments 113-118, wherein:

the inhibitor is a selective inhibitor of the target protein tyrosine kinase; and/or the inhibitor inhibits the target protein tyrosine kinase with a half-maximal inhibitory concentration (IC$_{50}$) that is at least 10 or at least 100 times lower than that of the IC$_{50}$ of the inhibitor for any protein tyrosine kinase or TEC family kinase distinct from the target protein tyrosine kinase, and/or inhibits the target protein tyrosine kinase with an IC50 at least 2, at least 10 or at least 100 times lower than that the IC50 value of the inhibitor for both ITK and BTK; and/or the inhibitor inhibits the target protein tyrosine kinase with a half-maximal inhibitory concentration (IC$_{50}$) of less than or less than about 1000 nM, 900 nM, 800 nM, 600 nM, 500 nM, 400 nM, 300 nM, 200 nM, 100 nM or less.

120. The method of any of embodiments 113-119, wherein the inhibitor is a small molecule, peptide, protein, antibody or antigen-binding fragment thereof, an antibody mimetic, an aptamer, or a nucleic acid molecule.

121. The method of any of embodiments 113-120, wherein the inhibitor is selected from the group consisting of the compound of Formula (II), ONO/GS-4059, Compound 30 or Compound 38,GDC-0834; RN-486; CGI-560; CGI-1764; HM-71224; CC-292; ONO-4059; CNX-774; and LFM-A13.

122. The method of any of embodiments 113-121, wherein the inhibitor comprises the compound of Formula (II), or an enantiomer, pharmaceutically-acceptable salt, solvate, hydrate, co-crystal, polymorph or prodrug thereof or a pharmaceutical composition comprising any of the foregoing.

123. The method of any of embodiments 113-122, wherein the T cells comprise CD4+ or CD8+ cells.

VIII. EXAMPLES

The following examples are included for illustrative purposes only and are not intended to limit the scope of the invention.

Example 1: Assessment of CAR-Expressing T Cell Phenotype and Function in the Presence of an Inhibitor of a TEC Family Properties of CAR-expressing T cells in the presence of an inhibitor of a TEC family kinase, ibrutinib or the compound of Formula (II), were assessed in in vitro studies.

To generate CAR-expressing T cells, T cells were isolated by immunoaffinity-based enrichment from three healthy human donor subjects, and cells from each donor were activated and transduced with a viral vector encoding an anti-CD19 CAR. The CAR contained an anti-CD19 scFv, an Ig-derived spacer, a human CD28-derived transmembrane domain, a human 4-1BB-derived intracellular signaling domain and a human CD3 zeta-derived signaling domain. The nucleic acid construct encoding the CAR also included a truncated EGFR (tEGFR) sequence for use as a transduction marker, separated from the CAR sequence by a self-cleaving T2A sequence.

CAR-expressing CD4+ and CD8+ cells were mixed 1:1 for each donor, individually, and the pooled cells for each donor assessed in vitro under various conditions.

A. Cytolytic Activity

CAR T cells generated as described above were plated in triplicate on Poly-D-Lysine plates and then co-cultured with ibrutinib-resistant, CD19-expressing target cells (K562 cells transduced to express CD19, K562-CD19) at an effector to target (E:T) ratio of 2.5:1. The targets cells were labeled with NucLight Red (NLR) to permit tracking of target cells by microscopy. Ibrutinib was added to the cultures at concentrations of 5000, 500, 50, 5 and 0.5 nM (reflecting a dosage range covering doses observed to be supraphysiologic (500 nM) and Cmax (227 nM)). The compound of Formula (II) was added to the cultures at concentrations of 5000, 500, 50, 5 and 0.5 nm (reflecting a dosage range covering doses observed to be supraphysiologic (5000 nM) and $C_{max}$ (1.8 µM)). CAR-T cells incubated in the presence of target cells in the absence of the inhibitor were used as an "untreated" control. Cytolytic activity was assessed by measuring the loss of viable target cells over a period of four days, as determined by red fluorescent signal (using the IncuCyte® Live Cell Analysis System, Essen Bioscience). Percent (%) of target killing was assessed by measuring area under the curve (AUC) for normalized target cell count over time and normalizing the inverse AUC (1/AUC) values by defining a 0% value (target cells alone) and a 100% value (CAR+ T cells co-cultured with target cells in vehicle control).

Figure 1A:
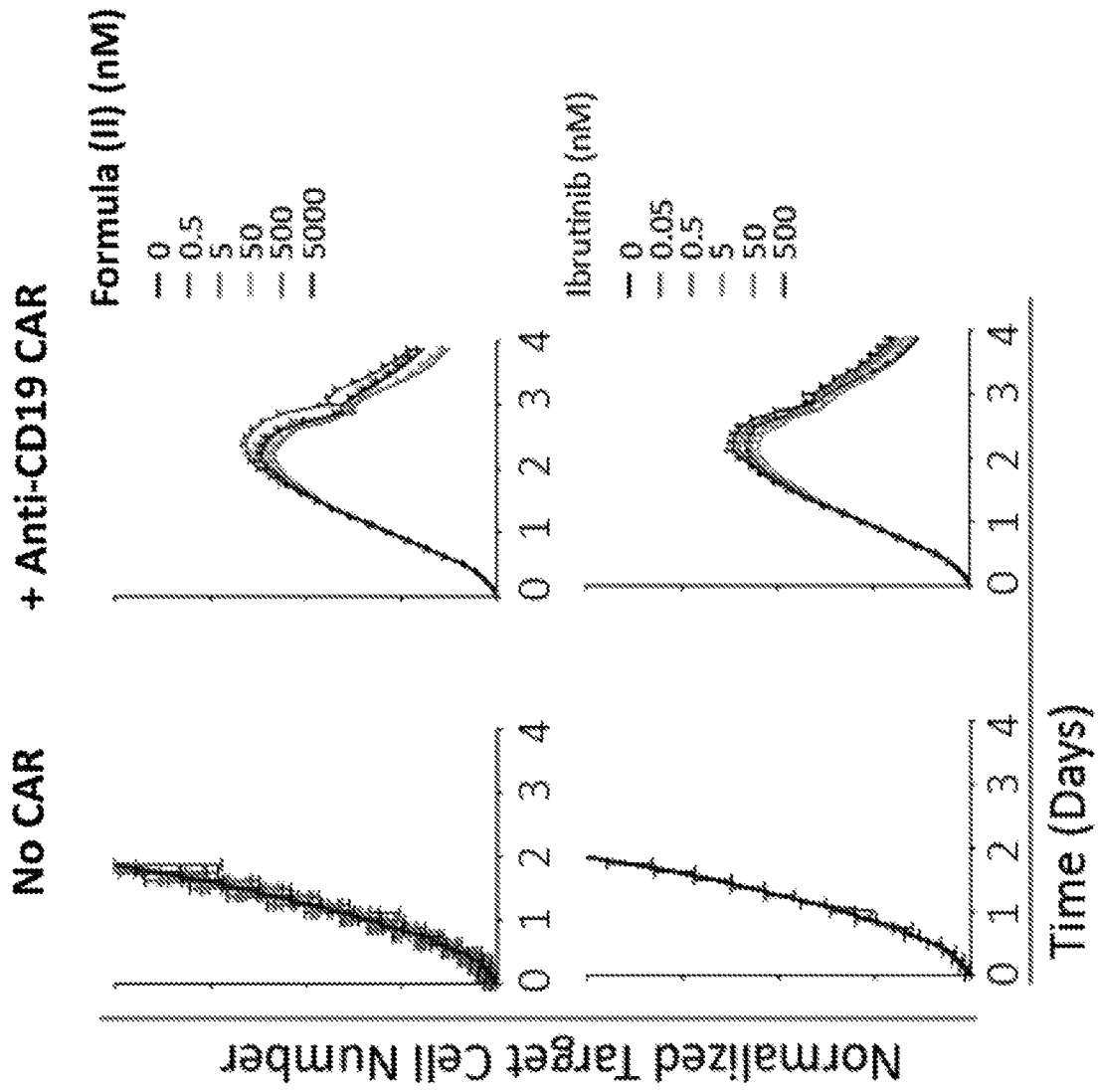
FIG. 1A shows graphs of normalized target cell numbers assessing target-specific cytolytic activity in triplicate wells co-cultured with CAR T cells with ibrutinib or the compound of Formula (II) (mean±SEM).
Figure 1B:
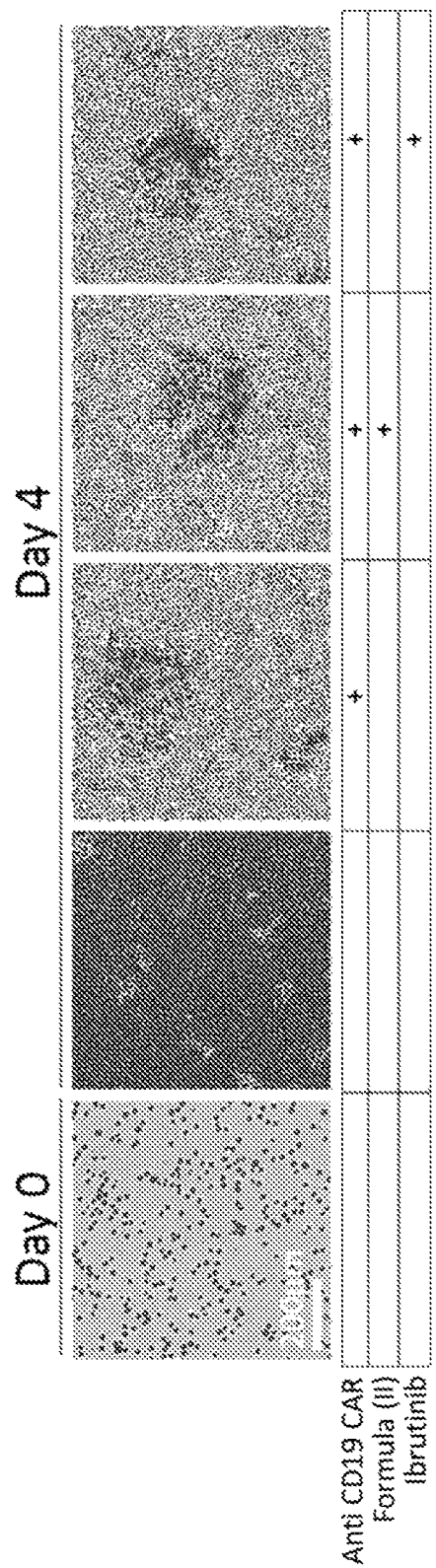
FIG. 1B shows a representative image of target cells (NucLight Red K562.CD19 cells) co-cultured with CAR T cells at an effector to target ratio (E:T) of 2.5:1 at the start and end of the cytotoxic assay.

As shown by microscopy, after an initial period of target cell growth, anti-CD19 CAR T cells from all donors were able to reduce the target cell number over a period of four days, thus demonstrating effective killing in the assay (FIG. 1A). A representative image of target cells co-cultured with CAR T cells at the start and end of the cytotoxic assay is shown in FIG. 1B.

Figures 1C, 1D:
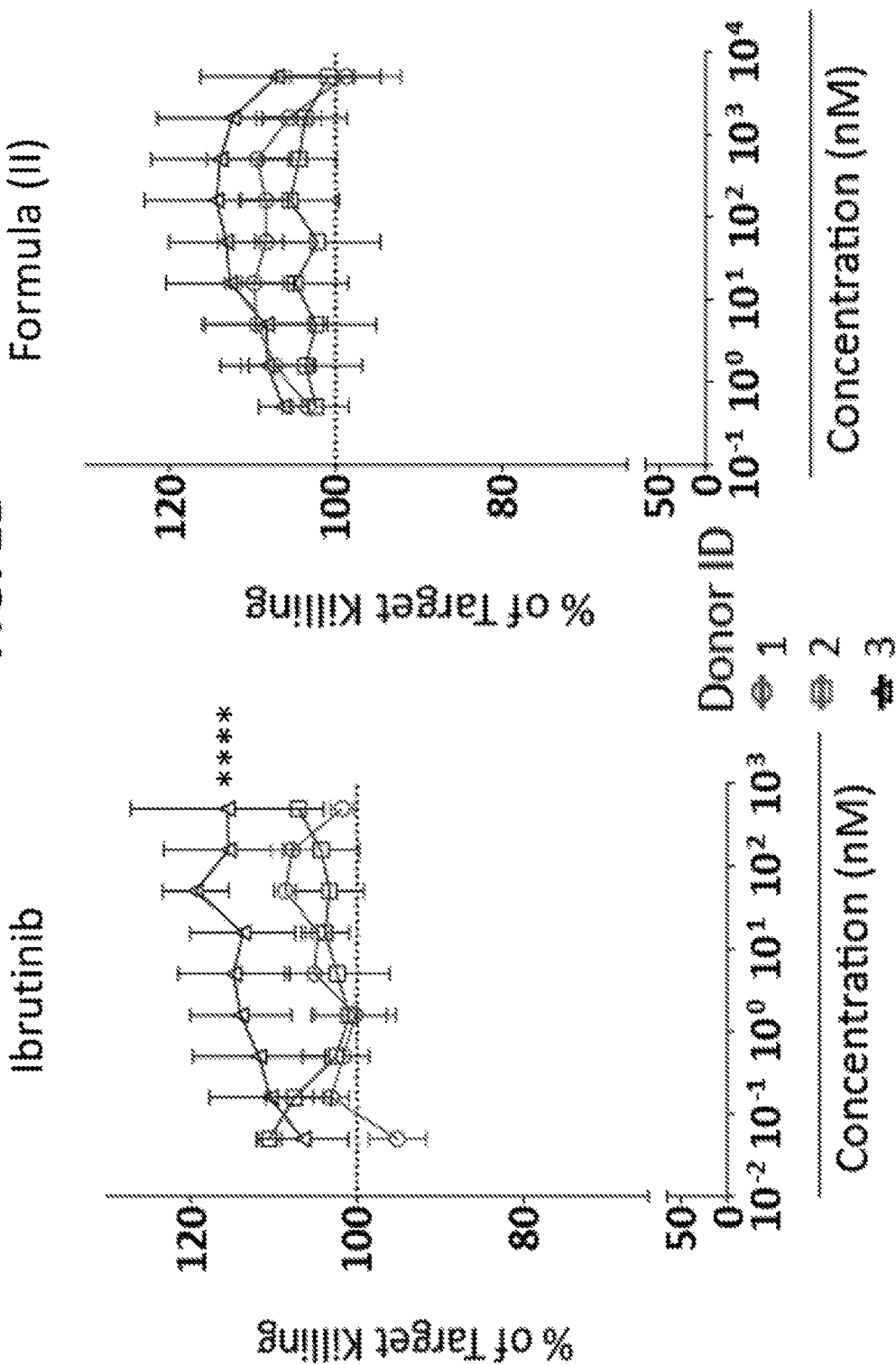
FIG. 1C and FIG. 1D shows the results of a study assessing target-specific cytolytic activity of anti-CD19 CAR T cells in the presence or absence of ibrutinib or the compound of Formula (II), respectively. The graphs show data from three independent donors and are normalized to untreated control (100%). The mean±SEM are depicted and statistically significant differences are indicated $P<0.00001$ (****).

Target-specific cytolytic activity by CAR-T cells against target cells, in the presence or absence of a range of doses of ibrutinib or the compound of Formula (II), was normalized to results for untreated controls. As shown in FIG. 1C, for two donors, ibrutinib did not significantly impact cytolytic activity, even when the concentrations were increased to supra-physiological levels (500 nM). The addition of ibrutinib, at all concentrations tested during the co-culture, did not inhibit the cytolytic function of the anti-CD19 CAR T cells. However, a modestly increased target cell killing was observed for one donor treated with ibrutinib (P<0.0001) (FIG. 1C). FIG. 1D also shows that similar results were observed for cells from each of the same three donors when treated with the compound of Formula (II) at concentrations from 50 to 5000 nM, a range including a dose observed to be supraphysiologic (5000 nM) and an observed Cmax (1.8 µM). Thus, both inhibitors were observed to have no negative impact on cytolytic function of CAR-T cells at dose ranges spanning Cmax or supraphysiologic doses assessed.

B. Expression of CAR-T Cell Surface Makers.

To assess various phenotypic markers of anti-CD19 CAR T cells cultured in the presence of ibrutinib or the compound of Formula (II), a panel of activation markers on CAR+, CD4+ and CD8+ cells (from three donors) were tracked over 4 days following stimulation with irradiated K562 target cells expressing the CD19 cognate antigen. CAR-T cells generated as described above were plated at 100,000 cells/well on 96 well Poly-D-Lysine coated plates. Irradiated K562-CD19 target cells were added at an effector to target ratio of 2.5:1. Cells were cultured for up to 4 days in the absence of inhibitor, or in the presence ibrutinib (concentrations of 5000, 500, 50, 5 and 0.5 nM) or in the presence of the compound of Formula (II) (concentrations 5000, 1582, 500, 158 and 50 nM), for the duration of the culture. Cells were harvested at 1, 2, 3, and 4 days, and were analyzed by flow cytometry for T cell activation and differentiation surface markers CD69, CD107a, PD-1, CD25, CD38, CD39, CD95, CD62L, CCR7, CD45R$^o$ and for EGFRt (a surrogate marker for CAR-transduced cells).

Figure 2B:
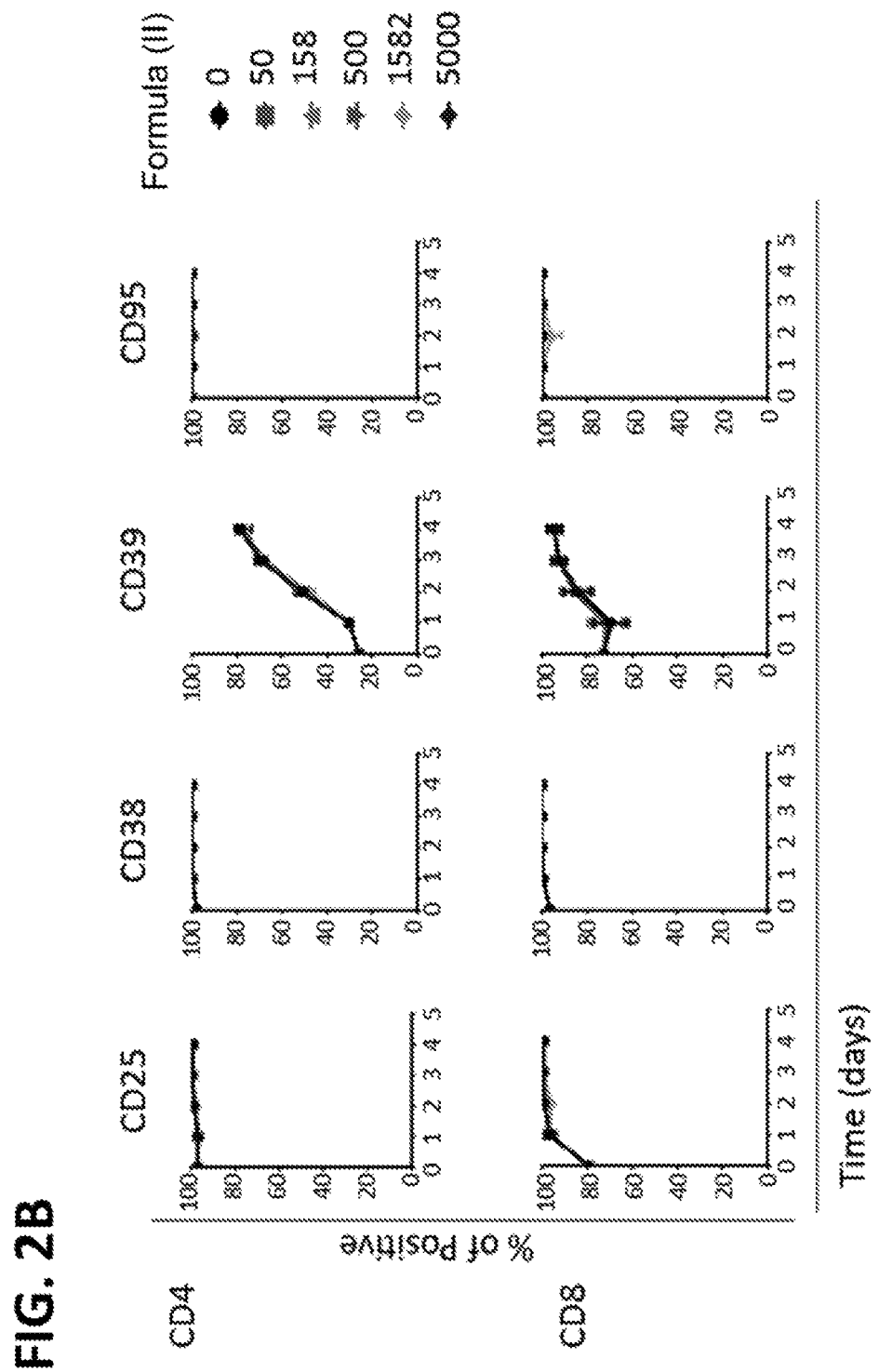
Figure 2C:
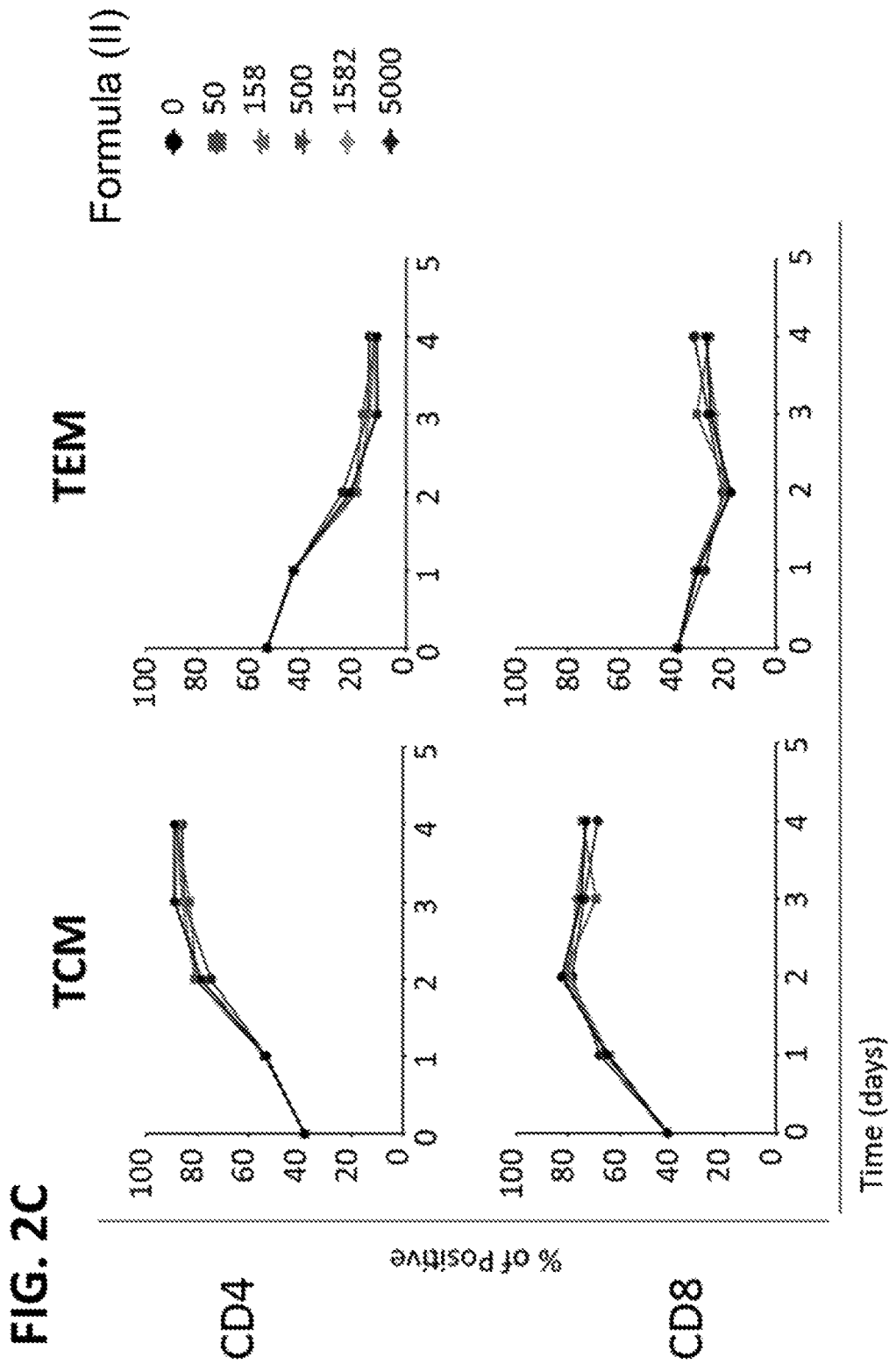
FIG. 2C and FIG. 2D show representative results of CAR T cell from one donor-derived cells for the percentage of TCM (CCR7+CD45RA−) and TEM (CCR7−CD45RA−) over four days after initial stimulation in the presence of ibrutinib or the compound of Formula (II), respectively.
Figure 2D:
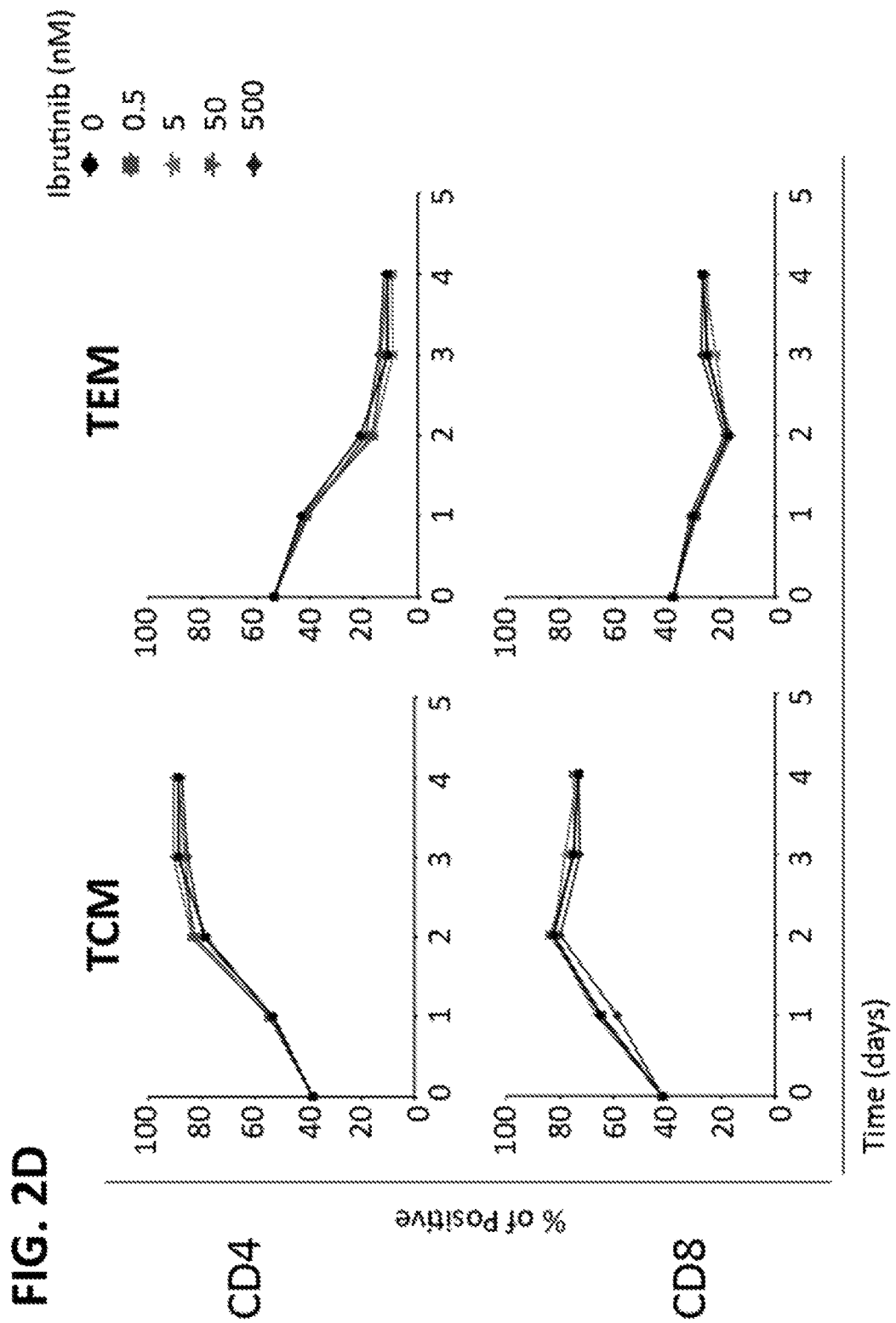
Figure 2E:
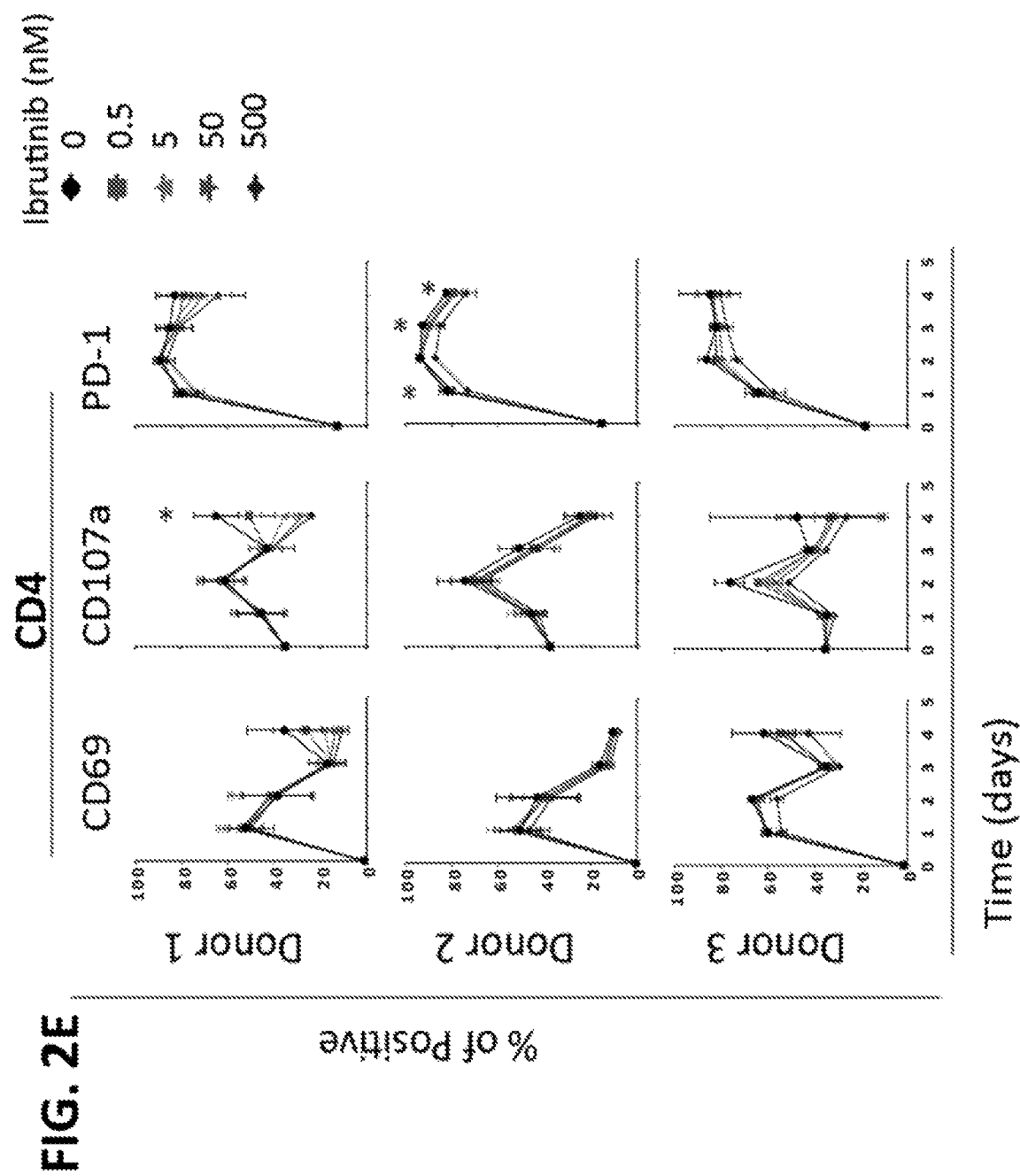
Figure 2H:
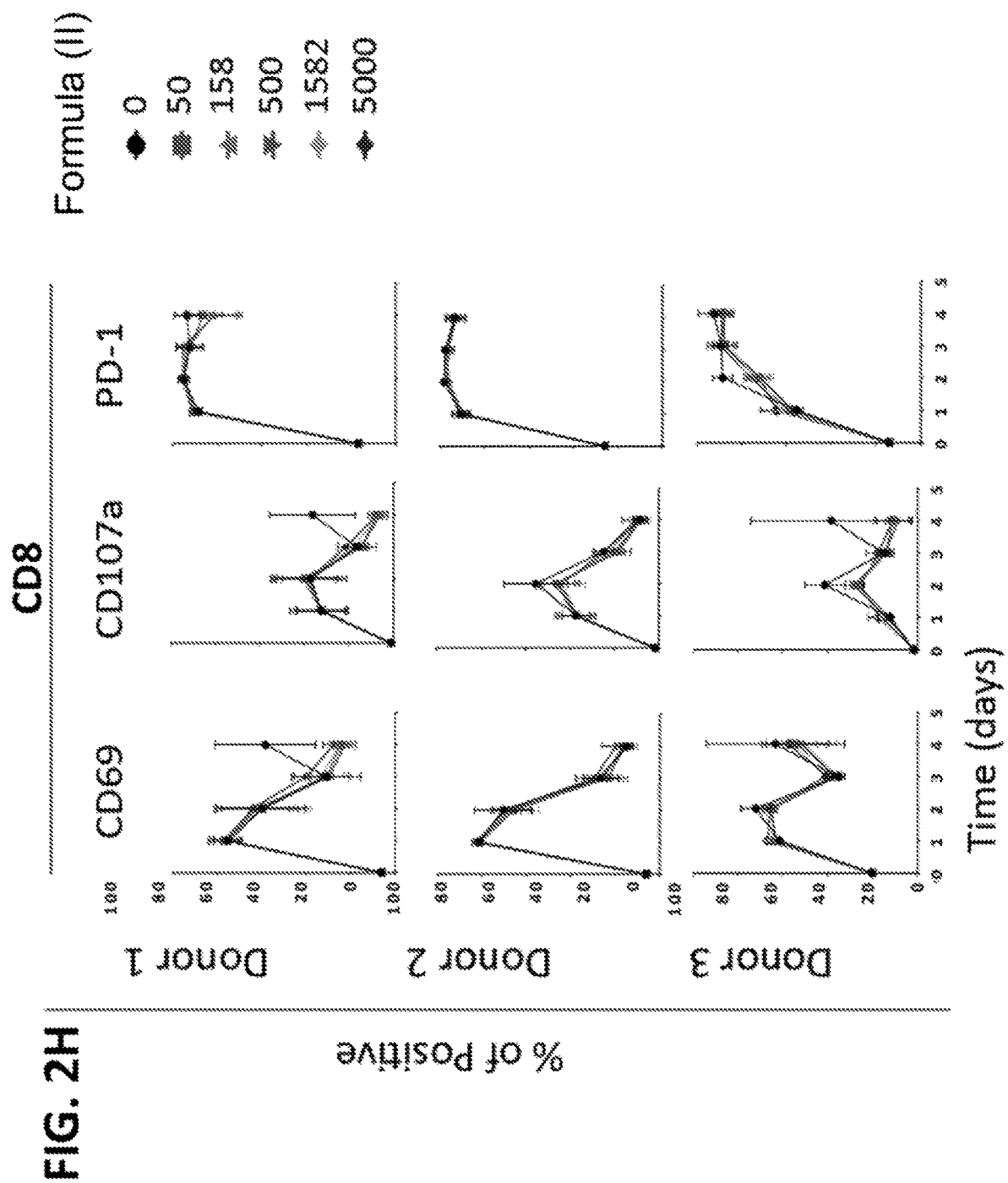

Across the 3 different anti-CD19 CAR T cell donors, ibrutinib at concentrations of 5000, 500, 50, 5 and 0.5 nM had no significant effect on expression of the EGFRt surrogate marker, or on any of the activation markers CD25, CD38, CD39, CD95 or CD62L, or on any of the T cell phenotypic markers assessed in this study (CCR7, CD62L and CD45R$^o$), consistent with a conclusion that ibrutinib did not significantly impact the activation state and/or differentiation subtype of the T cells in this assay. Similar results were observed for culture in the presence of the compound of Formula (II). FIGS. 2A and 2B depict results for exemplary markers. The results in FIGS. 2C and 2D show that treatment with ibrutinib or the compound of Formula (II), respectively, did not affect the phenotype of cells as central (TCM) or effector (TEM) memory subsets as assessed by the expression of CCR7 and CD45RA. As shown in FIGS. 2E and 2F, there was a subtle decrease in expression levels of CD69, CD107a or PD-1 when CD4+ or CD8+ cells, respectively, were cultured in the presence of ibrutinib. Similar results were observed for culture in the presence of the compound of Formula (II) (FIGS. 2G and 2H). Some donor variability over time and magnitude was observed.

C. Cytokine Production

Figure 3A:
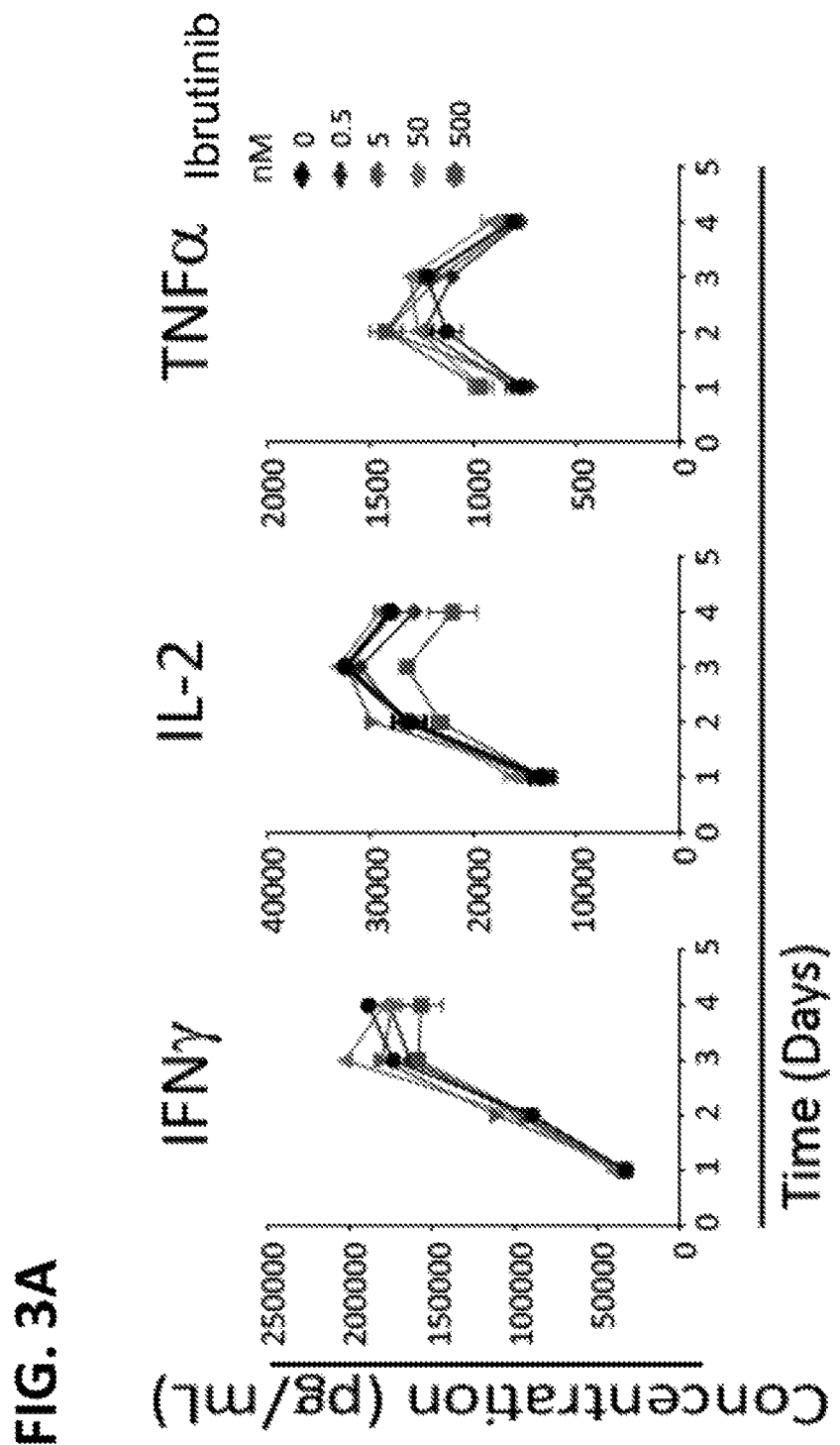
FIG. 3A and FIG. 3B shown measurement of IFN-gamma, IL-2 and TNF-alpha from supernatant of CAR T cells from one donor-derived cells stimulated with target cells at an E:T of 2.5:1 and treated with ibrutinib or the compound of Formula (II), respectively.
Figure 3B:
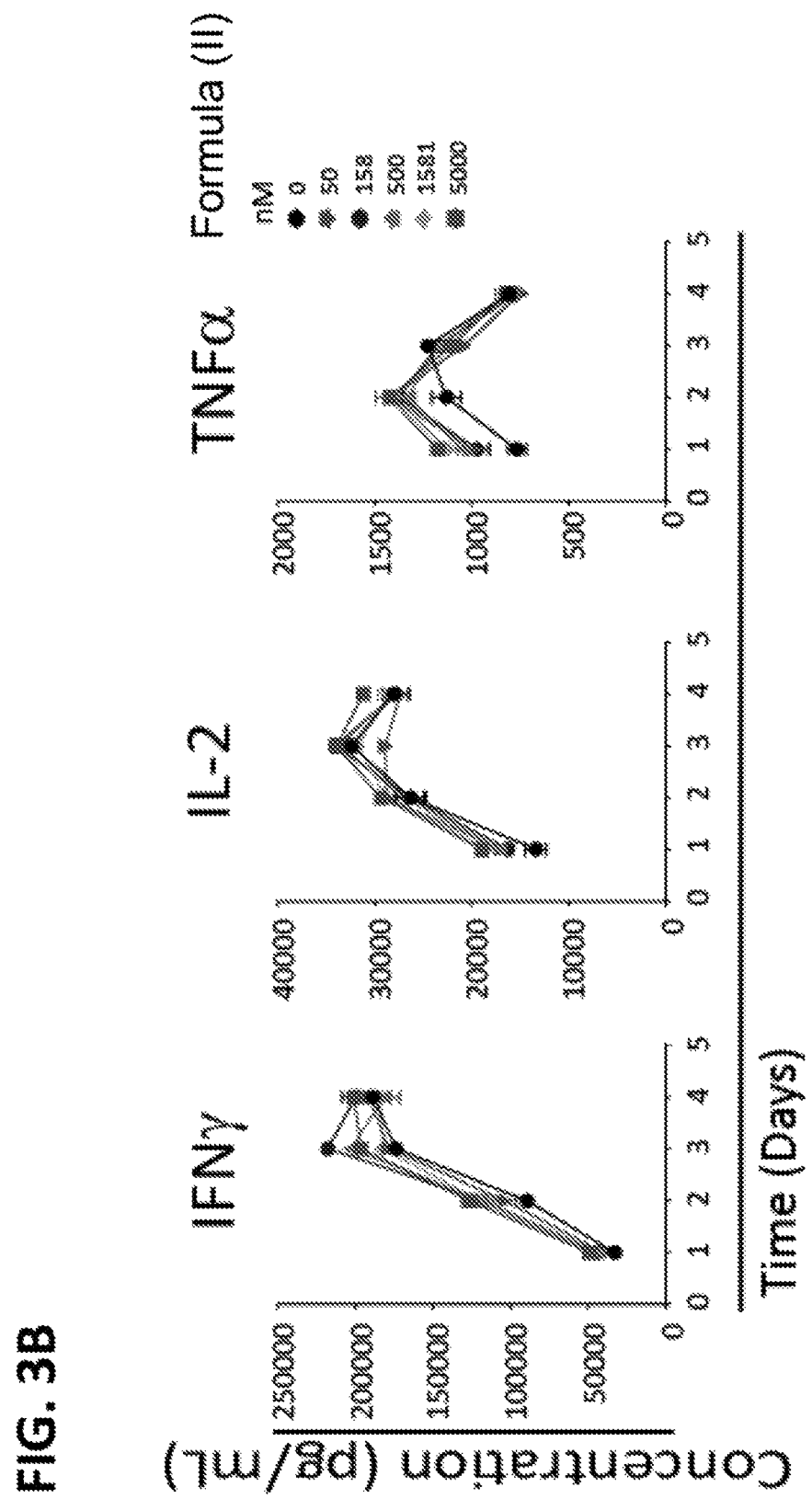
Figure 3C:
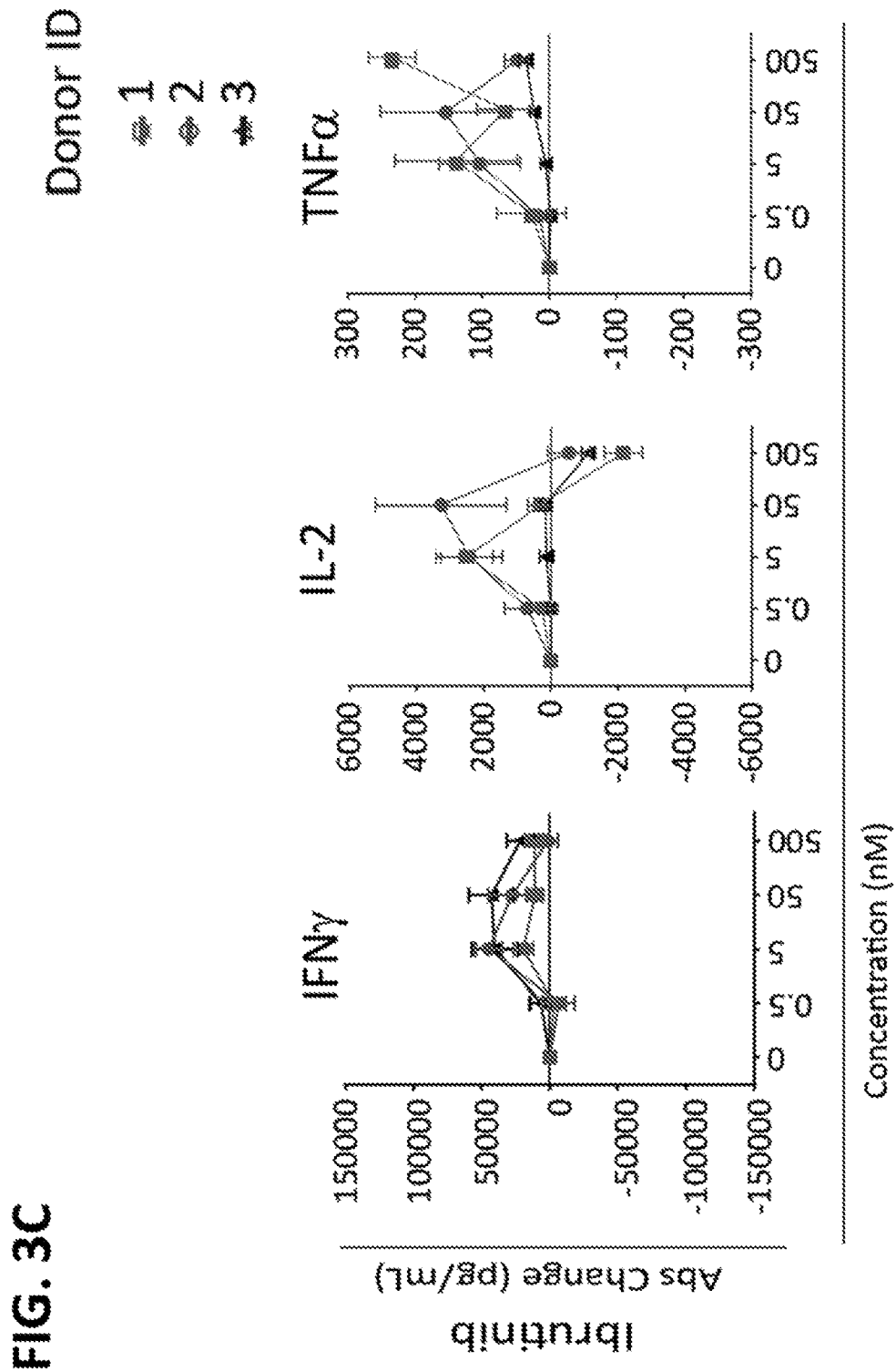
FIG. 3C depicts percentage change in a readout of secreted cytokine, IFN-gamma, IL-2 and TNF-alpha, after stimulation of CAR-T cells for 2 days in the presence of ibrutinib compared to untreated controls, in cells derived from three donors, in two 2 independent assays.
Figure 3D:
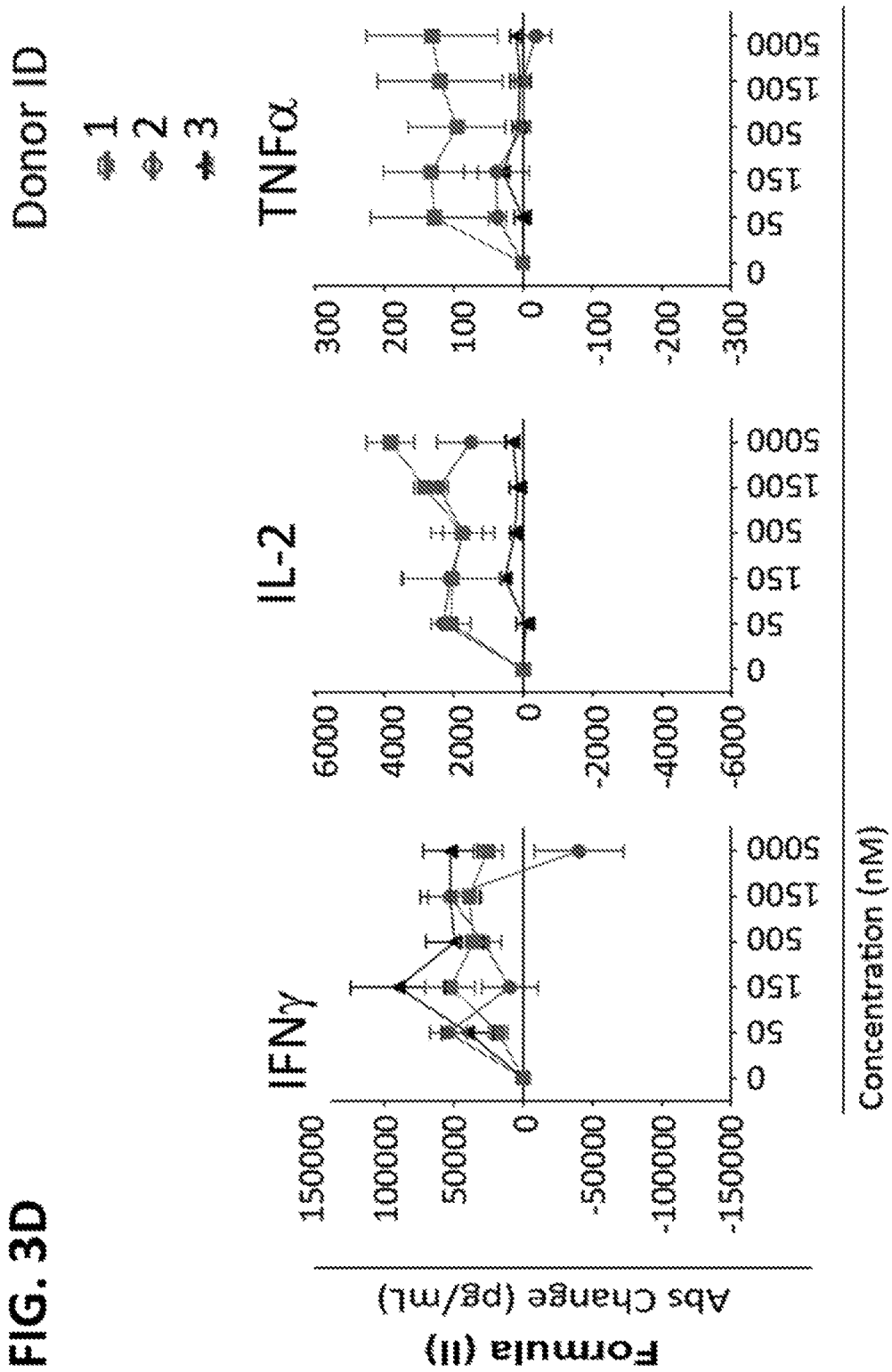
FIG. 3D depicts percentage change in a readout of secreted cytokine, IFN-gamma, IL-2 and TNF-alpha, after stimulation of CAR-T cells for 2 days in the presence of the compound of Formula (II) compared to untreated controls, for three donors in 2 independent assays.

The production of cytokines by anti-CD19 CAR T cells cultured in the presence or absence of ibrutinib or the compound of Formula (II) were assessed by assessing cytokine levels in the supernatants of co-cultures of CAR-T cells and irradiated K562-CD19 target cells. CAR-T cells generated as described above were plated at 100,000 cells/well on 96 well Poly-D-Lysine coated plates. Irradiated target cells (K562-CD19) were added at an effector to target ratio of 2.5:1. Cells were cultured for up to 4 days in the absence of inhibitor, in the presence of the compound of Formula (II) at concentrations of 50, 150, 500, 1500 or 5000 nM, or in the presence of ibrutinib at concentrations of 0.5, 5, 50 or 500 nM. Culture supernatants were harvested at day 2, 3 or 4, and IFNγ, IL-2 and TNFa were measured from the culture supernatants using cytokine kits from Meso Scale Discovery (MSD). The secreted IFNγ, IL-2, and TNFα levels from three healthy donor derived anti-CD19 CAR T cell lots over time following co-culture with irradiated K562.CD19 target cells in the presence of ibrutinib or the compound of Formula (II) is shown in FIG. 3A and FIG. 3B, respectively. Absolute change in cytokine production, 2 days after stimulation, of CAR-T cells generated from donor 2 in cells treated with ibrutinib (FIG. 3C) or the compound of Formula (II) (FIG. 3D), each in 2 independent experiments (mean±SEM), was determined. As shown in FIGS. 3C and 3D, physiological concentrations of ibrutinib and the compound of Formula (II), respectively, did not significantly inhibit cytokine concentrations. Although the magnitude of responses differed between donors, ibrutinib or the compound of Formula (II) overall did not inhibit CAR T cytokine production following stimulation with antigen-specific K562.CD19 cells. The compound of Formula (II) modestly increased cytokine production in some donors, and similar effects were observed with 50 nM of ibrutinib. In contrast, a mean decrease in IL-2 of 19.6% or 1200 pg/mL was observed with 500 nM ibrutinib ($P<0.05$) (FIG. 3C). Similar results were obtained when IL-4 and IL-10 were measured.

D. Serial Restimulation

The ability of cells to expand ex vivo following repeated stimulations in some aspects can indicate capacity of CAR-T cells to persist (e.g., following initial activation) and/or is indicative of function and/or fitness in vivo (Zhao et al. (2015) Cancer Cell, 28:415-28). Anti-CD19 CAR-T cells generated as described above were plated in triplicate at 100,000 cells/well on 96 well Poly-D-Lysine coated plates, and irradiated target cells (K562-CD19) were added at an effector to target ratio of 2.5:1. Cells were stimulated in the presence of 500 and 50 nM ibrutinib or 1581 and 158 nM of the compound of Formula (II), harvested every 3-4 days and counted, and cultured for restimulation with new target cells using the same culture conditions and added concentration of ibrutinib or the compound of Formula (II) after resetting cell number to initial seeding density for each round. A total of 7 rounds of stimulation during a 25 day culture period were carried out.

For each round of stimulation, the fold change in cell number and the number of doublings was determined. The results for population doublings are shown in FIGS. 4A and 4B, for ibrutinib and the compound of Formula (II), respectively. In this study, neither inhibitor was observed to impact the initial growth of the CAR+ T cells. Expansion kinetics were similar in all treatment groups after three rounds of stimulation (day 11), as observed by fold change and number of population doublings. By day 18, however, for CAR+ T cells generated from two of the three donors in this study, expansion (as measured by population doublings), following multiple rounds of restimulation, was observed to be enhanced by the presence of ibrutinib or the compound of Formula (II), at each of the concentrations assessed for the respective inhibitors as indicated by enhanced cell numbers and increased numbers of population doublings. The cells derived from the two donors in which these differences were observed, generally, as compared to those derived from the other donor, performed less well in the serial restimulation assay in the absence of either inhibitor.

FIGS. 4C and 4D summarize the results of the number of cells in culture at day 18 (5 rounds of restimulation) after stimulation for the three donors in the presence of ibrutinib or the compound of Forumla (II), respectively. As shown, a statistically significant increase in cell number after 18 days of the serial stimulation assay was observed. In particular, after five rounds of stimulation (day 18), CAR T cells from donor 2 treated with either ibrutinib or the compound of Formula (II) at the highest concentrations had significantly ($P<0.05$) increased cell counts relative to control cells. Non-significant, increased cell counts were also observed for cells from donor 3 treated with ibrutinib or the compound of Formula (II) at the highest concentration tested. When assessing cell counts across control conditions, cells derived from donors 2 and 3 exhibited inferior performance to donor 1 cells in this assay. Also, the cells derived from the two donors in which these differences were observed, generally, as compared to those derived from the other donor, performed less well in the serial restimulation assay in the absence of either inhibitor. Notably, these donors with inferior performance benefited from treatment with ibrutinib or the compound of Formula (II) in this assay. The results were consistent with the utility of ibrutinib or the compound of Formula (II) or other Btk (or other TEC family kinase) inhibitor, including selective inhibitors that do not inhibit Itk, to improve function, survival and/or expansion of T cells impaired in one or more factors impacting T cell function, survival and/or proliferative capacity. For example, such combinations may improve T cell function and/or persistence following antigen encounter, even in the case of kinase inhibitors not capable of specifically inhibiting Itk.

E. TH1 Phenotype

An assay was carried out to assess the skewing of anti-CD19 CAR T cells towards a TH1 phenotype when cultured in the presence of ibrutinib or the compound of Formula (II). Ibrutinib has been observed to limit $T_h2$ CD4 T cell activation and proliferation through the inhibition of ITK (Honda, F., et al. (2012) Nat Immunol, 13(4): 369-78). A serial restimulation assay was performed as described above and cells were harvested at various times and analyzed by flow cytometry to assess percentage of TH1-phenotype (assessed as CD4+CXCR3+CRTH2-) T cells or TH2-phenotype (assessed as CD4+CXCR3-CRTH2+). Representative plots for cells cultured with and without indicated concentrations of ibrutinib or the compound of Formula (II) is shown in FIG. 5A, and percentage of TH1 cells following culture over the course of the serial restimulation, and under various concentrations of ibrutinib or the compound of Formula (II), is shown in FIGS. 5B and 5C, respectively.

The presence of ibrutinib, but not the compound of Formula (II), was observed in this assay to increase the percentage of CAR+ T cells observed to exhibit a TH1 phenotype, after serial stimulation, and the effect was observed to be greater with increasing concentrations of ibrutinib. During the 18-day serial stimulation period, the percentage of CAR T TH1 cells increased for all three donors under control conditions (FIG. 5B). 500 nM ibrutinib further enhanced the percentage of TH1 cells ($P<0.01$), whereas no significant effects were observed with the compound of Formula (II) treatment (FIG. C). The compound of Formula (II) has been reported to have >200 times lower affinity for ITK compared with ibrutinib (Byrd, J. C., et al.

(2016) N Engl J Med, 374(4): 323-32), indicating that ibrutinib-mediated TH1 skewing could be influenced by off-target ITK activity.

No significant effects of either inhibitor on additional CAR T activation or memory markers were observed in CAR T cells isolated from the serial stimulation assay (FIGS. 5D and 5E, compound of Formula (II); and FIGS. 5F and 5G, ibrutinib).

Example 2: Enhancement of Anti-Tumor Activity of CAR-Expressing T Cells in the Presence of an Inhibitor of a TEC Family Kinase A disseminated tumor xenograft mouse model was generated by injecting NOD/Scid/gc−/−(NSG) mice with cells of a CD19+Nalm-6 disseminated tumor line, identified to be resistant to BTK inhibition.

On day zero (0), NSG mice were intravenously injected with $5 \times 10^5$ Nalm-6 cells expressing firefly luciferase. Beginning at day 4 and daily for the duration of the study, mice were treated with a vehicle control or were treated with ibrutinib, in each case by daily oral gavage (P.O.) at 25 m/kg q.d. To permit assessment of the effect of a combination therapy with the inhibitor, a suboptimal dose of anti-CD19 CAR T cells from two different donors were i.v. injected into the mice at $5 \times 10^5$/mouse at day 5. As a control, mice were administered the vehicle control or ibrutinib but without administration of the CAR-T cells. Eight (N=8) mice per group were monitored.

Following treatment as described above, tumor growth over time was measured by bioluminescence imaging and the average radiance ($p/s/cm^2/sr$) was measured. Results are shown in FIG. 6A for tumor growth over time from mice treated with ibrutinib and CAR T cells. Analysis of the results from the same study monitoring tumor growth at greater time points post-tumor injection from two different donors is shown in FIG. 6B. As shown, ibrutinib treatment alone had no effect on tumor burden in this ibrutinib-resistant model compared to vehicle treatment. In contrast, mice administered CAR-T cells and ibrutinib exhibited a significantly decreased tumor growth compared to mice treated with CAR-T cells and vehicle control ($p<0.001$, ***).

The combined administration of CAR T and ibrutinib also was observed to result in significantly increased survival compared with the CAR T and vehicle condition, as shown by Kaplan Meier curves showing survival of tumor bearing mice treated with ibrutinib and CAR T cells. As shown in FIG. 6C, mice treated with CAR-T cells and ibrutinib exhibited an increased median survival compared to the group receiving the suboptimal anti-CD19 CAR T cell dose+vehicle. Analysis of the results from the same study monitoring survival at greater time points post-tumor injection from two different donors is shown in FIG. 6D, which showed that the combined administration of CAR T and ibrutinib also was observed to result in significantly increased survival compared with the CAR T and vehicle condition, ($p<0.001$, ***).

Example 3: Assessment of CAR-Expressing T Cell Phenotype, Function and Anti-Tumor Activity In Vivo in the Presence of an Inhibitor of a TEC Family Kinase NSG mice described in Example 2 were intravenously injected on day 0 with $5 \times 10^5$ Nalm-6 cells expressing firefly luciferase. Beginning at day 4 and daily for the duration of the study, mice were treated with a vehicle control or were treated daily with an inhibitor of a TEC family kinase, either ibrutinib or the compound of Formula (II), in drinking water (D.W.) at 25 mg/kg/day. A bridging experiment confirmed that administration of ibrutinib by drinking water was equivalent to oral gavage administration (data not shown). To permit assessment of the effect of a combination therapy with the inhibitor, a suboptimal dose of anti-CD19 CAR T cells was i.v. injected into the mice at $5 \times 10^5$/mouse at day 5. As a control, mice were administered the vehicle control without administration of the CAR-T cells or inhibitor.

Following treatment as described above, the tumor growth and percent survival of treated mice was determined. As shown in FIG. 7A, mice treated with anti-CD19 CAR-T cells and either ibrutinib or the compound of Formula (II) exhibited an increased median survival compared to the group receiving the suboptimal anti-CD19 CAR T cell dose+vehicle ($p<0.001$). The compound of Formula (II) or ibrutinib, administered in combination with CAR T, also significantly ($P<0.001$) decreased tumor growth (FIG. 7B) compared with the CAR T administered with vehicle alone. The results were similar using anti-CD19 CAR-T cells generated by engineering T cells derived from two different donors.

Pharmacokinetic analysis of CAR+ T cells was analyzed in blood and bone marrow from mice having received anti-CD19 CAR+ T cells from one donor-derived cells, and that had been treated with vehicle, ibrutinib or the compound of Formula (II) (3 mice per group), Samples were analyzed to assess presence and levels of EGFRt+ CAR T cells and/or tumor cells at day 7, 12, 19 and 26 post CAR+ T cell transfer. As shown in FIGS. 7C and 7E, a significant increase in circulating CAR+ T cells was observed in mice treated with ibrutinib and the compound of Formula (II), respectively, as compared to those treated with CAR+ T cells and vehicle, consistent with a greater expansion of CAR-T cells in the blood in the presence of the inhibitor. At day 19 post CAR-T cell transfer, a significant increase in the number of cells in the blood was observed after treatment with ibrutinb (FIG. 7D; * $p<0.05$) and the compound of Formula (II) (FIG. 7E; *** $p<0.001$), respectively. As shown in FIGS. 7G and 7H, significantly fewer tumor cells were detected in the blood or bone marrow in mice in which the CAR+ cell treatment was combined with treatment with ibrutinib or the compound of Formula (II), respectively, as compared to with vehicle alone.

Ex vivo immunophenotyping also was performed on CAR+ T cells harvested from bone marrow at day 12 post-CAR T from mice that received CAR+ T cells and that had been treated with vehicle, ibrutinib or the compound of Formula (II) (n=3 mice per group). Cells were assessed for surface markers CD44, CD45RA, CD62L, CD154, CXCR3, CXCR4, PD-1 by flow cytometry and T-distributed stochastic neighbor embedding (t-SNE) high dimensional analysis was performed using FlowJo software. As shown in FIG. 8A, changes were observed in CAR+ T cells isolated from the bone marrow of animals having received CAR-T cells in combination with ibrutinib or the compound of Formula (II), as compared to with vehicle alone (control). Using multivariate t-SNE FACS analysis based on pooled analysis from three mice per group, 4 distinct population clusters were identified (FIG. 8B). FACs histograms showing the individual expression profiles of CD4, CD8, CD62L, CD45RA, CD44 and CXCR3 from the 4 gated t-SNE in FIG. 8A overlaid on the expression of the total population (shaded) is shown in FIG. 8C. The percentage and fold change of each t-SNE population in control mice or mice treated with ibrutinib or the compound of Formula (II), is shown in FIG. 8D. Statistically significant differences are indicated as P<0.95 (*), P<0.01 (), P<0.001 (*), P<0.0001 (****).

An increase in CD8+CD44$^{hi}$CXCR3$^{hi}$CD45RA$^{lo}$ CD62L$^{hi}$ (population 2) and CD4+ CD44$^{hi}$CXCR3$^{int}$CD45RA$^{hi}$ CD62L$^{hi}$ (population 4) was observed in the bone marrow of CAR T-treated mice also administered ibrutinib or the compound of Formula (II) as compared to control mice, at day 12 post CAR T transfer (FIG. 8B-8C). Mice treated with the compound of Formula (II) exhibited a greater enrichment of population 2 as compared to that observed in ibrutinib treated animals (populations 2 and 4 representing 29.2% and 8.4% of CAR-T cells in these mice, respectively), whereas a greater enhancement of population 4 was observed in ibrutinib-treated animals (15.2% compared to 4.4% of CAR-T cells) (FIG. 8D).

Example 4: Enhancement of Cytolytic Function of CAR-Expressing T Cells Manufactured from Diffuse Large B-Cell Lymphoma (DLBCL) Patients in the Presence of an Inhibitor of a TEC Family Kinase Anti-CD19 CAR-T cells were generated substantially as described in Example 1, except that T cells were isolated from two exemplary patients having diffuse large B-cell lymphoma (DLBCL). Cells were subjected to serial restimulation as described in Example 1.D, by co-culturing CAR+ T cells with K562-CD19 targets cells at an effector to target ratio of 2.5:1 and in the presence of 500 and 50 nM ibrutinib, harvesting cells every 3-4 days and restimulating under the same conditions after resetting cell number. Cells were subjected to serial restimulation over a 21 day culture period and monitored for cell expansion and cytotoxic activity.

As shown in FIG. 9A, cell expansion, as determined by the number of cell doublings, was observed during the 21 day culture period from cells derived from each individual subject. Ibrutinib did not inhibit the proliferation of CAR T cells derived from either patient (FIG. 9A), an observation consistent with previous data from healthy donor-derived CAR T cells. CAR+ T cells manufactured from cells derived from each individual subject demonstrated an increase in cytolytic function in the presence of 500 nM ibrutinib after 16 days of serial restimulation (P <0.001) (FIG. 9B). In cells derived from one patient, an increase in cytolytic activity after 16 days of serial stimulation was observed with 50 nM ibrutinib (P<0.01) (FIG. 9B). This increase in cytolytic activity is consistent with results from healthy donor cells (FIG. 1C, D).

Example 5: Assessment of Molecular Signature by RNA-Sea of CAR-Expressing T Cells Treated with Ibrutinib RNA was isolated from individual CAR-expressing cells, derived from three different donors, that had been treated for 18 days in a serial stimulation assay in the presence of ibrutinib (50 nM, 500 nM), the compound of formula (II) (1581 nM) or control (0 nM). RNA isolation was performed using the RNEasy Micro Kit (Qiagen). Samples were sequenced and RNASeq reads were mapped to the human genome (GRCh38) and aligned to the GENCODE release 24 gene model. RNAseq quality metrics were generated and evaluated to confirm consistency across samples. Differentially expressed genes were identified by imposing a log$_e$ fold change cutoff of 0.5 and a Benjamini-Hochberg adjusted false discovery rate (FDR) cutoff of 0.05.

As shown in the volcano plot in FIG. 10A, 500 nM ibrutinib significantly (FDR<0.05, absLog$_2$FC>0.5) altered the expression of 41 protein-coding genes. FIG. 10C shows a heat map of gene expression changes for the genes identified in FIG. 10A. In a separate experiment under similar culture conditions, only 3 genes were significantly altered (FDR<0.05, absLog$_2$FC>0.5) under treatment with the compound of formula (II) (1581 nM). FIG. 10B depicts a Volcano plot of expressed genes from day 18 serially stimulated CART cells treated with 1581 nM of the compound of Formula (II) compared with control.

Box plots of gene expression for two exemplary genes following treatment with different concentrations of inhibitor (50 nM or 500 nM) or control are shown in FIGS. 11A-B. Decreases in genes such as granzyme A (FIG. 11A) and increases in SELL/CD62L (FIG. 11B) are consistent with an effect of ibrutinib to dampen terminal-effector-like genes while enhancing genes associated with memory development. Furthermore, RNA-Seq revealed that genes associated with promoting TH1 differentiation were altered by ibrutinib, including upregulation of MSC, known to suppress TH2 programing (Wu, C., et al. (2017) Nat Immunol, 18(3): 344-353), and downregulation of HES6, HIC1, LZTFL1, NRIP1, CD38 and RARRES3, associated with the ATRA/Retinoic acid signaling pathway identified to inhibit TH1 development (Britschgi, C., et al. (2008) Br J Haematol, 141(2): 179-87; Jiang, H., et al. (2016) J Immunol, 196(3): 1081-90; Heim, K. C., et al. (2007) Mol Cancer, 6: 57; Nijhof, I. S., et al. (2015) Leukemia, 29(10): 2039-49; Zirn, B., et al. (2005) Oncogene, 24(33): 5246-51) (FIG. 11E-B-D). In support of the RNA-Seq results, a significant increase in CD62L expression was observed by flow cytometry after 18 days of serial stimulation in donors 2 and 3 (FIGS. 12A and 12B). Taken together, these results support that long term ibrutinib treatment may result in an increased TH1 and memory-like phenotype in CAR T.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |

| SEQ ID NO. | SEQUENCE | DESCRIPTION |
|---|---|---|
| 2 | GAATCTAAGTACGGACCGCCCTGCCCCCCTTGCCCT | spacer (IgG4hinge) (nt) Homo sapiens |
| 3 | ESKYGPPCPPCPGQPREPQVYTLPPSQEEMTKNQVSLTCLVKGFYPSDI AVEWESNGQPENNYKTTPPVLDSDGSFFLYSRLTVDKSRWQEGNVFSCS VMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDK SRWQEGNVFSCSVMHEALHNHYTQKSLSLSLGK | Hinge-CH2-CH3 spacer Homo sapiens |
| 5 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSL WNAGTSVTCTLNHPSLPPQRLMALREPAAQAPVKLSLNLLASSDPPEAA SWLLCEVSGFSPPNILLMWLEDQREVNTSGFAPARPPPQPGSTTFWAWS VLRVPAPPSPQPATYTCVVSHEDSRTLLNASRSLEVSYVTDH | IgD-hinge-Fc Homo sapiens |
| 6 | LEGGGEGRGSLLTCGDVEENPGPR | T2A artificial |
| 7 | RKVCNGIGIGEFKDSLSINATNIKHFKNCTSISGDLHILPVAFRGDSFT HTPPLDPQELDILKTVKEITGFLLIQAWPENRTDLHAFENLEIIRGRTK QHGQFSLAVVSLNITSLGLRSLKEISDGDVIISGNKNLCYANTINWKKL FGTSGQKTKIISNRGENSCKATGQVCHALCSPEGCWGPEPRDCVSCRNV SRGRECVDKCNLLEGEPREFVENSECIQCHPECLPQAMNITCTGRGPDN CIQCAHYIDGPHCVKTCPAGVMGENNTLVWKYADAGHVCHLCHPNCTYG CTGPGLEGCPTNGPKIPSIATGMVGALLLLLVVALGIGLFM | tEGFR artificial |
| 8 | FWVLVVVGGVLACYSLLVTVAFIIFWV | CD28 (amino acids 153-179 of Accession No. P10747) Homo sapiens |
| 9 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) Homo sapiens |
| 10 | RSKRSRLLHSDYMNMTPRRPGPTRKHYQPYAPPRDFAAYRS | CD28 (amino acids 180-220 of P10747) Homo sapiens |
| 11 | RSKRSRGGHSDYMNMTPRRPGPTRKHYQPYAPPRDFAAYRS | CD28 (LL to GG) Homo sapiens |
| 12 | KRGRKKLLYIFKQPFMRPVQTTQEEDGCSCRFPEEEEGGCEL | 4-1BB (amino acids 214-255 of Q07011.1) Homo sapiens |
| 13 | RVKFSRSADAPAYQQGQNQLYNELNLGRREEYDVLDKRRGRDPEMGGKP RRKNPQEGLYN ELQKDKMAEA YSEIGMKGER RRGKGHDGLY QGLSTATKDTYDALHMQALP PR | CD3 zeta Homo sapiens |
| 14 | RVKFSRSAEPPAYQQGQNQLYNELNLGRREEYDVLDKRRGRDPEMGGKP RRKNPQEGLYN ELQKDKMAEA YSEIGMKGER RRGKGHDGLY QGLSTATKDTYDALHMQALP PR | CD3 zeta Homo sapiens |
| 15 | RVKFSRSADAPAYKQGQNQLYNELNLGRREEYDVLDKRRGRDPEMGGKP RRKNPQEGLYN ELQKDKMAEA YSEIGMKGER RRGKGHDGLY QGLSTATKDTYDALHMQALP PR | CD3 zeta Homo sapiens |
| 16 | PGGG-(SGGGG)5-P- wherein P is proline, G is glycine and S is serine | linker |
| 17 | GSADDAKKDAAKKDGKS | linker |

| SEQ ID NO. | SEQUENCE | DESCRIPTION |
|---|---|---|
| 18 | MAAVILESIFLKRSQQKKKTSPLNEKKRLFLLTVHKLSYYEYDFERGRRGSKKG SIDVEKITCVETVVPEKNPPPERQIPRRGEESSEMEQISIIERFPYPFQVVYDE GPLYVFSPTEELRKRWIHQLKNVIRYNSDLVQKYHPCFWIDGQYLCCSQTAKNA MGCQILENRNGSLKPGSSHRKTKKPLPPTPEEDQILKKPLPPEPAAAPVSTSEL KKVVALYDYMPMNANDLQLRKGDEYFILEESNLPWWRARDKNGQEGYIPSNYVT EAEDSIEMYEWYSKHMTRSQAEQLLKQEGKEGGFIVRDSSKAGKYTVSVFAKST GDPQGVIRHYVVCSTPQSQYYLAEKHLFSTIPELINYHQHNSAGLISRLKYPVS QQNKNAPSTAGLGYGSWEIDPKDLTFLKELGTGQFGVVKYGKWRGQYDVAIKMI KEGSMSEDEFIEEAKVMMNLSHEKLVQLYGVCTKQRPIFIITEYMANGCLLNYL REMRHRFQTQQLLEMCKDVCEAMEYLESKQELHRDLAARNCLVNDQGVVKVSDF GLSRYVLDDEYTSSVGSKFPVRWSPPEVLMYSKESSKSDIWAFGVLMWEIYSLG KMPYERFTNSETAEHIAQGLRLYRPHLASEKVYTIMYSCWHEKADERPTFKILL SNILDVMDEES | Tyrosine-protein kinase BTK Homo sapiens |
| 19 | AACTGAGTGGCTGTGAAAGGGTGGGGTTTGCTCAGACTGTCCTTCCTCTCTGGA CTGTAAGAATATGTCTCCAGGGCCAGTGTCGTGCTcGATcGAGTcccAccilcc AAGTCCTGGCATCTCAATGCATCTGGGAAGCTACCTGCATTAAGTCAGGACTGA GCACACAGGTGAACTCCAGAAAGAAGAAGCTATGGCCGCAGTGATTCTGGAGAG CATCTTTCTGAAGCGATCCCAACAGAAAAGAAAACATCACCTCTAAACTTCAA GAAGCGCCTGTTTCTCTTGACCGTGCACAAACTCTCCTACTATGAGTATGACTT TGAACGTGGGAGAAGAGGCAGTAAGAAGGGTTCAATAGATGTTGAGAAGATCAC TTGTGTTGAAACAGTGGTTCCTGAAAAAAATCCTCCTCCAGAAAGACAGATTCC GAGAAGAGGTGAAGAGTCCAGTGAAATGGAGCAAATTTCAATCATTGAAAGGTT CCCTTATCCCTTCCAGGTTGTATATGATGAAGGGCCTCTCTACGTCTTCTCCCC AACTGAAGAACTAAGGAAGCGGTGGATTCACCAGCTCAAAAACGTAATCCGGTA CAACAGTGATCTGGTTCAGAAATATCACCCTTGCTTCTGGATCGATGGCAGTA TCTCTGCTGCTCTCAGACAGCCAAAAATGCTATGGGCTGCCAAATTTTGGAGAA CAGGAATGGAAGCTTAAAACCTGGGAGTTCTCACCGGAAGACAAAAAAGCCTCT TCCCCCAACGCCTGAGGAGGACCAGATCTTGAAAAAGCCACTACCGCCTGAGCC AGCAGCAGCACCAGTCTCCACAAGTGAGCTGAAAAAGGTTGTGGCCCTTTATGA TTACATGCCAATGAATGCAAATGATCTACAGCTGCGGAAGGGTGATGAATATTT TATCTTGGAGGAAAGCAACTTACCATGGTGGAGAGCACGAGATAAAAATGGGCA GGAAGGCTACATTCCTAGTAACTATGTCACTGAAGCAGAAGACTCCATAGAAAT GTATGAGTGGTATTCCAAACACATGACTCGGAGTCAGGCTGAGCAACTGCTAAA GCAAGAGGGGAAGAAGGAGGTTTCATTGTCAGAGACTCCAGCAAAGCTGGCAA ATATACAGTGTCTGTGTTTGCTAAATCCACAGGGGACCCTCAAGGGGTGATACG TCATTATGTTGTGTGTTCCACACCTCAGAGCCAGTATTACCTGGCTGAGAAGCA CCTTTTCAGCACCATCCCTGAGCTCATTAACTACCATCAGCACAACTCTGCAGG ACTCATATCCAGGCTCAAATATCCAGTGTCTCAACAAAACAAGAATGCACCTTC CACTGCAGGCCTGGGATACGGATCATGGGAAATTGATCCAAAGGACCTGACCTT CTTGAAGGAGCTGGGGACTGGACAATTTGGGGTAGTGAAGTATGGGAAATGGAG AGGCCAGTACGACGTGGCCATCAAGATGATCAAAGAAGGCTCCATGTCTGAAGA TGAATTCATTGAAGAAGCCAAAGTCATGATGAATCTTTCCCATGAAGCTGGT GCAGTTGTATGGCGTCTGCACCAAGCAGCGCCCATCTTCATCATCACTGAGTA CATGGCCAATGGCTGCCTCCTGAACTACCTGAGGGAGATGCGCCACCGCTTCCA GACTCAGCAGCTGCTAGAGATGTGCAAGGATGTCTGTGAAGCCATGGAATACCT GGAGTCAAAGCAGTTCCTTCACCGAGACCTGGCAGCTCGAAACTGTTTGGTAAA CGATCAAGGAGTTGTTAAAGTATCTGATTTCGGCCTGTCCAGGTATGTCCTGGA TGATGAATACACAAGCTCAGTAGGCTCCAAATTTCCAGTCCGGTGGTCCCCACC GGAAGTCCTGATGTATAGCAAGTTCAGCAGCAAATCTGACATTTGGGCTTTTGG GGTTTTGATGTGGGAAATTTACTCCCTGGGGAAGATGCCATATGAGAGATTTAC TAACAGTGAGACTGCTGAACACATTGCCCAAGGCCTACGTCTCTACAGGCCTCA TCTGGCTTCAGAGAAGGTATATACCATCATGTACAGTTGCTGGCATGAGAAAGC AGATGAGCGTCCCACTTTCAAAATTCTTCTGAGCAATATTCTAGATGTCATGGA TGAAGAATCCTGAGCTCGCCAATAAGCTTCTTGGTTCTACTTCTCTTCTCCACA AGCCCCAATTTCACTTTCTCAGAGGAAATCCCAAGCTTAGGAGCCCTGGAGCCT TTGTGCTCCCACTCAATACAAAAAGGCCCCTCTCTACATCTGGGAATGCACCTC TTCTTTGATTCCCTGGGATAGTGGCTTCTGAGCAAAGGCCAAGAAATTATTGTG CCTGAAATTTCCCGAGAGAATTAAGACAGACTGAATTTGCGATGAAATATTTT TTAGGAGGGAGGATGTAAATAGCCGCACAAAGGGGTCCAACAGCTCTTTGAGTA GGCATTTGGTAGAGCTTGGGGGTGTGTGTGGGGGTGGACCGAATTTGGCAAG AATGAAATGGTGTCATAAAGATGGGAGGGGAGGGTGTTTTGATAAAATAAAATT ACTAGAAAGCTTGAAAGTC | Tyrosine-protein kinase BTK Homo sapiens |

What is claimed:

1. A method of treatment of a cancer, the method comprising:
    (1) administering, to a subject having a cancer, T cells expressing a recombinant antigen receptor that specifically binds to an antigen associated with the cancer; and
    (2) administering to the subject a kinase inhibitor or a pharmaceutical composition comprising the inhibitor, wherein the inhibitor is the compound of Formula (II):

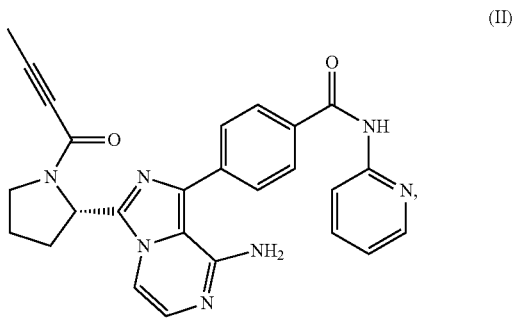 [SMILES: CC#CC(=O)N1CCC[C@H]1c1nc(-c2ccc(C(=O)Nc3ccccn3)cc2)c2c(N)nccn12]

(II)

or an enantiomer, pharmaceutically acceptable salt, solvate, hydrate, or prodrug thereof.

2. The method of claim 1, wherein:
    (i) the subject or the cancer (a) is resistant to ibrutinib or (b) comprises a population of cells that are resistant to ibrutinib;
    (ii) the subject or the cancer comprises a mutation or disruption in a nucleic acid encoding Bruton's tyrosine kinase (BTK), capable of reducing or preventing inhibition of the BTK by ibrutinib; or
    (iii) at the time of the administration in (1) and at the time of the administration in (2) the subject has relapsed following remission after treatment with, or been deemed refractory to treatment with ibrutinib.

3. The method of claim 2, wherein the mutation in the nucleic acid encoding BTK comprises a C481S or C481R substitution, or a T474I or T474M substitution.

4. The method of claim 1, wherein the cancer is selected from the group consisting of sarcomas, carcinomas, lymphomas, non-Hodgkin lymphomas (NHLs), diffuse large B cell lymphoma (DLBCL), leukemia, CLL, ALL, AML and myeloma.

5. The method of claim 1, wherein the T cells recognize an antigen selected from ROR1, B cell maturation antigen (BCMA), tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE Al, HLA-A2 NY-ESO-1, PSCA, folate receptor-a, CD44v6, CD44v7/8, avb6 integrin, 8H9, NCAM, VEGF receptors, 5T4, Fetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, 0-acetylated GD2 (OGD2), CE7, Wilms Tumor 1 (WT-1), a cyclin, cyclin A2, CCL-1, CD138, and a pathogen-specific antigen.

6. The method of claim 1, wherein the T cells comprise tumor infiltrating lymphocytes (TILs) or comprise genetically engineered T cells expressing a recombinant receptor that specifically binds to an antigen associated with the cancer.

7. The method of claim 6, wherein the T cells are genetically engineered T cells expressing a recombinant receptor and the recombinant receptor is a transgenic T cell receptor (TCR) or a chimeric antigen receptor (CAR).

8. The method of claim 7, wherein the recombinant receptor is a CAR and the CAR comprises an extracellular antigen-recognition domain that specifically binds to the antigen and an intracellular signaling domain comprising an ITAM.

9. The method of claim 8, wherein the intracellular signaling domain comprises an intracellular domain of a CD3-zeta (CD3ζ) chain.

10. The method of claim 8, wherein the chimeric antigen receptor (CAR) further comprises a costimulatory signaling region.

11. The method of claim 10, wherein the costimulatory signaling region comprises a signaling domain of CD28 or 4-1BB.

12. The method of claim 1, wherein the inhibitor irreversibly reduces or eliminates the activation of the target protein tyrosine kinase, specifically binds to a binding site in the active site of the target protein tyrosine kinase comprising an amino acid residue corresponding to residue C481 in the sequence set forth in SEQ ID NO:18, or reduces or eliminates autophosphorylation activity of the target protein tyrosine kinase.

13. The method of claim 1, wherein the inhibitor is administered concurrently with or subsequently to initiation of administration of the T cells.

14. The method of claim 1, wherein the inhibitor is administered subsequently to initiation of administration of the T cells.

15. The method of claim 14, wherein the inhibitor is administered within, or within about 1 week of the initiation of the administration of the T cells.

16. The method of claim 1, wherein the inhibitor is administered orally.

17. The method of claim 1, wherein the inhibitor is administered at a total daily dosage amount of between 50 mg/day and 250 mg/day.

18. The method of claim 1, wherein the inhibitor is administered in an amount that is about 200 mg/day.

19. The method of claim 1, wherein the administered T cells comprise CD4+T cells, CD8+T cells, or CD4+T cells and CD8+T cells.

20. The method of claim 1, wherein the administered T cells comprise administration of a dose comprising a number of cells between at or about $5\times10^5$ cells/kg body weight of the subject and at or about $1\times10^7$ cells/kg body weight of the subject.

21. The method of claim 1, wherein the administered T cells comprise administration of a dose comprising a number of cells between at or about $1\times10^7$ and at or about $2\times10^8$ total T cells comprising the recombinant receptor.

22. The method of claim 1, wherein the method further comprises administering a lymphodepleting chemotherapy prior to administration of the T cells.

23. The method of claim 1, wherein the method further comprises administering an immune modulatory agent to the subject, wherein the administration of the cells and the administration of the immune modulatory agent are carried out simultaneously, separately or in a single composition, or sequentially, in either order.

24. The method of claim 1, wherein the administered T cells exhibit increased or prolonged expansion or persistence in the subject as compared to a method in which the administered T cells are administered to the subject in the absence of the inhibitor.

25. The method of claim 1, wherein the method reduces tumor burden to a greater degree or for a greater period of time as compared to the reduction that would be observed with a comparable method in which the administered T cells are administered to the subject in the absence of the inhibitor.

26. The method of claim 10, wherein the costimulatory domain is a domain of 4-1BB.

27. The method of claim 1, wherein the inhibitor is administered for a time period up to 1 year after initiation of the administration of the T cells.

28. The method of claim 27, wherein the inhibitor is administered up to 3 months after initiation of the administration of the T cells.

29. The method of claim 1, wherein the inhibitor is administered orally.

30. The method of claim 1, wherein the inhibitor is administered twice a day.

31. The method of claim 27, wherein the inhibitor is administered twice a day.

32. The method of claim 1, wherein the administered T cells comprise cells that are autologous to the subject.

33. The method of claim 22, wherein the lymphodepleting chemotherapy comprises administering fludarabine or cyclophosphamide to the subject.

34. The method of claim 5, wherein the antigen is CD19.

35. The method of claim 1, wherein the inhibitor is administered before initiation of administration of the T cells.

36. The method of claim 1, wherein the inhibitor is administered twice a day for a cycle of 7, 14, 21, 28, 35 or 42 days.

37. The method of claim 1, wherein the inhibitor is administered for 1 to 24 cycles.

* * * * *